US012616572B2

(12) United States Patent
Sands et al.

(10) Patent No.: US 12,616,572 B2
(45) Date of Patent: May 5, 2026

(54) DEVICES, SYSTEMS, AND METHODS FOR A VALVE REPLACEMENT

(71) Applicant: ReValve Solutions, Inc., Irvine, CA (US)

(72) Inventors: Julie Logan Sands, McLean, VA (US); Kenneth Eugene Perry, Bainbridge Island, WA (US); Anthony Zoltan Zador, Irvine, CA (US); Kevin Stewart, Powell, TN (US); Behnood Miri, Irvine, CA (US); Nikolai Poulsen, Irvine, CA (US); Taylor Scheinblum, Vista, CA (US); Hieu Luong, Westminster, CA (US); Christopher Olson, Lake Forest, CA (US)

(73) Assignee: ReValve Solutions, Inc., Irvine, CA (US)

( * ) Notice: Subject to any disclaimer, the term of this patent is extended or adjusted under 35 U.S.C. 154(b) by 0 days.

(21) Appl. No.: 19/246,582

(22) Filed: Jun. 23, 2025

(65) Prior Publication Data

US 2026/0041551 A1 Feb. 12, 2026

Related U.S. Application Data

(63) Continuation-in-part of application No. 18/694,897, filed as application No. PCT/US2022/048304 on Oct. (Continued)

(51) Int. Cl.
| A61F 2/24 | (2006.01) |
| A61F 2/848 | (2013.01) |
| A61F 2/90 | (2013.01) |

(52) U.S. Cl.
CPC .... *A61F 2/2418* (2013.01); *A61F 2002/8486* (2013.01); *A61F 2/90* (2013.01); *A61F 2250/0039* (2013.01)

(58) Field of Classification Search
CPC .................................................. A61F 2/2418
See application file for complete search history.

(56) References Cited

U.S. PATENT DOCUMENTS

| 5,980,564 A | 11/1999 | Stinson |
| 6,290,674 B1 | 9/2001 | Roue et al. |
| (Continued) | | |

FOREIGN PATENT DOCUMENTS

| CA | 2623814 C | 4/2014 |
| CN | 106943207 A | 11/2018 |
| (Continued) | | |

*Primary Examiner* — Suba Ganesan
(74) *Attorney, Agent, or Firm* — Perkins Coie LLP

(57) ABSTRACT

Disclosed are valve replacement devices, systems, and methods. Valve replacement devices may comprise one- or two-piece systems comprising a receiver body (also called an adapter) and a valve assembly with replacement leaflets attached to and located within the receiver body. In two-piece systems, the valve assembly may be removable from the receiver body such that both can be delivered together or separately, and the receiver body may remain implanted while the valve assembly may be removed and replaced. Also described are devices, systems, and methods related to delivering, removing, and replacing a valve replacement. Such delivery methods may include transseptal insertion of a new minimum leaflet structure, and securement of the valve replacement using several securement type (e.g., supra-annular, sub-annular, radial, leaflet securement, etc.). Also described is a braided helical design that mimics the heart's natural movement, and a flange structure for assisting the functioning of the valve replacement.

30 Claims, 61 Drawing Sheets

Related U.S. Application Data 28, 2022, application No. 19/246,582, filed on Jun. 23, 2025 is a continuation-in-part of application No. 18/628,612, filed on Apr. 5, 2024, which is a continuation of application No. 18/275,988, filed as application No. PCT/US2022/015360 on Feb. 4, 2022, application No. 19/246,582, filed on Jun. 23, 2025 is a continuation-in-part of application No. 18/028,212, filed as application No. PCT/US2021/051828 on Sep. 23, 2021, now Pat. No. 12,575,928, application No. 19/246,582, filed on Jun. 23, 2025 is a continuation-in-part of application No. 17/925,590, filed as application No. PCT/US2021/032817 on May 17, 2021, application No. 19/246,582, filed on Jun. 23, 2025 is a continuation-in-part of application No. 17/921,070, filed as application No. PCT/US2021/038886 on Jun. 24, 2021, application No. 19/246,582, filed on Jun. 23, 2025 is a continuation-in-part of application No. 17/240,914, filed on Apr. 26, 2021.

(60) Provisional application No. 63/699,156, filed on Sep. 25, 2024, provisional application No. 63/407,624, filed on Sep. 17, 2022, provisional application No. 63/145,878, filed on Feb. 4, 2021, provisional application No. 63/082,035, filed on Sep. 23, 2020, provisional application No. 63/025,881, filed on May 15, 2020.

(56) References Cited

U.S. PATENT DOCUMENTS

| | | |
|---|---|---|
| 6,306,133 B1 | 10/2001 | Tu et al. |
| 6,632,241 B1 | 10/2003 | Hancock et al. |
| 7,018,401 B1 | 3/2006 | Hyodoh et al. |
| 7,329,279 B2 | 2/2008 | Haug et al. |
| 7,338,466 B2 | 3/2008 | Hart et al. |
| 7,556,646 B2 | 7/2009 | Yang et al. |
| 7,947,075 B2 | 5/2011 | Goetz et al. |
| 8,167,932 B2 | 5/2012 | Bourang et al. |
| 8,403,983 B2 | 3/2013 | Quadri et al. |
| 8,449,599 B2 | 5/2013 | Chau et al. |
| 8,500,798 B2 | 8/2013 | Rowe et al. |
| 8,568,472 B2 | 10/2013 | Marchand et al. |
| 8,568,475 B2 | 10/2013 | Nguyen et al. |
| 8,585,755 B2 | 11/2013 | Chau et al. |
| 8,628,571 B1 | 1/2014 | Hacohen et al. |
| 8,673,000 B2 | 3/2014 | Tabor et al. |
| 8,840,663 B2 | 9/2014 | Salahieh et al. |
| 8,858,621 B2 | 10/2014 | Oba et al. |
| 8,926,691 B2 | 1/2015 | Chau et al. |
| 8,992,604 B2 | 3/2015 | Gross et al. |
| 9,084,676 B2 | 7/2015 | Chau et al. |
| 9,168,131 B2 | 10/2015 | Yohanan et al. |
| 9,532,870 B2 | 1/2017 | Cooper et al. |
| 9,717,591 B2 | 8/2017 | Chau et al. |
| 9,744,031 B2 | 8/2017 | Girard et al. |
| 9,763,657 B2 | 9/2017 | Hacohen et al. |
| 9,763,778 B2 | 9/2017 | Eidenschink et al. |
| 9,763,780 B2 | 9/2017 | Morriss et al. |
| 9,867,700 B2 | 1/2018 | Bakis et al. |
| 9,867,704 B2 | 1/2018 | Lee et al. |
| 9,907,652 B2 | 3/2018 | Chau et al. |
| 9,962,260 B2 | 5/2018 | Krans et al. |
| 10,034,746 B2 | 7/2018 | Figulla et al. |
| 10,092,400 B2 | 10/2018 | Jimenez et al. |
| 10,111,748 B2 | 10/2018 | Chau et al. |
| 10,376,363 B2 | 8/2019 | Quadri et al. |
| 10,463,489 B2 | 11/2019 | Christianson et al. |
| 10,470,876 B2 | 11/2019 | Gurovich et al. |
| 10,531,951 B2 | 1/2020 | Spargias |
| 10,583,001 B2 | 3/2020 | Navia et al. |
| 10,743,992 B2 | 8/2020 | Krans et al. |
| 10,813,757 B2 | 10/2020 | Cooper et al. |
| 11,039,917 B2 | 6/2021 | Bruchman et al. |
| 11,123,186 B2 | 9/2021 | Landon et al. |
| 11,202,704 B2 | 12/2021 | Morriss et al. |
| 11,253,364 B2 | 2/2022 | Cooper et al. |
| 11,278,398 B2 | 3/2022 | Salahieh et al. |
| 11,633,279 B2 | 4/2023 | Rabito et al. |
| 11,679,236 B2 | 6/2023 | Von Oepen et al. |
| 11,872,123 B2 | 1/2024 | Schmitt |
| 11,883,287 B2 | 1/2024 | Cooper et al. |
| 11,911,264 B2 | 2/2024 | Chau et al. |
| 11,951,005 B2 | 4/2024 | Gross et al. |
| 11,969,163 B2 | 4/2024 | Hacohen et al. |
| 2002/0099432 A1 | 7/2002 | Yee |
| 2004/0186549 A1 | 9/2004 | Jayaraman |
| 2004/0243230 A1 | 12/2004 | Navia et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137693 A1 | 6/2005 | Haug et al. |
| 2005/0283231 A1 | 12/2005 | Haug et al. |
| 2006/0058872 A1 | 3/2006 | Salahieh et al. |
| 2006/0135968 A1 | 6/2006 | Schaller |
| 2007/0093869 A1 | 4/2007 | Bloom et al. |
| 2007/0244552 A1 | 10/2007 | Salahieh et al. |
| 2008/0221670 A1 | 9/2008 | Clerc et al. |
| 2008/0275540 A1 | 11/2008 | Wen |
| 2008/0300673 A1 | 12/2008 | Clerc et al. |
| 2009/0093826 A1 | 4/2009 | Warder-Gabaldon |
| 2009/0149872 A1 | 6/2009 | Gross et al. |
| 2009/0182404 A1 | 7/2009 | Shokoohi |
| 2009/0198315 A1 | 8/2009 | Boudjemline |
| 2010/0049313 A1 | 2/2010 | Alon et al. |
| 2011/0004299 A1 | 1/2011 | Navia et al. |
| 2011/0166636 A1 | 7/2011 | Rowe |
| 2011/0319988 A1 | 12/2011 | Schankereli et al. |
| 2012/0101571 A1 | 4/2012 | Thambar et al. |
| 2013/0018457 A1 | 1/2013 | Gregg et al. |
| 2013/0123912 A1 | 5/2013 | Tung et al. |
| 2013/0172992 A1 | 7/2013 | Gross et al. |
| 2013/0197629 A1 | 8/2013 | Gainor et al. |
| 2013/0304200 A1 | 11/2013 | McLean et al. |
| 2013/0338684 A1 | 12/2013 | Hausen |
| 2014/0005777 A1 | 1/2014 | Anderl et al. |
| 2014/0088696 A1* | 3/2014 | Figulla .................. A61F 2/2418 623/2.17 |
| 2014/0172083 A1 | 6/2014 | Bruchman et al. |
| 2014/0180014 A1 | 6/2014 | Ransden et al. |
| 2014/0296969 A1 | 10/2014 | Tegels et al. |
| 2014/0316516 A1 | 10/2014 | Vidlund et al. |
| 2014/0324164 A1 | 10/2014 | Gross et al. |
| 2014/0371844 A1* | 12/2014 | Dale .................... A61F 2/2418 623/2.11 |
| 2015/0142103 A1 | 5/2015 | Vidlund |
| 2015/0223934 A1 | 8/2015 | Vidlund et al. |
| 2015/0272731 A1 | 10/2015 | Racchini et al. |
| 2015/0327994 A1 | 11/2015 | Morriss et al. |
| 2015/0351903 A1 | 12/2015 | Morriss et al. |
| 2015/0359629 A1 | 12/2015 | Ganesan et al. |
| 2016/0089233 A1 | 3/2016 | Lee et al. |
| 2016/0256270 A1 | 9/2016 | Folan et al. |
| 2016/0310268 A1 | 10/2016 | Oba et al. |
| 2016/0331529 A1 | 11/2016 | Marchand et al. |
| 2017/0056175 A1 | 3/2017 | Chin et al. |
| 2017/0071766 A1 | 3/2017 | Düring et al. |
| 2017/0165066 A1 | 6/2017 | Rothstein |
| 2017/0172737 A1 | 6/2017 | Kuetting et al. |
| 2017/0189175 A1 | 7/2017 | Justino et al. |
| 2017/0266003 A1 | 9/2017 | Hammer et al. |
| 2017/0296332 A1 | 10/2017 | Harder |
| 2017/0367822 A1 | 12/2017 | Naor et al. |
| 2018/0049868 A1 | 2/2018 | Board et al. |
| 2018/0049873 A1 | 2/2018 | Manash et al. |
| 2018/0055629 A1 | 3/2018 | Oba et al. |
| 2018/0125647 A1 | 5/2018 | Nasr |
| 2018/0125648 A1 | 5/2018 | Nasr |
| 2018/0125649 A1 | 5/2018 | Nasr |
| 2018/0125650 A1 | 5/2018 | Nasr |
| 2018/0125651 A1 | 5/2018 | Nasr |

(56) References Cited

U.S. PATENT DOCUMENTS

| | | | |
|---|---|---|---|
| 2018/0193138 A1 | 7/2018 | Vidlund | |
| 2018/0250126 A1 | 9/2018 | O'Connor et al. | |
| 2018/0256321 A1 | 9/2018 | Zhang et al. | |
| 2018/0256327 A1 | 9/2018 | Perszyk et al. | |
| 2018/0325660 A1 | 11/2018 | Mauch et al. | |
| 2018/0325664 A1 | 11/2018 | Gonda et al. | |
| 2019/0053897 A1 | 2/2019 | Levi et al. | |
| 2019/0060060 A1 | 2/2019 | Chau et al. | |
| 2019/0209311 A1 | 7/2019 | Zhang et al. | |
| 2019/0240006 A1 | 8/2019 | Chodór | |
| 2019/0240008 A1 | 8/2019 | Salahieh et al. | |
| 2019/0254816 A1 | 8/2019 | Anderson et al. | |
| 2019/0269839 A1 | 9/2019 | Wilson et al. | |
| 2020/0030092 A1 | 1/2020 | Tuval et al. | |
| 2020/0163761 A1 | 5/2020 | Hariton et al. | |
| 2020/0253728 A1 | 8/2020 | Tayeb et al. | |
| 2020/0276014 A1 | 9/2020 | Burkart et al. | |
| 2020/0306037 A1 | 10/2020 | Siegel et al. | |
| 2020/0375731 A1 | 12/2020 | Ratz et al. | |
| 2021/0000593 A1 | 1/2021 | Rahmig et al. | |
| 2021/0030536 A1 | 2/2021 | Kaleta | |
| 2021/0068948 A1 | 3/2021 | Jimenez et al. | |
| 2021/0068950 A1 | 3/2021 | Quill et al. | |
| 2021/0077256 A1 | 3/2021 | Pellegrini et al. | |
| 2021/0330455 A1 | 10/2021 | Sands et al. | |
| 2022/0031452 A1 | 2/2022 | Alleleyn et al. | |
| 2022/0117732 A1 | 4/2022 | Tuval et al. | |
| 2022/0296367 A1 | 9/2022 | Hoang et al. | |
| 2023/0125281 A1 | 4/2023 | Alleleyn | |
| 2023/0200983 A1 | 6/2023 | Sands et al. | |
| 2023/0240846 A1 | 8/2023 | Sands et al. | |
| 2023/0320847 A1 | 10/2023 | Rowe et al. | |
| 2023/0355379 A1 | 11/2023 | Verine et al. | |
| 2023/0372085 A1 | 11/2023 | Sands et al. | |
| 2023/0372097 A1 | 11/2023 | Morrissey et al. | |
| 2024/0008978 A1 | 1/2024 | Nawalakhe et al. | |
| 2024/0081994 A1 | 3/2024 | Cooper et al. | |
| 2024/0122701 A1 | 4/2024 | Sands et al. | |
| 2024/0374381 A1 | 11/2024 | Sands et al. | |
| 2024/0407915 A1 | 12/2024 | Kupumbati et al. | |
| 2024/0415643 A1 | 12/2024 | Sands et al. | |

FOREIGN PATENT DOCUMENTS

| | | |
|---|---|---|
| DE | 102015209537 A1 | 11/2016 |
| EP | 2537487 B1 | 4/2013 |
| EP | 2921139 B1 | 11/2018 |
| EP | 4138735 A2 | 3/2023 |
| JP | 2007526011 A | 9/2007 |
| JP | 2008541865 A | 11/2008 |
| JP | 2011509806 A | 3/2011 |
| JP | 2012500665 A | 1/2012 |
| JP | 2013512765 A | 4/2013 |
| JP | 2018523553 A | 8/2018 |
| WO | 2014153267 A2 | 9/2014 |
| WO | 2016110613 A1 | 7/2016 |
| WO | 2020058534 A1 | 3/2020 |
| WO | 2020073981 A1 | 4/2020 |
| WO | 2020109576 A1 | 6/2020 |
| WO | 2020109596 A1 | 6/2020 |
| WO | 2020157018 A1 | 8/2020 |
| WO | 2021185528 A1 | 9/2021 |
| WO | 2024020181 A1 | 1/2024 |

* cited by examiner

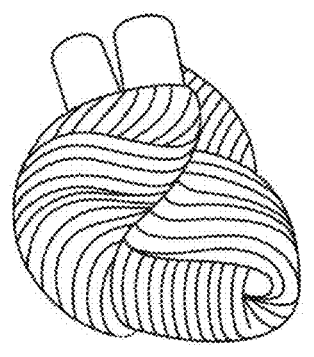
Ejection
Suction
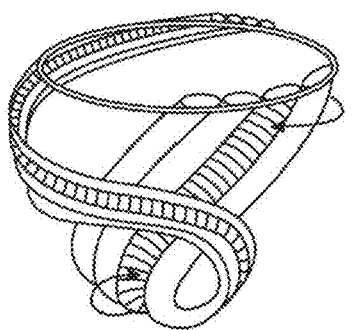 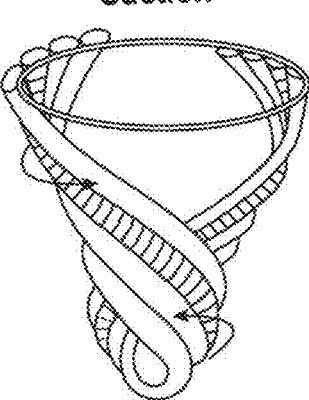
FIG. 2

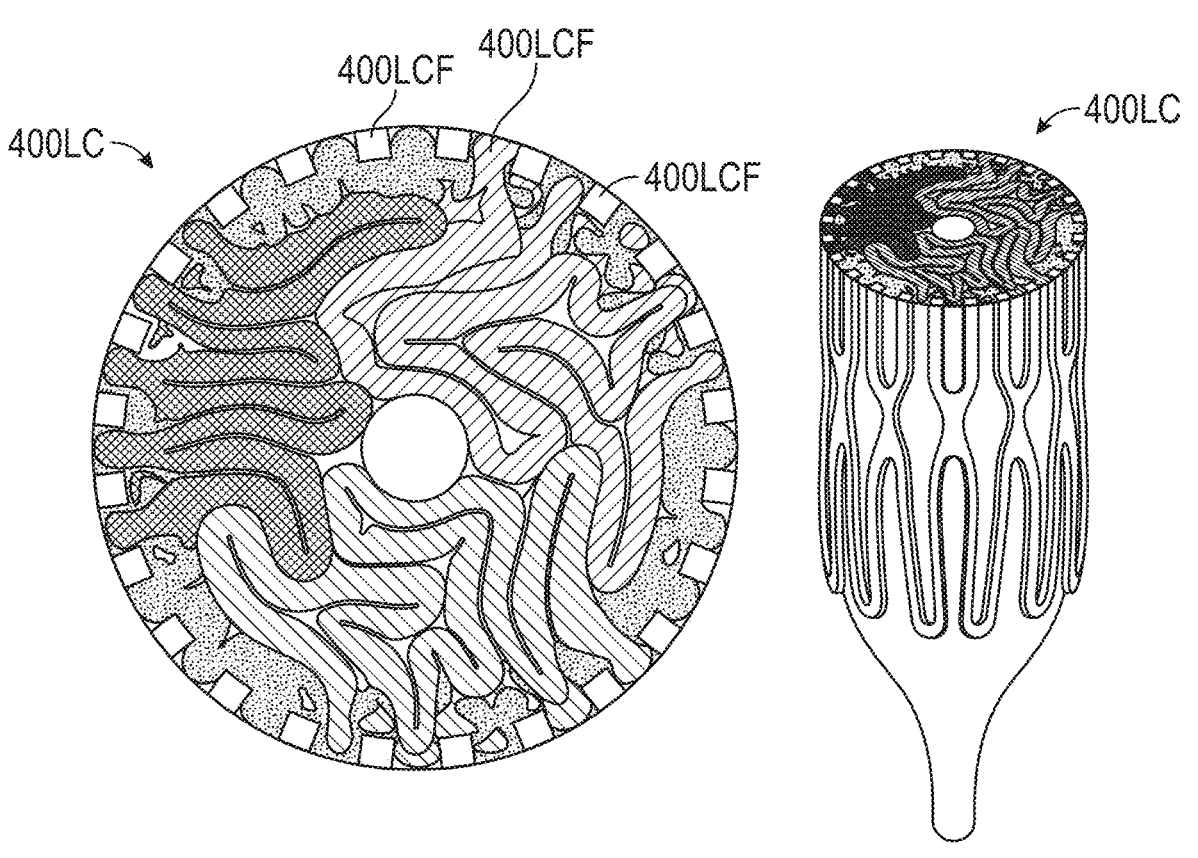
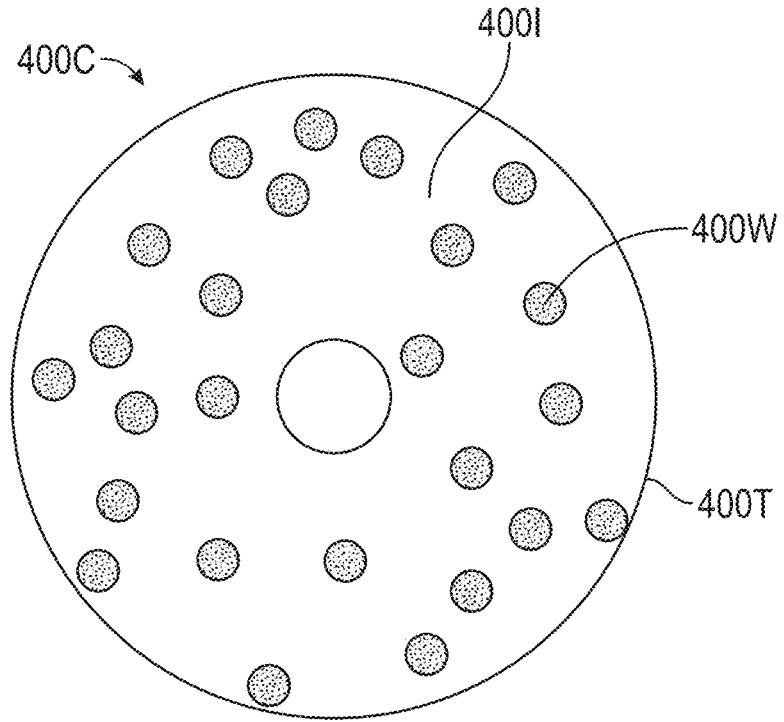
FIG. 24

Inflow (Atrial) Side

625a    625at    610    665

H₃

Lateral

Medial
H₂

630a

Outflow (Ventricular) Side

Inflow End
(Atrial Side)

1505b

1505a

1530c

1330b

Outflow End
(Ventricular
Side)

1330b

P2

φ°

150°

1505a

1505b

Medial
(M)

Lateral
(L)

1530c

210°

1330a

A2

5000

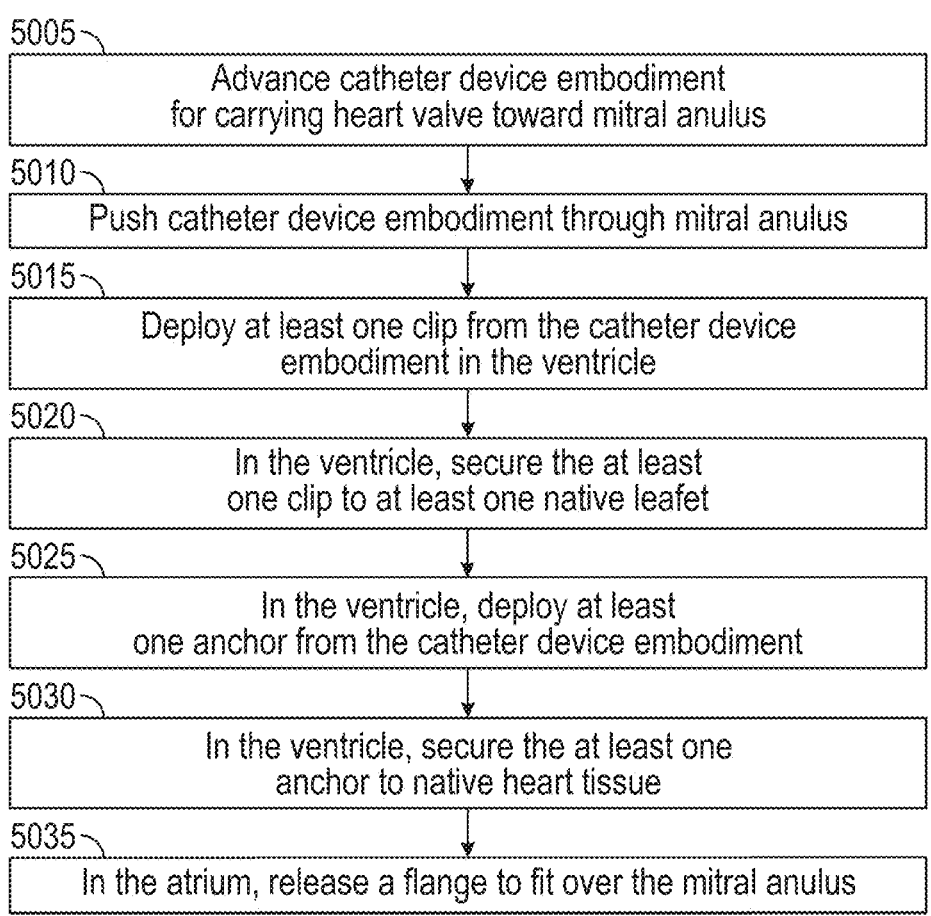

5005
Advance catheter device embodiment
for carrying heart valve toward mitral anulus 5010
Push catheter device embodiment through mitral anulus 5015
Deploy at least one clip from the catheter device
embodiment in the ventricle 5020
In the ventricle, secure the at least
one clip to at least one native leafet 5025
In the ventricle, deploy at least
one anchor from the catheter device embodiment 5030
In the ventricle, secure the at least one
anchor to native heart tissue 5035
In the atrium, release a flange to fit over the mitral anulus

DEVICES, SYSTEMS, AND METHODS FOR A VALVE REPLACEMENT

CROSS-REFERENCE TO RELATED APPLICATION(S)

This application claims priority to U.S. App No. 63/699,156, filed on Sep. 25, 2024. This application is a continuation in-part of U.S. application Ser. No. 18/694,897, filed on Mar. 22, 2024, which is a National Stage Entry of International App. No. PCT/US22/48304, filed Oct. 28, 2022, which claims priority and benefit to U.S. App. No. 63/407,624, filed Sep. 17, 2022. This application is a continuation in-part of U.S. application Ser. No. 18/628,612, filed on Apr. 5, 2024, which is a continuation of U.S. application Ser. No. 18/275,988, filed on Aug. 4, 2023, which is a National Stage Entry of International App No. PCT/US22/15360, filed Feb. 4, 2022, which claims priority and benefit to U.S. App. No. 63/145,878, filed Feb. 4, 2021. This application is a continuation in-part of U.S. application Ser. No. 18/028,212, filed Mar. 23, 2023, which is a National Stage Entry of International App. No. PCT/US21/51828, filed Sep. 23, 2021, which claims priority and benefit to U.S. App. No. 63/082,035, filed Sep. 23, 2020. This application is a continuation in-part of U.S. application Ser. No. 17/925,590, filed Nov. 15, 2022, which is a National Stage Entry of International App. No. PCT/US21/32817, filed May 17, 2021, which claims priority and benefit to U.S. App. No. 63/025,881, filed May 15, 2020. This application is a continuation in-part of U.S. application Ser. No. 17/921,070, filed Oct. 24, 2022, which is a National Stage Entry of International App. No. PCT/US21/38886, filed Jun. 24, 2021, which claims priority and benefit to U.S. App. No. 63/015,353, filed Apr. 24, 2020, and U.S. App. No. 63/025,881, filed May 15, 2020. This application is a continuation in-part of U.S. application Ser. No. 17/240,914, filed on Apr. 26, 2021, which claims priority and benefit to U.S. App. No. 63/015,353, filed Apr. 24, 2020, and U.S. App No. 63/025,881, filed May 15, 2020. The contents of the above-referenced applications are incorporated herein by this reference as though set forth in their entirety.

FIELD OF USE

The present disclosure relates generally to replacement heart-valve technology, and more specifically to devices, systems, and methods for delivering a valve replacement or replacing a valve replacement. Aspects of the disclosure also relate to unique features of the innovative replacement heart valve technology, including a helical braided wire design of the replacement heart valve frame and a multipoint anchoring system that utilizes a combination of supra-annular anchoring that anchors to the top of the annulus of the native heart valve, sub-annular anchoring that anchors to the bottom of the annulus of the native heart valve, and selectable and customizable radial force within the replacement heart valve that anchors within the annulus of the native heart valve. In embodiments, the innovative replacement heart valve technology includes a "floating valve" that is anchored in the atrium (for example by a flange) and in the ventricle (for example with leaflet clips and medial and lateral stabilizers) with a valve size that is minimally oversized in comparison to a native mitral valve annulus in one of more of the anterior-to-posterior (A-P) and commissure-to-commissure (C-C) directions, thereby providing a valve that effectively floats in the native annulus yet is anchored in position. In embodiments, the innovative replacement heart valve technology includes a posterior directionality (which may include a posterior tilt and/or posterior positioning of the replacement valve towards the posterior wall in the ventricle) whereby flow through the replacement valve from the atrium to the ventricle travels in a posterior direction relative to the mitral annulus and/or left ventricular apex (as opposed to directly towards the native heart's apex or anterior segment) and fosters a more natural vortex flow into the left ventricle and through the left ventricular outflow tract (LVOT). In embodiments, the atrial flange, leaflet clips and stabilizers create a geometrical bias towards a posterior direction when deployed within the native mitral valve thereby promoting vortex blood flow between the native atrium and native ventricle areas and left ventricle outflow tract (LVOT) preservation.

BACKGROUND

Heart valve intervention, such as full open-heart surgery, is often required to treat diseases of one or more of the four heart valves (which work together to keep blood properly flowing through the heart). Replacement and/or repair of a heart valve is often required when a valve is "leaky" (e.g., there is valve regurgitation) or when a valve is narrowed and does not open properly (e.g., valve stenosis). Heart valve replacement, such as mitral valve or tricuspid valve replacement, typically involves replacement of the heart's original (native) valve with a replacement mechanical and/or tissue (bioprosthetic) valve. Common problems with the replacement of valves and/or the frames carrying them include degradation of the leaflets (valve-like structure); breaking or failing frames, particularly with laser-cut nitinol frames; and undesirable changing in size of the native valve annulus. Replacement heart valves pose additional problems after they are implanted. For example, the replacement valve may move or migrate after it is placed in a desired location in the heart, or its location may not permit proper directional flow of blood through other parts of the organ, such as the outflow tract of the left ventricle.

Replacement valves are also not readily retrievable, most often because such removal can damage the surrounding heart tissue. This can be particularly problematic, for example, if the replacement valve is not properly and accurately placed into position when it is implanted in the native heart, as well as when the replacement valve starts failing, which may occur soon or years after initial implantation. An additional problem is that typical replacement valves, especially laser-cut valve frames, are relatively stiff and inflexible, resulting in a valve that does not flex with the dynamic movements of the pumping heart. Such inflexible valves do not conform to such dynamic movements, which can cause trauma to the heart surfaces, cause breaks in the frame itself, and otherwise cause or exacerbate problems during or after implantation. Thus, what is needed are treatment solutions for structural heart disease (e.g., mitral valve disease) that allow for ongoing treatment options and improving the long-term health of patients. Relatedly, there is a need for an effective Transcatheter Mitral valve replacement (TMVR) that can be simply and securely delivered while providing a platform for future intervention.

Also needed are devices, systems, and methods for a valve replacement that enables compact and secure delivery into the heart and convenient control of both the valve replacement during implantation as well as the expansion and retraction of the valve replacement when being implanted or removed/replaced via a catheter. Also needed are devices, systems, and methods for ensuring proper directional flow of blood through the heart during and after a valve replacement procedure. Also needed are devices, systems, and methods for ensuring that the replacement valve is placed into the proper position when being implanted in the native heart and prior to removing the current/prior valve.

Such devices, systems, and methods should provide the functionality of a one-piece system comprising both a receiver body with engaging mechanisms that secure to the heart and a valve assembly with replacement leaflets that are attached within the receiver body. Such devices, systems, and methods should also provide the functionality of a two-piece system comprising a receiver body and valve assembly that are compatible with each other yet wherein the valve assembly may be removable from the receiver body such that both can be delivered together or separately and such that the receiver body may remain implanted while the valve assembly may be removed and replaced. Some such devices, systems, and methods should also relate to delivering transcatheter therapies.

SUMMARY OF THE DISCLOSURE

The following presents a simplified overview of the example embodiments in order to provide a basic understanding of some embodiments of the present disclosure. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented herein below. It is to be understood that both the following general description and the following detailed description are exemplary and explanatory only and are not restrictive.

The present disclosure is directed to devices, systems, and methods for a valve replacement (also referred to as a prosthetic mitral valve, a replacement mitral valve, a replacement heart valve, a replacement valve, or a bioprosthetic valve) that serves the purpose of anchoring, sealing, and controlling the position of the leaflets and sub-valvular structure. The valve replacement may be highly flexible, resilient, fatigue resistant, and securable to the native valve tissue. And it is self-adapting, meaning it adapts to—and, in addition, supports—the natural movement of the heart. In an embodiment, the valve replacement comprises a collapsible prosthetic mitral valve that attaches to the native valve tissue and provides a sealing portion. In embodiments, the valve replacement comprises a receiver frame optimized for effective sealing and fixation to the native valve, wherein the design of the receiver frame is anatomically inspired and designed to maximize ventricular filling and minimize outflow tract obstruction. In embodiments, the receiver frame is a tubular frame that is designed to receive replacement leaflets in the form of a separate structure containing the replacement leaflets with the separate structure containing the replacement leaflets sized to nest within the tubular frame. In other embodiments, the receiver frame (also called a receiver or tubular frame) has replacement leaflets directly attached to its braided wire frame.

In some examples, the valve replacement includes a tubular frame with an inflow end and an outflow end. In some examples, the tubular frame may include at least one braided wire wound in a helical spiral direction. The helical spiral direction may begin at the inflow end and end at the outflow end. The tubular frame may be configured to lengthen and compress in relation to a heart contraction.

The valve replacement—whether as a one- or two-piece system—may further comprise a valve assembly, wherein the valve assembly comprises leaflets and is compatible to reside within the tubular frame. In some examples, the valve assembly is connected to the tubular braided frame, for example on the wireframe's diamond cell, and is configured to provide a seal between the inflow end and the outflow end. Attachment techniques such as certain knot locations, suture methods, and materials to the diamond cell allows for variability in the amount of extension allowed during crimping. This also allows for the load generated during leaflet closure to be spread across more of the wireframe, reducing potential for wire fretting.

The present disclosure also provides for a one- or two-piece valve replacement system that—due to its braided-wire frame design—is compressible to a smaller profile when compared to the prior art, wherein the smaller compressed profile allows for delivery via not only transapical approaches but also transfemoral and transseptal approaches. In embodiments, the valve replacement is constructed using a braided wire that is wrapped in an over-under fashion permitting the apices and crossing points of the braided wire structure to have a cylindrical helical movement, wherein the structure is free to move within a helical spiral form. In embodiments, shape set fabric and sewn nodes using sutures to sew the fabric to the frame provide upper and lower constraints within which the braided wire frame structure is still able to move with the helical movement of the heart.

In embodiments, a prosthetic mitral valve (also referred to herein as a replacement valve) is disclosed that comprises a tubular body (also referred to herein as a receiver, receiver body, adapter and adapter body) with a first braided wire, an inflow end and an outflow end, and a height between the inflow and outflow ends, a flange (also referred to as an atrial skirt and a sealing skirt) with a second braided wire woven into the first braided wire of the tubular body, the flange comprising a portion extending radially outwardly from an intermediate portion of the height of the tubular body and towards the inflow end of the tubular body, and the flange comprising a curved section and a D-shaped perimeter, wherein the flange's curved section comprises a convex section and a concave section with an inflection point therebetween. In embodiments, at least a portion of the flange's curved section is configured to rest in an intra-annular space of a native mitral annulus, at least a portion of the flange's concave portion is configured to rest in a supra-annular space of the native mitral annulus, at least a portion of the flange's D-shaped perimeter is configured to rest on top of the native mitral annulus, and wherein the flange resists migration of the prosthetic mitral valve towards the outflow end when deployed in the native mitral valve. In embodiments, the second braided wire of the flange comprises peaks along the D-shaped perimeter of the flange, wherein the peaks of the flange comprise a petal shape near the inflow end of the tubular body. In embodiments, the prosthetic mitral valve further comprises a medial stabilizer extending medially from a lower portion of the height of the tubular body at the outflow end, a lateral stabilizer extending laterally from a lower portion of the height of the tubular body at the outflow end, a posterior leaflet clip extending posteriorly from a lower portion of the height of the tubular body at the outflow end, the posterior leaflet clip configured to capture a P2 region of a native posterior mitral leaflet, and an anterior leaflet clip extending anteriorly from a lower portion of the height of the tubular body at the outflow end, the anterior leaflet clip configured to capture an A2 region of a native anterior mitral leaflet, wherein the medial and lateral stabilizers and posterior and anterior leaflet clips resist migration of the prosthetic mitral valve towards the inflow end. In embodiments, leaflet clips are also referred to herein as clips, leaflet anchors, and anchor clips and stabilizers are referred to as struts and anchor struts. In embodiments of the prosthetic mitral valve, the first braided wire of the tubular body comprises at least 8 peaks and no more than 16 peaks at the outflow end and at least 8 peaks and no more than 16 peaks at the inflow end of the tubular body. In embodiments, the second braided wire of the flange comprises at least 8 peaks and no more than 16 peaks at the outflow end of the tubular body and at least 8 peaks and no more than 16 peaks along the D-shaped perimeter of the flange. In an embodiment, the first braided wire of the tubular body comprises 12 peaks at the outflow end and 12 peaks at the inflow end of the tubular body and the second braided wire of the flange comprises 12 peaks at the outflow end of the tubular body and 12 peaks along the D-shaped perimeter of the flange. In other embodiments of the prosthetic mitral valve, the first braided wire of the tubular body comprises between 8 to 12 peaks at the outflow end and between 8 to 12 peaks at the inflow end of the tubular body and the second braided wire of the flange comprises between 8 to 12 peaks at the outflow end of the tubular body and between 8 to 12 peaks along the D-shaped perimeter of the flange. In embodiments, the inflow end of the prosthetic mitral valve points towards a left atrium when deployed in the native mitral valve and the outflow end points towards a left ventricle when deployed in the native mitral valve. In embodiments of the prosthetic mitral valve, at least a portion of the supra-annular space where the flange is configured to rest when deployed in the native mitral valve comprises an atrial floor of the left atrium, with at least a portion of the flange's D-shaped perimeter is configured to rest on top of the atrial floor when deployed in the native mitral valve and at least a portion of the flange's D-shaped perimeter is configured to rest at an aortic-mitral curtain area when deployed in the native mitral valve. In embodiments of the prosthetic mitral valve, at least a portion of the flange's D-shaped perimeter that is configured to rest on top of the atrial floor comprises a second circular section and the flange's curved section transitions into the D-shaped perimeter, wherein at least a portion of the flange's transition from the curved section into the D-shaped perimeter comprises a circular flange section that is configured to rest in an intra-annular space when deployed in the native mitral valve. In embodiments, the portion of the flange's transition from the curved section into the D-shaped perimeter comprises at least some of the convex portion and the inflection point of the flange's curved section. In embodiments, the peaks along the D-shaped perimeter of the flange comprise petal shapes configured to rest on a native atrial floor and native mitral annulus.

In embodiments, a prosthetic mitral valve is disclosed that comprises a receiver body (also called a tubular body) comprising a first braided wire, an inflow end and an outflow end, and a height between the inflow and outflow ends, a flange comprising a second braided wire woven into the first braided wire of the receiver body, the flange comprising a portion extending radially outwardly from an intermediate portion of the height of the receiver body and towards the inflow end of the receiver body, and the flange comprising a curved section and a D-shaped perimeter, wherein at least a portion of the flange's curved section is configured to rest in an intra-annular space of a native mitral annulus when deployed in a native mitral valve, and wherein at least a portion of the flange's D-shaped perimeter is configured to rest on top of the native mitral annulus when deployed in the native mitral valve, wherein the flange resists migration of the prosthetic mitral valve towards the outflow end. In embodiments, the prosthetic mitral valve further comprises a medial stabilizer formed from a wire that extends medially from a lower portion of the height of the receiver body at the outflow end, wherein the medial stabilizer extends from the second braided wire of the flange. In embodiments, the prosthetic mitral valve further comprises a lateral stabilizer formed from a wire that extends laterally from a lower portion of the height of the receiver body at the outflow end, wherein the lateral stabilizer extends from the second braided wire of the flange. In embodiments, the stabilizers are coupled to the flange or the receiver body by connecting the stabilizers to the braided wire of the flange or braided wire of the receiver body by welding, fusing, grafting, or mechanically coupling the wires together with a fastener. In other embodiments, the stabilizers are held by the braided wire of the flange or braided wire of the receiver body by a mechanical fit from the wires being interwoven (e.g., the stabilizer wire interwoven into the receiver or flange wires). In embodiments, the prosthetic mitral valve further comprises a posterior leaflet clip extending posteriorly from a lower portion of the height of the receiver body at the outflow end, the posterior leaflet clip configured to capture a P2 region of a native posterior mitral leaflet, wherein the posterior leaflet clip extends from the first braided wire of the receiver body and an anterior leaflet clip extending anteriorly from a lower portion of the height of the receiver body at the outflow end, the anterior leaflet clip configured to capture an A2 region of a native anterior mitral leaflet, wherein the anterior leaflet clip extends from the first braided wire of the receiver body, wherein the medial and lateral stabilizers and posterior and anterior leaflet clips resist migration of the prosthetic mitral valve towards the inflow end. In embodiments, the leaflet clips are coupled to the flange or the receiver body by connecting the leaflet clips to the braided wire of the flange or braided wire of the receiver body by welding, fusing, grafting, or mechanically coupling the wires together with a fastener. In other embodiments, the leaflet clips are held by the braided wire of the flange or braided wire of the receiver body by a mechanical fit from the wires being interwoven (e.g., the leaflet clip wire interwoven into the receiver or flange wires). In embodiments, the stabilizers and clips are connected to the same braided wire of the receiver body or flange and in other embodiments the stabilizers and clips are connected to different braided wires of the receiver body or flange. In embodiments, the stabilizers and clips are connected to the prosthetic mitral valve at the braided receiver body wire or braided flange wire along a height of the receiver body, including at a height that is in the top third, middle third or bottom third of the receiver body and other embodiments at a height that is in the top quarter, middle quarters or bottom quarter of the receiver body. Also, in embodiments, the braided flange is interwoven into the braided receiver body and the flange braid exits the receiver body along a height of the receiver body, including at a height that is in the top third, middle third or bottom third of the receiver body and other embodiments at a height that is in the top quarter, middle quarters or bottom quarter of the receiver body. In embodiments of the prosthetic mitral valve, the height of the receiver body is between 17 to 26 millimeters, with embodiments having a height of 17 mm, 17.5 mm, 18 mm, 18.5 mm, 19 mm, 19.5 mm, 20 mm, 20.5 mm, 21 mm, 21.5 mm, 22 mm, 22.5 mm, 23 mm, 23.5 mm, 24 mm, 24.5 mm, 25 mm, 25.5 mm, and 26 mm. In embodiments of the prosthetic mitral valve, the inner diameter (ID) of the receiver body is between 25 to 34 millimeters, with embodiments having an ID of 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, and 34 mm. In embodiments of the prosthetic mitral valve, the medial stabilizer comprises a height of between 7 to 15 millimeters and the lateral stabilizer comprises a height of between 7 to 15 millimeters, with height measured from the bottom (outflow end) of the receiver to the top (inflow end). In embodiments of the prosthetic mitral valve, the posterior leaflet clip comprises a height of between 10 to 18 millimeters and the anterior leaflet clip comprises a height of between 11 to 19 millimeters, with height measured from the bottom (outflow end) of the receiver to the top (inflow end). In embodiments of the prosthetic mitral valve, the anterior leaflet clip comprises a curved wire that exits the receiver body at a first location along the circumference of the receiver body and re-enters the receiver body at a second location along the circumference of the receiver body, wherein the first and second locations along the circumference of the receiver body are separated by a width of between 4 to 15 millimeters and the curved wire of the anterior leaflet clip comprises a widest point between the curved wire of between 8 to 16 millimeters. In embodiments of the prosthetic mitral valve, the posterior leaflet clip comprises a curved wire that exits the receiver body at a third location along the circumference of the receiver body and re-enters the receiver body at a fourth location along the circumference of the receiver body, wherein the third and fourth locations along the circumference of the receiver body are separated by a width of between 4 to 15 millimeters, wherein the curved wire of the posterior leaflet clip comprises a widest point between the curved wire of between 6 to 14 millimeters. In embodiments of the prosthetic mitral valve, the medial stabilizer comprises a curved wire that exits the receiver body at a fifth location along a circumference of the receiver body and re-enters the receiver body at a sixth location along the circumference of the receiver body, wherein the fifth and sixth locations along the circumference of the receiver body are separated by a width of between 4 to 15 millimeters and the lateral stabilizer comprises a curved wire that exits the receiver body at a seventh location along the circumference of the receiver body and re-enters the receiver body at an eighth location along the circumference of the receiver body, wherein the seventh and eighth locations along the circumference of the receiver body are separated by a width of between 4 to 15 millimeters. In embodiments of the prosthetic mitral valve, the curved wire of the medial stabilizer comprises a widest point between the curved wire of between 6 to 18 millimeters and the curved wire of the lateral stabilizer comprises a widest point between the curved wire of between 6 to 18 millimeters. The number and locations of the various locations along the circumference of the receiver body (or tubular body) where the clips and stabilizers enter and exit the receiver body can vary in embodiments.

In embodiments, a prosthetic mitral valve is disclosed comprising a tubular body comprising a first braided wire, an inflow end and an outflow end, and a height between the inflow and outflow ends, a flange comprising a second braided wire woven into the first braided wire of the tubular body, the flange comprising a portion extending radially outwardly from an intermediate portion of the height of the tubular body and towards the inflow end of the tubular body, and the flange comprising a curved section and a D-shaped perimeter, wherein at least a portion of the flange's curved section is configured to rest in an intra-annular space of a native mitral annulus when deployed in a native mitral valve, and wherein at least a portion of the flange's D-shaped perimeter is configured to rest on top of the native mitral annulus when deployed in the native mitral valve, wherein the flange resists migration of the prosthetic mitral valve towards the outflow end, a medial stabilizer extending medially from a lower portion of the height of the tubular body at the outflow end, wherein the medial stabilizer extends from the second braided wire of the flange, a lateral stabilizer extending laterally from a lower portion of the height of the tubular body at the outflow end, wherein the lateral stabilizer extends from the second braided wire of the flange, a posterior leaflet clip extending posteriorly from a lower portion of the height of the tubular body at the outflow end, the posterior leaflet clip configured to capture a P2 region of a native posterior mitral leaflet, wherein the posterior leaflet clip extends from the first braided wire of the tubular body, and an anterior leaflet clip extending anteriorly from a lower portion of the height of the tubular body at the outflow end, the anterior leaflet clip configured to capture an A2 region of a native anterior mitral leaflet, wherein the anterior leaflet clip extends from the first braided wire of the tubular body, wherein the medial and lateral stabilizers and posterior and anterior leaflet clips resist migration of the prosthetic mitral valve towards the inflow end. In embodiments, the stabilizers are formed from separate wires that are connected to the second braided wire of the flange (e.g., welded, grafted, coupled together) and extend from the second braided wire of the flange. And in embodiments, the leaflet clips are formed from separate wires that are connected to the first braided wire of the receiver/tubular body (e.g., welded, grafted, coupled together) and extend from the first braided wire of the receiver/tubular body.

In embodiments, a prosthetic mitral valve is disclosed, comprising a tubular body (also called a receiver or receiver body) comprising a first braided wire, an inflow end and an outflow end, and a height between the inflow and outflow ends, wherein the tubular body is undersized in comparison to a native mitral annulus of a native mitral valve in one or more of an anterior-to-posterior (A-P) and commissure-to-commissure (C-C) directions, wherein the tubular body does not exert radial force against the native annulus in the undersized directions when deployed in the native mitral valve. In embodiments, the height of the tubular body is between 17 to 26 millimeters and the tubular body has an inner diameter of between 25 to 34 millimeters. In embodiments, the tubular body in an uncompressed configuration has an inner diameter of at least 30 mm and is deliverable to the native mitral valve in a compressed configuration that is no more than 27Fr in diameter (in embodiments, the compressed configuration diameter being the outer diameter of the compressed tubular body or receiver body). In embodiments, the tubular body in an uncompressed configuration has an inner diameter of at least 29 mm and is deliverable to the native mitral valve in a compressed configuration that is no more than 26Fr in diameter (in embodiments, the compressed configuration diameter being the outer diameter of the compressed tubular body or receiver body). In embodiments, the tubular body in an uncompressed configuration has an inner diameter of at least 32 mm and is deliverable to the native mitral valve in a compressed configuration that is no more than 28Fr in diameter (in embodiments, the compressed configuration diameter being the outer diameter of the compressed tubular body or receiver body). In embodiments, the prosthetic mitral valve further comprises a flange comprising a second braided wire woven into the first braided wire of the tubular body, the flange comprising a portion extending radially outwardly from an intermediate portion of the height of the tubular body and towards the inflow end of the tubular body, and the flange comprising a curved section and a D-shaped perimeter. In embodiments, the prosthetic mitral valve further comprises a medial stabilizer extending medially from a lower portion of the height of the tubular body at the outflow end and a lateral stabilizer extending laterally from a lower portion of the height of the tubular body at the outflow end. In embodiments, the prosthetic mitral valve further comprises a posterior leaflet clip extending posteriorly from a lower portion of the height of the tubular body at the outflow end and an anterior leaflet clip extending anteriorly from a lower portion of the height of the tubular body at the outflow end. In embodiments, the leaflet clips and stabilizers extend from the tubular body at a lower half or a lower third portion or a lower quarter portion of the height of the tubular body. In embodiments, the flange extends from the tubular body at a middle third portion or a middle quarter portion of the height of the tubular body. In embodiments, the flange of the prosthetic mitral valve resists migration towards the outflow end when deployed in the native mitral valve and one or more of the posterior and anterior leaflet clips and medial and lateral stabilizers resist migration towards the inflow end when deployed in the native mitral valve.

Relatedly, devices, systems, and methods for delivering a valve replacement are also described herein. One method embodiment of delivering a replacement heart valve may include the step of advancing a catheter device for carrying a replacement heart valve toward a mitral annulus. The method embodiment may also include the step of pushing the catheter device through the mitral annulus. The method embodiment may also include the step of deploying a portion of the replacement valve in the native atrium before advancing the delivery catheter past the native mitral annulus. For example, in embodiments, an outflow portion of the valve replacement is deployed in a native atrium, without deploying the leaflet clips, before advancing the catheter device and replacement valve through the native mitral annulus and deploying the remainder of the replacement valve in the ventricle.

Still other advantages, embodiments, and features of the subject disclosure will become readily apparent to those of ordinary skill in the art from the following description wherein there is shown and described certain embodiments simply by way of illustration of various ways to carry out the subject disclosure. As will be realized, the present disclosure is capable of other different embodiments and its several details are capable of modifications in various obvious embodiments all without departing from, or limiting, the scope herein. Accordingly, the drawings and descriptions will be regarded as illustrative in nature and not as restrictive.

BRIEF DESCRIPTION OF THE DRAWINGS

The accompanying drawings, which are incorporated in and constitute a part of this specification, illustrate embodiments of the disclosure and together with the general description of the disclosure given above and the detailed description of the drawings given below, serve to explain the principles of the disclosure. In certain instances, details that are not necessary for an understanding of the disclosure or that render other details difficult to perceive may have been omitted.

FIG. 2 generally illustrates the helical functionality of the human heart.

FIG. 24 generally illustrates a comparison of a crimped laser cut valve versus a crimped braided valve of an embodiment of a valve replacement as disclosed herein.

FIGS. 31-32 generally illustrate embodiments of leaflet clips of a valve replacement as disclosed herein.

FIGS. 33-35 generally illustrate embodiments of a valve replacement as disclosed herein.

FIG. 80 is a flow diagram generally illustrating a method of delivering a replacement heart valve as disclosed herein.

DETAILED DESCRIPTION OF EMBODIMENTS

Before the present systems and methods are disclosed and described, it is to be understood that the systems and methods are not limited to specific methods, specific components, or to particular implementations. It is also to be understood that the terminology used herein is for the purpose of describing particular embodiments only and is not intended to be limiting. Various embodiments are described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

Figure 1:
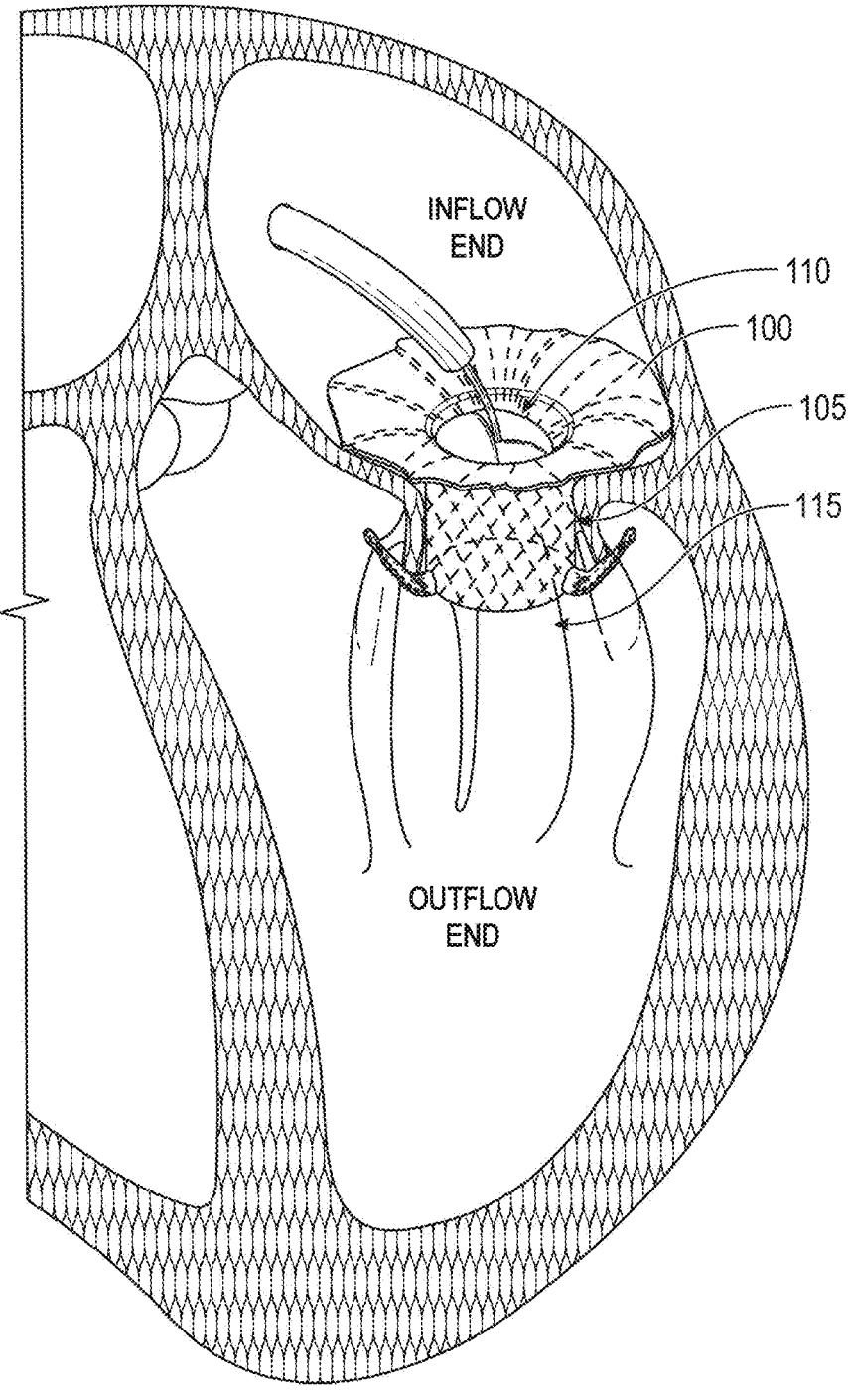
FIG. 1 generally illustrates an embodiment of a valve replacement as disclosed herein.

FIG. 1 generally illustrates an embodiment of a valve replacement as disclosed herein. FIG. 1 discloses an embodiment of a valve replacement (also referred to as a prosthetic mitral valve, a replacement mitral valve, a replacement heart valve, a replacement valve, or a bioprosthetic valve) 100 implanted in a malfunctioning mitral valve 105. The valve replacement 100, however, is not limited to compatibility with only the mitral valve 105 and may be also implanted in the tricuspid, aortic, or pulmonary valves (not shown). In an embodiment, the valve replacement 100 comprises a braided, collapsible frame and a braided valve-and-leaflet assembly that together serve to provide a sealing portion. The valve replacement may have an inflow end 110 (shown as facing the top side of the mitral valve 105 at the native atrium of the native mitral valve) and an outflow end 115 (shown as facing the bottom side of the mitral valve 105 at the native ventricle of the native mitral valve). The valve replacement allows for valve-in-valve placement, wherein embodiments of the valve-in-valve placement comprise replacing existing leaflets and valve assemblies without a reduction in area (such as by placing new material over existing material), and without compromising the functionality of the implanted valve replacement.

Braided Structures

The novel helical-braided designs of embodiments of the valve replacement purposefully leverage the natural helical movements of a beating human heart so as to balance both flexibility and strength. Studies of the human heart reveal that the mechanisms of ejection and suction are from a helical design of muscles in a "coil within a coil" formation, which are responsible for clockwise and counterclockwise rotation and functional activity. More specifically, the underlying anatomy of the human heart comprises a helical braid having a transverse basal loop of muscle for contraction that overlies an oblique helix that is responsible for ejection and suction within the heart.

The disclosed braided helical design is configured to put less stress on the individual components of the valve replacement because the valve replacement moves with the heart, i.e., the leaflets and anchors and other components have less stress and the valve replacement migrates less because its natural helical movement with the heart keeps it in place.

FIG. 2 generally illustrates the helical functionality of the human heart. As shown in FIG. 2, the twisting and untwisting motions within the heart are created by inner helical spirals within the descending and ascending apical loop muscle segments, with the heart having a natural clockwise torsion/contraction for ejection and a natural counterclockwise loosening/lengthening for suction. In heart disease, the natural helix of the heart becomes architecturally altered in shape.

Figure 3:
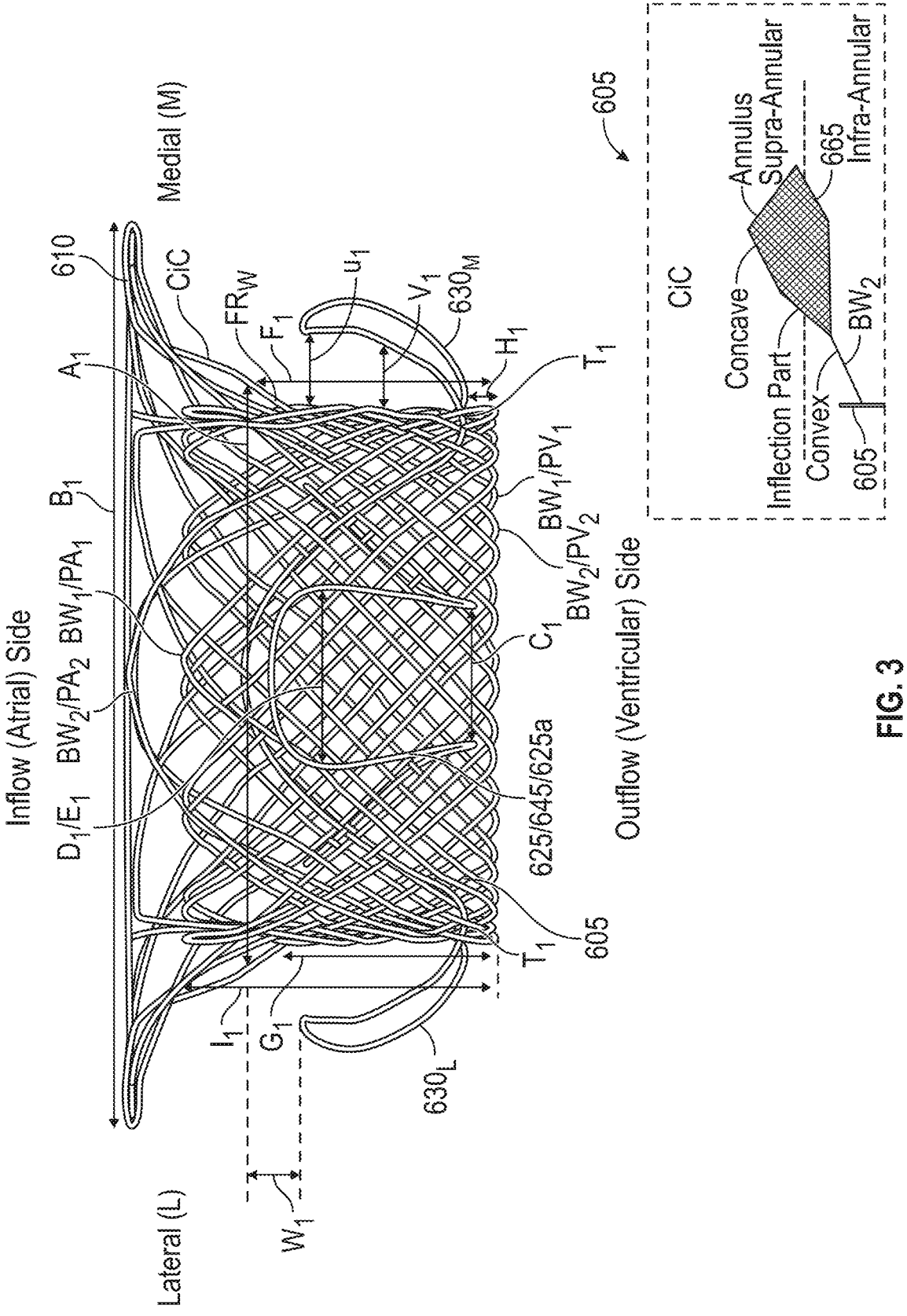
FIGS. 3-5 generally illustrate embodiments of a valve replacement as disclosed herein.
Figure 4:
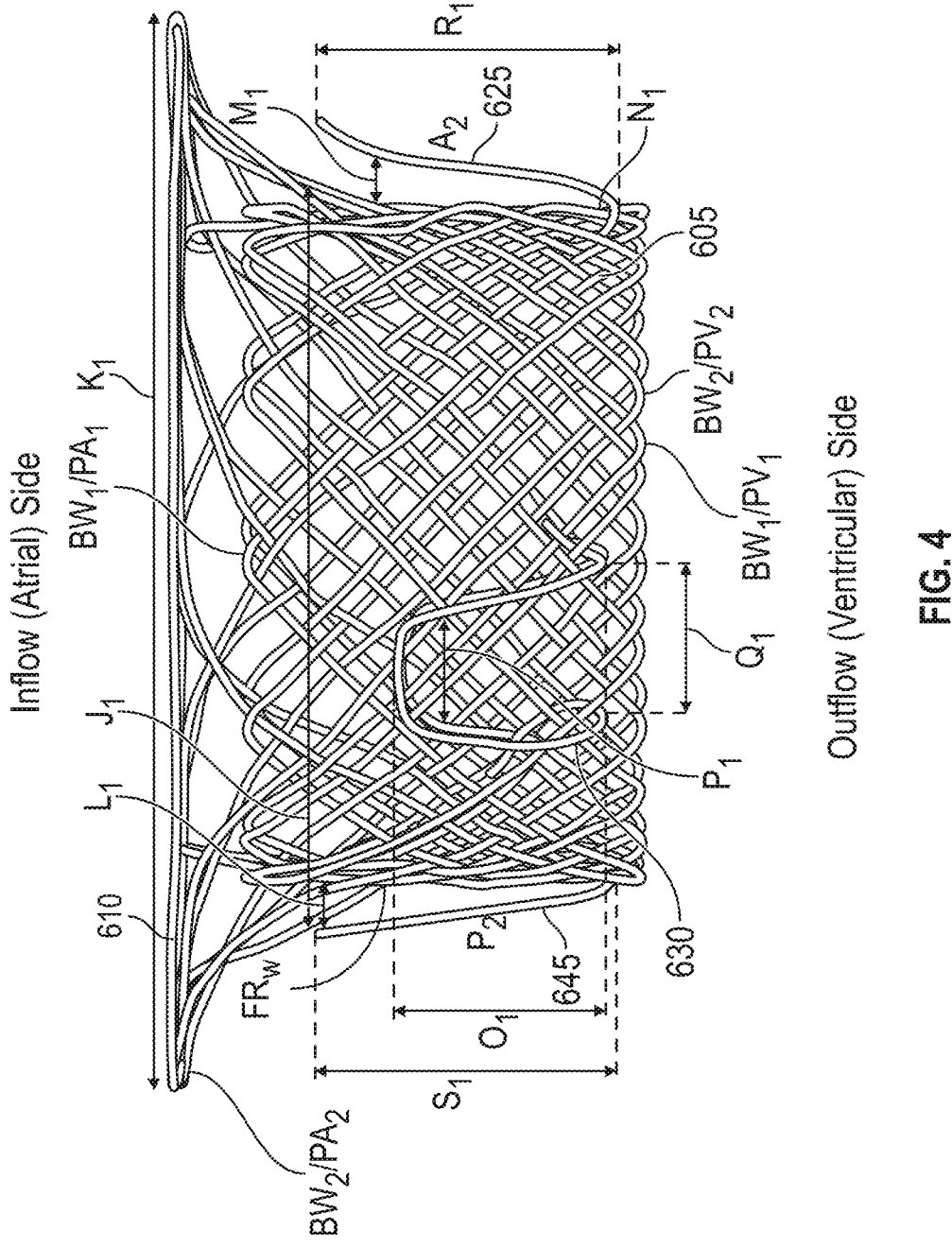
Figure 5:
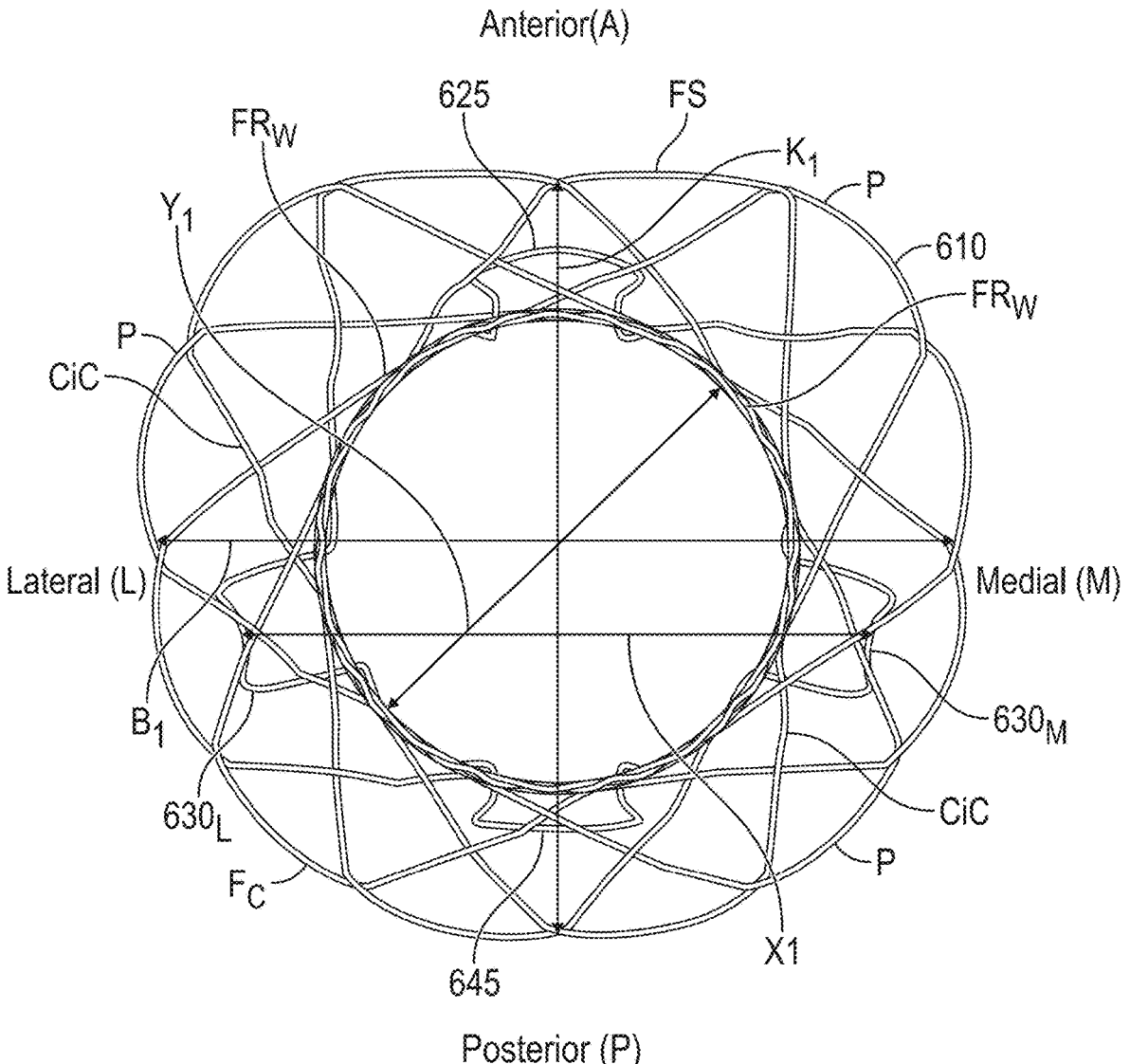
Figure 6:
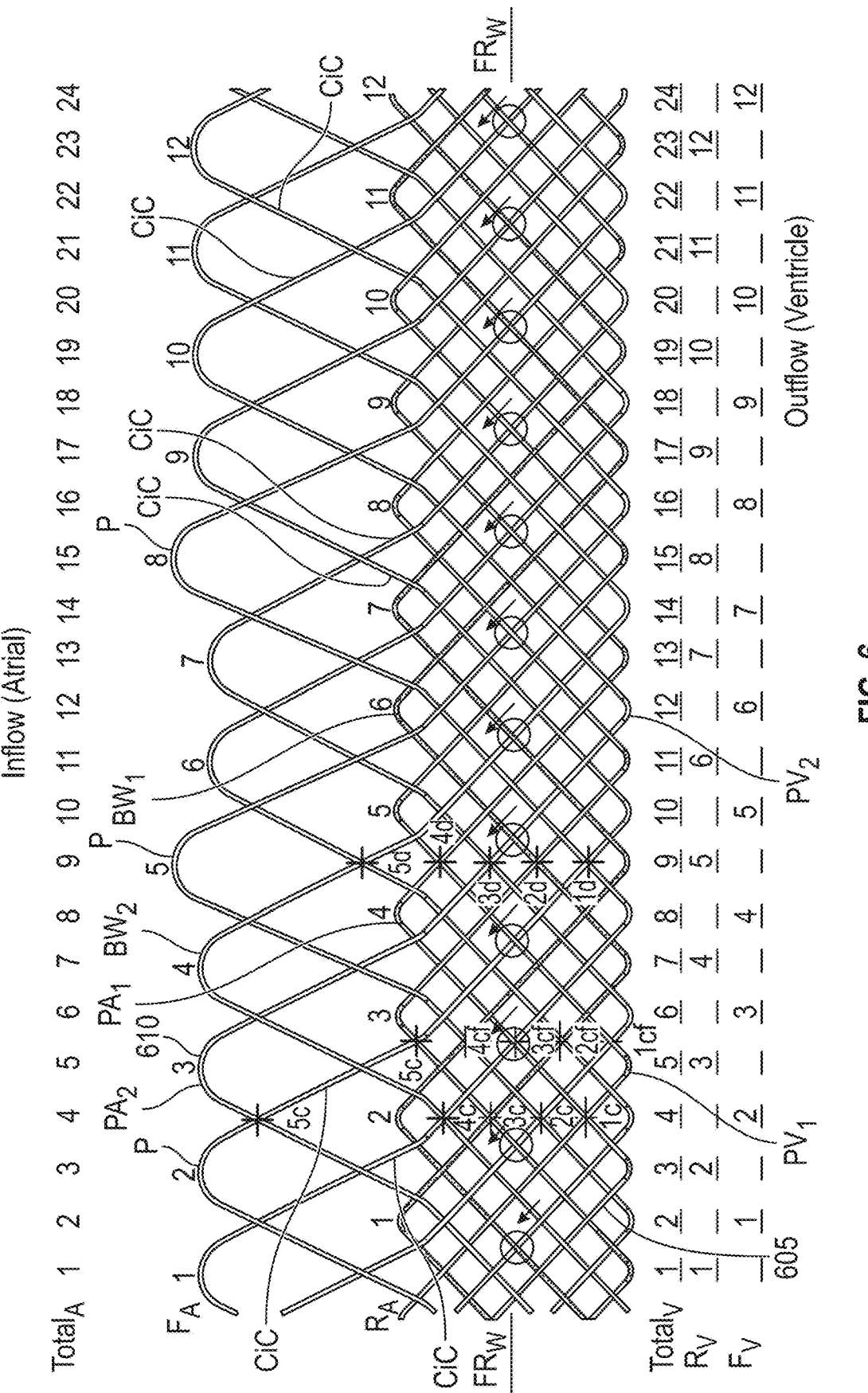
FIG. 6 generally illustrates an embodiment of an interwoven valve replacement and braid pattern as disclosed herein.
Figures 7, 8, 9, 10:
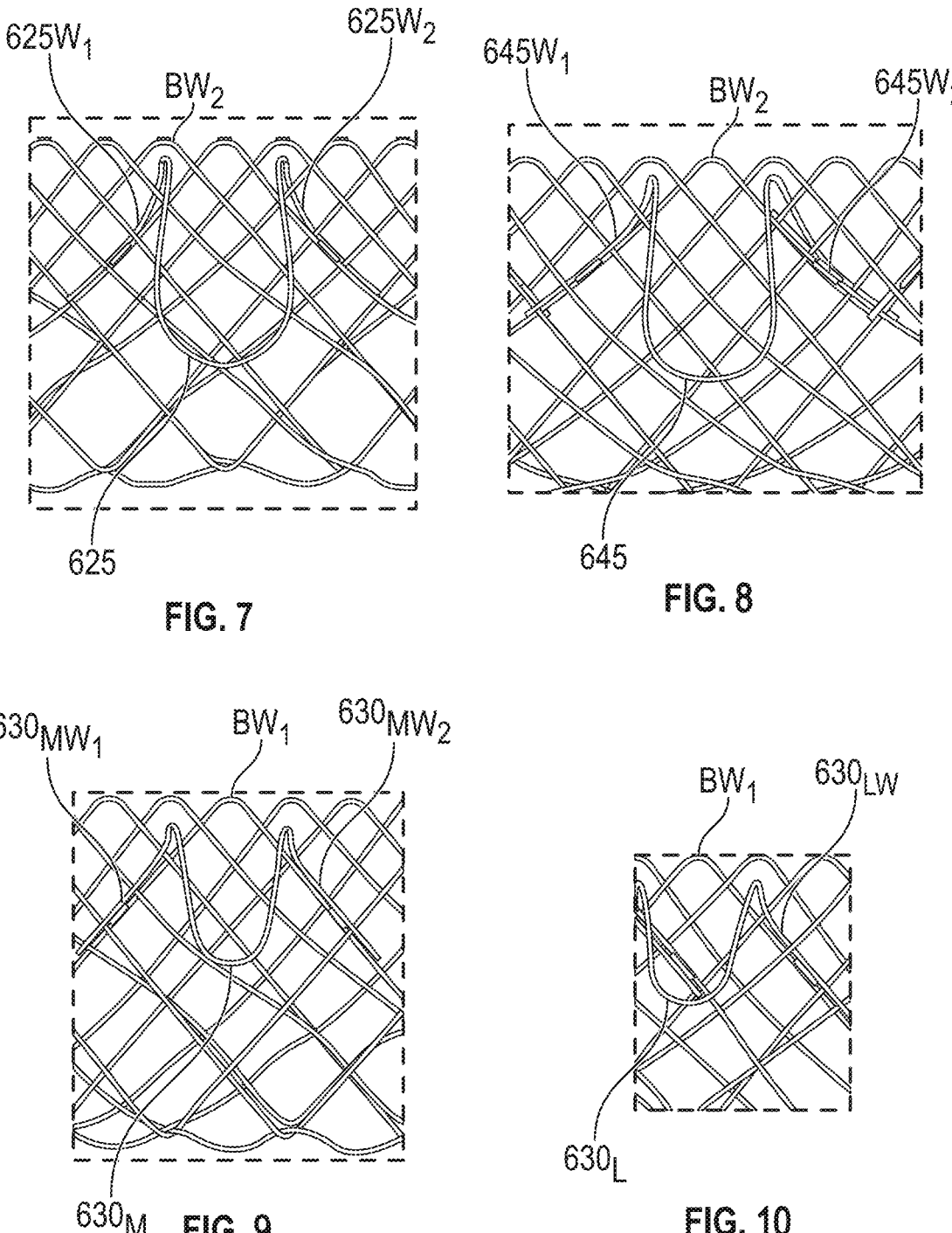
FIGS. 7-10 generally illustrate embodiments of leaflet clips and stabilizers as disclosed herein.
Figure 11:
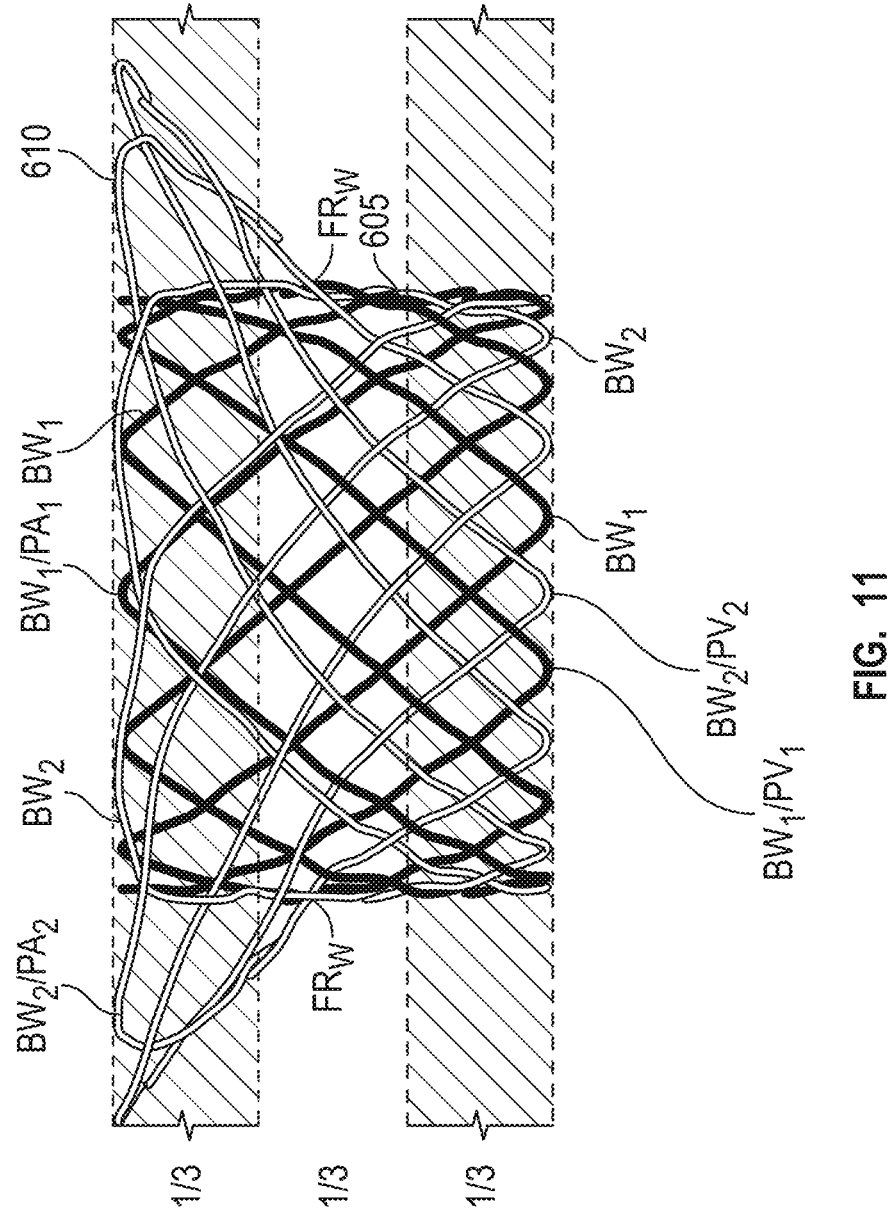
FIGS. 11-12 generally illustrate embodiments of a valve replacement as disclosed herein.
Figure 12:
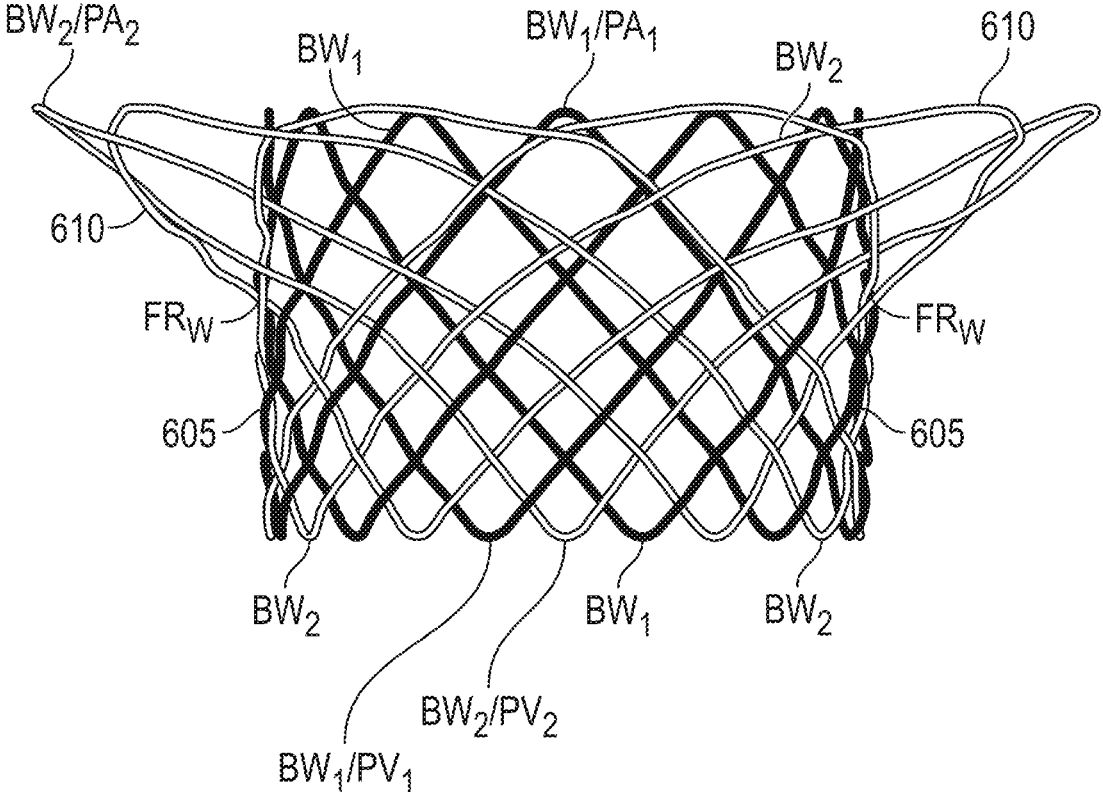

Referring to FIGS. 3, 4, 5, embodiments of a braided replacement valve are shown and referring to FIG. 6 (and FIG. 40), examples of braided patterns are shown and described. As disclosed herein, the frame of the valve replacement may incorporate helical architecture using braided wire technology and fabrication. The valve replacement comprises a tubular body (also referred to herein as a receiver, receiver body, adapter and adapter body) with a braided wire frame that has replacement leaflets therein forming a one-way replacement valve, where the receiver's frame may utilize overlapping helical strands that conform to the heart's natural movements and encourage central vortex flow through the replacement valve. For example, the valve replacement may not only facilitate contraction-like movements but also twisting, radial expansion, and other movements replicating movement of the heart. The receiver's frame may be made from braided wire. The properties of the frame, including densities and characteristics of the heart's anatomy, braiding design, wire thickness, etc., may facilitate not only the movements described above, but also accurize placement, maximize seal, and prevent migration, especially in coordination with an integrated and optimized anchoring system (and described in further detail below). In some embodiments, the receiver's frame may be made from materials that include wires with determined thickness and geometry to designed to increase strength.

As shown in FIGS. 3-20, embodiments of the valve replacement comprise a helical braided design that mimics and reinforces the normal helical and elliptical formation of the heart and its twisting/turning motions. In some embodiments, the helical braided design may form a wire frame. In some examples, the helical braided design may be braided so as to allow the frame to move in several (e.g., three) directions. Relatedly, the braided design may in some examples allow the frame to accommodate movement (e.g., from simultaneous compression and twisting) along the longitudinal axis and axis of rotation. In one embodiment, the helical braided design comprises a design wherein the braided wires resemble a frame that may move and/or flex (e.g., symmetrically to a helical axis) as it is compressed and/or elongated around an open center. In some embodiments, the helical braided design may implement tensegrity and/or floating compression principles by, e.g., shape setting the wires and frame into predetermined formations (e.g., to allow wires to slide across each other in a non-rigid manner). For example, since principles may assist in decoupling movement in the axial and rotation directions such that the device can move in three dimensions to accommodate movement of longitudinal axis and rotation while heart is beating. By way of further example, such movement may be free in a constrained range, which range may be defined by the shape setting of the nitinol and the fabric sewn onto the frame, to permit movement of braided frame wires along one another at the over-under braids within a predetermined range of movement in one or more (or any) directions.

Both the one-piece and two-piece systems may comprise the helical braided design. A normal heart develops ejection and suction as a functional consequence of the contraction integrity of the apical ellipse. The braided helical design of the valve replacement maximizes shortening and lengthening of the heart muscles, thereby reinforcing the desired apical ellipse of a healthy heart movement.

For example, as the human heart muscles compress and descend, the braided helical wires of the valve replacement—rather than be stiff—also compress and descend with the heart muscles, thereby reinforcing a natural spiral compression and descension of the heart muscle surrounding the braided wires. With the braided helical design, the valve replacement conforms to and reinforces the natural movement of the heart. The braided helical design of the valve replacement produces a twisting spiral coil that develops torsion in a clockwise direction. And as the human-heart muscles lengthen and fill, the braided helical design reinforces a natural spiral lengthening and filling of the braided wires with the surrounding heart muscle, resulting in an untwisting spiral coil within the replacement valve that develops an ejection force.

The novel braided helical design is significant for treating heart valves. By comprising a braided helical design, embodiments of the valve replacement reinforce the natural helical movement of the heart, and more naturally adapts and sits within the desired valve area. For example, embodiments of the valve replacement will tend to remain in the desired mitral or tricuspid valve area because the braided helical design will move (contract, twist and shorten, and untwist and lengthen) with the natural movements of the heart. This allows for the valve replacement to self-correct and seat within the valve area in a natural state, thus conforming to the heart's natural movements and encouraging central vortex flow.

The novel braided helical design thus facilitates a natural heart movement. In one embodiment, the valve replacement is held in place by the combined efforts of the flange and anchors, with the helical braided portion being in between the flange and anchors. The helical braided portion twists back and forth with the heart's natural movement, enabling a pumping-and-squeezing motion. The twisting motion, when the heart pumps, encourages flow of liquid through the valve replacement, thus allowing for better flow dynamics.

The braided wire architecture of embodiments of the valve replacement provides significant advantages over valve architectures that rely on laser cut or lattice structure frames or that have frame cell structures with fixed nodes along the replacement valve frame instead of a helical over-under braid pattern that permits the replacement valve frame to move with the natural helical movement of the native heart. Braided structures, such as those described herein in certain embodiments, provide collapsible scaffolding with a greater range and ability to contour to the native heart structure because the "nodes," where wires are wrapped in an over-under braiding style, may in some examples not be fixed and may be slid across each other to accommodate anatomical contouring. Such unfixed, sliding nodes having an over-under braiding style may allow greater flexibility and mobility than a pattern of fixed immovable nodes at intersection points of wires. Relatedly, in manufacturing, the flange embodiments deliberately position the most outer ring of braided nodes outward to minimize leakage between the braided wires and enhance the stiffness of the "D" perimeter. Additionally, the metallic braid may be selectively reinforced using soft components such as suture or cloth to stiffen specific regions of the frame. In one embodiment, suture may be utilize to link crossing nodes to fix them together and increase stiffness or reduce the ability of the nodes to slide relative to one another. Cloth may also be utilized to constrain the implant frame with radially or axially and modulate stiffness.

The braided wire frame of the valve replacement may comprise various wire embodiments, such as a single wire, two or more wires (for example, grafted or welded together), and a wire spliced of multiple wires. The wire(s) making up the valve replacement may be constructed of varying material, such as nitinol (NiTi), which has shape-memory characteristics and varies in dimensions, such as in diameter size. The valve replacement may comprise various types of wire, such as NiTi, stainless steel, cobalt chrome, and other types of implant metals. In other embodiments, the valve replacement may comprise polymer materials, such as biocompatible plastics and fiber-reinforced polymer. Some embodiments may comprise drawn-filled tubing (outside material NiTi and inside material some higher radiopaque material) for the valve replacement or portions of the valve replacement (e.g., anchors, or features desired to be seen under fluoroscopy). The valve replacement or portions of it may be made of hollow tubing. Additionally, flat wire or other cross-sections of wire may be chosen for portions of the valve replacement, such as to provide tailored/increased stiffness for anchors. Coatings may also be applied to nitinol wire to reduce friction and reduce fretting.

By integrating diverse wire thicknesses and braiding designs, in embodiments, the valve replacement conforms with various densities and characteristics (i.e., radial force and expansion) of the heart's anatomy. In embodiments, the braided frame enables the valve replacement to have a flexible and conformable performance, wherein the valve replacement self-adapts and moves with the heart while being forgiving to anatomical anomalies—similar to the heart's helical structure, as will be disclosed herein. Also, in embodiments, the composite nature of the wireframe and cloth covering enables the replacement valve to have a modulated stiffness with wire thicknesses and braid pattern, and also through selective cloth reinforcement and suture placement. The braided frame also facilitates placement of the valve replacement, maximizes its seal, and prevents migration with an integrated and optimized anchoring system. The braided frame geometry of the valve replacement allows for diverse application, such as being customizable to mitral and tricuspid anatomies; allows for fewer sizes to be needed to treat most disease states; promotes rapid prototyping; allows incorporation of various design features; promotes quicker design advancement with rapid evaluation and optimization of features; and is scalable using conventional processes. The braiding structure also allows for more degrees of freedom and opportunities for the wires to be in various positions.

An embodiment of fabricating the braided wire frame comprises oversizing the braided wire frame in relation to heart valve, which allows for more radial force for the same amount of material and geometry, thus allowing the frame to open up more fully and function better. Furthermore, it decreases the manufacturing tolerances involved in manufacturing the valve replacement. Oversizing the braided frame biases the wire frame structure so that there is less motion between the wires as they are predisposed with elastic strain energy to conform and adapt with greater radial force. As a result, the valves have higher degrees of consistency and the manufacturing tolerances associated with attaching the leaflets, for example, are greatly improved.

In one embodiment, the braided frame is wrapped and shape-set such that it has enough radial force to self-expand and be opened up to desired radial capacity while still being configured to fit within a catheter.

Embodiments of the valve replacement may range in diameter from 25 mm to more than 55 mm, and more specifically 25 mm-34 mm in some embodiments and a specific size of 32 mm and 29 mm in some embodiments. In embodiments, the inner diameter of the replacement valve is 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, 34 mm. In another embodiments, the wire frame is oversized, which comprises braiding the wire frame on a mandrel that is 25.4 mm in diameter (or 28.0 mm or 32.0 mm, depending on the desired valve size) and shape-setting it by treating it in 505° C. salt/sand bath. The frame is then removed from the initial mandrel and stretched over a 29 mm mandrel (or 31 mm or 33 mm, e.g., for larger valves) and shape-set again. Temporary strings (or other similar methods known to one skilled in the art) are then run through the loops and tied using a 25.4 mm mandrel as a reference diameter for the valve frame. This compresses the frame by spring loading the loops (though other embodiments may comprise other structures beyond loops, such as simple apices). The braided valve replacement may thus be shape-set at a larger diameter and then constrained to a smaller diameter and held with string until fabric is sewn onto the frame. In another manufacturing embodiment, the wire frame repeats a braid pattern over its length three times while wrapping five times around a circle.

Referring to FIG. 6, the replacement valve, in embodiments, comprises a 12×12 over/under weave of a first wire BW1 for the receiver 605 (12 peaks RA (or PA1) on the inflow or atrial side and 12 peaks RV (or PV1) on the outflow or ventricular side) and a 12×12 over/under weave of a second wire BW2 for the flange 610 (12 peaks FA (or PA2) on the inflow or atrial side and 12 peaks FV (or PV2) on the outflow or ventricular side), for a total of 24 peaks (TotalA) on the inflow or atrial side, and 24 peaks (TotalV) on the outflow or ventricular side with 24 wire crossings between each of the ventricle peaks TotalV. Other embodiments include weaves ranging from 8×8 to 16×16 of the first wire BW1 for the receiver 605 (between 8 to 16 peaks RA (or PA1) on the inflow or atrial side and between 8 to 16 peaks RV (or PV1) on the outflow or ventricular side) with embodiments having weaves of 8×8, 9×9, 10×10, 11×11, 12×12, 13×13, 14×14, 15×15, 16×16 as well as weaves with non-matching peaks on the atrial RA and ventricle RV sides (such as 8×9, 10×11, 16×12, 15×13, 14×12, etc . . . ) for all weave patterns of the receiver. Similarly, other embodiments include weaves ranging from 8×8 to 16×16 for the second wire BW2 for the flange 610 (between 8 to 16 peaks FA (or PA2) on the inflow or atrial side and between 8 to 16 peaks FV (or PV2) on the outflow or ventricular side) with embodiments having weaves of 8×8, 9×9, 10×10, 11×11, 12×12, 13×13, 14×14, 15×15, 16×16 as well as weaves with non-matching peaks on the atrial FA and ventricle FV sides (such as 8×9, 10×11, 16×12, 15×13, 14×12, etc.,) for all weave patterns.

In embodiments, the flange wire BW2 and receiver wire BW1 are interwoven in an over-under fashion (first wire under, second wire over, and alternating over/under up the weave), with crossing points for the wires. For example, in one pattern, the weave of the replacement valve includes a flange wire BW2 and a receiver wire BW1 interwoven in an over-under fashion for a section of the replacement valve followed by section of the replacement valve having the receiver wire BW1 interwoven on itself (without the flange wire BW2) and a section of the replacement valve having the flange wire BW2 interwoven on itself (without the receiver wire BW1). In embodiments, the section of the replacement valve where the flange wire BW2 exits the flange/receiver interwoven area is marked at FRw and is circled with an arrow pointing up in a right to left fashion. Where the flange wire BW2 exits the flange/receiver interwoven area FRw is the beginning of where the flange wire BW2 forms the curved section CiC and the petals P at the flange peaks FA at the inflow (atrial) end. In embodiments, the flange wire BW2 and receiver wire BW1 are each made from the same gage wire and in embodiments the flange wire BW2 and receiver wire BW1 are each made from different gage wires. For example, in embodiments, the flange wire BW2 and receiver wire BW1 are each made from a gage wire that is between 0.0100"-0.0200" gage wire, including embodiments with between 0.0150"-0.0180" gage wire and between 0.0160"-0.0175" gage wire, and including embodiments with 0.0100", 0.0105", 0.0110", 0.0115", 0.0120", 0.0125", 0.0130", 0.0135", 0.0140", 0.0145", 0.0150", 0.0155", 0.0160", 0.0165", 0.0170", 0.0175", 0.0180", 0.0185", 0.0190", 0.0195", and 0.0200" gage wire, including embodiments where the flange wire BW2 and receiver wire BW1 are different (for example, a flange wire BW2 of 0.0175" gage and a receiver wire BW1 of 0.0150"), embodiments where the flange wire BW2 and receiver wire BW1 are the same (for example, a flange wire BW2 and a receiver wire BW1 both being 0.0150" or 0.0175" gage wire), embodiments where the flange wire BW2 is a larger gage wire than the receiver wire BW1, and embodiments where the receiver wire BW1 is larger gage than the flange wire BW2.

In embodiments, for the 12×12 weave of the receiver wire BW1 interwoven with the 12×12 weave of the flange wire BW2, there are 5 over-under wire crossing points above each ventricle peak TotalV (as viewed from the outflow (ventricle) side up to the inflow (atrial) side), with the crossing points varying whether they are an odd numbered ventricle peak TotalV with a corresponding flange peak $F_A$ that forms a petal P on the inflow (atrial) side (for example ventricle peaks TotalV 1, 3, 5, 7, 9, 11, 13, 15, 17, 19, 21, and 23 with corresponding flange peaks FA 1, 2, 3, 4, 5, 6, 7, 8, 9, 10, 11, and 12) or an even numbered ventricle peak TotalV with a corresponding receiver peak RA on the inflow (atrial) side (for example ventricle peaks TotalV 2, 4, 6, 8, 10, 12, 14, 16, 18, 20, 22, or 24 with corresponding receiver peaks RA 1, 2, 3, 4, 5, 6, 7, 8, 9, 10, 11, and 12). Moreover, in embodiments, there are 5 over-under wire crossing points between each ventricle peak TotalV (as viewed from the outflow (ventricle) side up to the inflow (atrial) side), with the crossing points including where the flange wire BW2 exits the interweave from under a receiver wire BW1 at FRw and does not go under the receiver wire again as it continues up to form flange petals P at the flange's 610 inflow (atrial) side. (for example ventricle peaks TotalV 1, 3, 5, 7, 9, 11, 13, 15, 17, 19, 21, and 23 with corresponding flange peaks FA 1, 2, 3, 4, 5, 6, 7, 8, 9, 10, 11, and 12).

In embodiments, the flange 610 wire BW2 interweaves with the receiver 605 wire BW1 in an over-under fashion up to the third crossing point of the flange and receiver wires, as measured from the bottom (or between the second and third cells measured from the bottom). In embodiments, the weave pattern of the flange wire BW2 and receiver wire BW1, going from right to left on the weave pattern, the flange wire BW2 exits the interweave from under a receiver wire BW1 at FRw and does not go under the receiver wire again as it continues up and forms the flange's petals P at the flange's 610 inflow (atrial) side peaks FA (or PA2). In contrast, the flange wire BW2 going the opposite direction (going from right to left on the weave pattern) only interweaves with itself throughout the entire body of the valve. Beyond the third crossing point (or 2.5 cells up), the flange 610 and receiver 605 are still woven in an over-under fashion, but just with themselves (not interwoven).

In an embodiment, for example, there are five crossing points: 1$c$, 2$c$, 3$c$, 4$c$ and 5$c$ above the even numbered fourth ventricle peak TotalV4 (with corresponding receiver peak RA2 above it on the inflow (atrial) side). These over-under crossing points above the even numbered ventricle peak TotalV4 include a first crossing point 1$c$ (receiver/receiver wire BW1 crossing), a second crossing point 2$c$ (flange/flange wire BW2 crossing), a third crossing point 3$c$ (receiver/receiver wire BW1 crossing), a fourth crossing point 4$c$ (flange/flange wire BW2 crossing), and a fifth crossing point 5$c$ (flange/flange wire BW2 crossing). This pattern repeats itself for the other even numbered ventricle peaks TotalV. In this particular embodiment, for the even numbered ventricle peaks TotalV, the receiver/receiver wire BW1 crossing points stop after the third crossing point and the receiver peak RA in the atrium is between the last two flange wire BW2 crossings 4$c$ and 5$c$.

In this same embodiment, for example, there are five crossing points: 1$d$, 2$d$, 3$d$, 4$d$ and 5$d$ above the odd numbered ninth ventricle peak TotalV9 (with corresponding flange peak FA5 above it on the inflow (atrial) side). These over-under crossing points above the odd numbered ventricle peak TotalV9 include a first crossing point 1$d$ (flange/flange wire BW2 crossing), a second crossing point 2$d$ (receiver/receiver wire BW1 crossing), a third crossing point 3$d$ (flange/flange wire BW2 crossing), a fourth crossing point 4$d$ (receiver/receiver wire BW1 crossing), and a fifth crossing point 5$c$ (flange/flange wire BW2 crossing). This pattern repeats itself for the other odd numbered ventricle peaks TotalV. In this particular embodiment, for the odd numbered ventricle peaks TotalV, the flange/flange wire BW2 crossings and receiver/receiver wire BW1 crossing points alternate from top to bottom and have a flange petal P above the last (fifth) crossing point.

In this same embodiment, for example, there are also wire crossings between each of the ventricle peaks TotalV, with a wire crossing between each set of receiver ventricle peak RV and flange ventricle peak FV (crossing points between RV1 and FV1, RV2 and FV2, FV3 and RV3, FV4 and RV4, FV5 and RV5, FV6 and RV6, FV7 and RV7, FV8 and RV8, FV9 and RV9, RV 10 and FV 10, RV11 and FV 11, RV12 and FV12). These wire crossings between each of the ventricle peaks TotalV include wire crossings where the flange wire BW2 exits the flange/receiver interwoven area at FRw (flange wire BW2 wire exit circled with an arrow pointing up in a right to left fashion). There are five crossing points between each ventricle peak TotalV going from the outflow (ventricle) side up to the inflow (atrial) side. For example, between ventricle peaks TotalV 5 and 6 (between RV3 and FV3) there are crossing points: 1$cf$, 2$cf$, 3$cf$, 4$cf$ and 5$cf$. These over-under crossing points between the ventricle peaks include a first crossing point 1$cf$ (receiver wire BW1 top and flange wire BW2 bottom crossing), a second crossing point 2$cf$ (flange wire BW2 top and receiver wire BW1 bottom crossing), a third crossing point 3$cf$ (receiver wire BW1 top and flange wire BW2 bottom crossing), a fourth crossing point 4$cf$ (flange wire BW2 top and receiver wire BW1 bottom crossing), and a fifth crossing point 5$c$ (flange wire BW2 top and receiver wire BW1 bottom crossing). This pattern repeats itself for the other crossing points between the ventricle peaks TotalV. In this particular embodiment, once the flange wire BW2 exits the interweave from under a receiver wire BW1 at the third crossing point 3$cf$ along the line FRw, the flange wire BW2 does not go under the receiver wire again as it continues up and forms the flange's petals P at the flange's 610 inflow (atrial) side peaks F$_A$ (or PA2).

In embodiments, the petals P formed by the flange wire BW1 can vary in height or all be the same height. In embodiments, the flange petals P vary in height to form a D-shape, for example as shown in FIG. 22.

Figure 21:
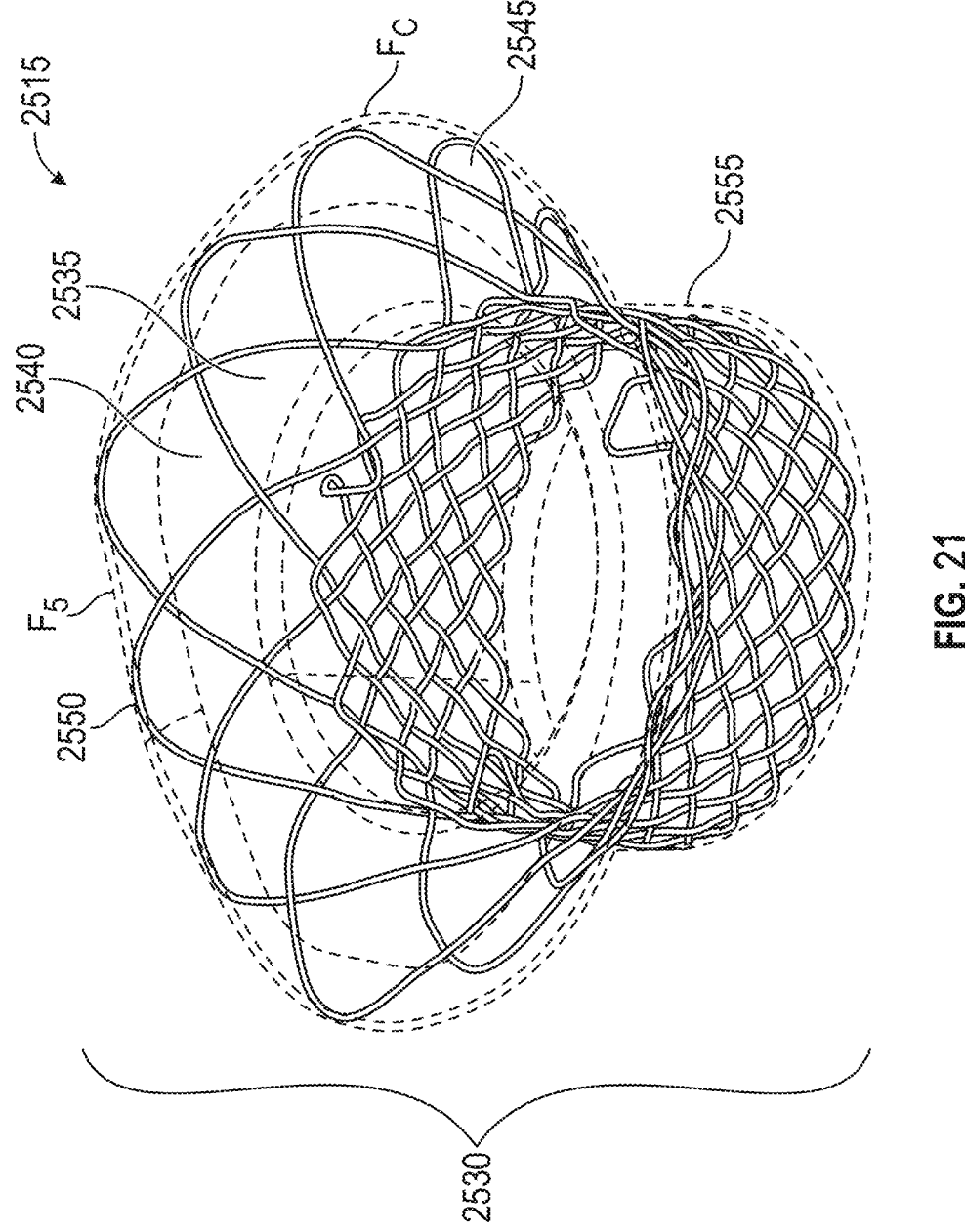
FIGS. 21-23 generally illustrate embodiments of the valve replacements as disclosed herein.
Figure 22:
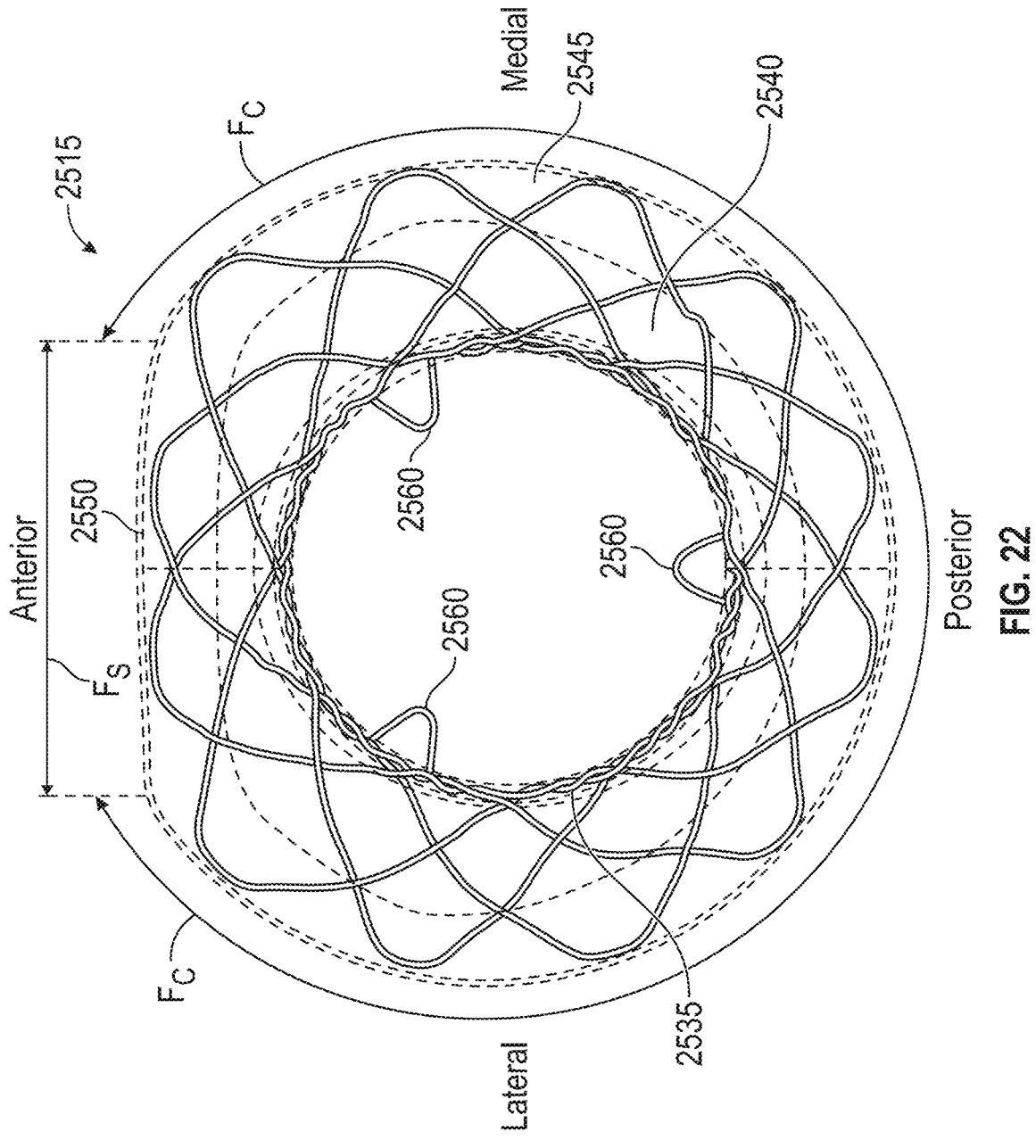
Figure 23:
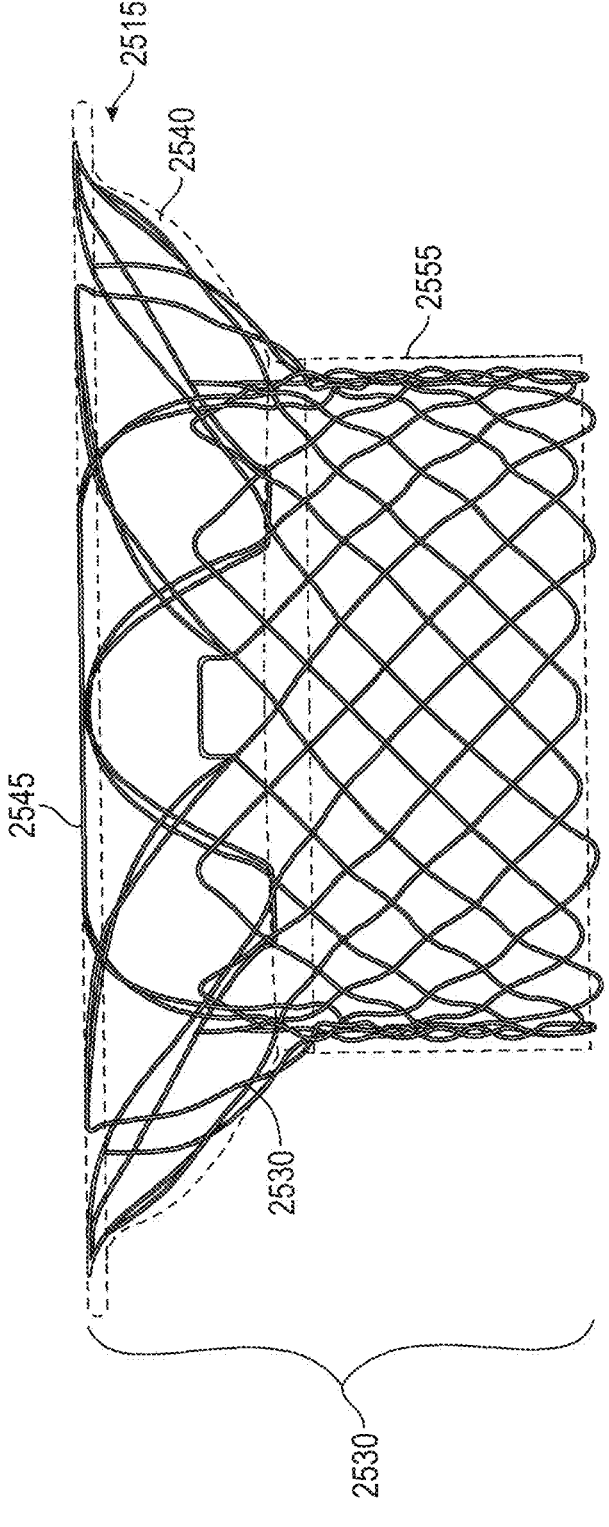

In particular, FIGS. 21, 22 and 23 illustrate an embodiment of a flange 2515 of the valve replacement comprising a contoured "funnel-like" shape fitted onto the annulus (as opposed to a "top hat"-shaped flange with a right-angle transition) as well as a D-shaped perimeter.

In embodiments, the frame of the flange 2515 may include one or more wires. For example, one embodiment may feature a flange 2515 with several (e.g., three) wires and have a braided structure. In some examples the wires of the flange may form looping petals P, terminating at extrados 2525. In some embodiments, the pedals may be uniform and shaped for predetermined placement corresponding to anatomy.

The angle between the intersection points 2520 of extrados 2525 may vary. In examples with a high angle (and potentially less wires), the braid may involve increased wire contact with the annulus, which may also involve a longer overall compressed length. Some such embodiments may have straighter, stiffer, and/or stronger contact with the annulus and a shorter overall compressed length.

Some flange 2515 examples and other related features may be created to have a specific desirable shape using a tooling or shape-setting process. This shape-set tooling may be derived from a geometric surface that has been carefully constructed to interface optimally with a diseased mitral annulus. In one such technique flange tips may be forced inward (toward the center of the implant). This may cause the wires to buckle in a controlled manner, potentially minimizing triangular gaps between wire extrados.

In some examples, the flange 2515 may be fabricated using a layer of material 2530 (e.g., "one-piece sock"), a contoured ring 2535 (with or without grooves), a contoured nesting ring 2540 (with or without grooves) and a top plate 2545 with a D-shaped perimeter 2550 ledge having a straight side Fs that is between $\frac{1}{5}^{th}$ to $\frac{1}{3}^{rd}$ of the perimeter of the flange 2515 and a circular or oval section Fc that is between $\frac{4}{5}^{th}$ and $\frac{2}{3}^{rd}$ of the perimeter of the flange 2515. The straight side Fs of the flange 2515 is designed to rest against and not block or press into native anatomy at the aortic-mitral curtain and to prevent cutting off blood flow circulation in the aortic tract. In embodiments, tooling to construct the flange 2515 can include top plates and nested contoured rings for producing the transition zone and D-shaped perimeter. In embodiments, before shape setting of the flange, the petals (or end loops of the flange) of the flange can be braided to be shorter at the D-shape perimeter straight side Fs than the other petals or ends of the flange around the oval or circular perimeter section Fc, for example, to accommodate the LVOT or aorto-mitral curtain. Components such the flange 2515 and its straight section Fs and oval or circular section Fc can be assembled with locator pins onto a cylindrical mandrel 2555 and together control the buckling of the wires during fabrication. The D-shape perimeter 2550 of the flange 2515 may be constructed to (optimally) seal the annulus, providing more coverage specifically at the native commissures and medial to the native commissures. In some embodiments, the braid itself and D-shape perimeter 2550 may provide a transition zone for anatomical features, for example having localized softness to accommodate the aorto-mitral curtain or LVOT.

In some embodiments, the layer of material 2530 may cover at least a portion or all of the flange 2515. In some embodiments, the top plate 2545, the first contoured ring 2535, and the second contoured ring 2540 may each have an underside surface, which in some examples may be covered by the layer of material 2530. In some embodiments, at least one of the underside surface of the top plate 2545, the underside surface of the first contoured ring 2535, and the underside surface of the second contoured ring 2540, and due in part to the braiding structure and orientation described herein, may be configured to contact at least a portion of native tissue so as to reduce gaps between the native tissue and the valve replacement incorporating the flange 2515.

In some embodiments, the first contoured ring 2535 may have a particular pattern or contours and the second contoured ring 2540 may have a pattern or contours, which may be distinct from each other. In addition, in some embodiments, the second contoured ring 2540 may have an outer edge and an inner edge. In some examples, the outer edge of the second contoured ring 2540 may be contiguous to the first contoured ring 2535 (and, e.g., an inner edge thereof). In some examples, the inner edge of the second contoured ring 2540 may be contiguous to the cylindrical mandrel 2555 or heart valve adapter frame.

In an embodiment, shown in FIG. 6, the flange petals P have heights up to their corresponding flange atrial peaks $F_A$, with petals P being the same height at flange peaks $F_A$1, 2, 3 and 4 as well $F_A$9, 10, 11 and 12, with petals P formed at flange peaks $F_A$5 and 8 being taller and petals P formed at flange peaks $F_A$6 and 7 being shorter. The two longer flange peaks $F_A$5 and 8 form the ends of the straight side Fs of the D-shape perimeter and the two shorter flange peaks $F_A$6 and 7 being the middle portion of the straight side Fs of the D-shape perimeter. The other flange peaks $F_A$1, 2, 3 and 4 as well $F_A$9, 10, 11 and 12 having the same height form the circular portion Fc of the flange.

As shown in FIG. 3 (and other Figures), the flange's 610 curved portion CiC is wider in the M-L direction than the A-P direction because in the native anatomy the M-L anatomy is wider than the A-P anatomy and the flange belly needs to be wide enough in the M-L and A-P directions to provide effective sealing during systole and prevent migration in the ventricular direction. Moreover, in embodiments, the flange's belly width J1 in the anterior-posterior (A-P) direction and belly width A1 in the medial-lateral (M-L) direction are located at a plane that intersects with the top of the P2 clip 645. In embodiments where the curved section CiC of the flange's 610 braided wire BW2 forms a flange belly CiC, the flange belly has a width A1 in the Medial-Lateral (M-L) direction of between 34 mm to 65 mm, including embodiments with the flange belly M-L width A1 being between 40-65 mm and between 50-60 mm, embodiments of A1 being 44 mm or 60 mm, and other embodiments with A1 being 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 mm, 50 mm, 50.5 mm, 51 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, 60 mm, 60.5 mm, 61 mm, 61.5 mm, 62 mm, 62.5 mm, 63 mm, 63.5 mm, 64 mm, 64.5 mm, 65 mm. Moreover, in embodiments where the curved section CiC of the flange's 610 braided wire BW2 forms a flange belly CiC, the flange belly has a width J1 in the Anterior-Posterior (A-P) direction of between 32 mm to 60 mm, including embodiments with the flange belly A-P width J1 being between 35-55 mm and between 40-50 mm, embodiments of J1 being 42 mm or 50 mm, and other embodiments with the flange belly A-P width J1 being 32 mm, 32.5 mm, 33 mm, 33.5 mm, 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 mmm, 50 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, and 60 mm.

As shown in FIG. 3, the flange's 610 curved portion CiC forms a belly with a curved or funnel shape that hugs the annulus of the native mitral valve where the curved portion CiC of the flange wire may flex and push outward to fill in gaps between the valve surfaces and the native anatomy. In some examples valve replacement embodiments, the transition zone may be between a flat flange portion (which may be configured to rest on top of annulus in the atrium) together with and including the funnel-like contoured ring of the flange and the adapter portion that radially pushes out into the annulus. Such a contoured transition portion may assist in promoting central vortex flow and provides improved sealing and anchoring. The funnel-like portion may have shape-set braided wire and material covering that is contoured and configured to fill in the gaps between native anatomy and the transition zone between the atrium and annulus heading towards the ventricle area. Additionally, this funnel shape provides additional surface for the native leaflets and annulus to contact, which minimizes the potential for leak.

Embodiments of the valve replacement may comprise compatibility with various-size catheters, such as 26F, 28F, 30F, 32F, and 34F. Due to the nature of the implant anchoring and sealing mechanisms, it enables compression (or crimping) into the potential catheter sizes listed. As the implant contains a single frame structure, multiple valve size configurations may be compressed into the same catheter size. As a result, multiple valve sizes may feature the same catheter size, and be configured to allow for treatment of a large range of patient native mitral annuli. This can include anterior-posterior dimensions of 26 mm-45 mm and medial-lateral (commissure to commissure) dimensions of 32 mm-53 mm. In particular, braided frames such as the embodiments disclosed herein enable the reduction of multiple stacked frames, that would otherwise be required in a laser cut frame. With a laser cut frame (also called a fixed lattice structure), in a single body construction a flange must exit the top of the laser cut frame as a continuation of the frame holding the leaflets because the lattice structure does not permit interweaving of additional structures. Also, in laser cut multi-frame constructions, a flange is typically a separate laser cut frame that is attached to another laser cut frame holding the leaflets, thereby increasing the amount of metal and structure of the laser cut implant and increasing the crimped profile of the laser cut frame. Moreover, a laser cut frame with fixed nodes does not have a buckling capacity that wire has in a braided structure. With embodiments of the innovative braided frame, as disclosed herein, a flange is able to be interwoven with the receiver's frame that holds the leaflets, thereby creating a single interwoven structure. With embodiments of the single interwoven structure, the flange and receiver wires are weaved together, thereby taking up less space than two separate structures and leaving more room within the replacement valve for replacement valve tissue (used for the replacement leaflets). Thus, with embodiments of the innovative interwoven replacement valve, more replacement valve tissue can be packed within a crimped braided valve while keeping the same or smaller crimp profile as a laser cut frame. The increased amount of tissue allows for a braided valve as disclosed herein to have a larger size valve (because more tissue is required for larger valve), which in turn permits a larger effective orifice area (EOA) in comparison to a laser cut frame with the same amount of tissue.

FIG. 24 generally illustrates the difference between a laser cut valve 400LC versus an embodiment of a braided replacement valve 400C as described herein. With a laser cut device 400C, the fixed nodes 400LCF along the perimeter of the laser cut valve crimp purely along the outer diameter eventually hitting a barrier around the perimeter at the fixed nodes 400LCF where metal contacts itself and does not permit further crimping. In contrast, with a braided configuration, such as with embodiments of a replacement valve 400C, there are not fixed nodes that determine the crimped profile. Instead, braided wire cross-sections 400W can move during crimping, thereby sliding across each other and permitting material to move and fit within free space 400I for tissue and cloth to reside. Thus, more tissue and cloth may fit within a similar sized braided replacement valve 400C than in a fixed node laser cut valve 400LC. Additionally, braided wire is inherently freer to move and buckle as compared to laser cut beams. Buckling and high degrees of deformation do not induce significant strains on nitinol wire, whereas a laser cut beam would experience damage during this crimping process (resulting in decreased fatigue life).

In embodiments, because of its compressible nature and braided structure, the braided wire frame design of the replacement valve 400C is compressible to between 6 mm to 10 mm such that it may be delivered in a catheter or delivery tube that is smaller than would be required for a laser cut frame or dual frame design with the same inner diameter without damaging the braided replacement valve because, for example, the wires in the braided configurations discussed herein can buckle and move past each other when the replacement valve is being compressed without damaging the wires. For example, in embodiments, the replacement valve 400C can have an inner diameter of at least 32 mm in an uncompressed configuration while deliverable to a native mitral valve in a compressed configuration that is no more than 28Fr in diameter (for example through a delivery tube 400T that is no more than 28Fr in diameter). In other embodiments, the replacement valve 400C can have an inner diameter of at least 29 mm while deliverable to a native mitral valve in a compressed configuration that is no more than 26Fr in diameter (for example through a delivery tube 400T that is no more than 26Fr in diameter). In other embodiments, the replacement valve 400C can have an inner diameter of at least 30 mm while deliverable to a native mitral valve in a compressed configuration that is no more than 27Fr in diameter (for example through a delivery tube 400T that is no more than 27Fr in diameter).

Flanges and Anchors of the Braided Wire Frame

In embodiments, and as described in other places in this disclosure, the replacement valve also comprises ventricular anchors and stabilizers, including in embodiments leaflet clips for anchoring to the anterior and posterior mitral leaflets (e.g., A2 clip 625, P2 clip 645, and other clips 625a) as well as stabilizers for providing stability and anchoring functionality in the medial and lateral ventricular regions, also called anchor struts or struts (e.g., medial stabilizer 630 and lateral stabilizer 630, stabilizers 630a). As described herein, the replacement valve is, in embodiments, a "floating valve" wherein the valve body "floats" in the native anatomy with at least a portion of the replacement valve does not make contact with the native anatomy. For example, where the replacement valve receiver body 605, which holds the replacement leaflets and one-way valve, is smaller than the size of the native annulus in one or more of the A-P and C-C directions. As a result, the valve body of the replacement valve floats within the native annulus from not having a uniform contact around the perimeter of the replacement valve within the native annulus. For this "floating valve" to be properly secure, and also provide the functionality described herein with regards to promoting forward vortex flow and a posterior tilt through the replacement valve and preservation of the LVOT, the "floating valve" must be properly secured on the atrial side (e.g., with embodiments of the flange 610 described herein) and properly secured on the ventricular side with clips and stabilizers. In embodiments, the clips and stabilizers have wider dimensions than the bioprosthetic valve, such that the anchoring of the replacement valve contacts tissue away from the replacement valve-thus enabling the replacement valve to "float" in the native anatomy. Similarly, in embodiments, the flange has a wider dimension than the native anatomy so that the flange belly contacts the native tissue and flexes when contracted (bimodal crush), so it minimizes crush on the replacement valve itself. Thus, in embodiments, the replacement valve is suspended in the native valve space by anchoring features.

In embodiments, the valve replacement is also designed to preserve native ventricular filling by orienting flow into the ventricle in such a way as to limit turbulence and maximize efficient flow, such as towards the posterior ventricle wall, between the papillary muscles. In embodiments, the valve replacement orients blood flow towards the posterior ventricle wall to mimic native blood flow between the native atrium and native ventricle of the native mitral valve.

In embodiments, the valve replacement is also designed to be anatomically customized with patient and disease state-specific sizing. Sizing may be based on anatomical data; for example, using a sizing tool to determine receiver diameter and flange length, while also optimizing valve orientation for both ventricle outflow consideration and ventricular efficiency. In the example, parameters of the sizing tool are fed to the parametric device model, which automatically creates the pattern for the shape-set tooling.

Figure 25:
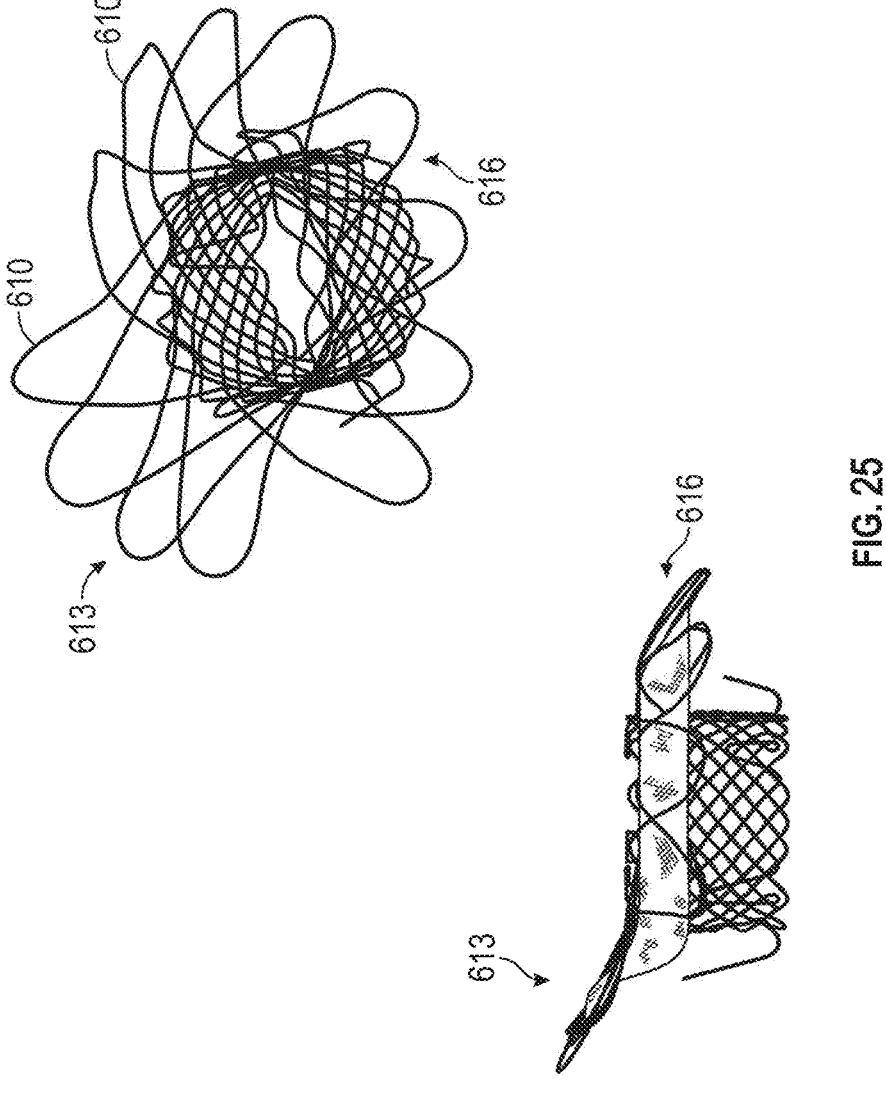
FIGS. 25-27 generally illustrate embodiments of a valve replacement as disclosed herein.

FIG. 25 generally illustrates an embodiment of the valve replacement as disclosed herein. As shown in FIG. 25, the valve replacement may comprise a receiver body 605 and one or more atrial flanges 610. In any receiver embodiment, a replacement valve comprising replacement leaflets can be sewn into the receiver body, thereby making the receiver a one-piece replacement valve design. In other embodiments, the receiver can be used to house a separate braided valve structure, making the receiver and separate braided valve structure combination a two-piece valve replacement design. In one embodiment wherein the replacement valve is applied to a native valve, such as a mitral valve, the circumference of the atrial flange 610 is separated into one-third 613 and two-thirds 616. The one-third portion 613 of the atrial flange 610 engages with the native fibrous aorta-mitral curtain and is formed at an angle that prevents the replacement valve being pulled into the LVOT. This feature also maximizes sealing during systole. The two-thirds portion 616 of the atrial flange 610 engages the native muscular wall and is formed at an angle that pulls the valve away from the LVOT and directs flow towards the apex of the ventricle, between the papillary muscles, or towards the ventricle wall. The flange may be configured as needed to seat within the 3D geometry (saddle shape) of the native mitral annulus. The flange contour may be adjusted to have variable height (or z-axis shape set) along the radial angles of the mitral annulus. This allows for variable contact, pressure, (or "corking") of the flange within the valve to enhance forward flow, fixation, and reduce regurgitation. In other embodiments, the receiver body and atrial flange function similarly or identically when applied to the tricuspid valve.

Figure 26:
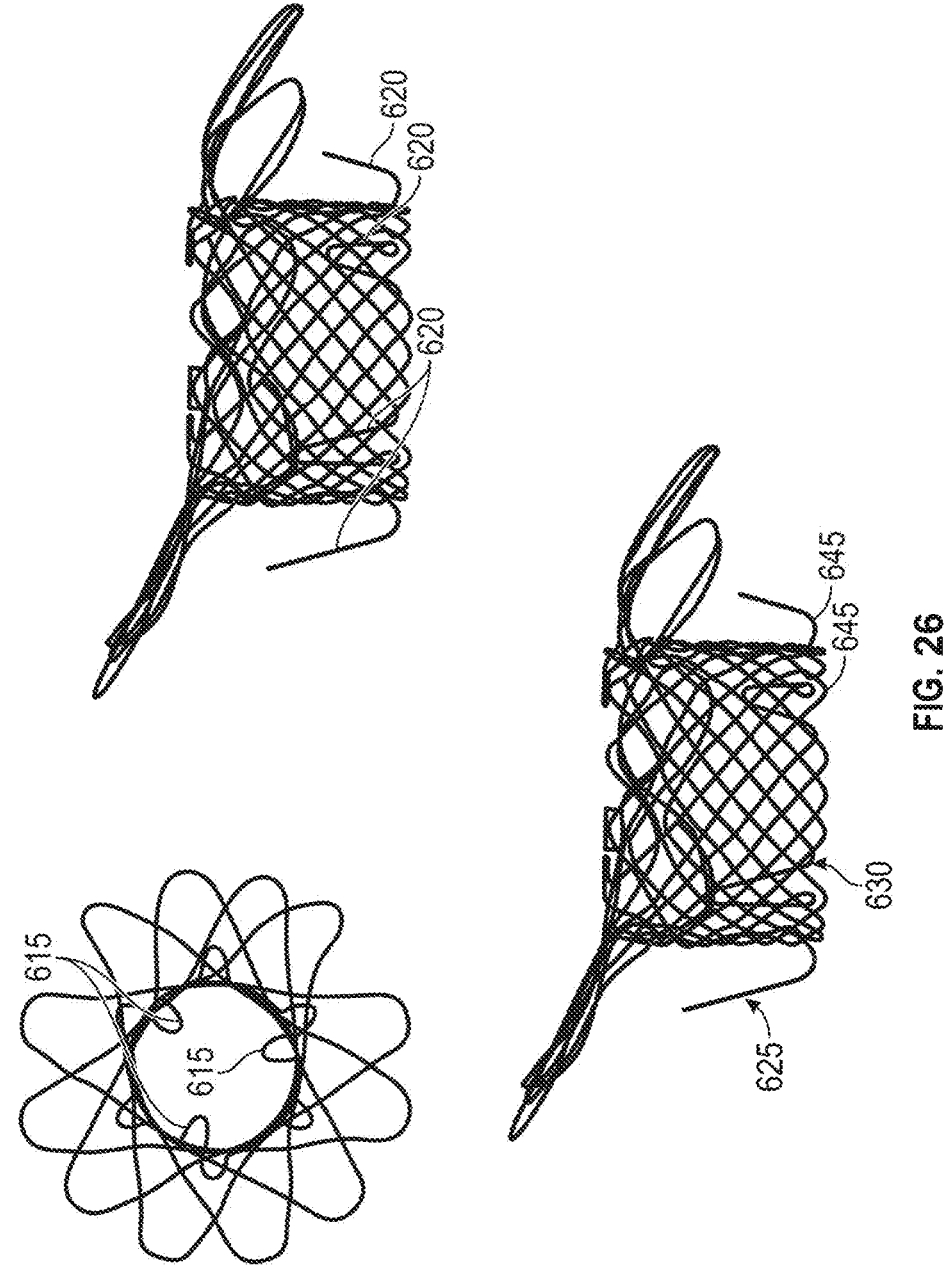

FIG. 26 generally illustrates an embodiment of the valve replacement as disclosed herein. As shown in FIG. 26, the receiver may comprise valve and retainers 615 within the inner frame of the receiver body. The receiver may also comprise sub-valvular anchors 620 for leaflet management. In one embodiment, the sub-valvular anchors 620 are made up of one or more of the following: anterior leaflet anchor 625 (also referred to herein as a clip, leaflet clip or anchor clip), anchor strut 630 (also known as a stabilizer), and posterior leaflet anchors 645 (also referred to herein as a clip, leaflet clip or anchor clip). For example, the receiver may comprise a single anterior leaflet anchor clip 625, two anchor struts 630 (or stabilizers), and three posterior leaflet anchor clips 645. The anchors may be configured to be biased in an upward atrial direction so as to be radially overlapping in relation to the receiver body. In embodiments, the anchor struts are inclined in the atrial direction and are configured to land, or anchor next to, fibrous landing zones within the native heart tissue and near the native heart valve being replaced. For example, in embodiments, the anchor struts (also referred to as stabilizers herein) are configured to be inclined towards the trigones in fibrous landing zones of the native heart. In embodiments, the anchor struts/stabilizers are also configured to be inclined towards the fibrous or muscular landing zones near the anterior or posterior leaflets of the native heart. Moreover, in embodiments, the medial stabilizer extends in between chordae into a medial sub-annular commissural area of a native heart when deployed within the native mitral valve and the lateral stabilizer extends in between chordae into a lateral sub-annular commissural area of the native heart when deployed within the native mitral valve. In embodiments, the medial and lateral stabilizers permit movement of the native mitral annulus (and native leaflets in embodiments) in the medial and lateral directions and resist migration of the prosthetic mitral valve towards the atrial end when deployed within a native mitral valve. In embodiments, stabilizers and clips are manufactured separately from the valve body and flange. This allows for the use of various wire diameters, as well as independent shape setting include angles, lengths, shape profiles, and heights. Following separate fabrication, stabilizers and clips may be attached to the valve body in various radial locations around the frame using common techniques such as welding. In embodiments, the stabilizers or clips are coupled to the flange or the receiver body by connecting the stabilizers and clips to the braided wire of the flange or braided wire of the receiver body by welding, fusing, grafting, or mechanically coupling the wires together with a fastener. In other embodiments, the stabilizers or clips are held by the braided wire of the flange or braided wire of the receiver body by a mechanical fit from the wires being interwoven (e.g., the stabilizer or clip wire interwoven into the receiver or flange wires). The radial locations along the receiver body where the stabilizers exit the receiver body and reach into the native anatomy when deployed can be configured to have the stabilizers land posterior to the trigone region of the native mitral valve. One embodiment places the stabilizers equally spaced at 150 degrees from the P2 clip along the circumference of the receiver body (which is tubular in embodiments), while another approximately 150 degrees from the A2 clip along the circumference of the receiver body. Other embodiments may adjust these angles within a range that points the stabilizers towards the native commissures of the native mitral valve. Stabilizers may also be unequally spaced to avoid native papillary structures.

Figure 27:
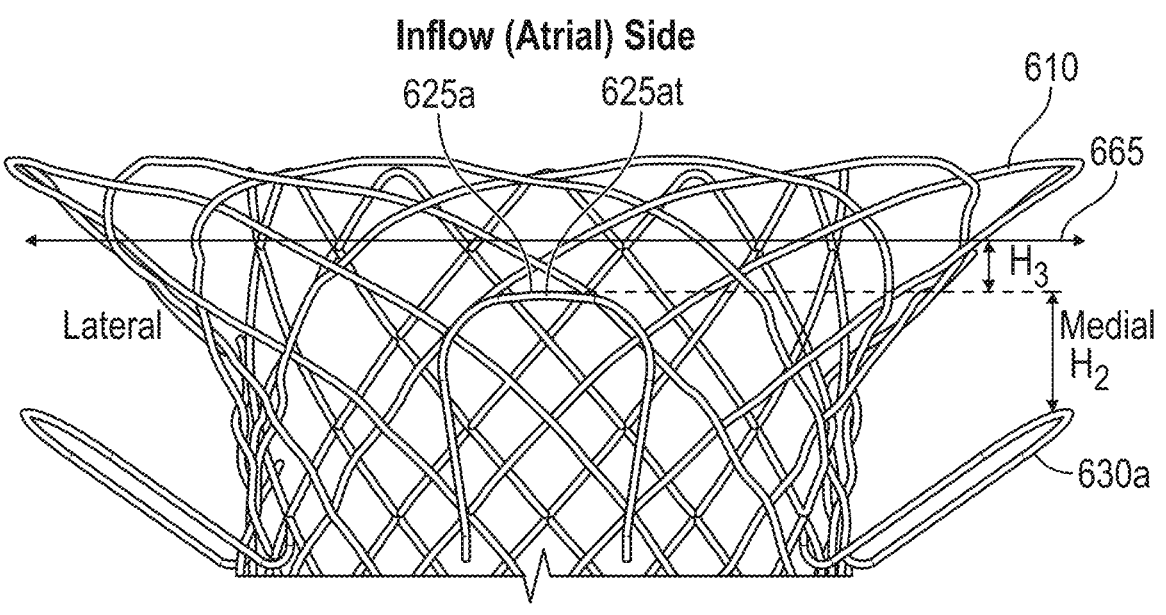
Figure 28:
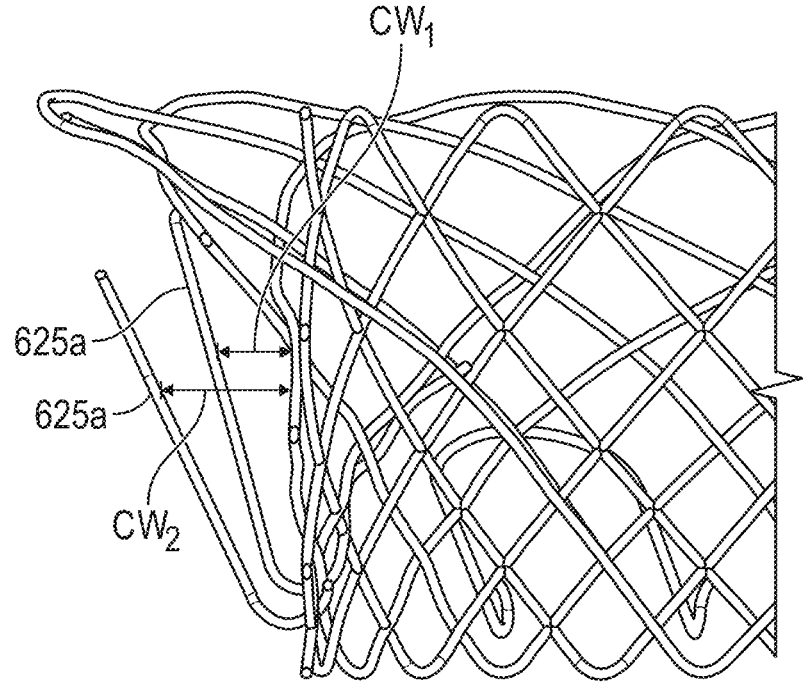
FIG. 28 generally illustrates embodiments of leaflet clips of a valve replacement as disclosed herein.

FIGS. 27 and 28 generally illustrate embodiments of the valve replacement as disclosed herein. The clips 625a are configured to extend at a more vertical angle towards the atrial direction, and therefore sit closer to the body of the valve replacement, than the stabilizers 630a, which extend in a more medial and lateral direction in relation to the body of the valve replacement. Accordingly, in the example shown, the height of the clip 625a at its highest point closest to the inflow or atrial side of the valve replacement is greater than the height of the stabilizer 630a at its highest point closest to the inflow or atrial side of the valve replacement. In embodiments, this height differential H2 between the height of the clip 625a and the height of the stabilizer 630a is between 0 mm to 6 mm, with embodiments having the height differential H2 between the clip and stabilizer being 0 mm, 1 mm, 2, mm, 3 mm, 4, mm, 5 mm, or 6 mm.

Having a greater height at the clip 625a than at the stabilizer 630a enables embodiments to correspond to a saddle shape of the native mitral annulus (represented by 665) and ventricular area near the native mitral annulus of the native heart. For example, in embodiments, the clip 625a can reach the higher part of the saddle shape of the native mitral annulus and ventricular area near the mitral annulus of the native heart, and in contrast, the stabilizer 630a can rest or lodge or be placed or secured in the lower part of the saddle shape of the native mitral annulus and ventricular area near the mitral annulus of the native heart.

However, the height differential H2 between clip 625a and stabilizer 630a can vary based on the heart anatomy of patients. For example, in the native mitral valve annulus area, there is a higher saddle shape in the anterior and posterior areas (including along the A2 and P2 leaflet areas) and lower saddle shape along the commissure-to-commissure areas. For some patients with a more pronounced saddle shape, a shorter stabilizer 630a (and increased height differential) can reduce instability as it more closely follows the native annular saddle shape. In the annulus of a highly diseased patient, the annulus may take on a flatter shape and as a result a taller stabilizer (reduced height differential) would be more appropriate. Thus, in some embodiments, clip 625a is higher than the stabilizer 630a in a range of 0 mm to 9 mm for height differential H2. In some embodiments, clip 625a is 3 mm to 8 mm higher than the stabilizer 630a for height differential H2. And in some embodiments, clip 625a is 2-3 mm higher than the stabilizer 630a for height differential H2. In embodiments, a higher clip provides for an easier staged deployment of the medial and lateral stabilizers. When the clips are in an appropriate position for final device placement such as against the annulus or behind the native A2/P2 leaflets, the stabilizers will naturally be exposed in a lower position due to the height differential. This allows for easier final positioning of the stabilizers as they are released in a more ventricular position. This position allows for easier placement of the stabilizers below the native annulus and reduces the need for additional atrio-ventricular motion of the system, reduces risk of losing clip position, thus simplifying final positioning, and also helps the stabilizers engage with native tissue (such as the native annulus, native chordae, and LV wall), but not pin leaflet material open.

In some embodiments, each clip 625*a* and/or stabilizer 630*a* corresponds to a particular leaflet. In some embodiments, each clip 625*a* and/or stabilizer 630*a* secures, clips, touches, restricts, and/or contains a particular leaflet. In some embodiments, each clip 625*a* and/or stabilizer 630*a* secures, clips, touches, restricts, and/or contains a particular leaflet in a particular sequence.

For example, in some embodiments, an A2 clip is first released to capture an A2 leaflet followed by a P2 clip released next to capture a P2 leaflet. In some embodiments, clip 625*a* may be used and configured to secure or clip the P2 leaflet with another clip on the opposite side of the valve replacement used and configured to secure or clip the A2 leaflet. In some embodiments, both clips, one clip on a first side and the other clip on opposite sides of the valve replacement (the two clips 180 degrees separated from each other) are simultaneously released and used to capture A2 leaflet first, followed by the P2 leaflet, or in some embodiments, used to capture the P2 leaflet first followed by the P2 leaflet, and in some embodiments, the A2 and P2 leaflets are captured simultaneously. In some embodiments, stabilizers (e.g., 630*a*) are also released to engage native anatomy, such as native chordae, native annulus, native LV wall, and native leaflets—e.g., P1/P3 leaflet areas in some embodiments. In some embodiments, there are two stabilizers 630*a* spaced equidistant from the P2 clip. Because P1/P3 leaflets are shorter than a P2 leaflet, the stabilizers (e.g., 630*a*) being shorter than the P2 clip 625*a* make it possible/easier to engage native anatomy in the native sub annular space (such as native P1/P3 locations on native leaflets) without having to move the device delivery system down into the ventricle. And reducing such movement after engaging the A2 and P2 leaflets (with the clips—e.g., 625*a*) makes it easier to maintain engagement of A2 and P2 native leaflet locations with the clips while then engaging other native anatomy (e.g., P1/P3 leaflets) with the stabilizers (e.g., 630*a*). In embodiments, the stabilizers 630*a* do not capture leaflets, but instead rest near the leaflets in the ventricular saddle shape of the native mitral annulus.

In some embodiments, opposite the P2 clip 625*a* on the replacement valve body is an A2 clip, which is used and configured to secure or clip the A2 leaflet. Some embodiments vary a degree of angle between the leaflet clip relative to the valve body itself. In some embodiments, such as that shown in FIGS. 27 and 28, the clip (e.g., an A2 clip or a P2 clip) may be situated almost vertically (e.g., about 180 degrees or parallel to the valve body). Increasing that angle, e.g., by shape setting the clip 625*a* out further may increase a window to capture a leaflet (e.g., an A2 leaflet), and thus result in that procedure becoming easier to achieve. In some embodiments the capture window of the shape set clip 625*a* is 25 degrees or less, for example in other embodiments the capture window of the shape set leaflet clip 625*a* is 20 degrees, 15 degrees, 10 degrees, 5 degrees or less than 5 degrees. As shown in FIG. 28, there is a smaller capture window CW1 and a larger capture window CW2. In embodiments, the P2 clip is minimally extended from the valve body (<6 mm), which enables the bioprosthetic valve to reside in a more posterior position within the annulus. In embodiments, the P2 clip has a distance between the P2 clip and the receiver between 4 mm to 6 mm. The flexible flange also enables this by conforming to the annulus on the posterior side. This minimal posterior valve projection ensures a posterior position of the valve when implanted and helps enable posterior vortex flow. In embodiments, the valve replacement is anchored to the native annulus in part by the tips of the clips engaging with the underside of the native annulus in the ventricle from below and the flange engaging with the topside of the native annulus in the atrium from above. In some of these embodiments, a distance H3 between where the clip tip 625at engages the native annulus 665 from below (on the ventricular side) and the flange 610 engaging the top of the native annulus from above (on the atrial side) is 5 mm or less, including a gap of 4 mm, 3.5 mm, 3 mm, 2.5 mm, 2 mm, 1.5 mm, 1 mm, or less.

In some examples, shorter stabilizers 630*a* may also prevent "kickstanding" of the replacement valve towards the LVOT. This may enable the replacement valve to point more posteriorly, with the benefit of maintaining posterior vortex flow and LVOT preservation. On the other hand, taller stabilizers 630*a* may angle the replacement valve more anterior.

In some embodiments, as depicted in FIGS. 27 and 28, the geometry of the leaflet clips 625*a* permit native leaflet motion/wrapping around the valve body for sealing by having drop loops of the clips low on the receiver's frame, with the clips pulling the native leaflets close to the valve body and creating a seal around the valve body and native leaflets, thereby encouraging native leaflet motion. In embodiments, the drop loops of the clips are on the ventricular aspect of the frame so the bulk of the leaflet can fit above them which allows for them to seal/move against the frame. In embodiments, as shown in FIG. 28, the drop loop of the leaflet clip 625*a* (with the drop loop being the curved section of the clip exiting the valve receiver before the clip eventually turns upward in an atrial direction) can take various forms and angles to accommodate the native leaflets and promote clip and flange anchoring and maintain acceptable crimp profile (two variations of leaflet clips 625*a* shown with different drop loop geometries, with the larger drop loop resulting in the clip extending further away in an axial direction from the valve receiver). For example, in embodiments, a first drop loop results in a 3 mm distance between the tip of the clip and the receiver body and in another embodiment a larger drop loop results in a 6-8 (plus or minus 1 mm) distance between the tip of the clip and the receiver body. In embodiments, the drop loop of the clip transitions into a straight section pointing in the atrial direction and then transitions into a mid-clip radius to angle out into a curved extended section reaching out to further areas of the saddle shape of the native heart. Clips with a mid-clip radius after the drop loop are particularly useful in larger valve sizes since the clip can extend further into a flatter annulus saddle shape. In embodiments, the drop loop of the leaflet clip provides a trough where the native leaflet is able to be captured in a more natural position, thereby permitting the native leaflet to move with the anatomical movement of the heart but also seal against the replacement valve body (or receiver), thereby helping prevent paravalvular leak and providing an anchoring function. In embodiments with clips 625*a* having drop loops and atraumatic capturing of the native leaflets, the replacement valve is able to be minimally oversized and still capture but not freeze the native leaflets.

Figure 29:
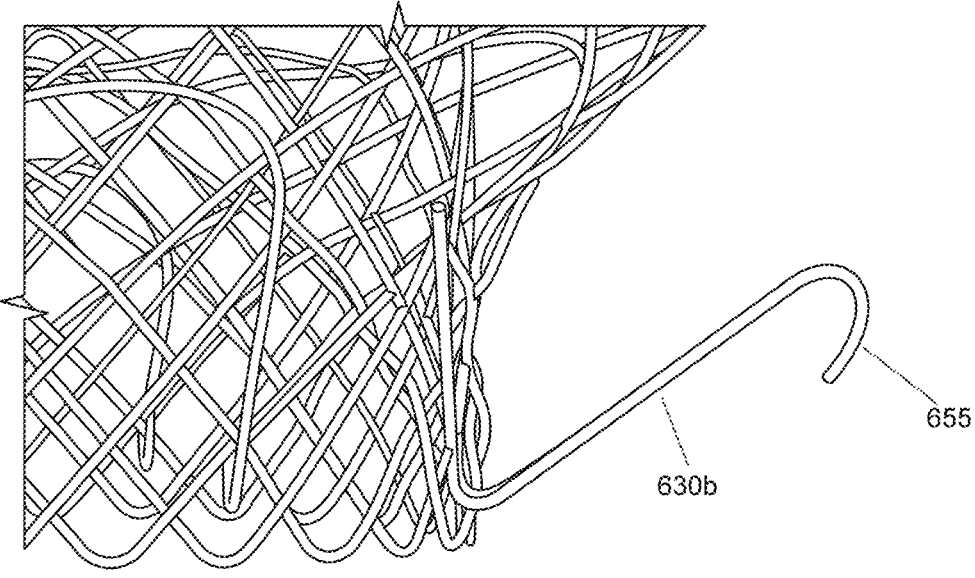
FIGS. 29-30 generally illustrate embodiments of stabilizers of a valve replacement as disclosed herein.
Figure 30:
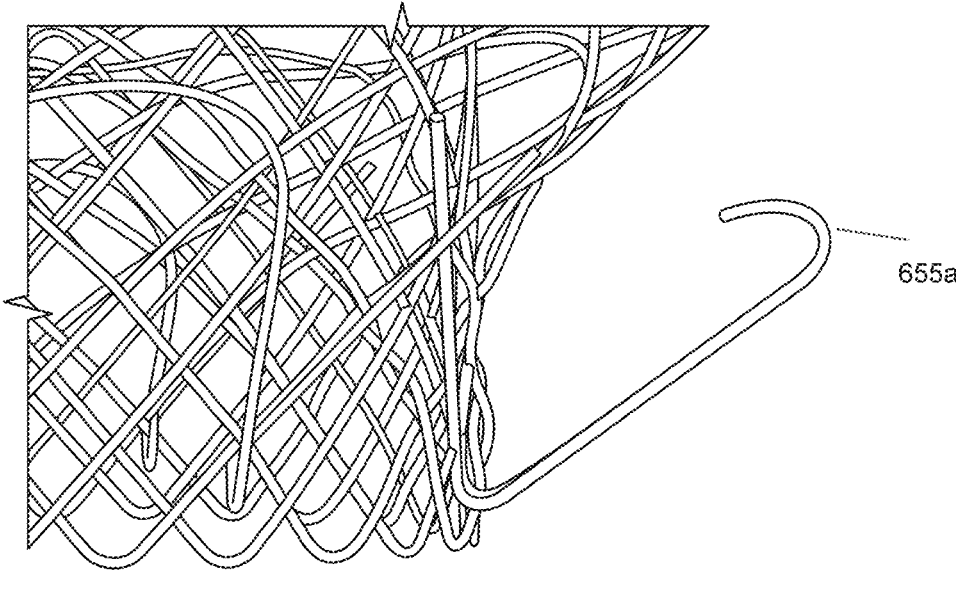

FIGS. 29 and 30 generally illustrate an embodiment of the valve replacement (also referred to as "replacement valve" and "prosthetic mitral valve") as disclosed herein. When deployed outwardly, the stabilizer 630*b* touches or makes contact with a part of the surrounding heart anatomy. The curved edges 655, 655*a* of the stabilizer 630*b* spread the load/forces of such contact over a larger surface area of the anatomy, and are less traumatic on the native tissues.

While tip geometry may vary according to embodiment, one embodiment utilizes a round tip with a straight side profile. A round end may further assist or ensure navigation through chords during deployment. Stabilizer width may also be increased to engage with native chordae and increase chordal support for anchoring purposes. Degree of curvature at the round end may also vary. in the side profile. In some embodiments, the curved both ends or edges 655, 655*a* of the stabilizer 630*b* may curve down towards the LV, and/or up towards to annulus, which as explained above may additionally spread load out on wall/annular contact. Some tip embodiments may vary with the objective of being atraumatic. As discussed herein as well, the leaflets clips can also have a "ski tip" (for example on the A2 leaflet clip) and padding on the clip (for example padding on the P2 leaflet clip) for creating a more atraumatic surface for the clips where they interact with the native tissue.

In some embodiments, clips and stabilizers (e.g., 625*a*, 630*a*, 630*b*) are braided in/welded into the receiver body such that the drop loops can bend into the open cell area during crimping as well as during cyclic in vivo motion. In embodiments, the drop loop of the clip and stabilizer extends out from a cell opening in the braided structure near the outflow end, less than ¾ of the way down the diamond opening with a target of ½. This ensures that during deflection as well as crimping the drop loop pushes inward into free space and does not contact the frame.

In some embodiments, the stabilizers 630*a* have a wingspan sufficient to extend from the valve body to the heart tissue. Stabilizers may increase or decrease in wingspan correspondingly with the annulus size and left ventricular cavity size (sub-valvular size), and therefore larger and smaller valve size than those described below are contemplated. For instance, there is generally an offset between annulus size and sub-valvular size. More specifically, by way of example, at about 5 mm below the annulus, the mitral valve opening in some examples is on average about 5.6 mm larger than the annulus itself in diastole. Analysis has also shown that a C-C (also referred to as medial-lateral) maximum distance of 46 mm will provide coverage of much of the patient population. Therefore, to ensure contact between the stabilizer and the surrounding heart tissue during systole and diastole, the stabilizers should have a wingspan (measured horizontally from the valve body) greater than 51 mm. In some embodiments, that wingspan has a length range of between 40-74 mm, 50-65 mm, and 51 mm to 59 mm (plus or minus 3 mm in embodiments). And in some embodiments, the stabilizers 625*a* have a wingspan of 55 mm or 58 mm (plus or minus 2 mm in embodiments). Note that in order to cover additional size ranges, the target C-C dimension (also called the medial-lateral dimension) may change and the stabilizer wingspan offset will follow, which is true for both smaller and larger size implants. For example, in embodiments, there is flange 610 size to stabilizer 625 wingspan X1 ratio. For example, for a flange 610 size in the M-L direction B1, there are possible configurations in embodiments with B1 being between 47 mm and 70 mm, between 50-65 mm, and between 53-63 mm, with embodiments having flange size B1 in the M-L direction of 54 mm, 58 mm, 62 mm, or 63 mm, and embodiments having a B1 span of 47 mm, 47.5 mm, 48 mm, 48.5 mm, 49 mm, 49.5 mm, 50 mm, 50.5 mm, 51 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, 60 mm, 60.5 mm, 61 mm, 61.5 mm, 62 mm, 62.5 mm, 63 mm, 63.5 mm, 64 mm, 64.5 mm, 65 mm, 65.5 mm, 66 mm, 66.5 mm, 67 mm, 67.5 mm, 68 mm, 68.5 mm, 69 mm, 69.5 mm, and 70 mm. In embodiments, stabilizers have a wingspan X1 from medial stabilizer to lateral stabilizer between 40 mm to 74 mm, between 40-60 mm, between 46-60 mm, and with embodiments including wingspans X1 of 46 mm, 48 mm, 52 mm, 56 mm, 58 mm, and 60 mm and embodiments having stabilizer wingspans X1 of 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 mm, 50 mm, 50.5 mm, 51 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, 60 mm, 60.5 mm, 61 mm, 61.5 mm, 62 mm, 62.5 mm, 63 mm, 63.5 mm, 64 mm, 64.5 mm, 65 mm, 65.5 mm, 66 mm, 66.5 mm, 67 mm, 67.5 mm, 68 mm, 68.5 mm, 69 mm, 69.5 mm, 70 mm, 70.5 mm, 71 mm, 71.5 mm, 72 mm, 72.5 mm, 73 mm, 73.5 mm, and 74 mm. In embodiments, the ratio of the flange width B1 in the M-L direction to the corresponding stabilizer 630 wingspan X1 can be between 0.8 to 0.9 and higher. For example, an embodiment with a larger flange 610 size B1 in the M-L direction of 62 or 63 mm, the stabilizers can have a slightly smaller wingspan X1, for example in the range of 56 mm to 60 mm (including 58 mm), resulting in a ratio of X1/B1 of 0.90 to 0.97. An embodiment with a medium flange 610 size B1 in the M-L direction of 58 mm, the stabilizers can have a slightly smaller wingspan X1, for example in the range of 52 mm to 56 mm, resulting in a ratio of X1/B1 of 0.89 to 0.96. An embodiment with a smaller flange 610 size B1 in the M-L direction of 54 mm, the stabilizers can have a slightly smaller wingspan X1, for example in the range of 46 mm & 48 mm to 52 mm, resulting in a ratio of X1/B1 of 0.85 & 0.89 to 0.96. The flange size in any direction, including M-L, can be combined with a range of stabilizer wingspans X1 depending on anatomy and other dimensions of the replacement valve.

Stabilizer embodiments may vary in dimensions, e.g., in width at the tip/end. While shorter/a lower range of widths may assist in navigating chords more effectively, larger widths may assist force/load distribution and may engage native chords to provide additional support for the replacement valve and help maintain its stability within the native anatomy. In some embodiments, stabilizer widths may range between about 4 mm to 15 mm, including embodiments with a stabilizer width of 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, and 15 mm, and in some embodiments may have a 6 mm-15 mm tip/end width, including embodiments with a stabilizer tip width of 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, and 15 mm. Such a range may be adequate for commercially available repair devices to better navigate chords, with widths in this range being tested and verified to be sufficiently flexible to accommodate additional contact from the native chords. In embodiments, clips, on the other hand, which may rest in chord free zones, are wider with a width range of 10-14 mm at the tip/end.

Some stabilizer embodiments may have bases with the same or similar widths as tips, which in some examples may entail simpler braiding configurations. Some stabilizer embodiments may have bases with smaller widths than tips. In some embodiments, the stabilizer width may be 50% smaller at the base than at the tip. The wider tip width in comparison with the base may assist in ensuring that chords come to rest in a more native position.

Figures 31, 32, 33, 34, 35:
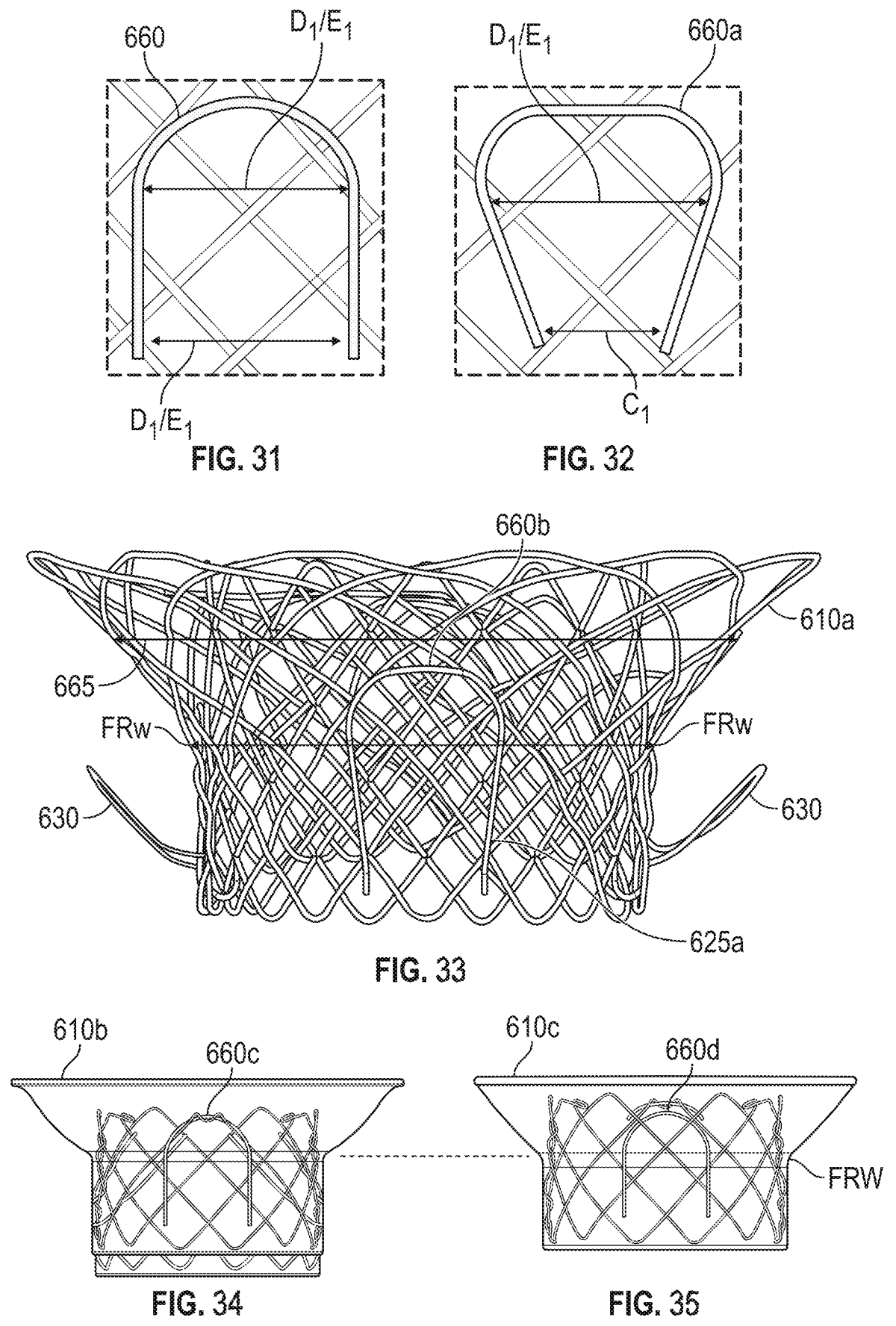

FIGS. 31 and 32 generally illustrate embodiments of the valve replacement as disclosed herein. More specifically, FIG. 31 shows close-up views of a previous tip design 660 of a clip (e.g., 625a), and FIG. 32 shows an updated tip design 660a of a clip (e.g., 625a). In embodiments, the P2 clip has the flat top and the A2 clip is rounded at the end with a ski tip.

Some tip design embodiments may conform to heart anatomy and shape(s) thereof, and in particular on the annulus. For example, the embodiments shown are specifically P2 clips 625a. And the FIG. 32 updated tip design 660a has a larger, more elongated, flatter top surface. As mentioned above, part of (e.g., the higher part of the saddle shape of) the native mitral annulus may rest or lodge or be placed or secured over the clip 625a. Accordingly, the FIG. 32 updated tip design 660a with its larger top surface provides a better landing spot for the annulus, by spreading a load across a longer surface.

Some clip designs may conform or be based on a specific the anatomy of a leaflet corresponding to the clip. For example, the P2 leaflet may have chordae that end at a narrower position than chordae of an A2 leaflet. Accordingly, some P2 clip embodiments feature narrowed bases (in comparison to tips) to reduce or prevent chordal interaction and potential damage to those chords. Notwithstanding differences in clips, e.g., A2 and P2 clips, embodiments of the replacement valve have the A2 and P2 clips braided into the receiver's frame at the same height symmetrical to one another along the receiver's frame. Also, in embodiments, the clips maintain the same distance relationship between the flange and clip tips to ensure a leaflet base "clamping" effect with the nitinol spring force. In other embodiments of the replacement valve, leaflet clips can be braided into the receiver's frame at various heights that may not be symmetrical to one another along the receiver's frame.

In addition to clip designs, certain operations and order of operations may also be based on particular leaflet anatomy. For example, as explained in more detail elsewhere in this disclosure an A2 leaflet may be longer on average than a P2 leaflet. Accordingly, in some embodiments, an A2 leaflet may be engaged (e.g., with an A2 clip drop loop) before the P2 leaflet. Engaging the A2 leaflet first may cause the device to pivot about A2 leaflet, and potentially point the device towards the posterior side of the left ventricle (see, for example, FIGS. 57 and 60). This, in turn, may assist in preserving LVOT and enabling more natural posterior vortex flow.

In some embodiments, the P2 clip tip 660a (or other clips—e.g., an A2 clip) may include padding (made from e.g., cloth, tissue, etc., placed under an outer layer of cloth covering) to make the edge more atraumatic. For example, the padding may further increase the surface area further spread the load and/or act as a "cushion." Other clip and stabilizer tip designs may also assist in spreading a load, such as additional wireframe structures (e.g., coil tips, "potato masher" designs, etc.). Some clip and stabilizer tip designs (e.g., for an A2 clip) may also feature a "ski tip"

profile added to assist in spreading a load (more atraumatic). In embodiments, the ski tip design also enables easier native leaflet engagement as it more naturally opens into a wider capture window distance and also enables better visualization on echocardiograms because an operator can identify which clip, stabilizer or other anchor feature is shown based on the specific edge of the tip. Such designs and profiles for spreading loads may be accomplished using padding and/or shape setting.

FIG. 33 generally illustrates an embodiment of the valve replacement as disclosed herein. In some embodiments, the tip 660b of a clip 625a touches the underside of a native annulus just below where the flange of the replacement valve is resting on the top of the native annulus when the valve replacement is deployed within a native mitral valve. For example, line 665 shows approximately where an annulus may rest on the flange 610a, and a small distance to the top tip 660b of the clip 625a. In some examples, the tip 660b of the P2 clip 625a is at the annulus 665 and define an interaction point of the device with the flange. In some examples, the part of the annulus that falls or lies below the flange 610a to rest on the tip 660b of the clip 625a helps anchor or secure the anulus into a desired position. In embodiments, a distance between where the flange 610a rests on a native mitral annulus and the top tip 660b of the clip 625a is between 3 to 6 mm and is 4 mm in embodiments.

As explained elsewhere in the disclosure, some embodiments may entail flanges that connect (e.g., are interweaved/braided in/welded) at different vertical coordinates along the receiver. These different "flange takeoff locations" relative to the receiver may allow use with receivers having increased height. In some embodiments increasing receiver height may result in the receiver being moved further into the atrium. This in turn may result in a tradeoff of decreased ventricular projection, made possible by the flange being interweaved at a different location than the top of the receiver, which may be beneficial in some aspects. In this manner, in some embodiments the ventricular projection may be reduced to 16 mm or less. In other embodiments, the ventricular projection is reduced to 15 mm, 14 mm, 13 mm, 12 mm, 10 mm, and less than 10 mm. In these embodiments, the flange is woven lower on the valve receiver, thereby reducing the ventricular projection of the valve receiver and increasing the height in the atrium. Similarly, the attachment points of the clips and stabilizers can be modified on the receiver to accommodate the relative receiver and flange height. In some embodiments, increased receiver height may improve valve performance in some aspects (EOA, coaptation, etc.). The point of entry of the flange into the receiver body allows for variation in the braid structure, support, and dimensional configuration of the implant. Should the flange be woven in at a more atrial position, it naturally provides a more robust structural support to the receive body as there is additional receive body surface with wire points crossing leading to additional structural support. This support must be balanced with the geometric position of the flange entry into the receive body, as an atrial entry position would lead to additional ventricular projection. Embodiments weave the flange wires in at approximately 8 mm to 12 mm from the outflow of the valve, including an embodiment at 11 mm, providing both additional structural support where it is needed the most (commissural attachment), while minimizing ventricular projection of the implant to approximately 15 mm. Additionally, the shape of the flange may be adjusted to modify ventricular projection while maintaining the same entry point into the receiver. As an example, one embodiment may have the flange run tightly close to the receiver body towards the atrium, followed by a bulbous outward shape. This would increase ventricular projection, whereas an embodiment that immediately contours outward from the entry point would minimize ventricular projection. This feature would allow for additional valve sizes that require modified flange diameters to use the same receive entry point in the braid. These feature sets are not achievable using traditional laser cut frames as the flange weaves into the receive wire at the id-section of the receive body. Traditional laser cut frames require the flange to exit the atrial-most end of the implant frame.

In embodiments, the clips are connected or coupled to the receiver (e.g., welded) at any height along the receiver length. In embodiments, the clips are coupled to the flange or the receiver body by connecting the stabilizers and clips to the braided wire of the flange or braided wire of the receiver body by welding, fusing, grafting, or mechanically coupling the wires together with a fastener. In other embodiments, the clips are held by the braided wire of the flange or braided wire of the receiver body by a mechanical fit from the wires being interwoven (e.g., the clip wire interwoven into the receiver or flange wires). In some examples, having the clips connected or coupled to the receiver at any height along the receiver length may assist in maintaining a same/similar relationship to the flange as well as drop loop location for leaflet insertion depending on where the flange is woven into the replacement valve body.

FIGS. 34 and 35 generally illustrates an embodiment of the valve replacement as disclosed herein. FIG. 34 shows a valve design with clip 660c welded into the receiver body at a height with the top of the clip 660c meeting near the underside of the flange 610b such that when deployed in native mitral valve, the flange 610b underside rests on the top of the native annulus and the top of the clip 660c rests on the underside of the native annulus, thereby creating an anchoring force between the flange and the clip. This anchoring dynamic is possible in other embodiments, for example in FIG. 35 where the flange 610c is woven at a lower location on the replacement valve body and the clip 660d is welded into the replacement valve body at a lower location, thereby maintaining the distance between the bottom of the flange 610c and the top of the clip 660d and permitting the same type of anchoring relationship between the native annulus when the replacement valve is deployed in the native mitral valve. As can be seen, when an annulus rests on the flange 610c of a valve with the clip 660d, there is a similar distance from the flange 610c to the native annulus to the clip 660d as there is from the flange 610b to the native annulus to the clip 660c.

In addition, as discussed elsewhere in this disclosure, the flange 610c need not be flush with the top of (e.g., a receiver portion of) the valve. Rather, flange 610c may be connected at and extend from a lower point of the valve (e.g., from receiver). In some embodiments, the flange 610c can be woven into the valve (e.g., the receiver) along any portion of its height. One benefit of this design is that the less of the receiver need intrude into the ventricle. This, in turn, may assist preserving LVOT and reducing interaction with native papillary structures.

In some embodiments, the valve may be oversized in the A-P (anterior-posterior) and C-C (commissure-commissure, also referred to as M-L or medial-lateral) directions in the native anatomy. For instance, in some examples, the valve diameter along the C-C may be 40 mm to 42 mm (plus or minus 2 mm), while the distance from A2 to P2 may be about 38 mm (plus or minus 2 mm).

As the anchoring mechanism of the A2 and P2 leaflet clips ensure repeatable device orientation within the native anatomy, the bioprosthetic valve leaflets may be repeatably oriented relative to the native anatomy. As the A2/P2 distance of the native valve is generally smaller than the C-C distance, the bioprosthetic valve commissure positioning may be pre-specified to optimize performance when crushed in the A2/P2 direction. This orientation includes an embodiment where a commissure is located at the P2 leaflet clip area of the replacement valve. By placing a bioprosthetic leaflet commissure directly at P2, the valve will perform in a predictable fashion when under crush. This position optimizes for leaflet redundancy, coaptation, as well as opening and forward flow when in a crushed position. Additionally, this aligns with predicate surgical implantation best practices in terms of commissural alignment. With a replacement valve having a posterior leaflet clip (P2 clip) next to a commissure of the three leaflet bioprosthetic one-way valve in the middle of the valve replacement embodiment (see FIGS. 58 and 63), a crush of the replacement valve in the AP (anterior-posterior) direction in vivo during outflow through the replacement valve causes beneficial outflow turbulence that helps with Neo-LVOT. This AP crush also helps the replacement valve settle into a beneficial posterior position during the cardiac cycle in vivo.

Figure 36:
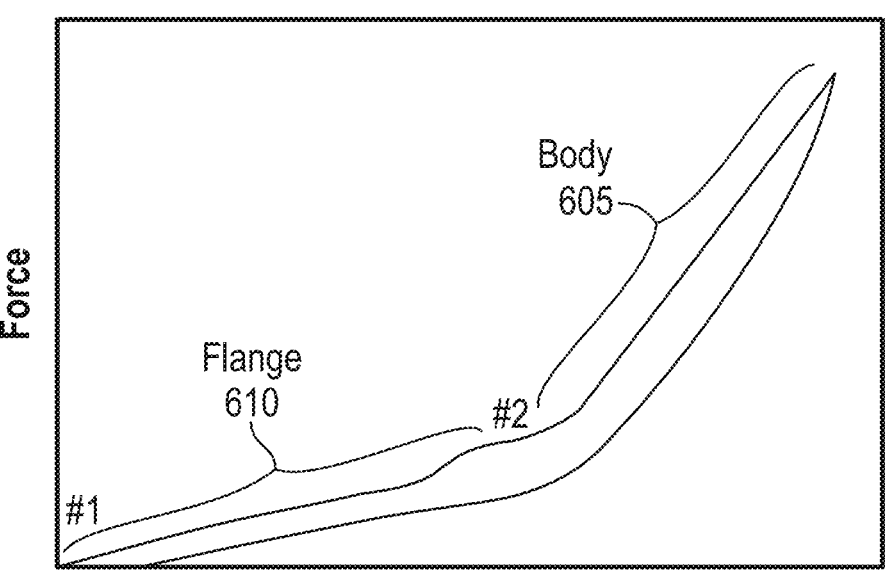
FIG. 36 generally illustrates crimping forces and displacements for embodiments of a valve replacement as disclosed herein.

FIG. 36 generally illustrates the bi-modal crush behavior of the valve replacement, including different crush resistances from the braided flange 610 and receiver 605. As shown in FIG. 36, in the starting position, the replacement valve has no crush force applied and the flange 610 and receiver 605 are not displaced. In the second position, there is a nominal crush of 25% coming down on the replacement valve, which crushes and displaces the braided flange 610 but does not crush the receiver 605. This ability to apply force to the replacement valve and displace the flange 610 but not the receiver 605 is due to the braided nature of the replacement valve and how part of the flange 610 is interwoven into the receiver 605 with the flange 610 having a separate weave outside the receiver 605 forming the petals and curved section on the flange 610 (as described elsewhere in this disclosure, see, e.g., FIGS. 3, 4, 5, 6, 11, 12, 17, 18). When the replacement valve is crushed, the petals and curved section on the flange 610 are displaced first, before the receiver 605, without the receiver wires 605 being crushed and displaced. Thus, with the interwoven flange 610 and receiver 605, as described herein, the flange 610 petals and curved wire outside the receiver 605 are able to be crushed and displaced before the receiver 605 deforms, such that the receiver 605 will still function as a valve replacement with the replacement leaflets coapting even when the flange 610 is crushed and displaced. The flange 610 is able to be crushed and not have a detrimental effect on the receiver's 605 function because the wires of the flange 610 and receiver 605 are different wires, with the portion of the flange 610 being crushed (e.g., the petals) not being directly connected to the receiver 605 wire. Thus, the crushed petals of the flange 610 can be displaced, causing the flange 610 wires to move past each other and displace without forcing the receiver 605 wire to be displaced. The flange 610 wire can move along and slide past itself, including at flange 610 wire crossings and even at crossings of flange 610 and receiver 605 wire, because the flange 610 and receiver 605 wires are not fixed together and do not have fixed nodes, unlike other dual frame systems or laser cut frames where the parts of the system are connected together and have fixed nodes that transfer force to the rest of the systems and deform downstream. The bi-modal crush of the replacement valve also comes from the flange 610 having half the weave density of portions of the receiver 610. The flange 610 has a single wire weave comprising the flange 610 wire that is outside the receiver 605, with that flange 605 wire forming the flange's 610 curved wire and petals (12 petals in embodiments) outside the receiver 605. In contrast, the receiver 605 has twice the wire density in portions with the flange 610 wire and the receiver 605 wire forming an interwoven pattern having 24 peaks at the outflow end of the replacement valve. This gives the receiver 605 twice the wire density as the flange 610 in the lower portion of the receiver 605. Thus, the receiver 610 has greater crush resistance than the flange 605, thereby contributing to the replacement valve's bi-modal crush resistance, especially at the lower portions of the receiver 605 with the greater weave density, as well as portions of the receiver 605 that are not interwoven with the flange 605 wire. Because the replacement valve has a bi-modal crush resistance and the receiver 610 is not displaced or crushed even when the flange 610 is under crush and being displaced, the replacement valve is a floating valve, with the flange 610 taking force and being crushed and enabling the receiver 610 and the replacement leaflets to float within the native anatomy and function without being crushed or displaced by the force applied to the flange 610.

Figure 37:
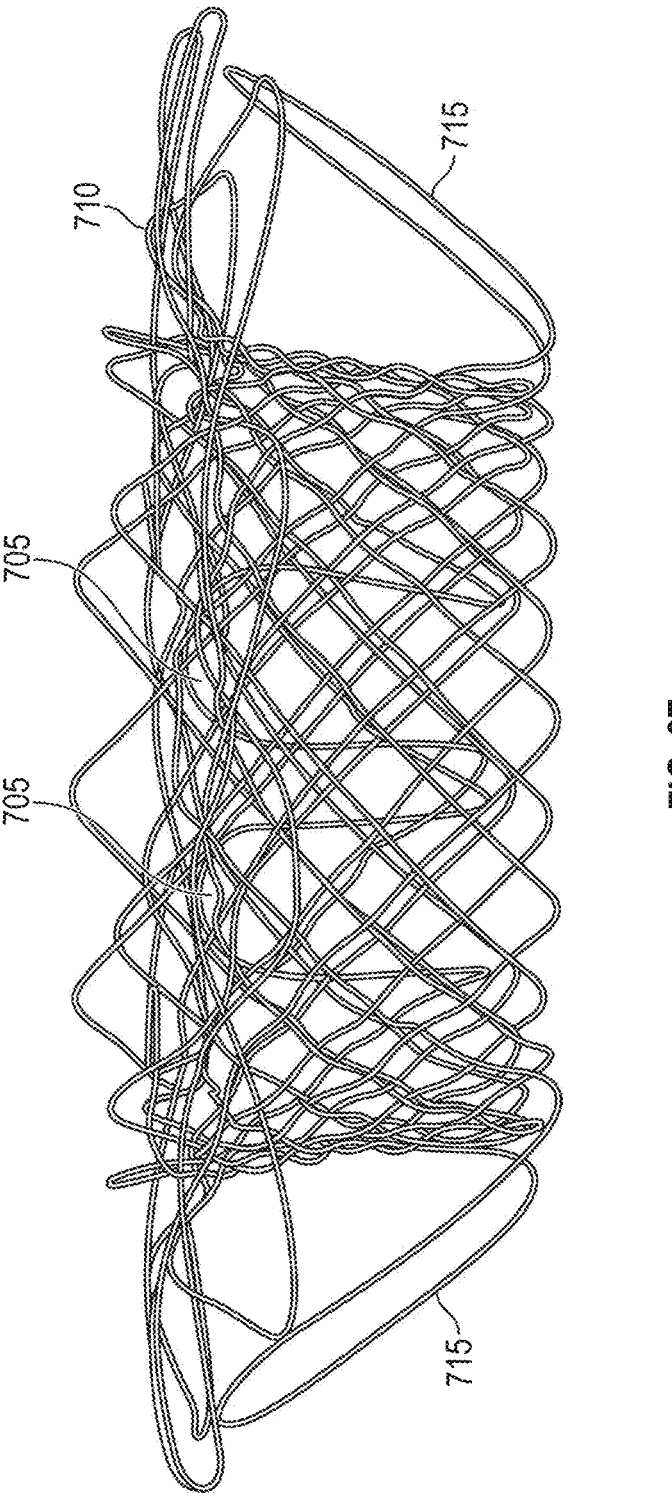
FIGS. 37-39 generally illustrate embodiments of a valve replacement as disclosed herein.

FIG. 37 generally illustrates an embodiment of the valve replacement as disclosed herein. FIG. 37 shows an embodiment of a wire braid frame that the receiver is comprised of. The wire braid frame may comprise a 24-point braid pattern, with double posterior leaflet anchors 705, wherein the double posterior leaflet anchors 705 are used to maintain symmetry and additionally provide twice the structural anchoring. The wire braid frame may also comprise dual stabilization anchors 715. Also shown is that the wire braid frame may have the anchor locations available in 15-degree increments.

The anchors may be, in some embodiments, an extension of the tubular braided frame and extend out from the outflow end to function as an engagement attachment. In other embodiments, the wire braid frame of a receiver may have anchors that are grafted, welded, or fused on. For example, FIG. 37 shows the combination of a larger gage wire (0.0175"-0.02") (represented by the stabilization anchors 715) and smaller gage wire (0.012-0.0175") (represented by the posterior leaflet anchors 705 and further represented by additional wires 710) by means of a joining operation at the interface between the varying-size wires. The connection interface may be a weld or a weld with a support tube.

Embodiments of welding used may be in relation to the material that the valve replacement is comprised of. In an embodiment of the anchors comprising a hollow tubing (hypotube) material, the inside diameter of the hypotube mates perfectly with the diameter of the wire so that a simple weld or other helical weld pattern may be used to join the anchor to the frame. There, the ends of the hypotube may be chamfered so as to present a smooth transition with the attached wire. Radiopaque wire may be inserted inside the hypotube and positioned to be at the peaks of the anchors (such embodiment provides optimal fluoroscopic visualization) or anywhere along the hypotube for clinical visualization. In embodiments, hypotube anchors made of hypotube material can be chosen to have a greater stiffness or strength than the other wires used for the helical braided architecture of the replacement valve. Moreover, the hypotube material can be shaped to provide a longer surface area along a distal tip of the hypotube anchor that presses against the native heart anatomy to prevent migration of the replacement heart valve. A combination of greater stiffness and a longer surface area along a distal tip of the hypotube anchor distributes the anchor force of the replacement heart valve along a wider or greater area of the native heart anatomy, thereby decreasing the chances of damage to the native heart anatomy. Moreover, hypotube anchors provide opportunities for greater customization of the anchoring system because the hypotube anchor material can be sized and selected based on desired stiffness and contact area at the distal end of the anchor that anchors to the native heart anatomy.

Figure 38:
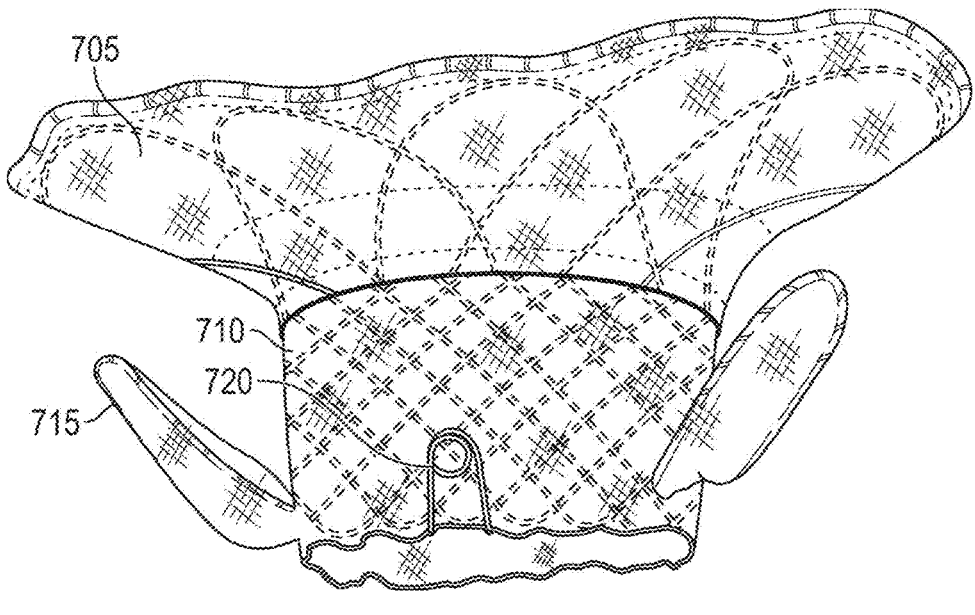
Figure 39:
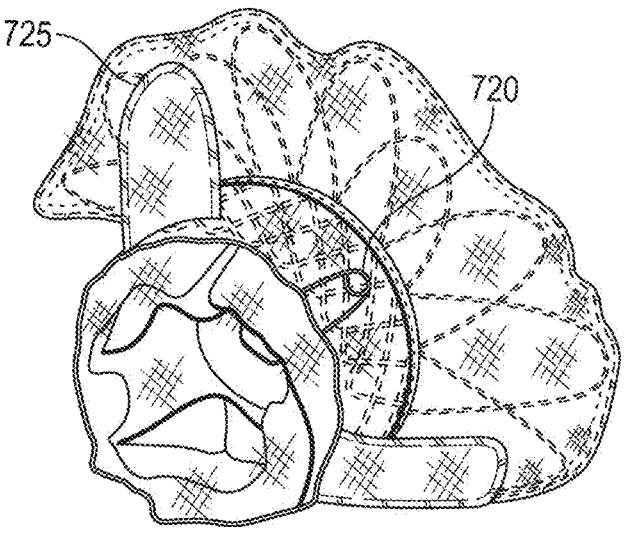

FIGS. 38 and 39 generally illustrate embodiments of the valve replacement as disclosed herein. The valve replacement embodiments of FIGS. 38 and 39 may include one or more anchor features. In one embodiment, as shown in FIG. 38, the valve replacement may comprise an atrial sealing skirt 705, a frame body 710, and an anchor feature 715 that are covered in a fabric for the purpose of flow sealing and/or encouraging (e.g., influencing either promoting or inhibiting) tissue growth after implantation. The anchor feature 715 may be strut or a stabilization anchor 715, which may assist in preventing migration of the valve replacement into the atrium. In some examples, the stabilization anchor 715 or a portion thereof may be configured or designed to rest on a specific area of the annulus (e.g., the trigone area). The embodiment may further comprise an anchor feature 720 that in some embodiments may not be covered in a fabric. In some embodiments, that anchor feature 720 may be or include a clip 720 or a hanger designed or configured to hold native leaflets. FIG. 39 shows a valve replacement comprising anchor features that may be posterior leaflet anchors (or struts) 725 and clips 720. In other embodiments, the clips and anchors are covered in fabric.

Figure 40:
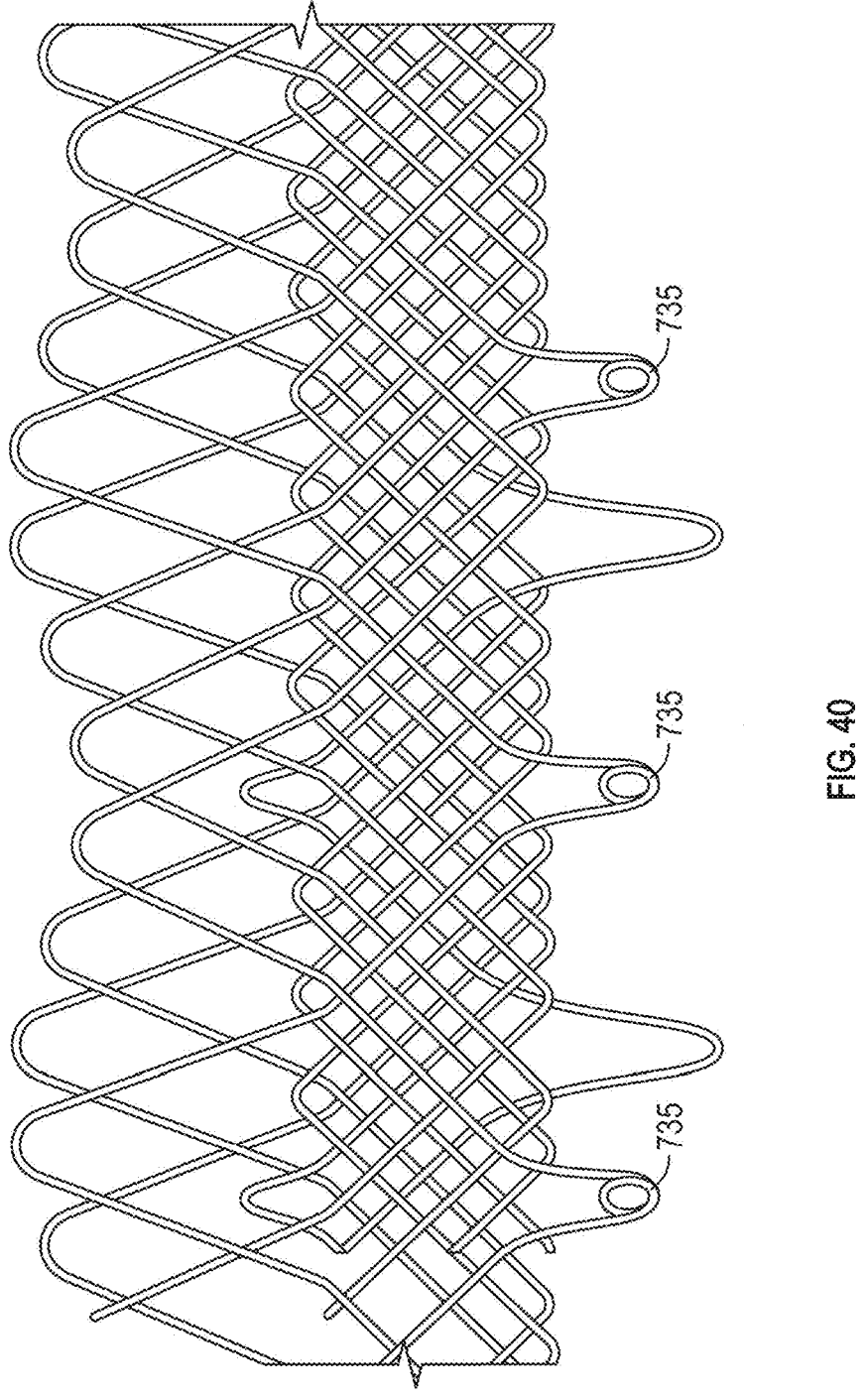
FIG. 40 generally illustrates an embodiment of an interwoven valve replacement and braid pattern as disclosed herein.

FIG. 40 generally illustrates an embodiment of the valve replacement as disclosed herein. FIG. 40 shows an embodiment of the valve replacement comprising a clip component 735 for the purpose of improving delivery control, via secure attachment of the valve replacement to a delivery catheter, and for the purpose of improving the efficiency and efficacy of leaflet attachment. FIG. 40 shows a flat-pattern schematic of a wire frame with a clip 735, wherein the clip 735 may be a looped portion of the wire frame extending out from the main body of the wire frame. In some embodiments, a clip 735 may be positioned at two or more separate locations around the circumference of the valve replacement. In other embodiments, clips 735 may be shape-set 180° such that they can provide for a hook shape to clip onto the native valve leaflets. For example, once the valve replacement is released from a delivery system, the clips 735 may attach onto the native valve leaflets, providing securement of the valve replacement. In embodiments, the clips envelope the native anterior and/or posterior leaflets of the native heart valve, mitral, or tricuspid for example. In embodiments, the clips wrap around the native leaflets to prevent the replacement heart valve from migrating into the atrium of the native heart. In embodiments, the clips are made of hypotube material comprising a hollow tubing (hypotube) material that has an inside diameter that mates with a wire of the helical wrapped wire of the frame of the valve replacement (including the receiver of the one-piece and two-piece systems).

Various embodiments of the valve replacement may comprise various quantities of anchors (including leaflet clips and stabilizers) at various angles and orientations. For example, one embodiment comprises six anchors, another embodiment comprises 3 anchors, and another comprises three anchors. In embodiments, the valve replacement comprises medial and lateral stabilizers oriented around a leaflet clip on an anterior side of the implant and in another, the valve replacement comprises medial and lateral stabilizers oriented around a leaflet clip on a posterior side of the implant. For example, in an embodiment applicable to the mitral valve, the valve replacement comprises two stabilizers/anchor struts (one medial and one lateral) and a leaflet clip in the A2 region of the anterior leaflet with a 150° angle (plus or minus 5 degrees and plus or minus 10 degrees in embodiments) between the medial and lateral stabilizers/anchor struts. In this embodiment, the A2 anchor (or A2 clip) anchors to the anterior leaflet at or near the A2 region (as explained further with regard to FIG. 8G) of the anterior leaflet and the A2 anchor (or A2 clip) is symmetric between the two anchor struts. In another embodiment applicable to the mitral valve, the valve replacement comprises two stabilizers/anchor struts (one medial and one lateral) and a leaflet clip in the P2 region of the anterior leaflet with a 150° angle (plus or minus 5 degrees and plus or minus 10 degrees in embodiments) between the medial and lateral anchors with the P2 anchor (or P2 clip) anchoring to the posterior leaflet at or near the P2 region of the posterior leaflet and the P2 anchor (or P2 clip) being symmetric between the two anchor struts. In another embodiment applicable to the tricuspid valve, the valve replacement comprises three anchors with a uniform 120°/120°/120° spacing of the anchors (or clips) to capture each leaflet of the tricuspid valve. Other angles and geometries are possible and within the scope of this disclosure.

Figure 58:
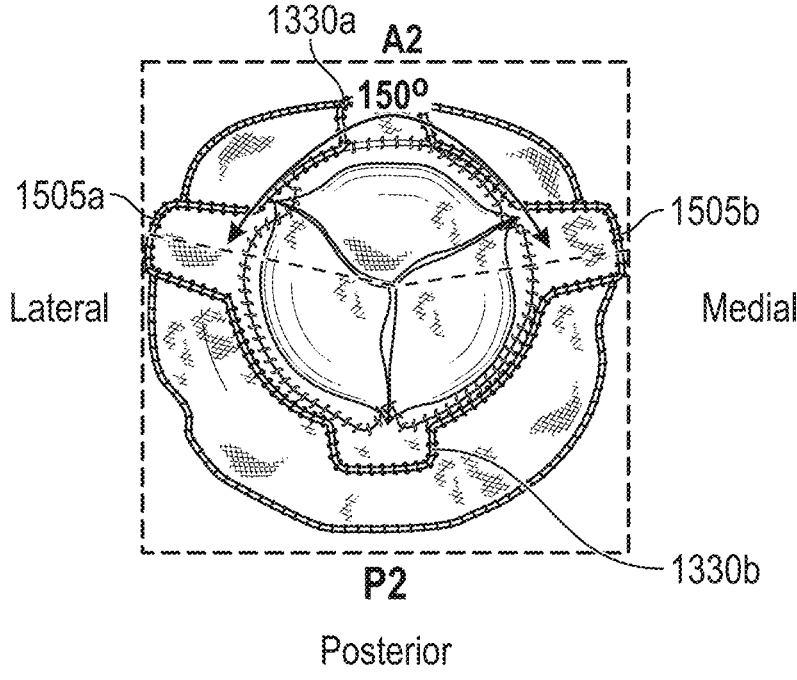
Figures 62, 63:
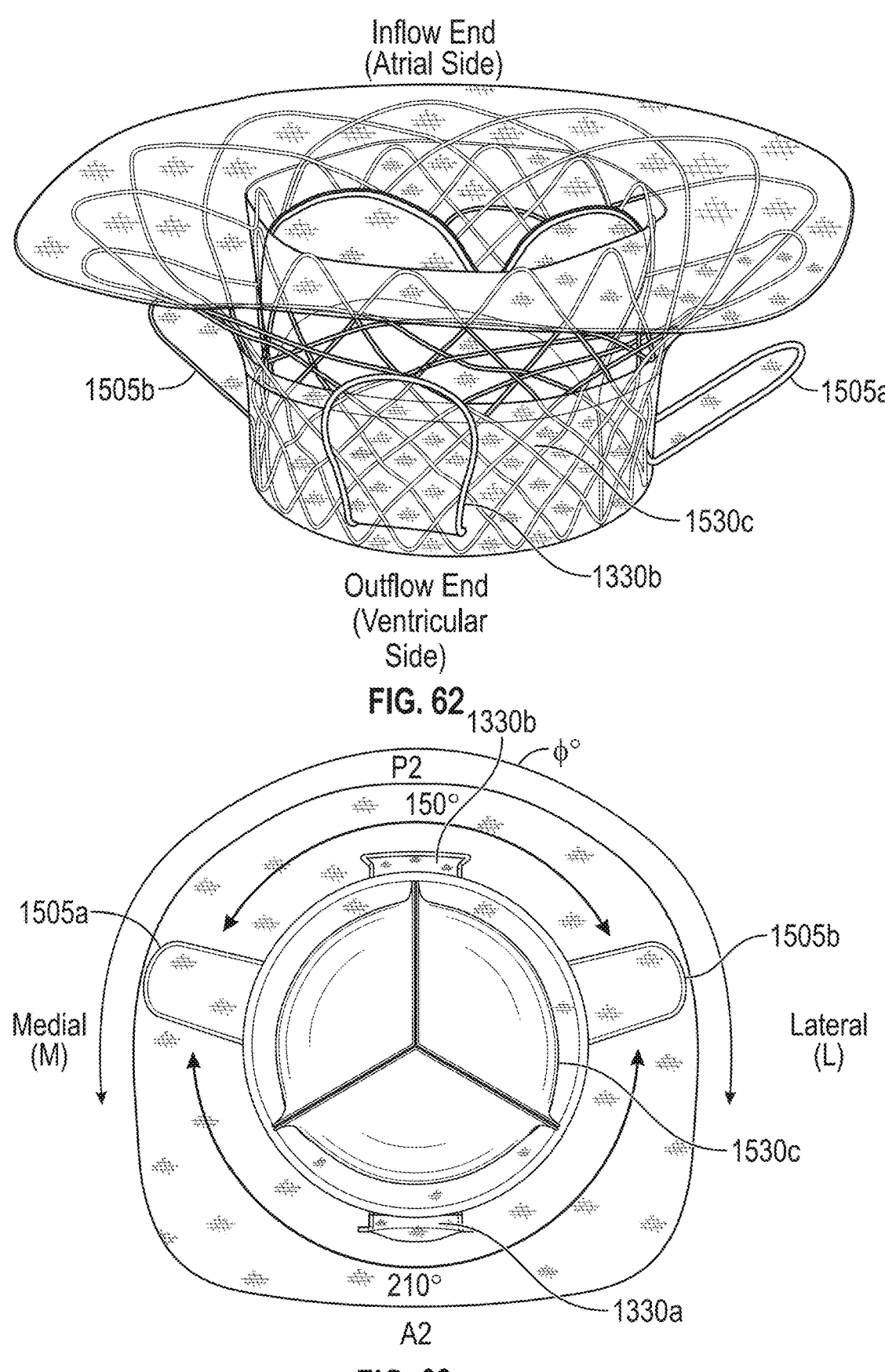
FIGS. 62-70 generally illustrate embodiments of a valve replacement as disclosed herein.

In other embodiments, for smaller hearts, the valve replacement comprises a 150° angle (plus or minus 5 degrees) between an upper medial and lateral anchor struts with the A2 anchor (or A2 clip) being approximately symmetric between the two upper anchor struts, and a 180° angle (plus or minus 5 degrees) between a lower medial and lateral anchor struts with the P2 anchor (or P2 clip) being approximately symmetric between the two lower anchor struts. In other embodiments, for larger hearts, the valve replacement comprises a 150° angle (plus or minus 5 degrees) between an upper medial and lateral anchor struts with the A2 anchor (or A2 clip) being approximately symmetric between the two upper anchor struts, and a 210° angle (plus or minus 5 degrees) between a lower medial and lateral anchor struts with the P2 anchor (or P2 clip) being approximately symmetric between the two lower anchor struts (as shown in FIGS. 58 and 63).

In other embodiments, the angle between the anchor struts, also referred to as stabilizers, varies based on the anatomy of the valve being replaced. For example, in a mitral valve replacement, the stabilizers include a medial strut extending in a medial direction radially outwardly from the ventricular end of the valve replacement and a lateral strut extending in a lateral direction radially outwardly from the ventricular end of the valve replacement.

In embodiments, the stabilizers, including medial and lateral struts, permit movement of the native mitral annulus in the medial and lateral directions, while the posterior and anterior leaflet clips permit movement of the native mitral annulus in the posterior and anterior directions, when deployed within a native mitral valve. At the same time, the stabilizers and clips provide an anchoring function when deployed within a native mitral valve, with the medial and lateral struts and posterior and anterior leaflet clips providing a resistance against migration of the prosthetic mitral valve towards the atrial end. In embodiments, the medial strut extends in between chordae into a medial sub-annular area of a native heart when deployed within the native mitral valve and the lateral strut extends in between chordae into a lateral sub-annular area of the native heart when deployed within the native mitral valve.

The geometry of the stabilizers is designed to help ensure avoidance of interaction with either the anterior or posterior leaflets while providing a stabilizing function. Similarly, the leaflet clips and stabilizers allow for native leaflet motion/wrapping around the valve body for sealing by having the drop loops of the clips and stabilizers low on the frame in the LV, with the clips pulling the native leaflets close to the valve body and creating a seal around the valve body and native leaflets, thereby encouraging native leaflet motion. In embodiments, the drop loops of the clips and stabilizers are on the ventricular aspect of the frame so the bulk of the leaflet can fit above them which allows for them to seal/move against the frame.

The anchors (which include clips) may be made of the same wire as the braided frame or different wire-whether it be different in material and size. This provides a novel aspect: The ability to have thicker and/or more durable wire for the anchors allows for the anchors-which are required to attach to the valve tissue and maintain the valve replacement in place—to be stronger and/or firmer, without comprising the flexibility of the body frame. This enables the valve replacement to remain firmly and securely positioned within the heart valve while still allowing the valve replacement to move and function in accordance with the heart's natural movements.

Another novel aspect is the synchronization between the flanges and the anchors. Once implanted, the flanges provide a downward force on the heart tissue as the anchors provide an upward force. These two forces exerted by the valve replacement further secure it in place without compromising the fluidity of the braided body frame or the functionality of the leaflets and does not have an axial force (or other force) that interferes with the natural torsional or radial motion of the native heart or the native heart motion. Instead, the replacement valve in embodiments provides an axial pinch that still allows freedom of torsion and crush in the native anatomy. Moreover, as discussed herein, the flange design also encourages forward flow through the valve (reducing chance for competitive flow around the valve). In embodiments, the flange design encourages forward flow through the valve (reducing chance for competitive flow around the valve) with the flange conforming around the annulus into a funnel shape leading to the valve leaflets. Flange conformability, flange funnel shape, as well as generally larger diameter dimensions ensure the native valve and annulus are covered and flow does not go around the replacement valve and is instead directed through bioprosthetic valve (also referred to herein as the replacement valve).

As discussed herein and in reference to all the Figures and embodiments, the geometry and placement of each feature in the innovative valve replacements discussed herein provide many functional improvements over prior devices. For example, with use of the innovative flange, anchoring, and braided architecture, embodiments of the valve replacement discussed herein provide best in class LVOT preservation, best in class EOA, best in class valve diameter with minimal ventricular projection, among other improvements, and all without need to rely on outward radial force within the native annulus for anchoring. No other replacement valve provides these benefits.

With reference to the Figures, including in particular FIGS. 3 through 20, valve replacement embodiments are described and shown with ranges for dimensions and elements. In embodiments, a valve replacement (also referred to herein as a prosthetic mitral valve) comprises a receiver body 605 (also referred to herein as an adapter, adapter body, a receiver, and a tubular body) and a flange 610 (also referred to herein as an atrial skirt and a sealing skirt) interwoven into the receiver body 605. In embodiments, as discussed in this disclosure, the flange 610 need not be flush with the top of the receiver body 605. Instead, the flange 610 can be interwoven with the receiver body 605 and extend from any portion of the height of the receiver body 605 at various flange/receiver exit points FRw along the height I1 of the receiver body 605 and along the circumference of the receiver body 605, thereby providing strength to the receiver body 605 where the flange is interwoven with the receiver body 605 as well as forming the flange 610 portions that exit the receiver body 605 and rest on top of the native mitral annulus and that rest in an intra-annular space of the native mitral annulus when deployed in a native mitral valve. In embodiments, the flange's 610 weave in location FRw into the receiver body 605 (and hence the location along the receiver 605 where the braided flange 610 exits the receiver body 605 and forms a curved section CiC that eventually transitions into and forms the flange's petals P) is between 8 mm to 12 mm from the outflow (ventricular) side of the receiver 605, with FRw being in embodiments 8 mm, 9 mm, 10 mm, 11 mm, and 12 mm from the bottom of the receiver 605 (also the bottom of the replacement valve in embodiments). In embodiments, the flange's 610 weave in location FRw into the receiver body 605 (and hence the location along the receiver 605 where the braided flange 610 exits the receiver body 605 and forms the curved section CiC that eventually transitions into and forms the flange's petals P) is in an intermediate portion of the height of the receiver (tubular body) 605. In embodiments, the intermediate portion of the receiver's height where the flange 610 enters and exits the receiver body 605 at height FRw is in a middle third portion of the receiver's height I1, with the receiver having a height I1 between 17 mm to 26 mm in embodiments.

Figure 18:
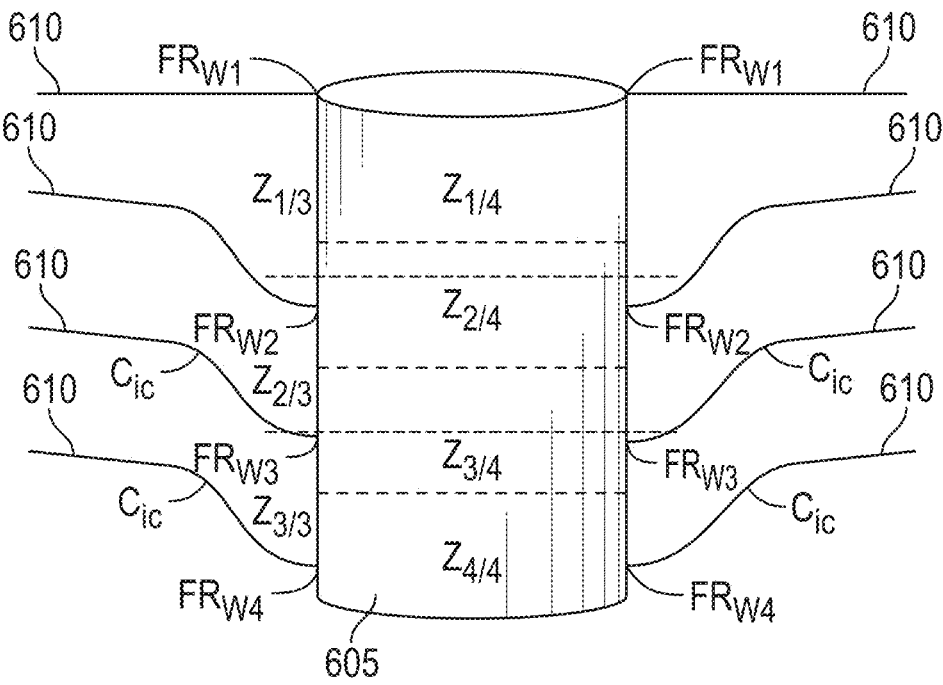

In other embodiments, the flange's 610 weave in location FRw into the receiver body 605 (or location where the flange exits the receiver body 605 and forms curved section CiC) is at any location along the height I1 of the receiver (tubular body) 605. For example, as shown in FIG. 18, the receiver body 605 is shown divided in thirds (with a Z1/3 at the inflow end, Z2/3 as the middle third, and Z3/3 at the outflow end) and is also shown with the receiver body 605 divided in fourths (with a Z1/4 at the inflow end, Z2/4 and Z3/4 as the middle portions, and Z4/4 at the outflow end) with the weave in location FRw into the receiver body 605 (or location where the flange exits the receiver body 605) at several possible locations along the height of the receiver (tubular body) 605. For example, the flange 610 can exit the receiver body 605 in a top third Z1/3 of the receiver body, for example at FRw1 (depicted at the top of the receiver body 605 at the inflow end), a middle third Z2/3 of the receiver body, for example at FRw2, or a bottom third Z3/3 of the receiver body, for example at FRw3 or FRw4 (depicted at the bottom of the receiver body 605 at the outflow end). In other embodiments the flange 610 can exit the receiver body 605 in a top quarter Z1/4 of the receiver body, for example at FRw1, a middle half Z2/4 or Z3/4 of the receiver body, for example at FRw2 or FRw3, or a bottom quarter Z4/4 of the receiver body, for example at FRw4. Moreover, in embodiments, the flange 610 wire that exits the receiver body 605 need not be curved (like CiC) and instead can take other forms, such as a flat flange wire FRw1 that rests on top of the native annulus when deployed, for example as shown at the top of the receiver body 605 at the inflow end Z1/3 or Z1/4. In other embodiments, the flange 610 wire that exits the receiver body 605 is curved (like CiC), for example as shown on the receiver body 605 at Z2/3 & Z3/3 or Z2/4, Z3/4 & Z4/4.

In embodiments, the receiver body 605 is formed by a first braided wire BW1 that is braided by wrapping a nitinol wire in an over-under fashion around a cylindrical mandrel core, thereby intertwining the wire to form a braided structure comprising with 12 peaks PA1 (peaks also referred to as extrados) at the inflow (atrial) side and 12 peaks (extrados) PV1 at the outflow (ventricular) side. The flange 610 is then formed by interweaving a second braided wire BW2 that is braided by wrapping a nitinol wire in an over-under fashion around a cylindrical mandrel core with the first braided wire BW1 of the receiver 605, thereby intertwining the two wires BW1 and BW2 to form a braided structure comprising at the outflow (ventricular) side 12 peaks PV1 for the receiver 605 and 12 peaks PV2 for the flange 610, with the peaks alternating side-by-side and numbering 24 consecutive peaks along the outflow (ventricular) side of the replacement valve. Also, at the inflow (atrial) side of the replacement valve, the flange 610 is formed by one of the two interwoven wires BW1 and BW2 to form a braided flange structure. In embodiments, the replacement valve's two interwoven wires BW1 and BW2 form a structure comprising 12 peaks PA1 for the receiver 605 and 12 peaks PA2 for the flange 610, with the peaks alternating and numbering 24, but with the 12 peaks PA1 of the receiver 605 forming the inflow side of the receiver 605 and the 12 peaks PA2 of the flange 610 forming 12 petals P (also called looping petals) around the circumference of the flange 610. Formation and shape setting of the flange 610, including its petals P, is discussed elsewhere in this disclosure, including the D-shape of the flange 610 that, in embodiments, is configured to seat within the 3D geometry (saddle shape) of the native mitral annulus and wherein at least a portion of the flange's 610 D-shaped perimeter is configured to rest on top of the native mitral annulus when deployed in the native mitral valve.

In other embodiments, the receiver body 605 is formed by braiding the nitinol wire in an over-under fashion around a cylindrical mandrel core thereby intertwining the wire to form a braided structure comprising between 8 to 12 peaks PA1 (extrados) at the inflow (atrial) side and between 8 to 12 peaks (extrados) PV1 at the outflow (ventricular) side and the flange 610 is formed by interweaving a second braided wire BW2 with the first braided wire BW1 of the receiver 605, thereby intertwining the two wires BW1 and BW2 to form a braided structure comprising at the outflow (ventricular) side between 8 to 12 peaks (including embodiments with 8, 9, 10, 11 or 12 peaks) PV1 for the receiver 605 and between 8 to 12 peaks (including embodiments with 8, 9, 10, 11 or 12 peaks) PV2 for the flange 610 and with the peaks alternating side-by-side and numbering between 16 to 24 consecutive peaks (extrados) (including embodiments with 16, 17, 18, 19, 20, 21, 22, 23, or 24 peaks) along the outflow (ventricular) side of the replacement valve and between 8 to 12 peaks (including embodiments with 8, 9, 10, 11 or 12 peaks) PA2 of the flange 610 forming between 8 to 12 petals (including embodiments with 8, 9, 10, 11 or 12 petals) P (also called looping petals) around the circumference of the flange 610. In embodiments where the flange 610 wire BW2 is interwoven into the receiver 605 wire BW1, the area of the receiver body 605 where the flange wire BW2 is interwoven with the receiver body 605 (labeled G1 from the outflow end to the flange take-off point FRw towards the inflow side) is stronger because it has the two wires BW1 and BW2 woven together, thereby providing a fortified region for attaching replacement leaflets within the receiver body 605. In embodiments, the height G1 of the receiver body 605 where the flange 610 is woven into the receiver body (and also where the flange takes off from the receiver body and starts forming the petals P) is between 6 mm to 14 mm or between 8-12 mm from the outflow end of the receiver body 605, with height G1 being 11 mm in an embodiment, and other embodiments having a height G1 of 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, and 14 mm.

In embodiments, the flange 610 petals P are shape set and braided to form a D-shape circumference with flat section Fs configured to rest on a aorta-mitral curtain and a rounded, curved or circular section Fc that sits on the remainder of the native annulus, with the D-shape helping preserve the LVOT, accommodating the aortic sinus and curtain, preventing migration of the replacement valve into the native ventricle, directing flow towards the apex of the ventricle, and maximizing sealing during systole. In embodiments with the D-shape flange 610, because of the flat section Fs and the rounded, curved or circular section Fc, the flange 610 has different dimensions in the A-P (Anterior-Posterior) direction K1 and M-L (Medial-Lateral) direction B1. In embodiments, the A-P dimension K1 is smaller because of the flat section Fs of the flange 610 and the M-L dimension B1 is larger because the petals P of the flange 610 are configured to extend into the larger M-L directions of the native anatomy. In other embodiments, the A-P dimension K1 is larger than the M-L dimension B1. In embodiments, the flange 610 has a K1 dimension between 40 mm to 66 mm, between 48-60 mm, between 48-58 mm, including embodiments of K1 being 48 mm, 52 mm, 56 mm, and 58 mm, and embodiments with K1 being 40 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 mm, 50 mm, 50.5 mm, 51 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, 60 mm, 60.5 mm, 61 mm 61.5 mm, 62 mm, 62.5 mm, 63 mm, 63.5 mm, 64 mm, 64.5 mm, 65 mm, 65.5 mm, and 66 mm. In embodiments, the flange 610 has a B1 dimension between 47 mm to 70 mm, between 50-65 mm, and between 53-63 mm, including embodiments of B1 being 52 mm, 54 mm, 58 mm, 62 mm and 63 mm, and embodiments of B1 being 47 mm, 47.5 mm, 48 mm, 48.5 mm, 49 mm, 49.5 mm, 50 mm, 50.5 mm, 51 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, 60 mm, 60.5 mm, 61 mm, 61.5 mm, 62 mm, 62.5 mm, 63 mm, 63.5 mm, 64 mm, 64.5 mm, 65 mm, 65.5 mm, 66 mm, 66.5 mm, 67 mm, 67.5 mm, 68 mm, 68.5 mm, 69 mm, 69.5 mm, and 70 mm. In some embodiments having a D-shaped flange 610, the ratio of the smaller K1 dimension to the larger B1 dimension include a ratio of between 0.88 to 0.92 (e.g., K1 48 mm/B1 54 mm, K1 52 mm/B1 58 mm, K1 56 mm/B1 62 mm, K1 58 mm/B1 63 mm).

In embodiments, the receiver body 605 has a height I1 that is between 17 mm to 26 mm, with embodiments of I1 being between 20-25 mm, between 22 mm and 23 mm, and other embodiments having a receiver body height I1 of 17 mm, 17.5 mm, 18 mm, 18.5 mm, 19 mm, 19.5 mm, 20 mm, 20.5 mm, 21 mm, 21.5 mm, 22 mm, 22.5 mm, 22.9 mm, 23 mm, 23.5 mm, 24 mm, 24.5 mm, 25 mm, 25.5 mm, and 26 mm. Moreover, because the receiver body 605 is braided and reinforced with the flange 610 interweaving along portions of the height I1 of the receiver body 605, the receiver body 605 is able to have, in embodiments, a larger receiver inner diameter Y1 (also referred to as EOA) of between 25 mm to 34 mm, between 29-32 mm, and with embodiments having a receiver inner diameter Y1 of 29 mm and 32 mm and embodiments having an inner diameter Y1 of 25 mm, 25.5 mm, 26 mm, 26.5 mm, 27 mm, 27.5 mm, 28 mm, 28.5 mm, 29 mm, 29.5 mm, 30 mm, 30.5 mm, 31 mm, 31.5 mm, 32 mm, 32.5 mm, 33 mm, 33.5 mm, and 34 mm. This combination of shorter receiver height in relation to the receiver's EOA provides several benefits over exiting valves, including less ventricular projection with a corresponding larger EOA. In embodiments of the replacement valve disclosed herein, the receiver's body height I1 in relation to its inner diameter (EOA) Y1 is a ratio of 0.6 to 0.75, including embodiments with a ratio of 0.7 (e.g., an embodiment with a receiver height of between 22-23 mm and an EOA of 32 mm (ratio between 0.68-0.72) and an embodiment with a receiver height of between 19-20 mm and EOA of 29 mm (ratio between 0.65-0.69)). In other embodiments, the receiver's body height I1 in relation to its inner diameter (EOA) Y1 is a ratio of 0.7 to 0.8, including embodiments with a ratio of 0.8 (e.g., an embodiment with height of 26 mm and EOA of 32.5 mm). In embodiments, the ratio of the receiver body's height I1 (I1 embodiments include height of between 22-23 mm) to the flange's width B1 in the M-L direction (B1 embodiments include 54 mm, 58 mm, 62 mm, 63 mm) includes ratios of 0.3-0.42 and in embodiments, the ratio of the receiver body's height I1 (I1 embodiments include height of between 22-23 mm) to the flange's width K1 in the A-P direction (B1 embodiments include 48, 52, 56, 58 mm) includes ratios of 0.3-0.48.

In embodiments where the flange 610 is braided in such a way that it exits the receiver body 605 at a location FRw other than the top of the inflow side of the receiver 605, the replacement valve provides the largest EOA with a reduced ventricular projection because the flange 610 exiting along the height I1 of the receiver 605 at a flange/receiver weave in location FRw means only the portion of the receiver body 605 below the flange/receiver weave in location FRw is pointed towards the outflow (ventricular) side (receiver 605 ventricular projection F1) and the portion of the receiver body 605 above the flange/receiver weave in location FRw is pointed towards the inflow (atrial) side. Thus, the lower the Flange/Receiver weave in location FRw along the height I1 of the receiver 605 (lower pointing towards the ventricular side), the less of the receiver 605 height I1 that will project into the native ventricle (receiver 605 ventricular projection F1). In embodiments, the receiver body's 605 ventricular projection F1 is between 11 mm to 18 mm or between 12-16 mm, with embodiments having a ventricular projection F1 of 16 mm, and other embodiments having an F1 of 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, and 18 mm. In some embodiments with reduced ventricular projection, the replacement valve's large EOA in relation to the ventricular projection F1 provides a ratio of 0.50 (e.g., embodiment with F1 of 16 mm and EOA Y1 of 32 mm).

Moreover, in embodiments where the flange 610 wire BW2 exits the receiver body 605 at a location FRw and extends radially outward from the receiver body (tubular body) 605 (e.g., extends radially outward from an intermediate portion of the height I1 of the receiver 605), the portion of the flange's wire BW2 that extends radially outward from the receiver body 605 comprises a curved section CiC that transitions into and forms the flange's petals P. In embodiments, the curved section CiC (between the exit point FRw and the petals P) of the flange wire BW2 comprises a parabolic curve and in some embodiments comprises a convex section and a concave section with an inflection point therebetween. In embodiments, the curved section CiC of the flange's 610 braided wire BW2 forms a flange belly CiC with at least a part of the convex portion configured to rest in an inter-annular space of the native mitral annulus and at least a part of the concave portion configured to rest in a supra-annular space of the atrium when deployed in the native mitral valve. In embodiments, the convex portion of the flange belly wire CiC exits the receiver body 605 at space FRw and forms a surface or line that curves upward (towards the atrial side) and outward towards the native annulus, thereby configured to come in contact with the native annulus and rest in an intra-annular space when implanted in the native mitral valve. In embodiments, the concave portion of the flange belly wire CiC past the inflection point (where the surface or line transitions from convex to concave) forms a surface or line that curves inwards and is shaped at its ends to form petals P of the flange 610, with at least a portion of the concave portion configured to come in contact with the native annulus and then rest in a supra-annular space when implanted in the native mitral valve with the petals P configured to rest on top of the native annulus in the atrium.

In embodiments, the flange 610 wire BW2 exits the receiver body 605 at a location FRw and extends radially outward from the receiver body (tubular body) 605 (e.g., extends radially outward from an intermediate portion of the height I1 of the receiver 605), the portion of the flange's wire BW2 that extends radially outward from the receiver body 605 comprises a curved section CiC that transitions into and forms the flange's petals P. In embodiments, the curved section CiC (between the exit point FRw and the petals P) of the flange wire BW2 comprises a parabolic curve and in some embodiments comprises a convex section and a concave section with an inflection point therebetween. In embodiments, the curved section CiC of the flange's 610 braided wire BW2 forms a flange belly CiC with at least a part of the convex portion configured to rest in an inter-annular space of the native mitral annulus and at least a part of the concave portion configured to rest in a supra-annular space of the atrium when deployed in the native mitral valve. In embodiments, the convex portion of the flange belly wire CiC exits the receiver body 605 at space FRw and forms a surface or line that curves upward (towards the atrial side) and outward towards the native annulus, thereby configured to come in contact with the native annulus and rest in an intra-annular space when implanted in the native mitral valve. In embodiments, the concave portion of the flange belly wire CiC past the inflection point (where the surface or line transitions from convex to concave) forms a surface or line that curves inwards and is shaped at its ends to form petals P of the flange 610, with at least a portion of the concave portion configured to come in contact with the native annulus and then rest in a supra-annular space when implanted in the native mitral valve with the petals P configured to rest on top of the native annulus in the atrium Referring to FIG. 6, the replacement valve, in embodiments, comprises a 12×12 over/under weave of a first wire BW1 for the receiver 605 (12 peaks RA (or PA1) on the inflow or atrial side and 12 peaks RV (or PV1) on the outflow or ventricular side) and a 12×12 over/under weave of a second wire BW2 for the flange 610 (12 peaks FA (or PA2) on the inflow or atrial side and 12 peaks FV (or PV2) on the outflow or ventricular side), for a total of 24 peaks (TotalA) on the inflow or atrial side, and 24 peaks (TotalV)

on the outflow or ventricular side with 24 wire crossings between each of the ventricle peaks TotalV.

In embodiments, the flange wire BW2 and receiver wire BW1 are interwoven in an over-under fashion (first wire under, second wire over, and alternating over/under up the weave), with crossing points for the wires. For example, in one pattern, the weave of the replacement valve includes a flange wire BW2 and a receiver wire BW1 interwoven in an over-under fashion for a section of the replacement valve followed by section of the replacement valve having the receiver wire BW1 interwoven on itself (without the flange wire BW2) and a section of the replacement valve having the flange wire BW2 interwoven on itself (without the receiver wire BW1). In embodiments, the section of the replacement valve where the flange wire BW2 exits the flange/receiver interwoven area is marked at FRw and is circled with an arrow pointing up in a right to left fashion. Where the flange wire BW2 exits the flange/receiver interwoven area FRw is the beginning of where the flange wire BW2 forms the curved section CiC and the petals P at the flange peaks $F_A$ at the inflow (atrial) end.

In embodiments, there are 5 over-under wire crossing points above each ventricle peak TotalV (as viewed from the outflow (ventricle) side up to the inflow (atrial) side), with the crossing points varying whether they are an odd numbered ventricle peak TotalV with a corresponding flange peak FA that forms a petal P on the inflow (atrial) side (for example ventricle peaks TotalV 1, 3, 5, 7, 9, 11, 13, 15, 17, 19, 21, and 23 with corresponding flange peaks FA 1, 2, 3, 4, 5, 6, 7, 8, 9, 10, 11, and 12) or an even numbered ventricle peak TotalV with a corresponding receiver peak RA on the inflow (atrial) side (for example ventricle peaks TotalV 2, 4, 6, 8, 10, 12, 14, 16, 18, 20, 22, or 24 with corresponding receiver peaks RA 1, 2, 3, 4, 5, 6, 7, 8, 9, 10, 11, and 12). Moreover, in embodiments, there are 5 over-under wire crossing points between each ventricle peak TotalV (as viewed from the outflow (ventricle) side up to the inflow (atrial) side), with the crossing points including where the flange wire BW2 exits the interweave from under a receiver wire BW1 at FRw and does not go under the receiver wire again as it continues up to form flange petals P at the flange's 610 inflow (atrial) side. (for example ventricle peaks TotalV 1, 3, 5, 7, 9, 11, 13, 15, 17, 19, 21, and 23 with corresponding flange peaks FA 1, 2, 3, 4, 5, 6, 7, 8, 9, 10, 11, and 12).

In embodiments, the flange 610 wire BW2 interweaves with the receiver 605 wire BW1 in an over-under fashion up to the third crossing point of the flange and receiver wires, as measured from the bottom (or between the second and third cells measured from the bottom). In embodiments, the weave pattern of the flange wire BW2 and receiver wire BW1, going from right to left on the weave pattern, the flange wire BW2 exits the interweave from under a receiver wire BW1 at FRw and does not go under the receiver wire again as it continues up and forms the flange's petals P at the flange's 610 inflow (atrial) side peaks FA (or PA2). In contrast, the flange wire BW2 going the opposite direction (going from right to left on the weave pattern) only interweaves with itself throughout the entire body of the valve. Beyond the third crossing point (or 2.5 cells up), the flange 610 and receiver 605 are still woven in an over-under fashion, but just with themselves (not interwoven).

In an embodiment, for example, there are five crossing points: 1c, 2c, 3c, 4c and 5c above the even numbered fourth ventricle peak TotalV4 (with corresponding receiver peak RA2 above it on the inflow (atrial) side). These over-under crossing points above the even numbered ventricle peak TotalV4 include a first crossing point 1c (receiver/receiver wire BW1 crossing), a second crossing point 2c (flange/flange wire BW2 crossing), a third crossing point 3c (receiver/receiver wire BW1 crossing), a fourth crossing point 4c (flange/flange wire BW2 crossing), and a fifth crossing point 5c (flange/flange wire BW2 crossing). This pattern repeats itself for the other even numbered ventricle peaks TotalV. In this particular embodiment, for the even numbered ventricle peaks TotalV, the receiver/receiver wire BW1 crossing points stop after the third crossing point and the receiver peak RA in the atrium is between the last two flange wire BW2 crossings 4c and 5c.

In this same embodiment, for example, there are five crossing points: 1d, 2d, 3d, 4d and 5d above the odd numbered ninth ventricle peak TotalV9 (with corresponding flange peak $F_A5$ above it on the inflow (atrial) side). These over-under crossing points above the odd numbered ventricle peak TotalV9 include a first crossing point 1d (flange/flange wire BW2 crossing), a second crossing point 2d (receiver/receiver wire BW1 crossing), a third crossing point 3d (flange/flange wire BW2 crossing), a fourth crossing point 4d (receiver/receiver wire BW1 crossing), and a fifth crossing point 5c (flange/flange wire BW2 crossing). This pattern repeats itself for the other odd numbered ventricle peaks TotalV. In this particular embodiment, for the odd numbered ventricle peaks TotalV, the flange/flange wire BW2 crossings and receiver/receiver wire BW1 crossing points alternate from top to bottom and have a flange petal P above the last (fifth) crossing point.

In this same embodiment, for example, there are also wire crossing points between each of the ventricle peaks TotalV, with a wire crossing between each set of receiver ventricle peak RV and flange ventricle peak FV (crossing points between RV1 and FV1, RV2 and FV2, FV3 and RV3, FV4 and RV4, FV5 and RV5, FV6 and RV6, FV7 and RV7, FV8 and RV8, FV9 and RV9, RV 10 and FV 10, RV11 and FV 11, RV12 and FV12). These wire crossings between each of the ventricle peaks TotalV include wire crossings where the flange wire BW2 exits the flange/receiver interwoven area at FRw (flange wire BW2 wire exit circled with an arrow pointing up in a right to left fashion). There are five crossing points between each ventricle peak TotalV going from the outflow (ventricle) side up to the inflow (atrial) side. For example, between ventricle peaks TotalV 5 and 6 (between RV3 and FV3) there are crossing points: 1cf, 2cf, 3cf, 4cf and 5cf. These over-under crossing points between the ventricle peaks include a first crossing point 1cf (receiver wire BW1 top and flange wire BW2 bottom crossing), a second crossing point 2cf (flange wire BW2 top and receiver wire BW1 bottom crossing), a third crossing point 3cf (receiver wire BW1 top and flange wire BW2 bottom crossing), a fourth crossing point 4cf (flange wire BW2 top and receiver wire BW1 bottom crossing), and a fifth crossing point 5c (flange wire BW2 top and receiver wire BW1 bottom crossing). This pattern repeats itself for the other crossing points between the ventricle peaks TotalV. In this particular embodiment, once the flange wire BW2 exits the interweave from under a receiver wire BW1 at the third crossing point 3cf along the line FRw, the flange wire BW2 does not go under the receiver wire again as it continues up and forms the flange's petals P at the flange's 610 inflow (atrial) side peaks $F_A$ (or PA2).

In embodiments, the petals P formed by the flange wire BW1 can vary in height or all be the same height. In embodiments, the flange petals P vary in height to form a D-shape (for example as shown and discussed in reference to FIGS. 21-23). In an embodiment, shown in FIG. 6, the flange petals P have heights up to their corresponding flange atrial peaks FA, with petals P being the same height at flange peaks FA1, 2, 3 and 4 as well FA9, 10, 11 and 12, with petals P formed at flange peaks FA5 and 8 being taller and petals P formed at flange peaks FA6 and 7 being shorter.

In embodiments where the curved section CiC of the flange's 610 braided wire BW2 forms a flange belly CiC, the flange belly has a width A1 in the Medial-Lateral (M-L) direction of between 34 mm to 65 mm, between 40-65 mm and between 50-60 mm, including embodiments with the flange belly M-L width A1 being 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 mm, 50 mm, 50.5 mm, 51 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, 60 mm, 60.5 mm, 61 mm, 61.5 mm, 62 mm, 62.5 mm, 63 mm, 63.5 mm, 64 mm, 64.5 mm, 65 mm. Moreover, in embodiments where the curved section CiC of the flange's 610 braided wire BW2 forms a flange belly CiC, the flange belly has a width J1 in the Anterior-Posterior (A-P) direction of between 32 mm to 60 mm, including embodiments with the flange belly A-P width J1 being between 35-55 mm and between 40-50 mm, embodiments of J1 being 42 mm or 50 mm, and embodiments of J1 being 32 mm, 32.5 mm, 33 mm, 33.5 mm, 34 mm, 34.5 mm, 35 mm, 35.5 mm, 36 mm, 36.5 mm, 37 mm, 37.5 mm, 38 mm, 38.5 mm, 39 mm, 39.5 mm, 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 mmm, 50 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, and 60 mm. The flange's 610 curved portion CiC is wider in the M-L direction than the A-P direction because in the native anatomy the M-L anatomy is wider than the A-P anatomy and the flange belly needs to be wide enough in the M-L and A-P directions to provide effective sealing during systole and prevent migration in the ventricular direction. Moreover, in embodiments, the flange's belly width J1 and A1 are located at a plane that intersects with the top of the P2 clip 645.

In embodiments, and as described in other places in this disclosure, the replacement valve also comprises ventricular anchors and stabilizers, including in embodiments leaflet clips for anchoring to the anterior and posterior mitral leaflets (e.g., A2 clip 625, P2 clip 645, and other clips 625a) as well as stabilizers for providing stability and anchoring functionality in the medial and lateral ventricular regions, also called anchor struts or struts (e.g., medial stabilizer 630 and lateral stabilizer 630, stabilizers 630a). As described herein, the replacement valve is, in embodiments, a "floating valve" wherein the valve body "floats" in the native anatomy with at least a portion of the replacement valve does not make contact with the native anatomy. For example, where the replacement valve receiver body 605, which holds the replacement leaflets and one-way valve, is smaller than the size of the native annulus in one or more of the A-P and C-C directions. As a result, the valve body of the replacement valve floats within the native annulus from not having a uniform contact around the perimeter of the replacement valve within the native annulus. For this "floating valve" to be properly secure, and also provide the functionality described herein with regards to promoting forward vortex flow and a posterior tilt through the replacement valve and preservation of the LVOT, the "floating valve" must be properly secured on the atrial side (e.g., with embodiments of the flange 610 described herein) and properly secured on the ventricular side with clips and stabilizers. In embodiments, the clips and stabilizers have wider dimensions than the bioprosthetic valve, such that the anchoring of the replacement valve contacts tissue away from the replacement valve-thus enabling the replacement valve to "float" in the native anatomy. Similarly, in embodiments, the flange has a wider dimension than the native anatomy so that the flange belly contacts the native tissue and flexes when contracted (bimodal crush), so it minimizes crush on the replacement valve itself. Thus, in embodiments, the replacement valve is suspended in the native valve space by anchoring features.

With reference to FIGS. 13, 14, 15, 16, 19, 20, as well as the other Figures in this description, various embodiments of the replacement valve are shown deployed in a native mitral valve with the replacement valve 605 floating in the native anatomy. A replacement valve is shown comprising a valve body 605 with a replacement one-way valve therein, a flange 610 interwoven into the valve body 605 with the flange 610 exiting the valve body 605 at the atrial (inflow) end of the replacement valve, an anterior leaflet clip 625 and a posterior leaflet clip 630 attached to the replacement valve on the ventricular end of the replacement valve, and stabilizers attached to the medial and lateral sides of the replacement valve on the ventricular end of the replacement valve. As can be seen in these embodiments, the replacement valve is a "floating valve" with the valve body 605 "floating" in the native anatomy with portions of the valve body 605 not contacting the native mitral annulus anatomy. For example, the replacement valve receiver body 605, which holds the replacement leaflets and one-way valve, is smaller than the size of the native annulus in one or more of the anterior-posterior (A-P) directions and medial-lateral (M-L) directions (also referred to as the commissure-to-commissure ("C-C") directions). As a result, the valve body 605 floats within the native annulus because the perimeter of the valve's body 605 does not have a uniform contact around the native annulus. In embodiments, the valve body 605 does not come in contact with at least a portion of the native annulus anatomy, including in one or more of the A-P and C-C directions. In some embodiments, the valve body 605 does not come in contact with the native annulus anatomy once deployed with the valve body 605 relying on the interwoven flange 610 for securement on the atrial (inflow) side and on the clips 625/645 and stabilizers 630 for securement on the ventricular (outflow) side. As can be seen in these embodiments, the clips 625/645 and stabilizers 630 have wider dimensions than the valve body 605, such that the anchoring of the replacement valve contacts tissue away from the valve body 605. Similarly, in embodiments, the flange 610 has a wider dimension than the native anatomy where it exits the valve body 605 (at FRw at the native annulus) and the curved wire CiC of the flange belly contacts the native tissue at the native annulus and atrium, thereby holding the valve body 605 away from the native annulus anatomy and enabling the replacement valve's body 605 to "float" in the native mitral valve. Moreover, because the flange's curved wire CiC (which forms the flange's belly and petals) is wider than the native mitral annulus anatomy and holds the valve body 605 away from the native anatomy, the flange 610 is able to flex when contracted by the native heart (bimodal crush) and minimize any crush on the valve body 605. Thus, in embodiments, the replacement valve is suspended in the native valve space by the flange that resists migration of the replacement valve towards the ventricle end when deployed within a native mitral valve.

In embodiments, the replacement valve is anchored on the ventricle (outflow) side by the clips 625/645 and stabilizers 630 to provide sub-annular securement and prevent migration of the valve replacement into the atrium. For example, an anterior leaflet clip 625 is secured to an A2 region of the native anterior leaflet in an atraumatic fashion, e.g., without pinching or grabbing the anterior leaflet, but instead capturing the anterior leaflet and enveloping it between the clip 625 and the receiver body 605. Similarly, a posterior leaflet clip 645 is secured to a P2 region of the native posterior leaflet in an atraumatic fashion, e.g., without pinching or grabbing the posterior leaflet, but instead capturing the posterior leaflet and enveloping it between the clip 625 and the receiver body 605. In embodiments, the P2 clip 645, once deployed, comes in contact with the posterior portion of the native annulus in the ventricle with the flange 605 anchoring on the posterior portion of the annulus in the atrium, thereby providing an anchor above and below the posterior region of the native annulus with the flange pushing down from the atrium and the P2 clip pushing up from the ventricle for securement of the replacement valve, providing both an anchor and posterior tilt for vortex flow. In these embodiments, the valve body 605 can come in contact with a portion of the native leaflets, as they are enveloped by the A2 and P2 clips 625/645, and still float within the native annulus.

Figures 13, 14:
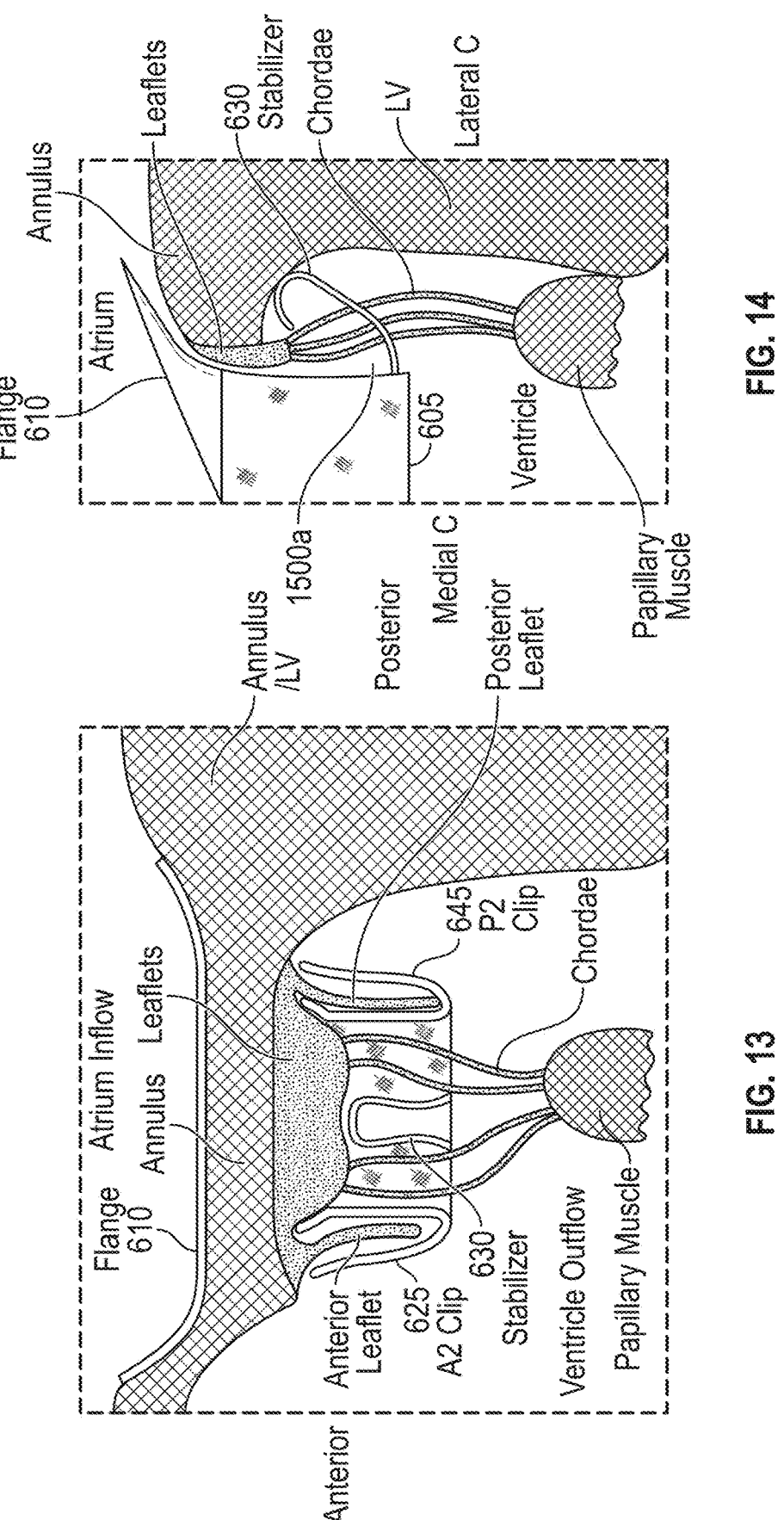
FIGS. 13-16 generally illustrate embodiments of a valve replacement deployed in a native mitral valve as disclosed herein.
Figures 15, 16:
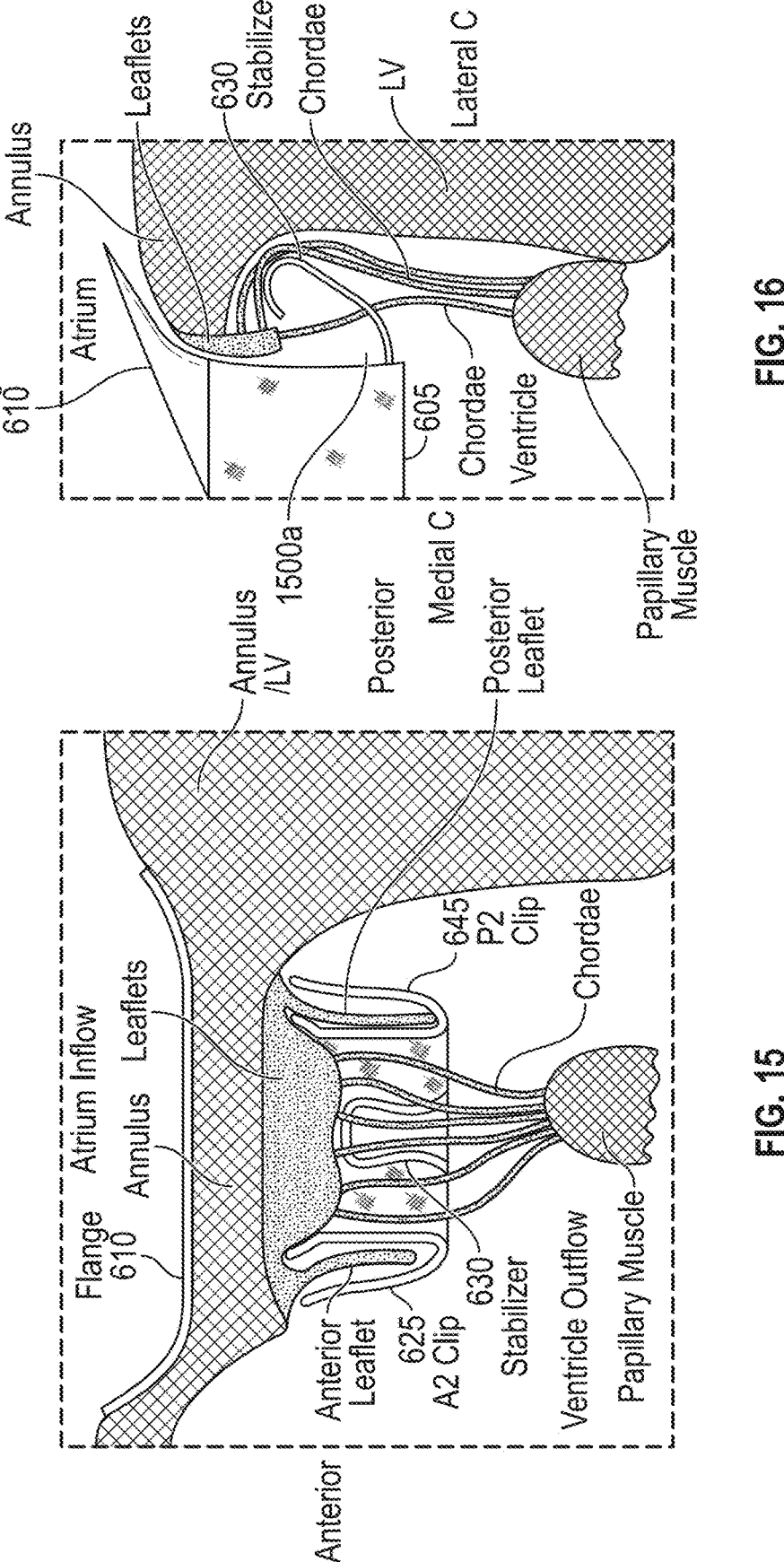
Figure 17:
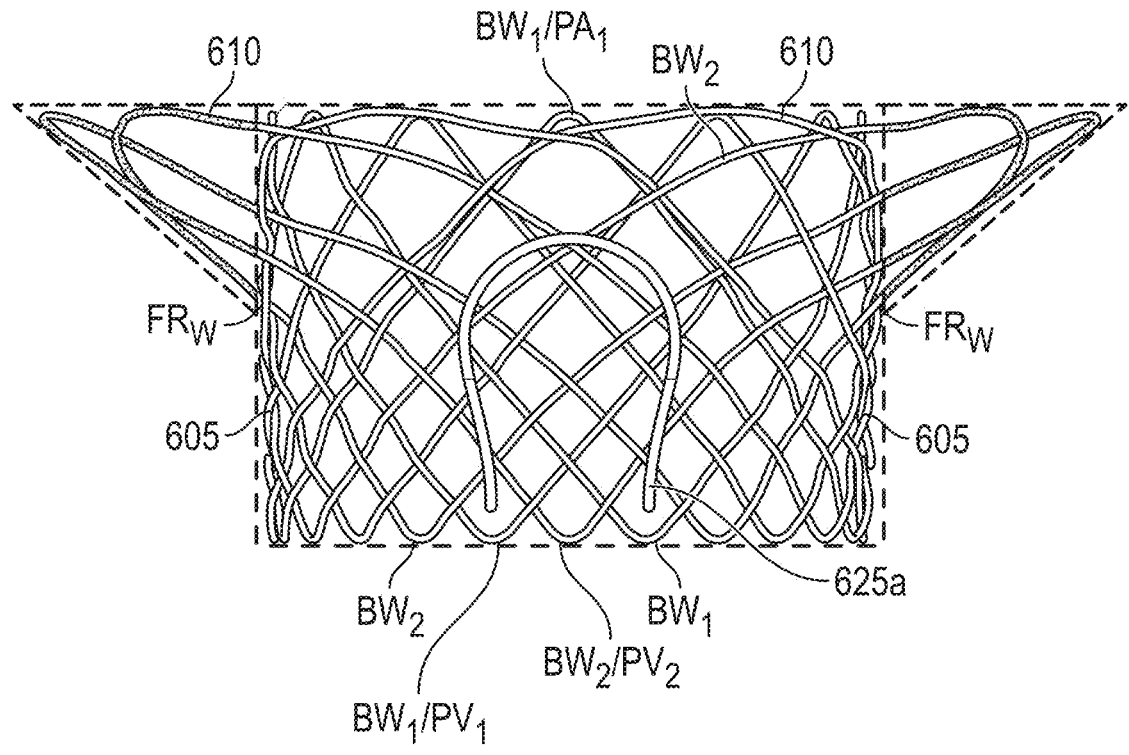
FIGS. 17-18 generally illustrate embodiments of a valve replacement as disclosed herein.
Figure 19:
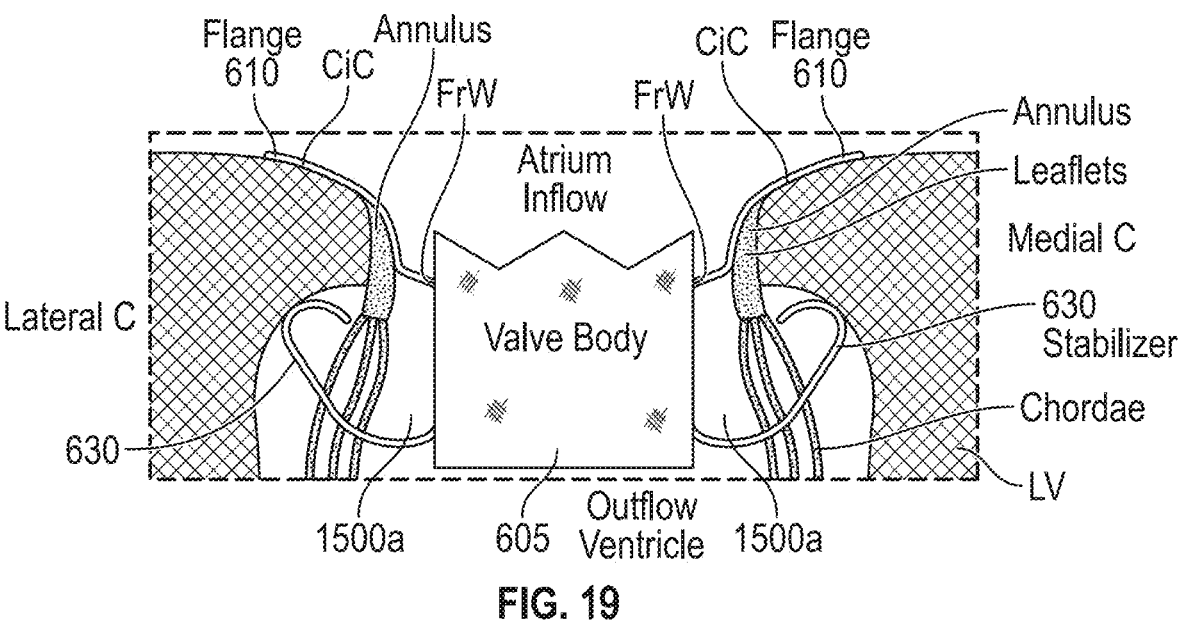
FIGS. 19-20 generally illustrate embodiments of a valve replacement deployed in a native mitral valve as disclosed herein.
Figure 20:
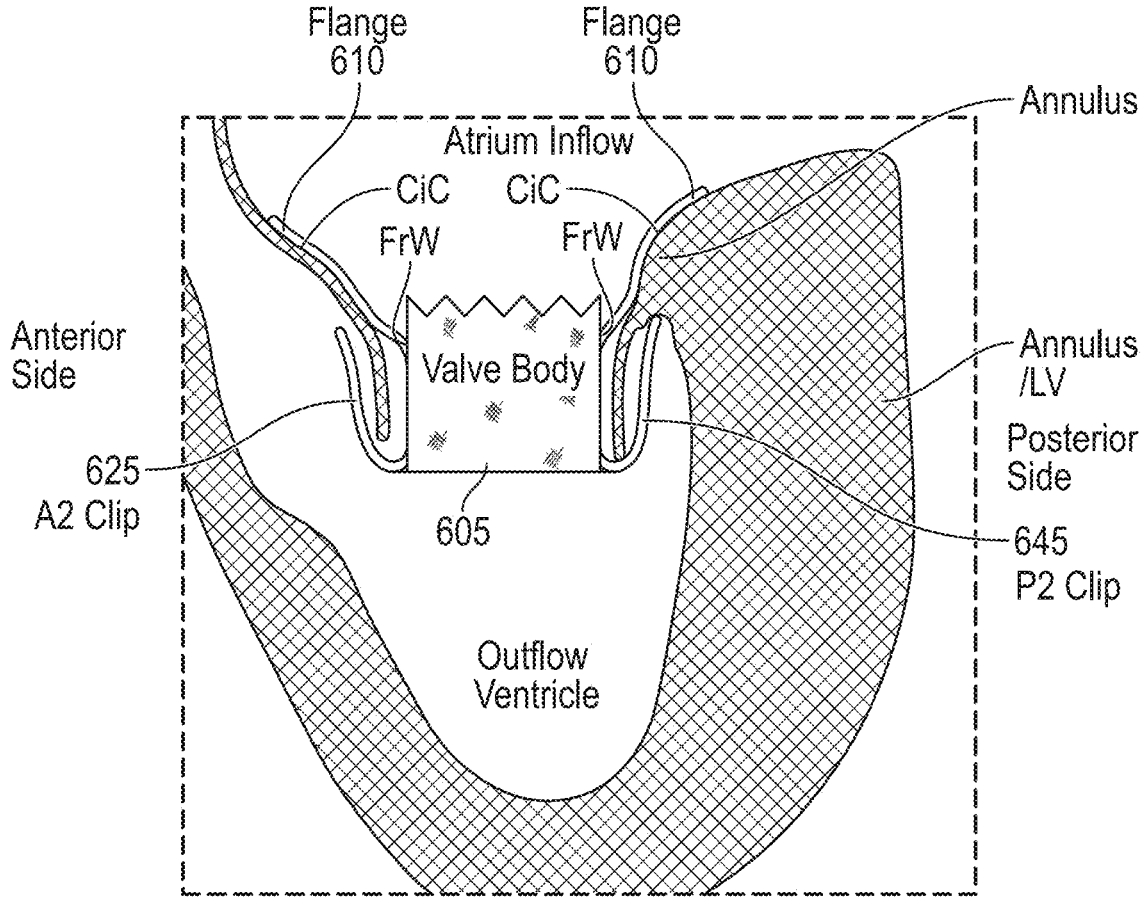

In embodiments, the stabilizers 630 are longer and reside higher on the valve body 605 than the clips and are therefore designed and/or configured to press against the native anatomy (e.g., the fibrous or muscular landing zones of the lateral and medial walls of the left ventricle behind the anterior or posterior leaflets of the native mitral valve). In some embodiments, the stabilizers 630 extend into and rest against native anatomy, for example the wall of the left ventricle behind the native chordae and behind the native leaflets. In some embodiments, there may be desired target areas of native tissue for the anchors. For example, the medial stabilizer 630 may rest on/in the medial area of native ventricle heart tissue while the lateral stabilizer 630 may rest on/in the lateral area of native ventricle heart tissue. In other embodiments, the stabilizers 630 are configured to rest in and anchor against the native heart trigone areas, inter-commissural areas, underneath leaflets, and/or underneath chordae near the annulus of the native heart valve being treated. For example, in embodiments, the stabilizers 630 are inclined towards the lateral and medial areas of the native left ventricle near the anterior or posterior leaflets of the native heart. Moreover, in embodiments, one or more of the stabilizers extend in between chordae into a lateral and/or medial sub-annular commissural area of a native heart when deployed within the native mitral valve (for example as seen in FIGS. 13, 14, 19). In embodiments, one or more of the stabilizers extend into the native chordae and push the chordae into a lateral and/or medial sub-annular commissural area of a native heart when deployed within the native mitral valve (for example as seen in FIGS. 15 and 16). In other embodiments one stabilizer 630 can extend into the native chordae and another stabilizer 630 extend through the native chordae. In embodiments, the medial and lateral stabilizers 630 as well as the leaflet clips 625/645 permit movement of the native mitral annulus (and native leaflets in embodiments) in the medial, lateral directions (by stabilizers) and anterior and posterior directions (by clips) and resist migration of the prosthetic mitral valve towards the atrial end when deployed within a native mitral valve. Thus, in embodiments, the replacement valve is suspended in the native valve space by these stabilizer and leaflet clip features and resist migration of the replacement valve towards the atrial end when deployed within a native mitral valve.

With reference to all of the Figures, including in particular FIGS. 3-20, valve replacement embodiments are described and shown with ranges for dimensions and elements, including for the flange, clips and stabilizers that enable the replacement valve to be securely suspended in the native valve anatomy. In embodiments, the replacement valve includes one of more leaflet clips, for example, in embodiments, a leaflet clip for the anterior leaflet and a leaflet clip for the posterior leaflet. With specific height, width and relational dimensions, the clips and stabilizers are designed to provide functionality in concert with the other aspects of the replacement valve, such as with the flange. For example, with the anchor and flange configurations disclosed herein, a replacement valve will provide in embodiments a beneficial posterior tilt, elimination of mitral regurgitation (MR), preservation of the LVOT, as well as the benefits of a "floating valve", as described herein, that are not present in competing devices such as laser cut/multi frame valves.

In embodiments, a replacement valve includes anchors at the outflow (ventricular) side of the replacement valve, for example leaflet clips 624a, with a leaflet clip 625 for the anterior leaflet (also called an anterior leaflet clip) and a leaflet clip 645 for the posterior leaflet (also called a posterior leaflet clip). In embodiments, because the anterior leaflet is typically larger in the human anatomy, the anterior leaflet clip 625 is larger and wider than the posterior leaflet clip 625. In other embodiments, the leaflet clips 625 are the same size or varying sizes depending on the application. Moreover, in embodiments the replacement valve includes stabilizers 630/630a (also called anchor struts) at the outflow (ventricular) side of the replacement valve, for example a stabilizer 630M on the medial side of the replacement valve and a stabilizer 630L on the lateral side of the replacement valve.

The leaflet clips and stabilizers are, in embodiments, constructed from wire(s), including for example nitinol wire, and are shaped into specific geometries for attachment to the braided wire of the receiver body 605. In embodiments, the leaflet clips and stabilizers are each constructed from different wires, the same wires, or a combination of wires. In embodiments, the leaflet clips and stabilizers are attached to or woven from the same wire as the receiver body 605, and in embodiments, the leaflet clips and stabilizers are attached to or woven from the same wire as the flange 610. In embodiments, the leaflet clips and stabilizers are attached to the receiver body 605 at a lower portion towards the outflow (ventricular) end of the receiver body 605 and are each attached to at least two separate locations along the circumference of the receiver body 605. For example, in embodiments, the anterior leaflet clip 625 is attached to the receiver body 605 on a bottom half or lower third of the receiver body 605 along the circumference of the receiver body 605 at two locations, with one attachment location 625W1 on the flange wire BW2 that is braided into the bottom half or lower third of the receiver body 605 and with a second attachment location 625W2 on the flange wire BW2 that is braided into the bottom half or lower third of the receiver body 605. In embodiments, the posterior leaflet clip 645 is attached to the receiver body 605 on the bottom half or lower third of the receiver body 605 along the circumference of the receiver body 605 at two locations, with one attachment location 645W1 on the flange wire BW2 that is braided into the bottom half or lower third of the receiver body 605 and with a second attachment location 645W2 on the flange wire BW2 that is braided into the bottom half or lower third of the receiver body 605. Similarly, in embodiments, the medial stabilizer 630M is attached to the receiver body 605 on the bottom half or lower third of the receiver body 605 along the circumference of the receiver body 605 at two locations, with one attachment location 630MW1 on the receiver wire BW1 that is braided into the bottom half or lower third of the receiver body 605 and with a second attachment location 630MW2 on the receiver wire BW1 that is braided into the bottom half or lower third of the receiver body 605. In embodiments, the lateral stabilizer 630L is attached to the receiver body 605 on a bottom half or lower third of the receiver body 605 along the circumference of the receiver body 605 at two locations, with one attachment location 630LW1 on the receiver wire BW1 that is braided into the bottom half or lower third of the receiver body 605 and with a second attachment location 630LW2 on the receiver wire BW1 that is braided into the bottom half or lower third of the receiver body 605. In other embodiments, the leaflet clips and stabilizers are part of the receiver wire BW1 or the flange wire BW2 and are part of the interwoven braid pattern of the wires instead of separate wires attached to the receiver wire BW1 or the flange wire BW2. For example, in embodiments, instead of forming a peak at the inflow or outflow ends, the flange or receiver wire can be used to form a leaflet clip or stabilizer (see e.g., FIG. 40, where a clip 735 is formed from a looped portion of the wire frame and extends out from the main body of the wire frame). In embodiments, the stabilizers are formed from separate wires that are connected to the second braided wire of the flange (e.g., welded, grafted, coupled together) and extend from the second braided wire of the flange. And in embodiments, the leaflet clips are formed from separate wires that are connected to the first braided wire of the receiver/tubular body (e.g., welded, grafted, coupled together) and extend from the first braided wire of the receiver/tubular body. In embodiments, the leaflet clips and stabilizers are each made from the same gage wire and in embodiments the leaflet clips and stabilizers are each made from different gage wires. For example, in embodiments, the stabilizers 630/630a/630M/ 630L each comprise a larger gage wire (for example, between 0.0175"-0.0200" gage wire, including embodiments with 0.0175", 0.0180", 0.0185", 0.0190", 0.0195", and 0.0200" gage wire) and the leaflet clips 625/645/625a each comprise a smaller gage wire (for example, between 0.0120"-0.0175" gage wire, including embodiments with 0.0120", 0.0125", 0.0130", 0.0135", 0.0140", 0.0145", 0.0150", 0.0155", 0.0160", 0.0165", 0.0170", and 0.0175" gage wire). In embodiments, the stabilizers 630/630a/630M/ 630L and leaflet clips 625/645/625a each comprise between 0.0120"-0.0200" gage wire, including embodiments with between 0.0150"-0.0180" gage wire and between 0.0160"-0.0175" gage wire, and in other embodiments one or more of the stabilizers 630/630a/630M/630L and leaflet clips 625/645/625a comprise between 0.0160"-0.0175" gage wire.

In an embodiment, the leaflet clips and stabilizers are attached to or extend out of the receiver body 605 at a lower portion of the receiver body 605 towards the outflow (ventricular) end, for example at the bottom half or lower third of the height I1 of the receiver body 605. For example, in embodiments, the distance H1 from the outflow end of the receiver body 605 to where the leaflet clips and stabilizers exit the receiver body 605 is between 1 to 4 mm, between 1-1.5 mm (including 1.1 mm, 1.2 mm, 1.3 mm, 1.4 mm and 1.5 mm), between 1-2 mm, between 0-4 mm and between 0-2 mm, including embodiments of 0 mm, 1 mm, 1.5 mm, 2 mm, 2.5 mm, 3 mm, 3.5 mm, and 4 mm. In embodiments, as discussed elsewhere, the geometry of the leaflet clips 625/645/625a and stabilizers 630/630a/630M/630L have "drop loops" that are curved sections of wire clip exiting the valve receiver body 605 that curve downward towards the ventricular/outflow side before the clip or stabilizer eventually turns upward in an atrial/inflow direction. Thus, in embodiments, one or more of the clips and stabilizers exit the receiver body 605 at the outflow end and may extend down past the outflow end with the drop loops before turning back towards the atrial/inflow direction, with an H1 distance of between 0 mm to 2 mm down past the outflow end of the receiver body. In embodiments having drop loops, the geometry of the leaflet clip's 625/645/625a drop loop NI include a radius of between 0.8 mm to 3.5 mm, including embodiments with a drop loop radius of between 0 mm to 1 mm, 1 mm to 1.5 mm, 1.5 mm to 2 mm, 2 mm to 2.5 mm, 2.5 mm to 3 mm, 3 mm to 3.5 mm, and other embodiments with a drop loop radius NI of between 0 mm to 1 mm, 1 mm, 1.5 mm, 2 mm, 2.5 mm, 3 mm, and 3.5 mm. Also, in embodiments having drop loops, the geometry of the stabilizer's 630/630a/630M/630L drop loop T1 include a radius of between 0 mm to 4 mm, including embodiments with a drop loop radius of between 0 mm to 1 mm, 1 mm to 1.5 mm, 1.5 mm to 2 mm, 2 mm to 2.5 mm (including 2.2 and 2.3 mm), and other embodiments having a drop loop radius T1 of between 0 mm to 1 mm, 1.5 mm, 2 mm, 2.5 mm, 3 mm, 3.5 mm, and 4 mm. In embodiments, there is also a distance between the drop loops of the various clips and stabilizers. For example, in embodiments, the leaflet clips 625/645/625a have a width C1 between the two drop loops of each clip of between 4 mm to 15 mm and between 5-10 mm, including embodiments having a width C1 of 9 mm, and other embodiments with C1 being 4 mm, 4.5 mm, 5 mm, 5.5 mm, 6 mm, 6.5 mm, 7 mm, 7.5 mm, 8 mm, 9 mm, 10 mm, 11 mm, 11.5 mm, 12 mm, 12.5 mm, 13 mm, 13.5 mm, 14 mm, 14.5 mm, and 15 mm. Also, in embodiments, the stabilizers 630/630a/630M/630L have a width Q1 between the two drop loops of each stabilizer of between 4 mm to 15 mm, between 6-10 mm, or between 7-10 mm, including embodiments having a width Q1 of 8 mm, and other embodiments with Q1 being 4 mm, 4.5 mm, 5 mm, 5.5 mm, 6 mm, 6.5 mm, 7 mm, 7.5 mm, 8 mm, 9 mm, 10 mm, 11 mm, 11.5 mm, 12 mm, 12.5 mm, 13 mm, 13.5 mm, 14 mm, 14.5 mm, and 15 mm.

In embodiments, the distance C1 between the drop loops of the clips defines the distance between where the clips enter and exit the receiver body 605. For example, in embodiments of the prosthetic mitral valve, the anterior leaflet clip 625 comprises a curved wire that exits the receiver body 605 at a first location along the circumference of the receiver body and re-enters at a second location along the circumference of the receiver body and the posterior leaflet clip 645 comprises a curved wire that exits the receiver body 605 at a third location along the circumference of the receiver body and re-enters at a fourth location along the circumference of the receiver body, wherein the first and second locations and the third and fourth locations along the circumference of the receiver body 605 are each separated by a width of between 4 to 15 millimeters, which is the same distance C1 between drop loops of the leaflet clips 625/645/625a.

Similarly, the distance Q1 between the drop loops of the stabilizers 630/630a/630M/630L defines the distance between where the stabilizers enter and exit the receiver body 605. For example, in embodiments of the prosthetic mitral valve, the medial stabilizer 630M comprises a curved wire that exits the receiver body 605 at a fifth location along a circumference of the receiver body 605 and re-enters the receiver body at a sixth location along the circumference of the receiver body 605 and the lateral stabilizer 630L comprises a curved wire that exits the receiver body at a seventh location along the circumference of the receiver body 605 and re-enters the receiver body 605 at an eighth location along the circumference of the receiver body 605, wherein the fifth and sixth locations and the seventh and eighth locations along the circumference of the receiver body 605 are each separated by a width of between 4 to 15 millimeters, which is the same distance Q1 between drop loops of the stabilizers 630/630a/630M/630L.

The leaflet clips and stabilizers also have various geometries of width and height in embodiments designed to compliment one another and ensure a stable implant in vivo and provide the functionality discussed herein, such as proper anchoring, LVOT preservation, MR elimination, posterior tilt, vortex flow, and a floating valve. For example, in various embodiments, the leaflet clips 625/645/625a have a uniform width or a varying width along the height of the wire that comprises the clip portion that engages the native leaflets. In embodiments, the widest point DI of the anterior leaflet clip 625 is between 8 mm to 16 mm or between 10-14 mm, with an embodiment of DI being 11 mm or 12 mm, and other embodiments having a width DI of 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, and 16 mm. In embodiments, the anterior leaflet clip 625 has a wider portion than the posterior leaflet clip because the native anterior leaflet is typically larger, so the anterior leaflet clip can be made more robust. In embodiments, the widest point E1 of the posterior leaflet clip 645 is between 6 and 14 mm or between 8-12 mm, including embodiments having a width E1 of 11.3 or 11.5 mm, and other embodiments having a width E1 of 6 mm, 6.5 mm, 7 mm, 7.5 mm, 8 mm, 8.5 mm, 9 mm, 9.5 mm, 10 mm, 10.5 mm, 11 mm, 11.5 mm 12 mm, 12.5 mm, 13 mm, 13.5 mm, and 14 mm. For height, which includes in embodiments a height from a bottom of a drop loop to the highest point of the clip, the leaflet clips 625/645/625a have a height between 12 mm and 17 mm. In embodiments, the height R1 of the anterior leaflet clip 625 is between 11 mm to 19 mm or between 13-16 mm, including embodiments having a height R1 of 15 mm and 16 mm and other embodiments having a height R1 of 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, and 19 mm. In embodiments, the height S1 of the posterior leaflet clip 645 is between 10 mm to 18 mm, between 12-16 mm, and between 13-15 mm, including embodiments having a height S1 of between 14 mm and 15 mm and between 14 mm and 14.5 mm and other embodiments having a height of 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, and 18 mm.

In embodiments, the distance between a clip 624a to the receiver body 605 is between 2 mm to 12 mm, including embodiments with the distance between the clip 625a and the receiver body 605 being 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm. In embodiments, the A2 clip 625 has a distance MI between the A2 clip and the receiver being between 2 mm to 12 mm and between 4-10 mm and the P2 clip 645 has a distance L1 between the P2 clip 645 and the receiver body 605 being between 2 mm to 12 mm and between 4-10 mm, with embodiments of L1 being 4 mm, 5 mm, or 10 mm and corresponding MI being 2 mm, 4 mm, or 8 mm, and embodiments with L1 or MI being 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm. Thus, in embodiments, a capture window for the leaflet clip 625*a* to capture a native leaflet can vary depending on the particular clip (A2 clip vs P2 clip). For example, as shown in FIG. 28, there is a smaller capture window CW1 and a larger capture window CW2. In embodiments, the capture window is the distance between the leaflet clip 625/645/625*a* and the receiver body 605 and in embodiments the capture window for the P2 clip 645 is larger than the capture window for the A2 clip 625 and in other embodiments the capture window for the A2 clip 625 is larger than the capture window for the P2 clip 645.

For the stabilizers, in various embodiments, the stabilizers 630/630*a*/630M/630L have a uniform width or a varying width along the height of the wire that comprises the stabilizer portion that engages the native heart structure. In embodiments, the widest point P1 of the stabilizers 630/630*a*/630M/630L is between 6 mm to 18 mm, between 8-12 mm, or between 10-12 mm, including embodiments having a width P1 of 10 mm and embodiments of width P1 being 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, and 18 mm. For height, which includes in embodiments a height from a bottom of a drop loop to the highest point of the stabilizer, the stabilizers 630/630*a*/630M/630L have a height O1 between 7 mm and 20 mm or between 10-15 mm. In embodiments, the height O1 of the stabilizers 630/630*a*/630M/630L is between 7 mm to 15 mm, including embodiments having a height O1 of 10 mm, between 14-15 mm, and 15 mm, and embodiments of O1 being 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 14.8 mm, 15 mm, 15.5 mm, 16 mm, 16.5 mm, 17 mm, 17.5 mm, 18 mm, 18.5 mm, 19 mm, 19.5 mm, and 20 mm.

For the stabilizers, in embodiments, have a curved shape that bends in a convex loop and forms a surface or line that curves upward (towards the atrial side) and outward towards the native anatomy on either a lateral or medial area of the native anatomy below the native annulus in the ventricle when implanted in the native mitral valve. In embodiments, the stabilizers 630/630*a*/630M/630L have a maximum distance V1 along the curved surface measured from the receiver body 605 to the stabilizer of between 4 mm to 22 mm, between 10 mm to 22 mm, between 6 mm to 18 mm, and between 6-14 mm, with embodiments having a distance V1 of 6 mm, 8 mm, 10 mm, 12 mm, 14 mm, and embodiments having a V1 distance of 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, 17.5 mm, 18 mm, 18.5 mm, 19 mm, 19.5 mm, 20 mm, 21.5 mm, and 22 mm. In embodiments, the stabilizers 630/630*a*/630M/630L have a maximum distance U1 along the curved surface measured from the receiver body 605 to the tip of the stabilizer of between 3 mm to 14 mm, between 6-14 mm, and between 8-13 mm, with embodiments having a distance U1 of 8 mm and between 12-12.5 mm and embodiments having a U1 distance of 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, and 14 mm. In embodiments having multiple stabilizers 630/630*a*/630M/630L, for example a medial stabilizer 630M and a lateral stabilizer 630L, the stabilizers have a wingspan X1 designed to compliment each other and work with the other anchoring mechanisms. In embodiments, the distance between the tips of stabilizers 630M/630L on either side of the replacement valve include a wingspan X1 between 40 mm and 74 mm, between 40-60 mm, between 46-60 mm, and with embodiments including wingspans X1 of 46 mm, 48 mm, 52 mm, 56 mm, 58 mm, and 60 mm including embodiments having a wingspan distance X1 between stabilizer tips of 40 mm, 40.5 mm, 41 mm, 41.5 mm, 42 mm, 42.5 mm, 43 mm, 43.5 mm, 44 mm, 44.5 mm, 45 mm, 45.5 mm, 46 mm, 46.5 mm, 47 mm, 47.5 mm, 48 mm, 48.5 mm, 49 mm, 49.5 mm, 50 mm, 50.5 mm, 51 mm, 51.5 mm, 52 mm, 52.5 mm, 53 mm, 53.5 mm, 54 mm, 54.5 mm, 55 mm, 55.5 mm, 56 mm, 56.5 mm, 57 mm, 57.5 mm, 58 mm, 58.5 mm, 59 mm, 59.5 mm, 60 mm, 60.5 mm, 61 mm, 61.5 mm, 62 mm, 62.5 mm, 63 mm, 63.5 mm, 64 mm, 64.5 mm, 65 mm, 65.5 mm, 66 mm, 66.5 mm, 67 mm, 67.5 mm, 68 mm, 68.5 mm, 69 mm, 69.5 mm, 70 mm, 70.5 mm, 71 mm, 71.5 mm, 72 mm, 72.5 mm, 73 mm, 73.5 mm, and 74 mm.

Moreover, in order to provide a posterior tilt in embodiments and encourage proper anchoring, in various embodiments, the height of the stabilizers is lower than the height of the clips. For example, in embodiments, the distance W1 from the tip of the stabilizers 630/630*a*/630M/630L to the tip of one or more of the higher leaflet clips 625/645/625*a* is between 0 mm to 6 mm, between 2-4 mm, and between 3-5 mm, including embodiments having a distance W1 of 3 mm and embodiments having a W1 distance of 0 mm, 0.5 mm, 1 mm, 1.5 mm, 2 mm, 2.5 mm, 3 mm, 3.5 mm, 4 mm, 4.5 mm, 5 mm, 5.5 mm, and 6 mm.

Material Covering

In some embodiments, different materials are prepared prior to assembling into a continuous covering. In other embodiments, material may be added and receive a modification treatment post-assembly that is applied to only specific locations on the valve replacement.

In some valve replacement embodiments disclosed herein, tissue attachment and ingrowth may be promoted in an area that is desired to become anchored to the tissue, while cellular interaction can be limited to simple endothelialization or no response at all, to allow disturbance of part of the device at a later date without risk of tissue or thrombus embolization. Put simply, the varying material X1 used may be either conducive or non-conducive to chemical bonding. For example, in embodiments, the materials in contact between the inner portion of the receiver and the outer portion of the valve assembly do not bond, so as to allow for movement of both portions; whereas the material on the outside of the receiver bonds with human tissue. Thus, depending on the location, materials may be used such that cellular growth is inhibited or promoted.

Some valve replacement embodiments may be encased, either completely or partially, in a continuous material covering to elicit the type of physiological response that is desired as well as the mechanical behavior. Though the covering is continuous—as in there are no material gaps at the transitions of physical features—the materials may be modified locally in areas of the device to behave differently. For example, the material covering one side of the flange may be deliberately nonporous to facilitate sealing, while the material on the other side of the flange may be a knit that facilitates tissue ingrowth for anchoring. In embodiments, local stiffness of the implant due the braid structure and cloth composite nature results in selective stiffening of the implant and desired mechanical behavior for sealing, ingrowth, fixation, and durability. Alternatively, the flange could be alternating rings of nonporous and ingrowth material on both sides of the flange. These techniques can be applied to any surface of the device. In other embodiments, the valve replacement is covered in a cloth with additional slack material beyond the edge of the wireframe (for example at the edge of the flange covering and at the end of the outflow end of the replacement valve), which accounts for for-lengthening during crimping and allows the braid to expand during foreshortening without bunching up the braid at the ends of the cloth. In embodiments, additional slack material in the cloth covering reduces loading force and prevents cloth damage during crimping/deployment.

Material differences range from being entirely different materials-natural tissue or synthetic fabric—to physical and chemical surface modification, to obtain the desired mechanical and biocompatible properties. These modifica-tions can include but are not limited to coating, etching, mechanically biasing, ion infusion, various deposition tech-niques, and oxidizing/nitriding/carbiding. Modifications may be used in any combination to achieve the desired result.

Figure 41:
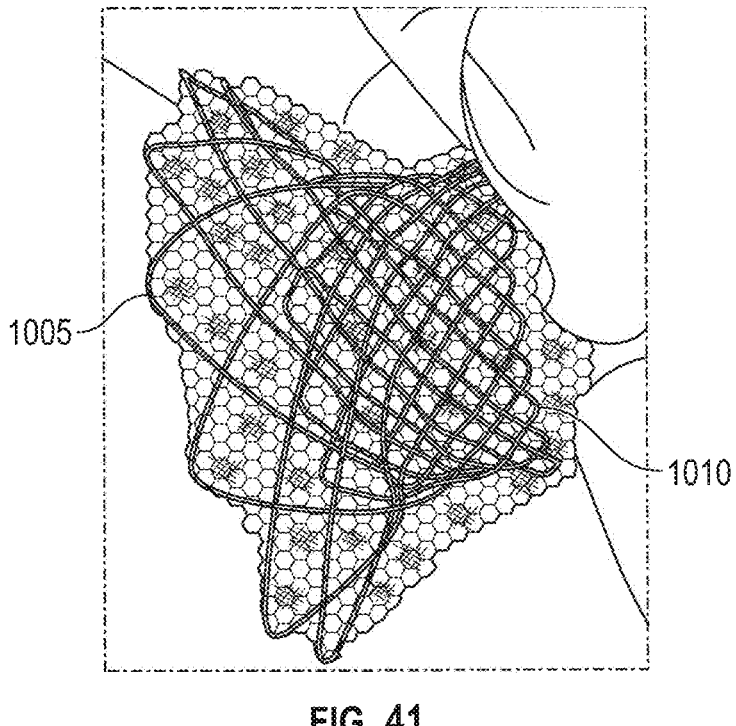
FIGS. 41-42 generally illustrate embodiments of a valve replacement as disclosed herein.
Figure 42:
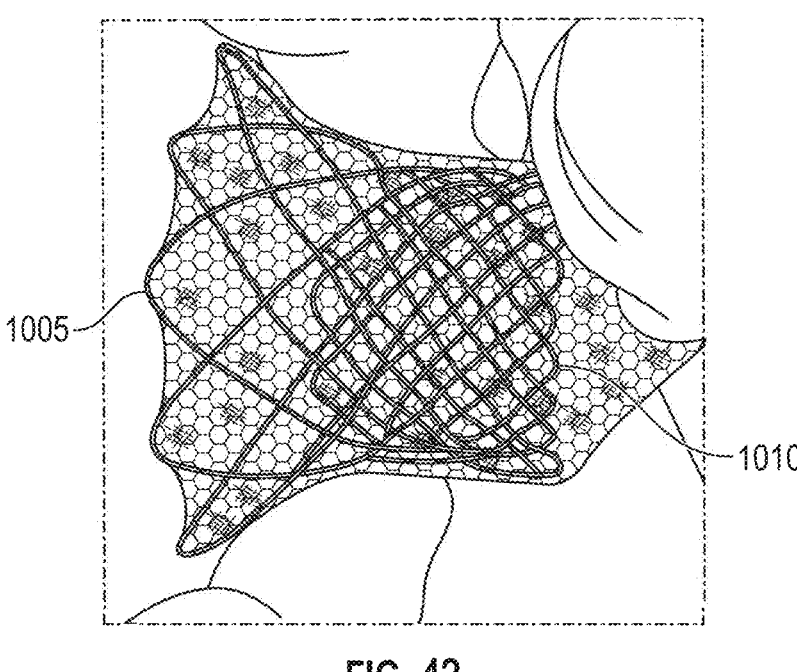

FIGS. 41 and 42 generally illustrate embodiments of a valve replacement as disclosed herein. As shown in FIGS. 41 and 42, an embodiment of the valve replacement may comprise a continuous piece of material around the outside of the frame. A continuous seal may be configured from the material (such as fabric) extending from an inflow edge 1005 of the valve replacement to the extrados 1010 of the body of the valve replacement. A strip of ingrowth fabric may be sewn around the inflow edge of the valve replace-ment, with a non-porous coating forming a continuous seal extending into the ventricle. Material can also be configured to fill spaces between the inner and outer fabric. For example, in an embodiment, filler fabric is selectively placed within the valve replacement to fill in spaces and gaps between the materials or areas where the frame and fabric have gaps.

The continuous surface of the fabric may be locally influenced and characterized for modulating or even con-tradicting properties, such as coating with medical polymer in locations where no tissue attachment is desired, hydrogels where space-filling or latent actions are desired, or a hydro-philic tissue adhesive. The continuous material structure of the fabric may be voluminous in nature, filling space and adapting the round heart valve to the asymmetrical shape of the valve annulus. Combined with other attachment meth-ods, an embodiment of the mitral-valve adapter fabricated with this method aids in engagement and attachment of the leaflet tissue and other sub-valvular structures. The partially porous fabric provides an improved seal for a replacement valve, enabling accommodation to irregular shaped anatomy through the compliance of the fabric. In embodiments, fabric is selectively treated by partial dipping in a coating that provides additional properties to the fabric, such as improved sealing.

In other embodiments, the valve replacement may be fabricated using a constraint to hold the valve replacement at a specific dimension while attaching material to influence device performance. A fabrication technique is disclosed, which acts to influence the disposition of a braided wire frame—removing the inherent freedom of movement and unpredictability that is present between relative members of the frame structure when in a load-free state. This technique involves restraining the radial expansion of the frame with a constraint, such as feeding some number of sutures through or around the structure to hold it at a specific dimension other than its unrestrained, "free" dimension. In subsequent fabrication steps, the structure is incorporated into an assembly that adopts this new configuration and considers this to be the final dimension. When the con-straints are removed from the braided frame, this braided frame tries to recover to its original "free" dimension-applying additional radial force to the surrounding structure while being constrained to the desired dimension.

The degree of radial force transmitted to the fabric mate-rial from the frame can be adjusted as required to achieve the optimal combination or performance properties. In particu-lar, the strain energy density of the structure can be more uniform. A greater stiffness is achieved (resulting in a better seal) with less material, resulting in a more low-profile structure. The suture finally provides a biasing of the struc-ture toward a desirable diameter and height for the valve structure.

To expand the concept further, structures that possess features described herein may be co-deployed singularly or with a connected design, so as to engage both the mitral and the aortic valve apparatus and/or annulus. The intent is to influence the leaflets of both valves, as well as the angulation of the valves relative to one another, to ensure the most effective management of flow through the ventricle and maximizing the efficiency of the outflow tract.

In some embodiments, the valve replacement is covered in a material that wraps around the frame in a continuous manner. Embodiments of the material are fabric and animal tissue. By using materials that can be locally modified to change characteristics such as porosity and surface rough-ness, a certain level of control over cellular interaction on the various parts of the device can be achieved. In other embodiments, the adapter body and atrial flange may be covered in fabric for the purpose of flow sealing and/or influencing (e.g., either promoting or inhibiting) tissue growth after implantation.

The material used further assists with the loading and deployment of the valve replacement. For example, the material may promote the valve replacement to function as a re-valve system, wherein a tubular braided fabric tube (coated with a polymer to decrease porosity to blood) surrounds the frame and constrains the diameter. This tube is sewn onto the frame, sometimes in conjunction with a leaflet panel, so that the strings can be removed and what remains is a pretensioned frame constrained by the fabric. In embodiments, an elastomer-coated, tubular knit, shape-set fabric is attached to the braided frame. In embodiments, dip-coated braided frames are utilized, such as a frame dipped in urethane, either as a whole device or partial. In other embodiments, treated panels are sewn onto the braded frames. In other embodiments, sections of treated fabric are cut into panels that are configured to be able to be sewn onto a at least partially circular surface, such as a flange.

Figure 43:
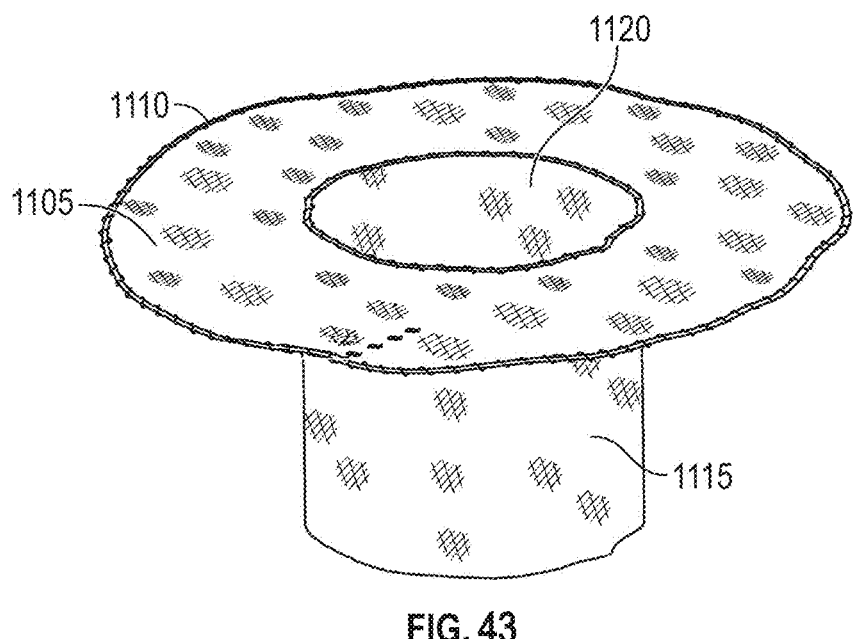
FIGS. 43-44 generally illustrate embodiments of fabric and material coverings for a valve replacement as disclosed herein.
Figure 44:
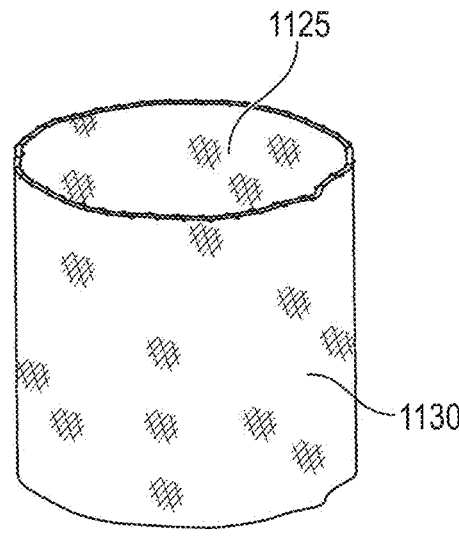

FIGS. 43 and 44 generally illustrate embodiments of the valve replacement as disclosed herein. More specifically, FIGS. 43 and 44 show various embodiments of the fabri-cation of material for the valve replacement, focused on the two-piece system, and is also consistent with a one-piece system as well. In embodiments, material for the various parts may be made of the same or different materials, respectively. Such materials may include, for example, a textured or hard-knitted style fabric or textiles, or bioresorb-able mesh (e.g., made from polymers), elastomeric scaf-folds, or other materials. Other materials with similar or different properties may be used, such as permeable or impermeable materials, with various degrees of elasticity, and stretchable in predetermined directions or any direction, and biocompatible materials.

FIG. 43 shows a flange outer material 1105, a flange rim material 1110, an outer receiver (also referred to as an adapter) cuff material 1115, and an inner adapter cuff material 1120 of the valve replacement. The flange outer material 1105 may form a circular top piece, wherein it may further have a coating to reduce fluid permeability. The flange rim material 1110 may form a circular bottom piece that stretches to allow expansion of the valve replacement when deployed. The outer adapter cuff material 1115 may constitute a cross-stitch that attaches the ends to create the tube-like shape. The inner adapter cuff material 1120 may comprise a running or cross-stitch that attaches the ends to create a tube shape, wherein the fabric of the inner adapter cuff material 1120 may have limited elasticity and either stitch maintains the integrity of the inner adapter cuff material 1120.

In one embodiment, the flange rim material 1110 and the outer adapter cuff material 1115 may be combined, either by cross-stitching or other method known to one skilled in the art, to form a secant bottom piece. The flange may be stitched furthest away from any anchor slots. The formed secant bottom piece may be positioned onto the bottom of the adapter or the one-piece system, wherein the shape-set thread around the body of the frame is cut and wrap-stitch is used to close or secure the anchor slots.

In another embodiment, the inner adapter cuff material 1120 may be attached to the inner opening of the flange outer material 1105 to form a top piece of material. The top piece or material may be slid over the top of the adapter or the one-piece system after which the fabric is wrap-stitched closest to the frame.

In another embodiment, the bottom piece of material and the top piece of material may be connected, such as by wrap-stitching at the bottom of the frame to connect the top piece of material to the bottom piece of material. For this, the fabric of the flange outer material 1105 and the flange rim material 1110 may be smoothed and held in place (such as with sewing clips) and connected around the wire flange (such as with a running stitch), wherein the border of the flange may be circular and not rigid. The excess fabric may be trimmed, and additional stitching may be added around the flange and each wire flange tip. Additional stitching may be performed along the wires to secure the fabrics together and keep flush against the wire flange. The stitching may be done to the second crossing of wires, followed to the next wire, and then up towards the tip of the wire flange. This process may be continued around the flange and repeated on the next set of wires.

One embodiment of the outer adapter cuff material 1115 may be folded in half and secured together (such as with a sewing clip), after which a blanket stitch may be performed around the edges. The blanket stitch allows the outer adapter cuff material 1115 to retain its shape without sinching the fabric. The outer adapter cuff material 1115 may be turned inside out and placed over the anchor wire, after which the outer adapter cuff material 1115 may be secured to the front and back of the anchor wire (such as with a running stitch). In this, the seam of the stitch (used to close the anchor slots) may be caught between the front and back fabric of the outer adapter cuff material 1115 to secure it to the adapter or one-piece system. The running stitch may encompass the front of the outer adapter cuff material 1115, the seam, and the back of the outer adapter cuff material 1115 along the base of the anchor wire. Once the outer adapter cuff material

1115 is secured at the base, a stitch may be continued along the anchor wire to keep the outer adapter cuff material 1115 from slipping or sliding on the anchor. Fabric may be slightly caught, wherein it is not loose enough to leave excess fabric but not tight enough to affect the shape of the wire.

In embodiments, stitching of the fabric to the replacement valve helical braided wire architecture performs several functions, including the following: sewing of fabric to the braided wire architecture helps constrain the braided wire of the replacement valve from migrating into the ventricle or atrium and helps prevent paravalvular leaks, while at the same time permitting slight movements along the unfixed nodes at the over-under braids to allow the replacement valve to move with the natural helical movements of the heart.

FIG. 44 shows an inner valve cuff material 1125 and an outer adapter cuff material 1130. In one embodiment, leaflets may be connected to the inner valve cuff material 1125, such as along a strip of fabric with a double running stitch along the belly of the leaflet, wherein the stitches are uniform across the leaflets to allow for proper valve opening and closing. The leaflet or commissure tabs may be exposed, such as by laser-cutting with slots at the top of the inner valve cuff material 1125 (wherein a strip of the inner valve cuff material 1125 may be folded in half, making sure that leaflets are aligned on top of each other; and wherein the ends of the inner valve cuff material 1125 may be attached to the junction of the belly and tabs with a double running stitch). Following the exposure of the leaflet tabs, the inner valve cuff material 1125 may be placed inside the valve assembly frame, the tabs may be pulled through commissure wires and laid flat between the leaflets and the inner valve cuff material 1125.

In one embodiment, the ends of the outer valve cuff material 1130 may be connected and the outer valve cuff material 1130 slid over the outside of the valve assembly frame.

In another embodiment, the inner valve cuff material 1125 and the outer valve cuff material 1130 may be connected together. After placing the inner valve cuff material 1125 on the inside of the valve assembly frame and the outer valve cuff material 1130 on the outside of the valve assembly frame, the two parts may be connected to the bottom of the frame (such as by tacking down both parts with a square knot) directly below commissure wires, and the parts may be stitched along the bottom of the frame. Following a commissure attachment, which is set forth in the following paragraph, both portions may be combined by sewing through the frame and the top of the valve assembly frame may be stitched. Additional steps may comprise, along the upper perimeter of the valve, stitching around the wires travelling from the commissures downwards and away from the peaks so as to create a z-shaped pattern. In this, the stitches may connect the inner fabric behind the leaflet and the outer valve cuff material 1130.

In an embodiment of a commissure attachment, leaflet tabs are fed through the commissures, wherein each tab folds towards its own leaflet and is wrapped around the commissure wires. The ends of the tabs may be held together against the entry of the tabs and secured together, such as with running stitches vertically and on the inside of the valve assembly. Stitching may continue in front and around the commissure, such as for 3-4 times, and entering and exiting at the location of the running stitch. Stitches may be perpendicular, comprising of embodiments such as a running stitch along the y-axis and a wrap-stitch along the x-axis.

In other embodiments of the fabrication of material for the valve replacement wherein the focus is on the one-piece system, a fabric for the various portions may comprise a stretchy and semi-transparent fabric; wherein the outer adapter cuff material 1115 and flange rim material 1110 may be sewn together to create the outer piece. Cross-stitch may be used to connect the edges of the outer adapter cuff material 1115 and to connect the outer adapter cuff material 1115 to the flange rim material 1110.

In a separate embodiment, a fabric for the portions comprises an inflexible and opaquer fabric where the coating is visible; wherein the inner adapter cuff material 1120 and flange outer material 1105 may be sewn together to create the inner piece. A running stitch may be used to connect the edges of the tubular inner adapter cuff material 1120 and a cross-stitch is used to connect the inner adapter cuff material 1120 to the flange outer material 1105.

For these embodiments focused on the one-piece system, an inner valve cuff material may be created, wherein leaflets are attached to the inner adapter cuff material 1120 and wherein leaflet tabs are placed through slots of the inner adapter cuff material 1120 where the junction of the inner adapter cuff material 1120 and tabs meet, with the leaflets held in place, such as with sewing clips. Using a double running stitch, the belly's edge of each leaflet is sewed to the inner adapter cuff material 1120. The tabs and top edge of the leaflet(s) are flushed and level with one another and the running stitch on each belly of the leaflet(s) is level and uniform. (Inconsistent stitches can lead to a defective valve.) After the leaflets are attached to the inner adapter cuff material 1120, the inner adapter cuff material 1120 is folded in half, keeping leaflets level and held in place. A double running stitch may then be sewn directly down from the junction of the leaflet tabs, continuing away from the leaflets with a running stitch back up towards the junction of the leaflet tabs. (The running stitch should be away from the leaflet belly.) Following these steps, the inner valve cuff material should create a tube.

A first set of materials may be created by connecting the inner valve cuff material from above to the flange outer material 1105, such as with a cross-stitch, wherein leaflets are away from the seam.

Once the first set of materials is created, it may be connected to a second set (e.g., the flange rim material 1110 and outer adapter cuff 1115 previously sewn together) by using a running stitch through the frame (between the double running stitch of the leaflet belly) and following the belly stitch of the leaflet(s) to secure both sets together. The tabs are then secured through the commissures and wrap-stich is used to connect the second set to the first set at the base of the frame. The deployment apertures are created, by cutting the fabric, before finishing the wrap-stich. Once connected, a beta-stitch is incorporated on the flange and anchors' cuff placements.

Engagement Structures

Embodiments of the valve replacement as disclosed herein are designed to be implanted and anchored with engagement structures in a malfunctioning native mitral valve, with the receiver (also called tubular body) having the replacement leaflets being deployed in the mitral valve, the flange (also called sealing skirt) being deployed against the floor of the left atrium, and leaflet clips and stabilizers being deployed in the native ventricle. In embodiments, the receiver is oriented at a slight angle (i.e., from 10-30 degrees relative to the plane of the flange), such that when deployed, the receiver is biased towards the posterior leaflet, encourages central vortex flow, and helps prevent obstruction of the left ventricular outflow tract obstruction (LVOT).

In embodiments, how the engagement structures of the replacement valve interact with the native anterior and posterior leaflets and the surrounding native anatomy determines how the replacement valve sits within the native anatomy and to the degree the replacement valve will have a posterior tilt, for example. In embodiments, the replacement valve has engagement structures that help determine how the replacement valve sits in the native anatomy and helps prevent migration of the replacement valve. These engagement structures include, for example, ventricular leaflet clips and stabilizers as well as an atrial flange.

Figure 45:
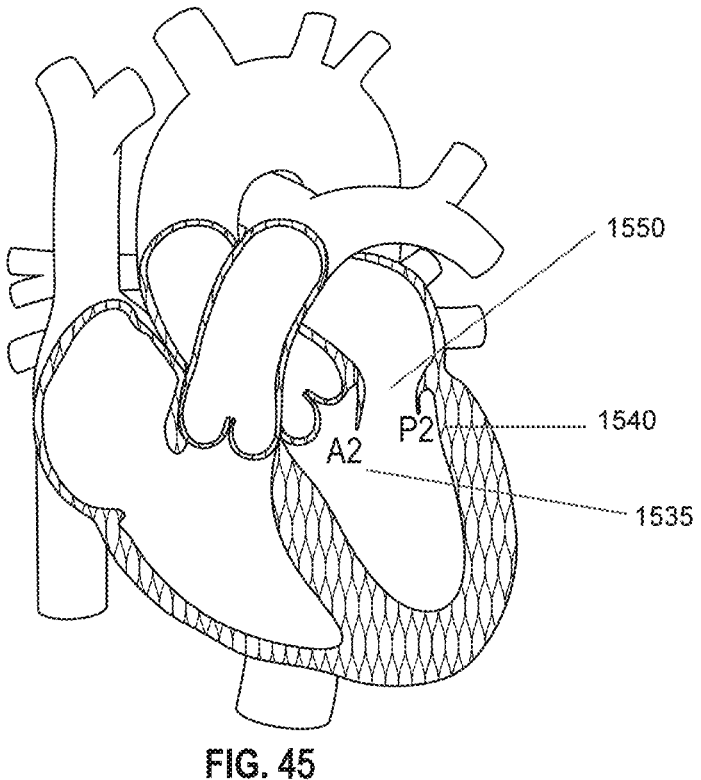
FIG. 45 generally illustrates a human heart and a native mitral valve with native leaflets.

FIGS. 45-66 generally illustrate embodiments of a valve replacement as disclosed herein. FIG. 45 shows a heart with a mitral valve 1550, with an anterior leaflet having an A2 region 1535 and a posterior leaflet with a P2 region 1540, with the anterior native leaflet and A2 region being longer and thicker than the native posterior leaflet and P2 region.

Figures 46, 47:
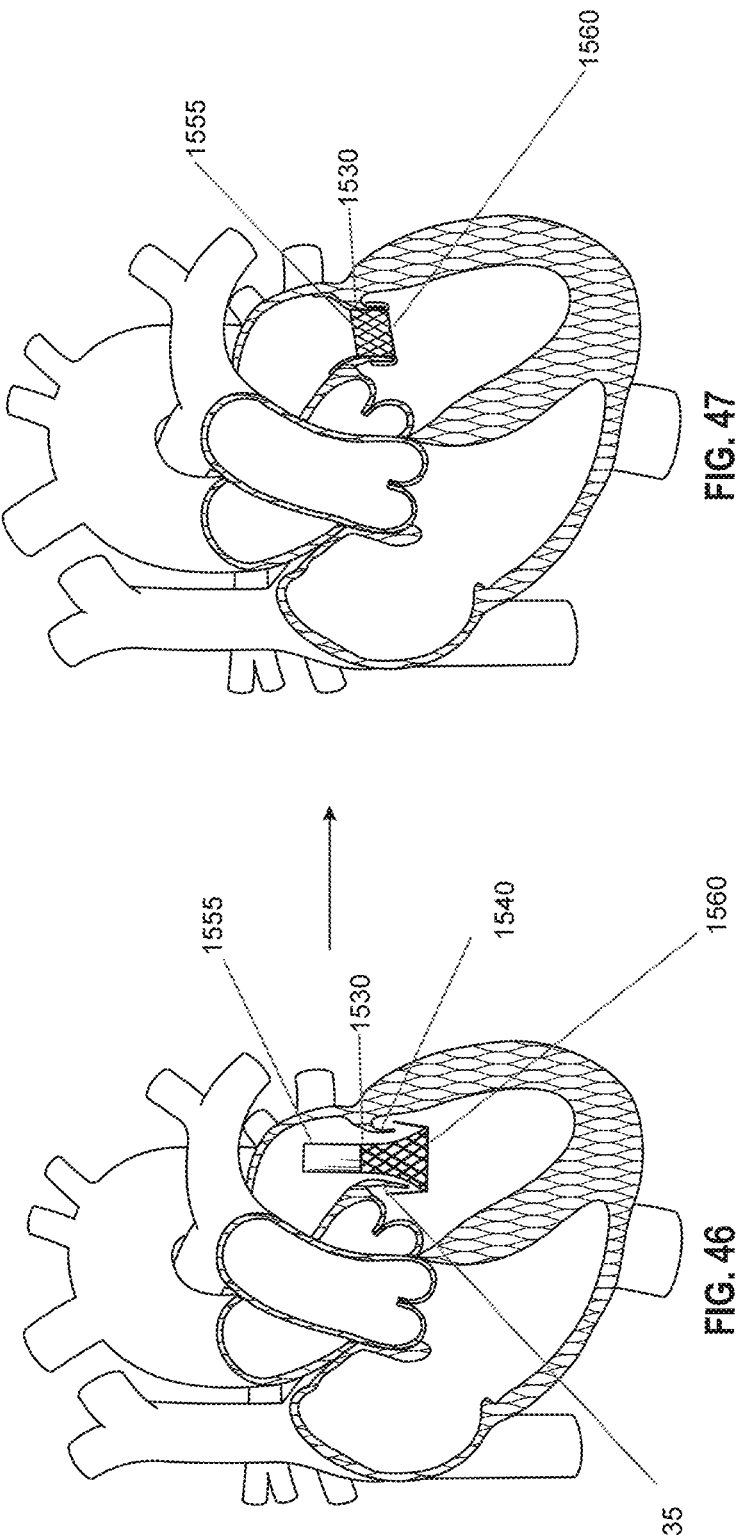
FIGS. 46-48 generally illustrate embodiments of a valve replacement deployed in a native mitral valve as disclosed herein.

FIGS. 46 and 47 show initial deployment of the valve 1530 in the heart. FIG. 46 shows capturing and attaching to the A2/P2 leaflets 1535, 1540. As explained in more detail elsewhere in the disclosure (and in Figure below), to ensure that the valve 1530 is not deployed until in the correct location, the rest of the receiver and flange may remain in a compressed position while and until the A2/P2 leaflets are captured. In other words, the top of the receiver 1555 (e.g., the flange, etc.) may not be released while the receiver bottom 1560 in the ventricle is released, until both 1555, 1560 are released as shown in FIG. 47.

Figure 48:
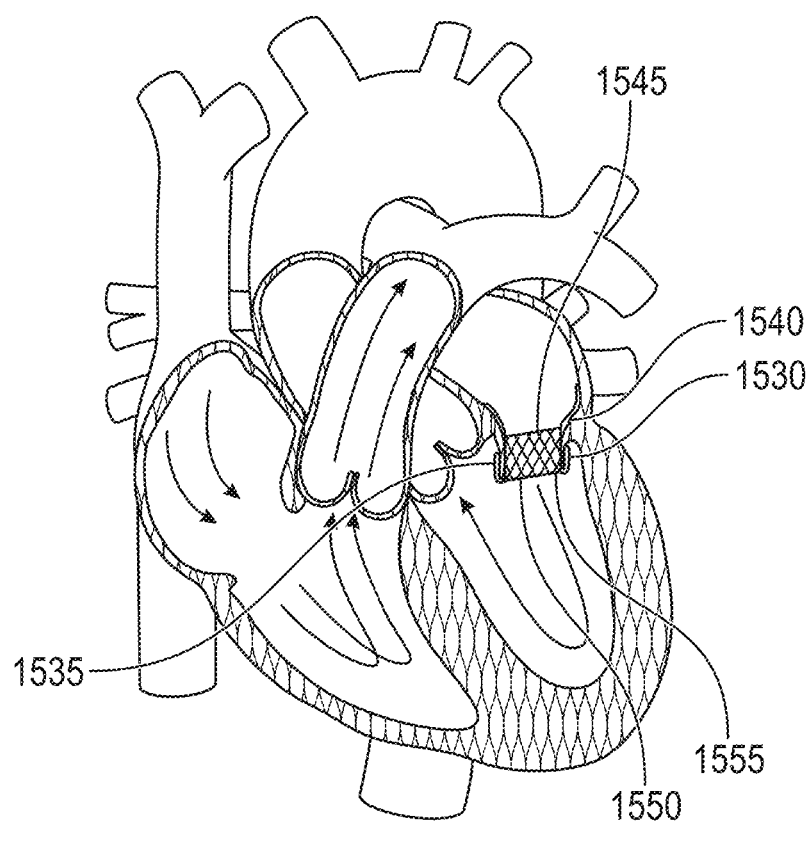

FIG. 48 shows a replacement heart valve 1530 connected with the A2 leaflet 1535 and the P2 leaflet 1540. One side is an inflow end 1545, while the opposite side of the heart valve is the outflow end 1555.

As the blood enters the inflow end 1545 into the mitral valve 1550 and heart valve 1530, the blood flow will follow the angulation of the bioprosthetic valve as implanted. This angle creates posterior vortex flow as the blood is directed posteriorly within the left ventricular cavity relative to the mitral annulus and/or left ventricular apex. To mimic this naturally occurring flow, the heart replacement valve 1530 may be tilted in place when installed.

Figure 49:
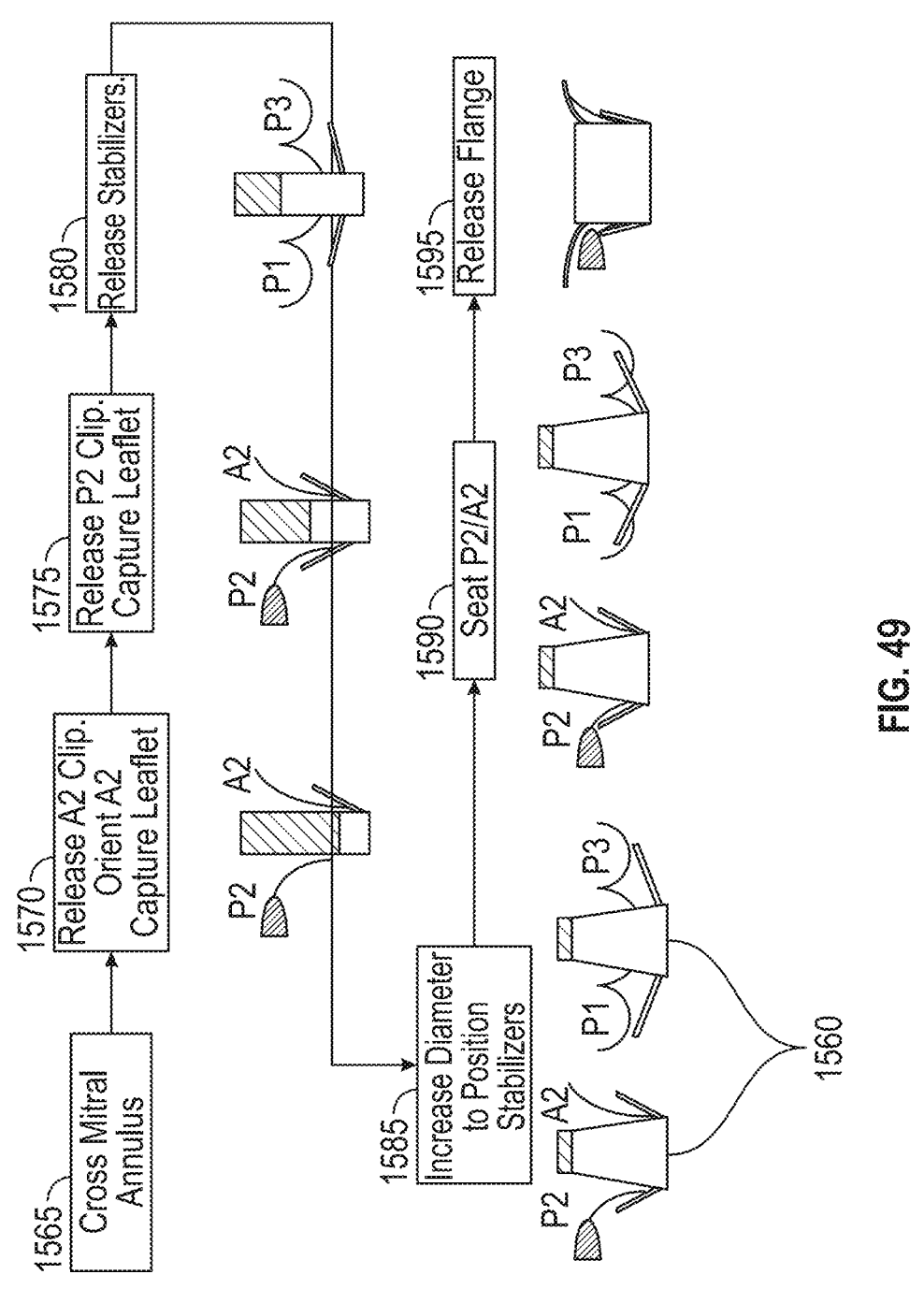
FIG. 49 is a flow diagram generally illustrating a method of deploying a replacement heart valve as disclosed herein.

FIG. 49 is a flowchart showing steps of deployments. In a first step 1565, the heart valve 1530 crosses the mitral annulus. In a second step 1570, part of the receiver bottom 1560 begins to deploy. Specifically, in some embodiments, an A2 clip is released, oriented to capture the A2 leaflet 1535, and captures the A2 leaflet 1535. In some embodiments, the orienting is accomplished using fluoroscopy and/or echocardiography to visualize the anchors and other metal features of the replacement valve. By orienting the A2 clip to the A2 leaflet at the beginning of the procedure, this ensures the remaining features of the valve are aligned properly to the native anatomy, including the P2 clip (at P2 leaflet), stabilizers (medial lateral positioning), and D-shaped flange. The A2 provides an imaging landmark that is relatively easy to identify using standard imaging techniques, thus allowing for the procedure to be adoptable by users of ordinary skill. Procedurally, this simplifies the positioning and orientation of the device. The delivery system may allow for rotation and independent manipulation of the implant to achieve proper rotational alignment of the A2 clip with the A2 leaflet. Additionally, by aligning the A2 clip to the A2 leaflet, the pre-sewn bioprosthetic commissures are aligned in an optimal fashion to accommodate A2-P2 crush, while maintaining hemodynamics.

In a third step 1575, another part of the receiver bottom 1560 begins to deploy. Specifically, in some embodiments, an P2 clip is released, oriented to capture the P2 leaflet 1540, and captures the P2 leaflet 1540. In some embodiments, this capturing will involve the P2 clip tip interacting/capturing the P2 leaflet 1540 at a middle part of the leaflet 1540.

In a fourth step 1580, after the clips have captured the A2/P2 leaflets 1535, 1540, stabilizers may be released. In some embodiments, the stabilizers are released below the edges of the leaflets. In a fifth step 1585, the diameter of the receiver bottom 1560 is increased, to help position the stabilizers (e.g., further outward). In some embodiments, the positions of the stabilizers may correspond to the P1 and P3 regions of the heart. In a sixth step 1590, the tips of the A2 and P2 clips are seated against annulus. And in a seventh step 1595, the flange is released over the annulus.

Figure 50:
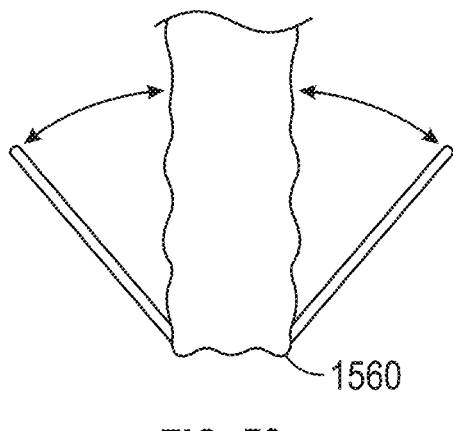
FIGS. 50-55 generally illustrate exemplary steps of deploying leaflet clips and stabilizers according to embodiments of a valve replacement as disclosed herein.
Figures 51, 52, 53:
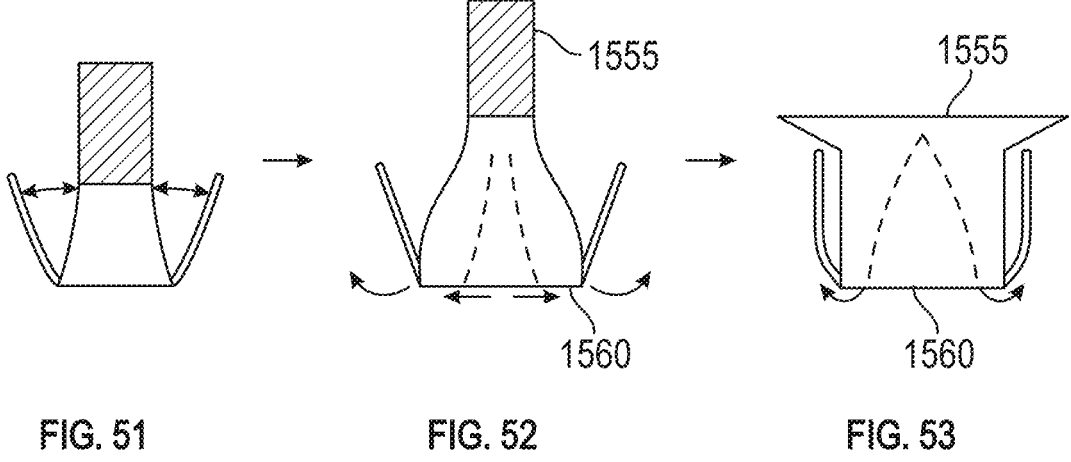

FIGS. 50-55 shows step-by-step of deployment arms/clips. FIG. 50 shows the initial release of the clips, prior to the expansion of the receiver bottom 1560. FIG. 51 shows the receiver bottom begin to expand laterally. FIG. 52 shows that after the clips release, and the receiver bottom continues to expand in a lateral direction, the clips after expand in a lateral direction with the rest of the receiver bottom 1560.

FIG. 53 shows that as the body expands further, including the top portion of the receiver 1555, the clips are directed into more vertically upright positions, resulting in less space between the receiver body and the clips. In some embodiments, the period between extension of the clips and the clips arriving at the upright position is referred to a capture window for capturing leaflets. Accordingly, the expansion of the receiver bottom 1560 first may increase capture window of the clips. Moreover, due to the final position of the clips, which can be upright or angled with a predetermined or residual angle, once the clips capture the leaflets during the capture window, the leaflets are more easily retained/secured in place due to the diminished/tighter space between receiver body wall and the clips, due to the expansion of the receiver, which then occupies more space.

Figures 54, 55:
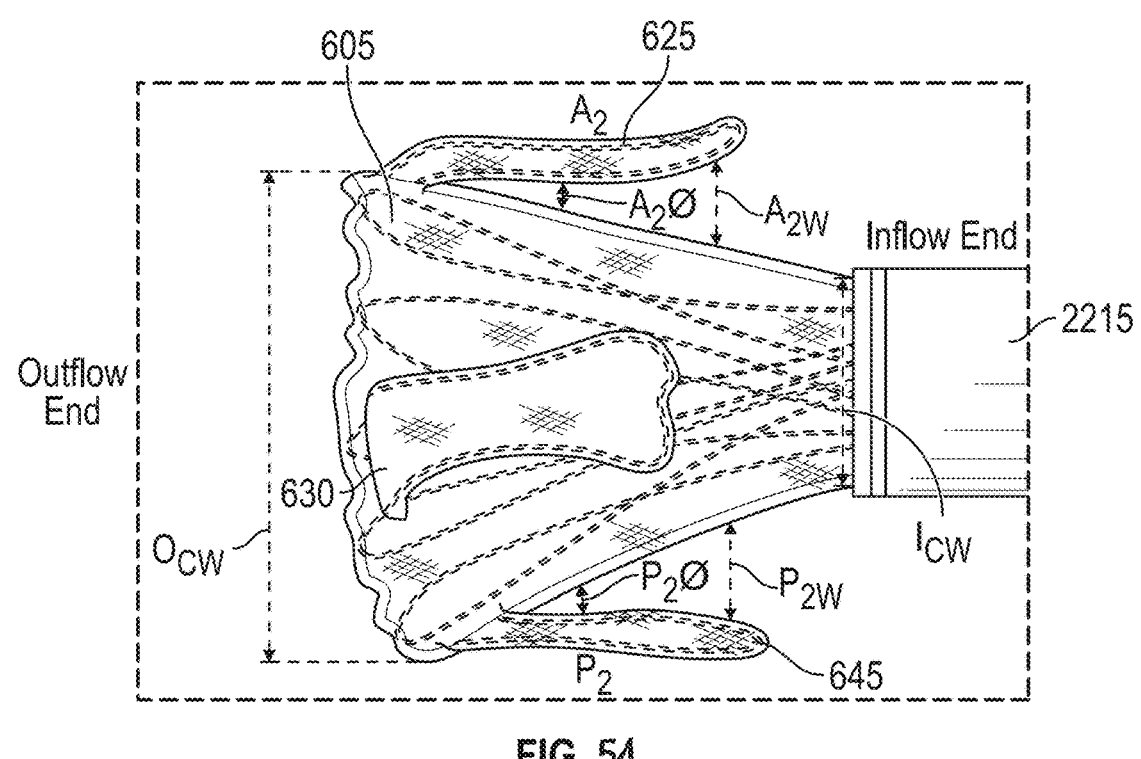

FIGS. 54 and 55 show expansion of embodiments of the replacement valve from a delivery tube. In an embodiment of the braided replacement valve, the receiver's tubular body 605 and flange 610 are compressible to a small diameter—such as 6 mm to 10 mm—such that they are delivered through a delivery tube 2215 that is between no more than 26Fr to 30Fr in inner diameter. For example, in embodiments, the replacement valve's receiver 605 can have an inner diameter of at least 30 mm in an uncompressed while deliverable to a native mitral valve in a compressed configuration that is no more than 28Fr in inner diameter (for example through a delivery tube 2215 that is no more than 28Fr in inner diameter). In other embodiments, the replacement valve's receiver 605 can have an inner diameter of at least 29 mm while deliverable to a native mitral valve in a compressed configuration that is no more than 26Fr in inner diameter (for example through a delivery tube 2215 that is no more than 26Fr in inner diameter). In other embodiments, the replacement valve's receiver 605 can have an inner diameter of at least 32 mm while deliverable to a native mitral valve in a compressed configuration that is no more than 30Fr in inner diameter (for example through a delivery tube 2215 that is no more than 30Fr in inner diameter). In other embodiments, the replacement valve's receiver 605 can have an inner diameter of at least 32 mm while deliverable to a native mitral valve in a compressed configuration that is no more than 28Fr in inner diameter (for example through a delivery tube 2215 that is no more than 28Fr in inner diameter). In embodiments, the replacement valve can have a flange width B1 in the M-L direction (B1 embodiments include 54 mm, 58 mm, 62 mm, 63 mm) and an inner diameter of the receiver body 605 of at least 32 mm while deliverable to a native mitral valve in a compressed configuration that is no more than 28Fr in inner diameter (for example through a delivery tube 2215 that is no more than 28Fr in inner diameter) and in other embodiments with these valve dimensions in a compressed configuration that is no more than 30Fr in inner diameter (for example through a delivery tube 2215 that is no more than 30Fr in inner diameter).

FIGS. 54 and 55 show partial deployment of the replacement valve such that the outflow end of the receiver 605 has been pushed out of the delivery tube 2215 and the stabilizers 630 and clips 625/645 have been released prior to the release and expansion of the receiver's 605 inflow end and flange 610. In this partially deployed configuration, the outflow end of the receiver 605 is not constrained and the inflow end is compressed in the delivery tube 2215. In this partially deployed configuration, with the inflow end in a compressed configuration, the capture window for the clips and stabilizers is greater than then fully deployed configuration, thereby providing additional room during delivery to properly place the clips and stabilizers in desired locations in the native anatomy prior to releasing the inflow end and fully releasing and deploying the replacement valve. For example, in embodiments, in a partially deployed configuration with the inflow end compressed and the outflow end released, a receiver 605 with an effective orifice area Ocw of 32Fr (10.6 mm) is being deployed from a delivery tube having an inner diameter of 28Fr. In this embodiment, the capture window between the A2 clip and the receiver is between 4 mm to 10 mm in width A2W from clip to receiver and between 15 to 30 degrees in angle A20 between clip to receiver, with embodiments having a capture window width A2W of between 4 mm to 6 mm and a capture window angle A20 of between 20 to 25 degrees. Similarly, the capture window between the P2 clip and the receiver is between 4 mm to 10 mm in width P2W from clip to receiver and between 15 to 30 degrees in angle P20 between clip to receiver, with embodiments having a capture window width P2W of between 4 mm to 6 mm and a capture window angle P20 of between 20 to 25 degrees. For the stabilizers 630, in this embodiment, the capture window between the first stabilizer and the receiver is between 4 mm to 10 mm in width SW1 from stabilizer to receiver and between 20 to 50 degrees in angle SO1 between the stabilizer and receiver, with embodiments having a capture window width SW1 of between 6 to 8 mm and a capture window angle A20 of between 30 to 40 degrees. Similarly, the capture window between the second stabilizer and the receiver is between 4 mm to 10 mm in width SW2 from stabilizer to receiver and between 20 to 50 degrees in angle SO2 between stabilizer to receiver, with embodiments having a capture window width SW2 of between 6 mm to 8 mm and a capture window angle SO2 of between 30 to 40 degrees.

Figures 56, 57:
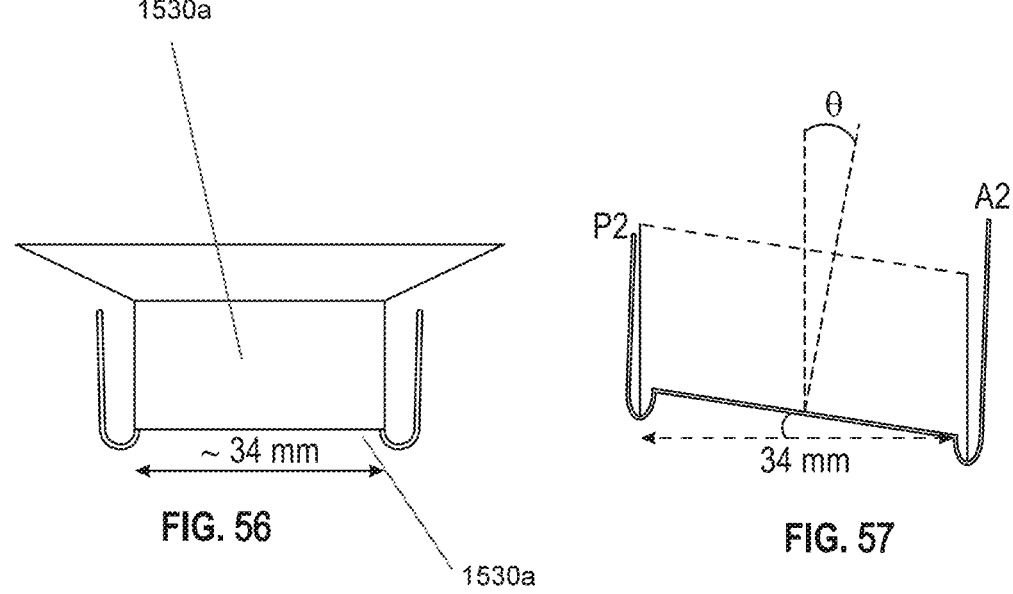
FIGS. 56-59 generally illustrate embodiments of a valve replacement as disclosed herein.

FIG. 56 shows a valve embodiment 1530a with particular dimensions, which may be a "floating valve." For example, post-expansion, valve embodiment 1530a may have a valve body roughly equal to the receiver bottom 1560a, with a diameter/width of 34 mm (plus or minus 3-5 mm). In some embodiments, a valve embodiment 1530a with a diameter/width of 34 mm is smaller than the size of an annulus, which has been measured in patients as having a native annulus diameter/width as between 38 mm and 41 mm (as measured from both the A-P and C-C directions). In other embodiments, where the replacement valve size is 34 mm OD and the native annulus is less than 34 mm (plus or minus 2-3 mm in embodiments and 27 mm in smaller embodiments), the valve embodiment 1530a still functions under radial pressure due to the replacement valves braided architecture crush resistance, minimal radial oversizing, and accommodation/funneling of the flange. Moreover, in smaller native annulus, replacement valve embodiments with a 34 mm OD (plus or minus 2-3 mm in embodiments) still "float" when deployed because the native annulus is not uniform, which has been measured in patients as being 33-35 mm in the A-P direction and 38-40 mm in the C-C direction. As a result, the valve body of the valve embodiment 1530a floats within the native annulus from not having a uniform contact around the perimeter of the replacement valve within the native annulus. In embodiments, the tubular body of the replacement valve is undersized in comparison to a native mitral annulus of a native mitral valve in one of more of an anterior-to-posterior (A-P) and commissure-to-commissure (C-C) directions, wherein the tubular body does not exert radial force against the native annulus in the undersized directions when deployed in the native mitral valve.

Further, with the annulus engaging with the tips of the clips and the flange, the receiver body of the valve embodiment 1530a need not directly contact the annulus. A floating valve will minimize damage to, ovalization of, the valve from heart tissue crushing the valve along the A-P axis. For some smaller patients, chordal tension across, the valve may still occur at the leaflet/LV level, but without propping open the annulus and preventing natural basal wall motion. In embodiments, the posterior positioning of the replacement valve due to low posterior projection of the P2 clip (<6 mm) and flange conformability also promotes vortex flow and protects the LVOT.

FIG. 57 shows an angle of tilt of the deployed replacement valve relative to the native mitral annulus with the tilt angle tilting towards the posterior side of the ventricle. As mentioned above, this posterior tilt angle may assist in creating a vortex flow and also aids in reducing LVOT obstruction by reducing the replacement valve's ventricular projection into the LVOT region on the anterior side of the native anatomy.

Figure 60:
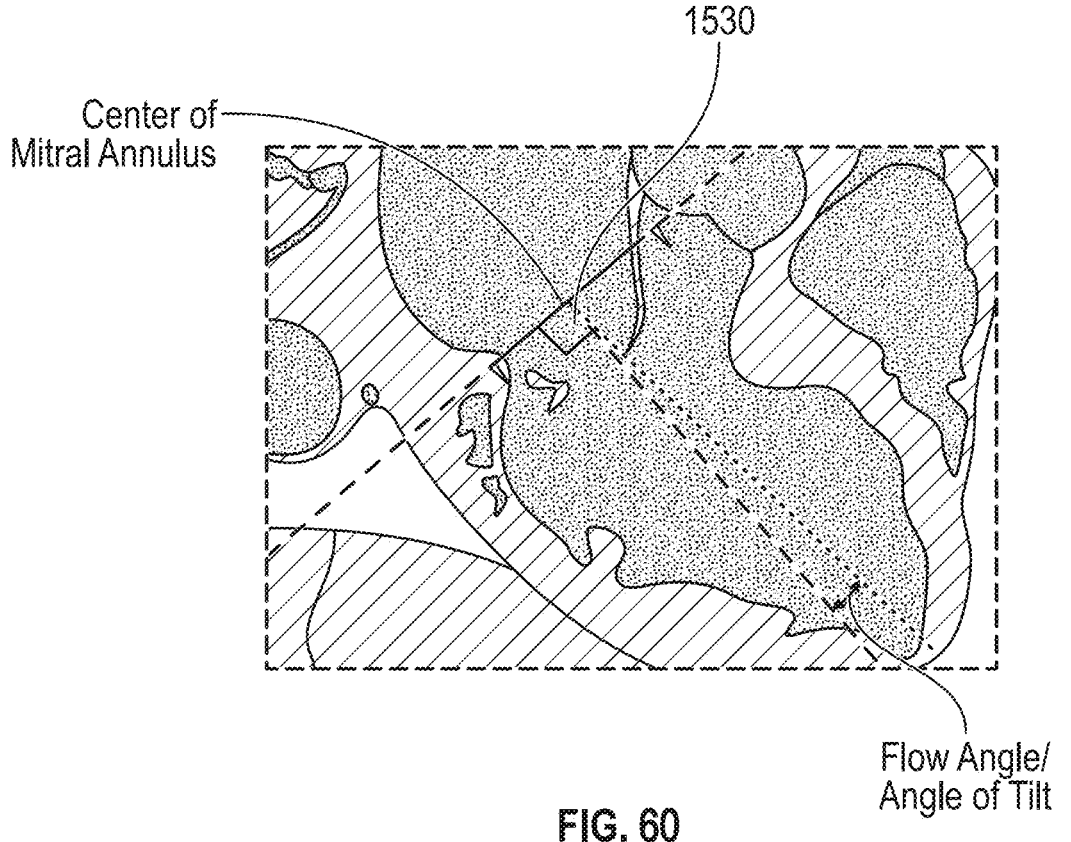
FIG. 60 generally illustrates an example image of a posterior tilt of an embodiment of a valve replacement as disclosed herein.

In some examples, a valve tilt/angle may be between 0 and 30 degrees relative to the mitral annulus. FIG. 60 shows an example image of angle offset measurement between the left ventricular apex and mitral annulus. In some embodiments, the calculated angle of tilt may be based on factors in addition to leaflet lengths, such as factors related to apex positioning, native annular anatomy, whether a flange will conform, and on clip lengths. For example, anterior and posterior leaflet clip length can be reduced or increased as well as where along the height of the receiver where the anterior and posterior leaflet clips exit the receiver, thereby affecting how deep into the leaflet clip the native leaflet sits within the leaflet clip (e.g., the higher the takeoff point is for the leaflet clip along the height of the receiver, the sooner the A2 or P2 native leaflets will hit the bottom of the corresponding anterior or posterior leaflet clip at its drop loop). In embodiments, the anterior leaflet clip (also called an A2 clip or A2 leaflet clip) and posterior leaflet clip (also called a P2 clip or P2 leaflet clip) can vary in length (also called the clip height, e.g., A2 clip height R1 and P2 clip height S1), including clip lengths that correspond to the native A2 and P2 lengths, plus or minus 5 mm, including embodiments with anterior or posterior clip lengths between 8 mm to 20 mm, including embodiments with 8 mm, 10 mm, 14 mm, 15 mm, and 20 mm (plus or minus 5 mm), as well as variations in the angle between the anterior or posterior leaflet clips and the receiver body, including angle ranges between 5 degrees to 25 degrees and embodiments with less than 25 degrees (plus or minus 5 degrees). Note that in FIG. 57, the anterior leaflet clip (A2 clip) is depicted as longer than the posterior leaflet clip (P2 clip). In embodiments, the A2 and P2 clips are the same length, in other embodiments the P2 clip is longer than the A2 clip, and in other embodiments the A2 clip is longer than the P2 clip.

In embodiments, the posterior tilt of the replacement valve is determined by the length of the native anterior and posterior leaflets in comparison to the heights (or lengths) of the replacement valve's anterior and posterior leaflet clips. For example, in an anatomy having average native leaflet lengths (native A2 length of 20.6 mm and native P2 length of 12.9 mm), a replacement valve with a posterior leaflet clip 645 shorter than the native P2 length (e.g., a posterior leaflet clip with a height of 8 mm) will have a larger angle of posterior tilt from the mitral valve (e.g., a posterior tilt angle of 12.8 degrees assuming a 34 mm inner diameter prosthetic valve dimension). In comparison, in that same anatomy having average native leaflet lengths (native A2 length of 20.6 mm and native P2 length of 12.9 mm), a replacement valve with a longer posterior leaflet clip 645 closer in length to the native P2 length (e.g., a posterior leaflet clip with a height of 14 mm) will have smaller posterior tilt from the mitral valve (e.g., a posterior tilt of 11 degrees assuming a 34 mm inner diameter prosthetic valve dimension). This difference of posterior tilt angle comes from, for example, the annular contact point of the posterior leaflet clip relative to the native P2 leaflet and annular contact point in the ventricle of the tip of the posterior leaflet clip.

In other examples, a longer native A2 leaflet length captured by an anterior leaflet clip 625 can also affect the posterior tilt of the replacement valve, with a longer native A2 leaflet pushing the anterior leaflet clip 625 and the replacement valve in the posterior direction. For example, in an anatomy having a longer than average native A2 leaflet length (native A2 length of 23 mm) and a shorter than average native P2 leaflet length (native P2 leaflet length of 11 mm), a replacement valve with a posterior leaflet clip 645 shorter than the native P2 length (e.g., a posterior leaflet clip with a height of 8 mm) and an anterior leaflet clip 645 shorter than the native A2 length (e.g., an anterior leaflet clip with a height of 15 mm) will have a larger angle of posterior tilt from the mitral valve (e.g., a posterior tilt angle of 19.4 degrees assuming a 34 mm inner diameter prosthetic valve dimension). In comparison, in that same anatomy having a longer than average native A2 leaflet length (native A2 length of 23 mm) and a shorter than average native P2 leaflet length (native P2 leaflet length of 11 mm), a replacement valve with a posterior leaflet clip 645 longer than the native P2 length (e.g., a posterior leaflet clip with a height of 14 mm) and an anterior leaflet clip 645 shorter than the native A2 length (e.g., an anterior leaflet clip with a height of 15 mm) will still have an above average angle of posterior tilt from the mitral valve (e.g., a posterior tilt angle of 14.8 degrees assuming a 34 mm inner diameter prosthetic valve dimension) because the native A2 leaflet is longer than average and will push the anterior leaflet clip and replacement valve in the posterior direction. In embodiments, a posterior tilt for a replacement valve in normal anatomy (e.g., an A2 length of between 17 mm to 23 mm and a P2 length of between 11 mm to 13 mm) with a posterior leaflet clip of between 10 mm to 18 mm will be between 2 degrees and 25 degrees, and in embodiments, the posterior tilt will be between 5 degrees and 20 degrees, with embodiments having a posterior tilt of 10 degrees and 15 degrees. In embodiments, the replacement valve tilt and ventricular projection is accomplished by, including but not limited to, the annular contact point of the P2 clip relative to the native P2 leaflet and annular contact point in the ventricle of the tip of the P2 clip as well as the stabilizers (medial and lateral) landing behind the posterior leaflet and within the saddle shape of the annular plane in the ventricle, combined with the larger A2 leaflet captured by the A2 clip and slightly pushing the replacement valve in the posterior direction, as described in greater detail in this disclosure. In addition to tilt, in embodiments, the posterior position of the replacement valve provides decreased ventricular projection. For example, in embodiments where the P2 clip has a smaller or minimal distance from the valve body (i.e., a smaller distance between the P2 clip and the receiver body when deployed), the replacement valve will have a more posterior position when deployed in the native mitral valve. In embodiments, the braided wire of the replacement valve also allows for the clips (including the P2 clip) to bend inward as they interact with the native wall (e.g., LV wall), further decreasing the posterior distance. A low profile on the posterior side of the replacement valve allows the replacement valve to be closer to the native posterior wall with a posterior tilt combined with proximity to the native posterior wall coming from clip distance from the receiver body. In embodiments (including as shown in FIGS. 3, 4, 5, 27, 28) the distance between the clip to the receiver body is between 2 mm to 6 mm, including embodiments with the distance between the clip and the receiver being 2 mm, 2.5 mm, 3 mm, 3.5 mm, 4 mm, 4.5 mm, 5 mm, 5.5 mm, and 6 mm. In embodiments, the A2 clip has a distance between the A2 clip and the receiver being between 2 mm to 4 mm and the P2 clip has a distance between the P2 clip and the receiver being between 4 mm to 6 mm. In embodiments, the stabilizer distance to the clips (A2 or P2 depending on the embodiments) is between 2 mm to 10 mm. In some embodiments, the height difference between the clip tip height and the stabilizer height is between 0 mm to 6 mm, including embodiments with a height differential of 0 mm, 0.5 mm, 1 mm, 1.5 mm, 2 mm, 2.5 mm, 3 mm, 3.5 mm, 4 mm, 4.5 mm, 5 mm, 5.5 mm, and 6 mm.

The flow angle of the replacement valve into the ventricle relative to the native mitral annulus is important as that mimics the way the native leaflets open and allow flow to move posteriorly. FIG. 60 shows the flow angle measured from the angle of a plane defined by the annulus to the native apex to the tilt of the replacement valve biased and tilted posteriorly in the ventricle (from the A2 and P2 clips and medial and lateral stabilizers). The angle of tilt of the replacement valve as deployed in the native mitral annulus is 4 degrees (plus or minus 3 degrees) relative to the annulus (as reflected in the table above). In other embodiments, the angle of tilt of the replacement valve as deployed in the native mitral annulus is 20 degrees (plus or minus 3 degrees), 15 degrees (plus or minus 3 degrees), 12 degrees (plus or minus 3 degrees), 8 degrees (plus or minus 3 degrees, 6 degrees (plus or minus 3 degrees) or 3 degrees (plus or minus 3 degrees) relative to the annulus. In embodiments, the tips of the stabilizers are up to 6 mm below the tip of the P2 clip, thereby enabling the tilt discussed above.

Figure 59:
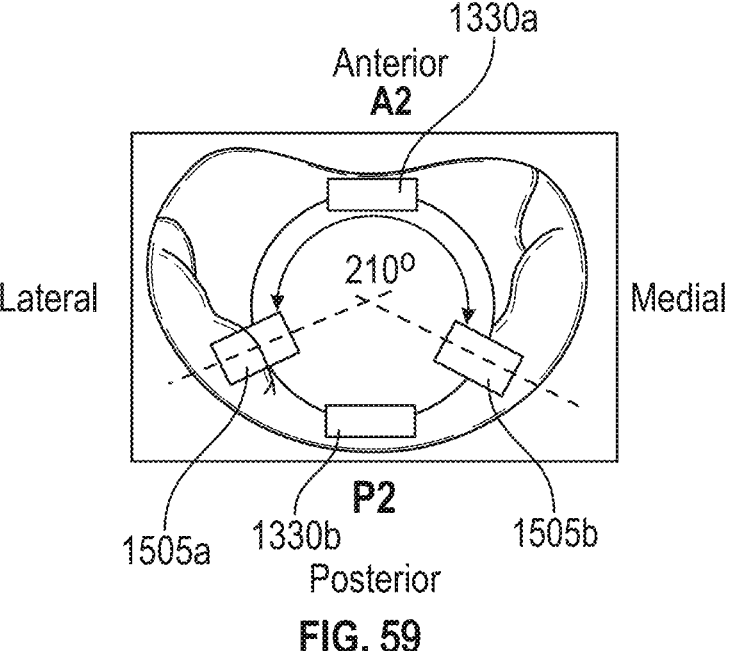

FIGS. 58 and 59 show how the positions of stabilizers and clips may be defined/described/measured in various ways, e.g., by determining the angles therebetween. In some embodiments, such angles and positions may be configured to ensure avoidance of interaction with either the anterior leaflet or major chords leading to the anterior leaflet.

In some embodiments, the distance or diameter from the medial and lateral anchors 1505a, 1505b to the anterior and posterior clips 1330a, 1330b may be in a range of 65° to 115°, and not necessarily 90°, and in some embodiments about 75°, from each other. In some examples, the design of the device 1530b is such that the medial and lateral anchors 1505a, 1505b and the anterior and posterior clips 1330a, 1330b are spaced so that appropriately grabbing the anterior and posterior leaflets 1535, 1540 using the clips 1330a, 1330b results in the medial and lateral anchors 2260, 2255 aligning with predesignated and proper positions for anchoring. Thus, unsheathing the anchors 1505a, 1505b assists in achieving full securement on the ventricular side.

For example, FIG. 58 shows a 150 angle between stabilizers off of an A2 clip, or 75 degrees to the right and 75 degrees to the left of the A2 clip, while FIG. 59 shows an opposite angle between stabilizers of 210 degrees.

Figure 61:
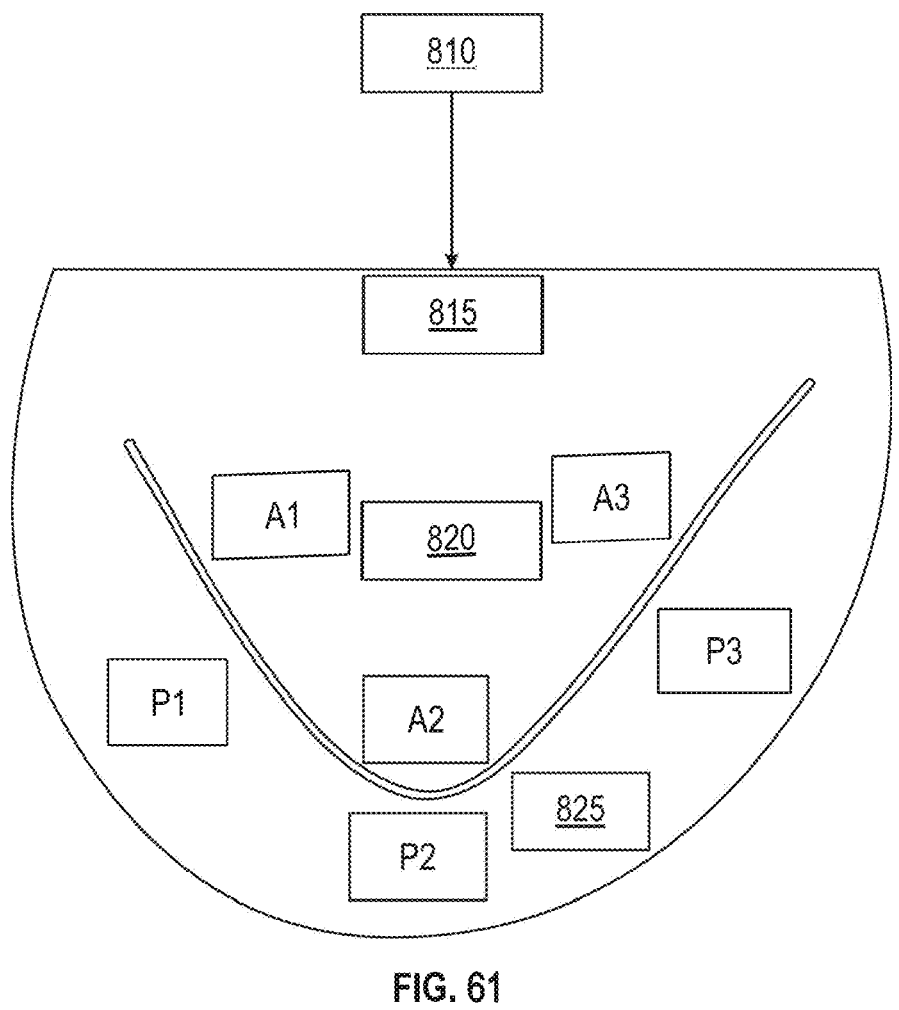
FIG. 61 generally illustrates areas of a native mitral valve as disclosed herein.

Other configurations may take into account features of the native anatomy, such as of the leaflets. For example, the A2 leaflet may be relatively large, strong, and structural, while P2 leaflet tend to be a bit thinner/shorter. FIG. 61 shows different regions of heart tissue. For example, FIG. 8G shows a diagram of an aortic mitral curtain 815, an anterior leaflet 820, and a posterior leaflet 825. The anterior leaflet 820 may be slightly larger than the posterior leaflet 825, as is typical for most human hearts. The anterior and posterior leaflets 820, 825 may also be divided into separate areas labeled, e.g., A2 and P2.

Accordingly, moving stabilizers to more posterior positions will provide additional support on that segment, as well as to the posterior annulus, while the A2 region may not need additional support. This also provides procedural redundancy as the P2 leaflet may be more difficult to visualize and capture.

FIG. 62 shows a close-up perspective view of a replacement heart valve 1530c with a flange sitting or connected at a point a below receiver top, and with stabilizers and clips situated at angles as described and shown above. In addition, FIG. 62 indicates an inflow end on the side of the flange and receiver top. FIG. 62 similarly indicates an outflow end opposite of the inflow end.

FIG. 63 shows a bottom view of a replacement heart valve 1530c, including showing the stabilizers at a particular angle from each other, and from clips. For example, in this embodiment, the medial and lateral stabilizers are 150 degrees separated from each other with the P2 clip symmetrically between the stabilizers (or 210 degrees separated from each other as measured relative to the A2 clip with the A2 clip symmetrically in between the medial and lateral stabilizers). Note that in embodiments, the leaflet clips wrap the native leaflets around the replacement valve body for sealing.

Figures 64, 65:
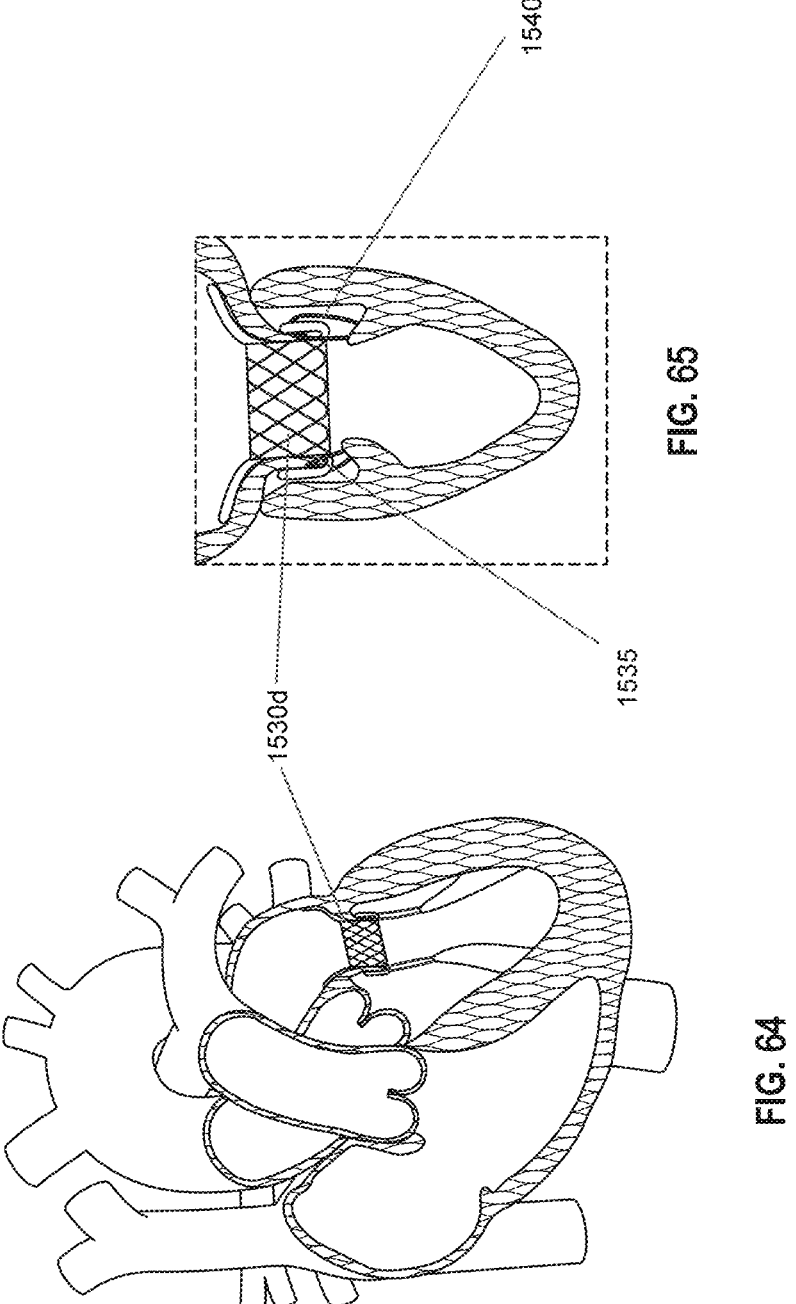

FIGS. 64 and 65 show deployment of a, and a deployed, heart valve 1530d, with FIG. 64 showing the A2/P2 clips and FIG. 65 showing the medial and lateral stabilizers, with both figures showing a final position of the replacement implant and how it is positioned (a) above the native papillary muscles, (b) with the native leaflets able to be positioned next to the replacement valve enabling sealing around the replacement valve, and (c) native chords being left intact or going around the replacement valve anchoring features.

As shown in FIG. 64, the stabilizers may begin to deploy in an outward and upright position. And as they are released (e.g., through pulling a suture wire/cord), as shown in FIG. 64, the stabilizers may extend outward further until touching the tissue of the mitral valve or ventricle sidewalls. In some embodiments, this may result is a space between the ventricle sidewalls or the mitral valve sidewalls and the receiver body, essentially allowing the heart valve 1530*d* to float in the mitral valve. This may have the benefit of avoiding "valve crush" at least in part, while also causing less trauma to surrounding tissue, and while also allowing some freedom of the heart valve 1530*d* to shift and move conforming to natural movements occurring in the heart, and without restricting those movements to some extent. FIG. 65 shows a close-up view of clips having captured the A2/P2 leaflets 1535, 1540.

Figure 66:
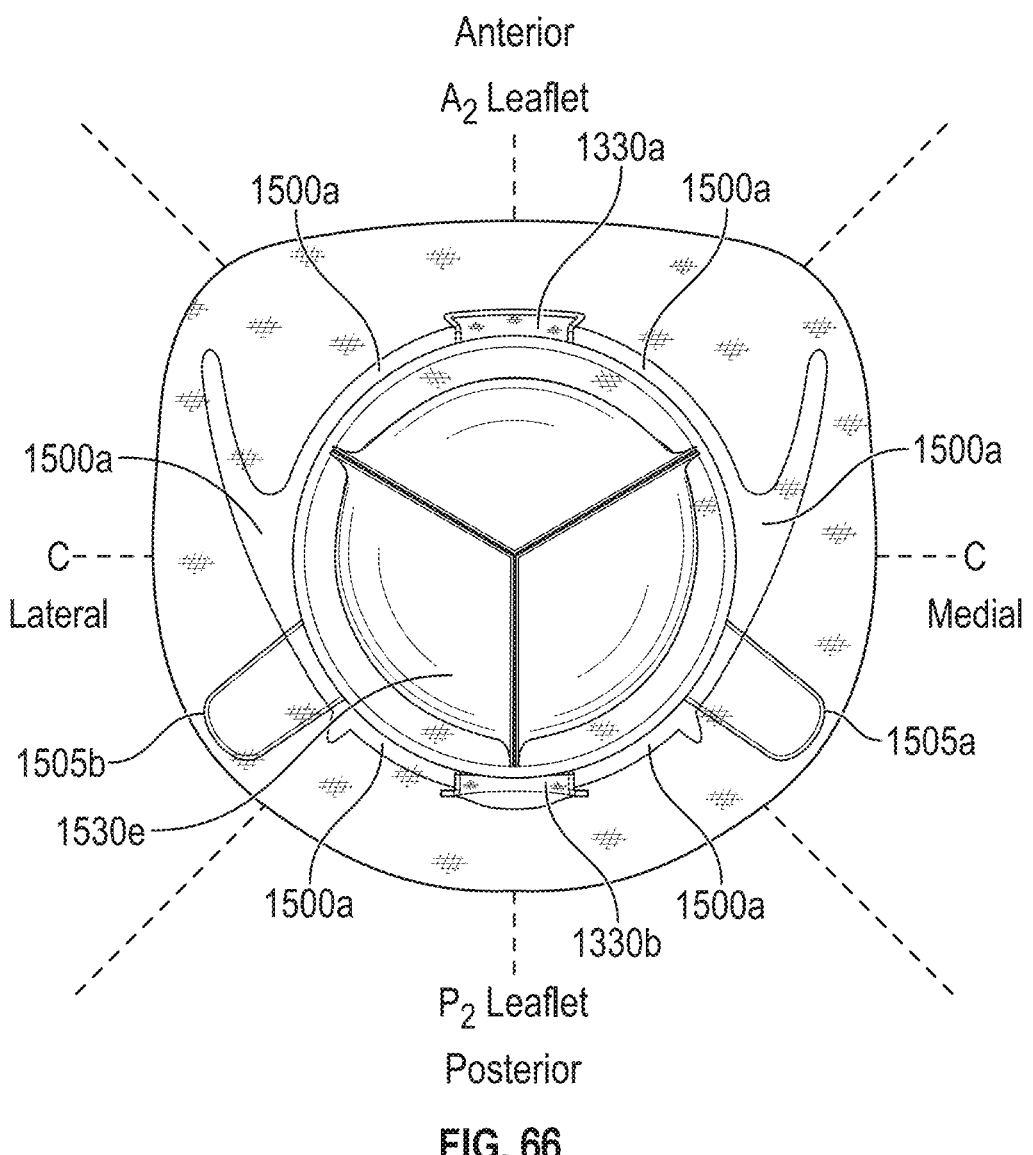
Figure 67:
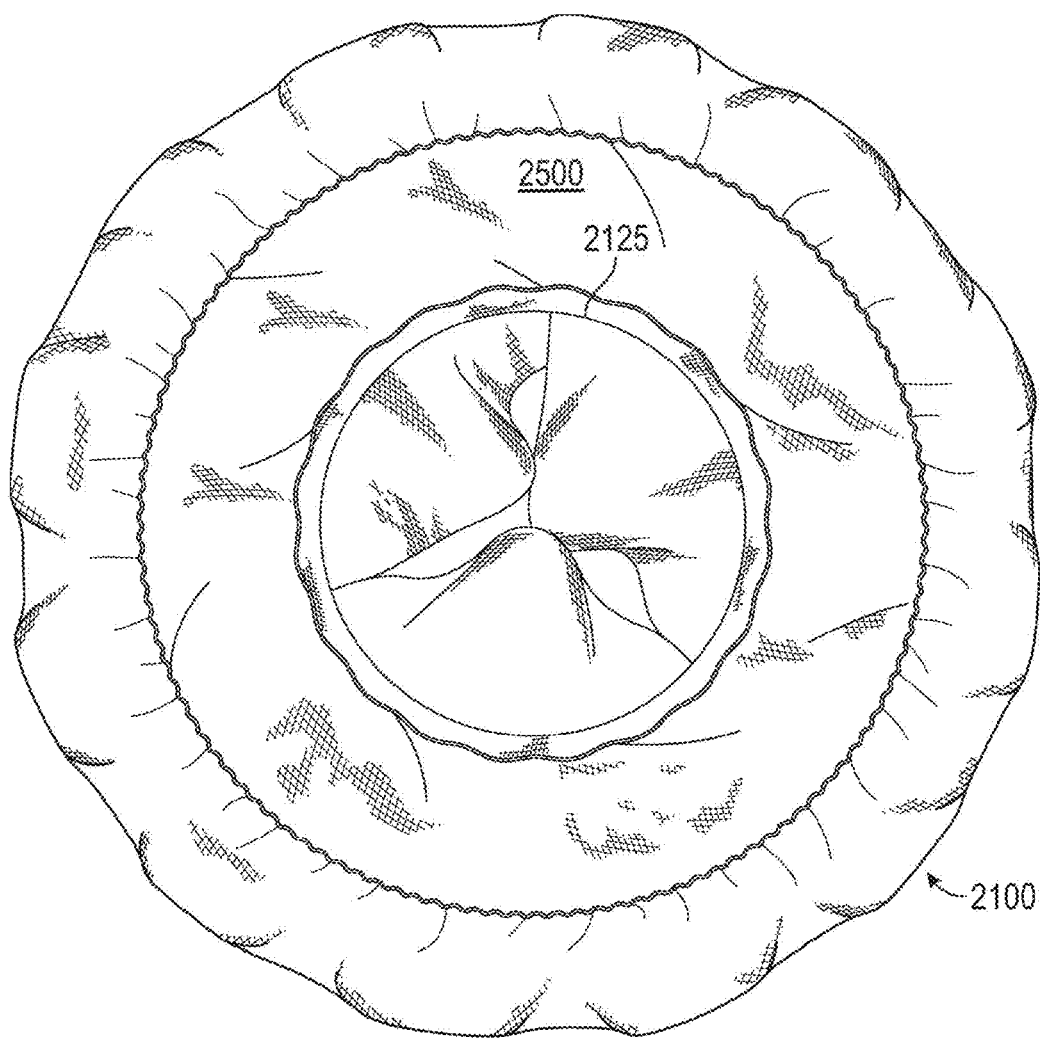
Figure 68:
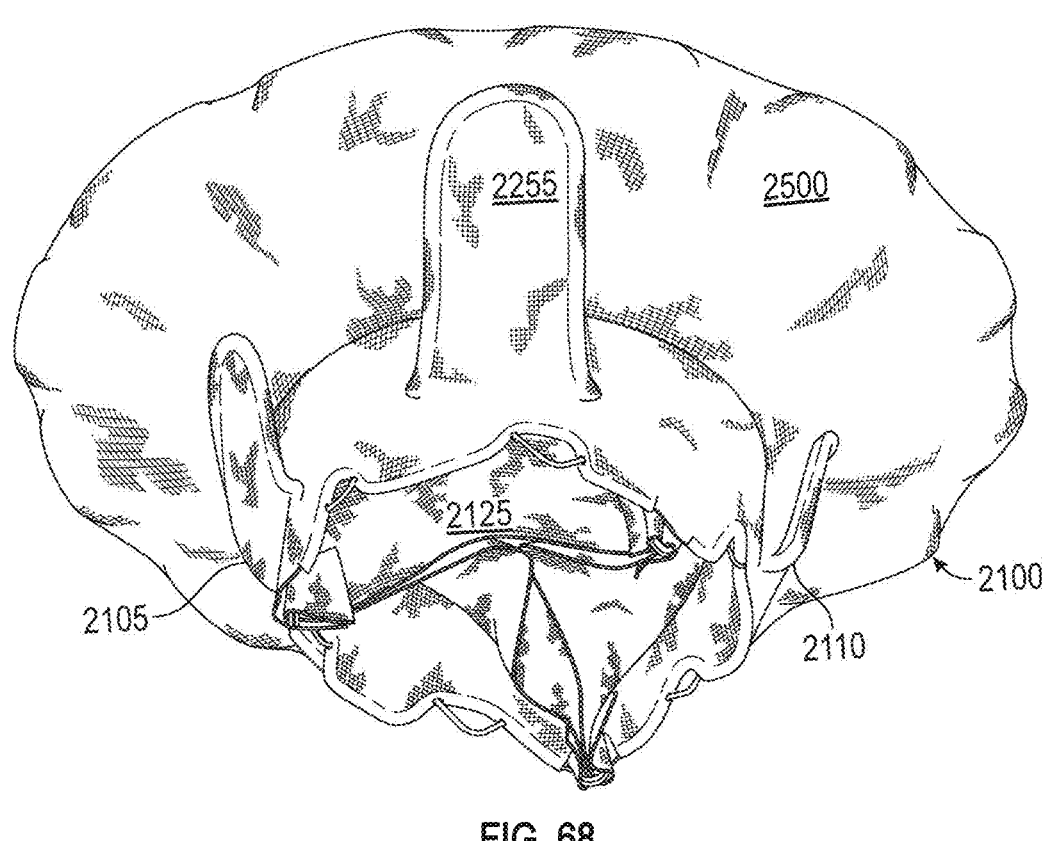
Figure 69:
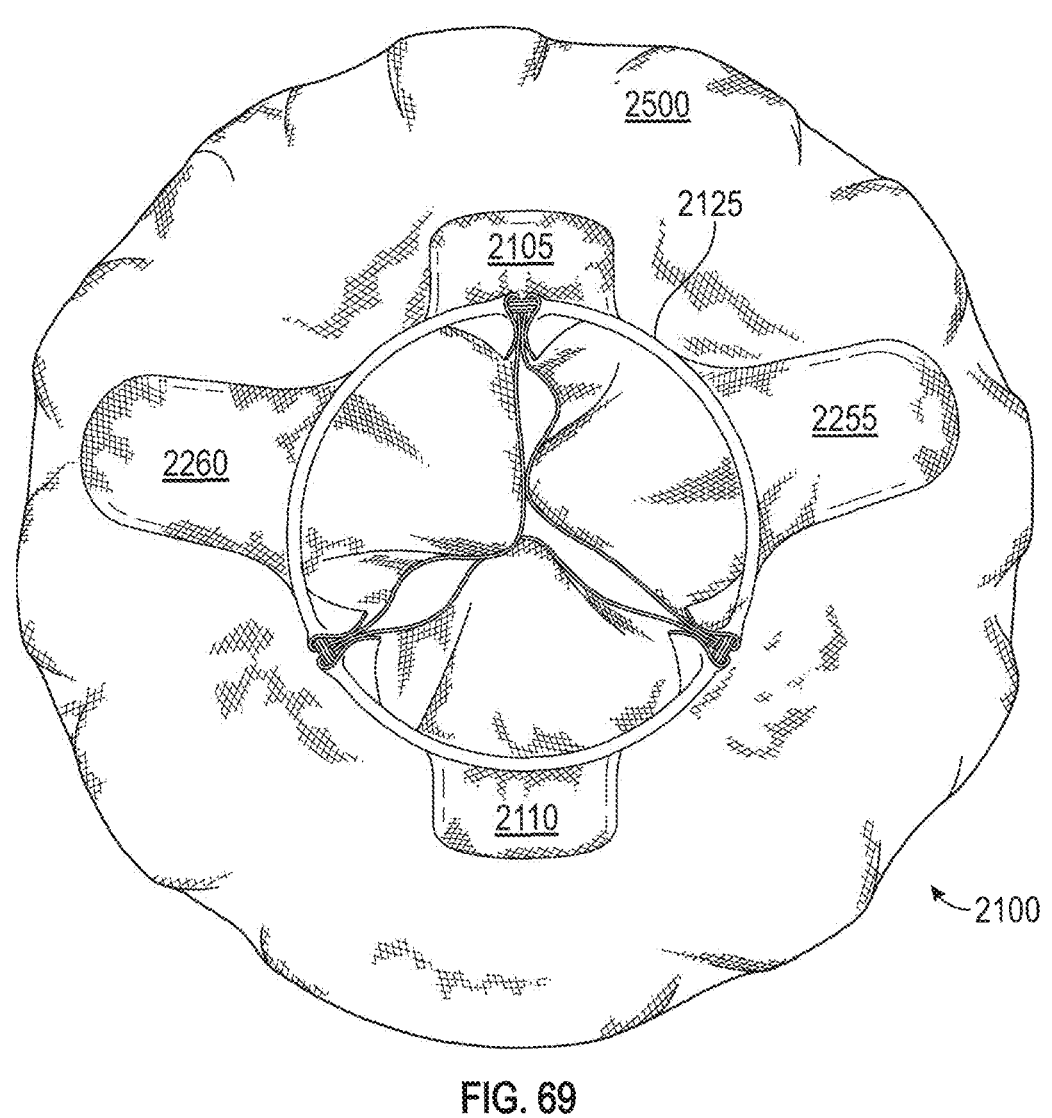
Figure 70:
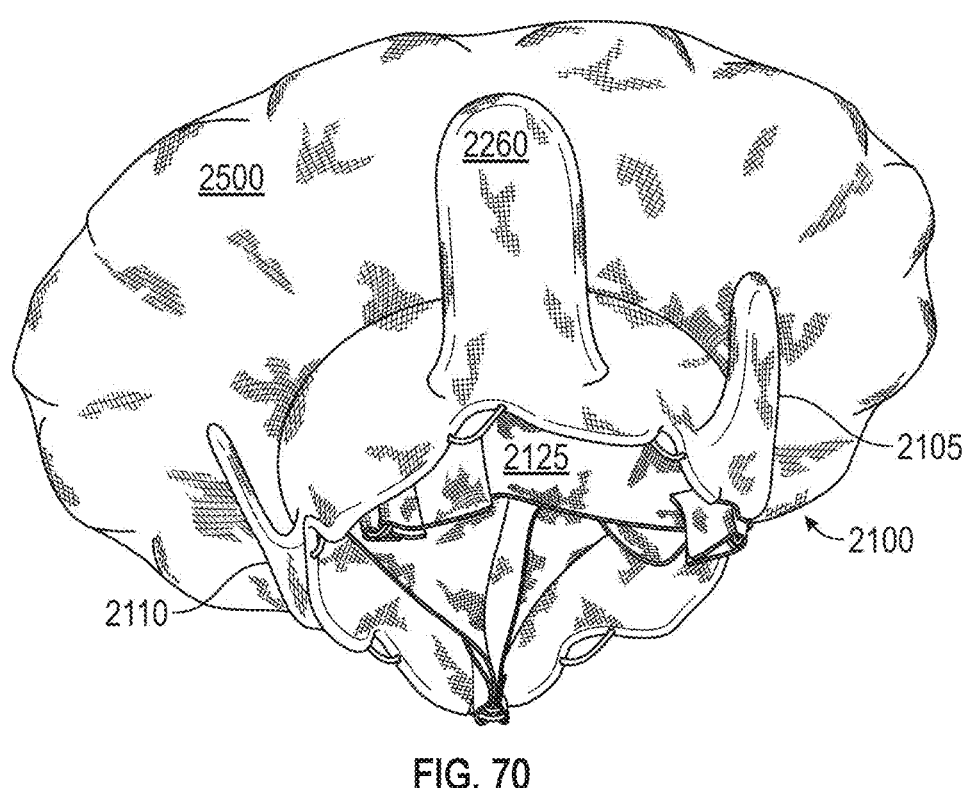

FIG. 66 shows a bottom view of a deployed heart valve 1530*e*. FIG. 66 further shows attachment of the heart valve 1530*e* and clips thereof with the A2 and P2 leaflets. FIG. 66 further shows stabilizers and a space 1500*a* between the ventricle sidewall tissue, or the sidewalls of the mitral valve, and the receiver body, bridged by the stabilizers. Accordingly, FIG. 66 shows the heart valve 1530*e* floating in the mitral valve and/or the upper portion of the ventricle chamber. FIGS. 50-57 also shows that the floating valve heart valve 1530*e* has a particular angle between stabilizers with respect to the clips, as described in more detail above. Moreover, due to the conformability of the braided wireframe implant, large size ranges of native anatomy may be accommodated from implantation in both the A-P and C-C direction.

In annuli with measurements less than the receiver outer diameter (34 mm in one embodiment), the receiver itself may ovalize or compress to accommodate the native annulus. This minimizes the floating effect of the valve in small anatomies, but the conformability allows for effective placement and adaptability to the native heart.

In annuli with measurements less than the flange effective diameter at the annular level (flange dimensions of 36-44 mm in one embodiment), the flange is designed to conform to the native heart size and motion. Due to the flexibility of the flange, minimal deformation of the receiver occurs, allowing the valve itself to "float" despite the flange contact with the annulus. This contact provides sealing in addition to redundant contact of the receiver and flange contours with native leaflet tissues. Additionally, the clips hang behind the native A2 and P2 leaflets, providing anchoring without deformation of the receiver. The stabilizers extend into the commissural sub-annular ventricular cavity, contacting mitral tissue, annulus, or left ventricular wall tissues. Based on published literature and internal anatomical analyses, on average the ventricular cavity is 5 mm larger than the annulus directly below the annular level. Based on this, the stabilizers may be designed to extend at a minimum 5 mm from the receiver and up to 15 mm depending on the anatomy to be treated. As a result, the stabilizers may extend in a commissural direction, engage tissue, and suspend the valve from the ventricular aspect. This suspension of the receiver occurs both with the clips and stabilizers, allowing the anchoring features to engage, and move with the native anatomy while not disrupting the performance of the bioprosthetic valve in the receiver.

In annuli with measurements larger than the flange effective diameter at the annular level (greater than 40 mm as an example), no direct annular contact is made with the flange at the annular level. Redundant tissue such as leaflets contact the receiver and flange to provide sealing, but the receiver is not deformed and thus floats within the anatomy. Clip and stabilizer distance from the valve may be modified to allow for proper suspension and engagement of the tissue for effective anchoring in these larger anatomies.

FIGS. 67-70 generally illustrate an embodiment of the valve replacement 2100 as disclosed herein. The valve replacement embodiment 2100 may show a system embodiment of and be used to perform method embodiments relating to TMVR.

Some solutions to TMVR described herein may utilize the valve replacement embodiment 2100 and involve several types of securement. For example, the valve replacement embodiment 2100 may feature one or more types of securement, and in some embodiments more than two securement mechanisms. For example, some valve replacement 2100 embodiments may utilize four-point securement. In some embodiments, such multipoint securement may be configured to distribute an implant's workload across an entire device by utilizing a combination of securement mechanisms. In contrast, some prior art devices may only utilize (or primarily use) the radial force (as described in more detail below)—essentially relying on "brute radial force"—for their positioning, securement, and sealing.

For example, one type is supra-annular securement. This may be accomplished in some embodiments through a flange being placed, clamped, or cinched onto the annulus or to ledges (e.g., mitral ledges) above the annulus. In embodiments, the flange may prevent migration into the ventricle and may be configured and/or designed to eliminate paravalvular leaks. Another type is sub-annular securement. Utilizing anchor features, which may be struts 2255, 2260 in some embodiments (and as described in more detail below), such securement may provide stability in the medial and lateral positions directly under the anatomy of the native heart valve in the sub-annular region. For example, in embodiments, the sub-annular anchors perform as struts or braces that permit slight movements of the valve replacement with the natural helical movement of the native heart, but constrains movement of the valve replacement, for example in medial and lateral positions or directions or in anterior and posterior directions, so that the valve replacement does not migrate into the atrium of the native heart or have paravalvular leaks.

Such sub-annular securement may also involve, or relate to, other anchor features, which may be clips for securing to native tissue, including leaflet securement. Some embodiments may thus utilize leaflet clips 2105, 2110. In some embodiments, the struts 2255, 2260 may be more elongated than the clips 2105, 2110, and jut outward farther from the device than the clips, with strut tips designed and/or configured to press against and jut into native anatomy (e.g., the trigone area). On the other hand, in some embodiments the clips might have a more curved shape, e.g., curving upward and bending inward toward the native leaflets, or otherwise similarly configured hold leaflets in place.

In some embodiments, the anchor features for securing native leaflets may be hangers, which may hang onto or capture the leaflets, rather than clips 2105, 2110 to clip onto the native leaflets. Such securement may prevent migration into the atrium and control movement of native leaflets. In some embodiments, and as described elsewhere herein, the aforementioned leaflet clips 2105, 2110 may be deployed before deployment of the struts 2255, 2260. Such sub-annular securement, for example, may be sufficiently restrictive enough to prevent the device embodiment 2100 from migrating into mitral area or creating leaks, yet loose enough to move with natural movement of the heart. Such movement, and in accordance with other aspects of this disclosure, may be facilitated by overlapping wire structure without many rigid fixed points. In embodiments, native leaflets may be captured by leaflet anchors or engagement attachment (e.g., clips), which in embodiments may hang on the native leaflets (rather than pinch the native leaflets) to prevent migration towards the native atrium, and anchor struts, which in embodiments transfer compressive loads to the native annulus or native anatomy near the native annulus in the inter-commissural zones below the annulus in the native ventricle area, to prevent migration into the native atrium.

With regard to leaflet securement, in some examples, different points in the native tissues may be associated with securement features. For instance, in some examples, the valve replacement embodiment 2100 may integrate four points for anchoring, sealing, and fixation. In the embodiment shown, two general points or regions of native leaflet tissue may be associated with two leaflet anchors or engagement attachment (e.g., clips) 2105, 2110 and two general points or regions of native tissue may be associated with two anchors or struts 2115, 2120. These multiple points of securement may provide stability while preserving the LVOT, preventing paravalvular leaks, and trauma to tissue associated with the native heart wall.

Such multi-point securement using the valve replacement embodiment 2100 may result in a highly flexible and conformable valving system. The system may encourage structural stability by preserving central flow through the valve.

Another type of securement is selective radial force securement. In some embodiments, directional radial force securement may be controlled through a receiver or adapter, which may assist in preventing migration while preserving the LVOT. Such radial force, in some examples, may be generated by oversizing a valve frame 2125 (e.g., a wrapped or braided nitinol wire frame around a mandrel) with respect to the annulus hole, pushing against the annulus walls. In some embodiments, the valve frame 2125 may be shape-set to about a 10% oversize in relation to the annulus hole, while permitting some limited movement. Such radial force securement may also prevent migration into the atrium and ventricle while preserving LVOT.

In addition, as explained elsewhere, the natural helical structures of features associated with valve frame 2125 embodiment may be based on the more holistic understanding of the nature of the heart and its motions. For example, such features may be configured to mimic the movement of a healthy heart using natural helical structures (as described above), by contracting and twisting with each beat of the heart.

Such features may include braided wire designs (as explained and shown elsewhere in more detail), which in some embodiments may offer increased flexibility and conformability. In addition to such braided wire design embodiments adapting to and moving with the heart, they may be configured to (by, e.g., integrating diverse and various wire thicknesses and braiding designs) forgive anatomical anomalies, and conform with various densities and characteristics (i.e., radial force and expansion) of the heart's anatomy.

Further, braided wire design embodiments may leverage nitinol strength through geometry and a unique braided wire architecture. Such architecture in some embodiments may purposely omit fixed nodes at crossing points of wires and permit the braided wires to move across one another in a controlled fashion. Such features may assist the replacement valve in moving with the natural helical movement of the heart. Some braided wire design embodiments may also facilitate placement in the native heart, maximize seal in the human anatomy, and prevent unwanted migration with an integrated and optimized novel securement system. Thus, such features may be designed based on recognition that the mitral valve is more than simply a structure to be "stented."

In contrast, some earlier valve frame designs by others (e.g., centering on laser cut nitinol on a lattice) may not feature such helical architecture or otherwise be configured for allowing similar dynamic movement. Rather, such prior art designs may often be limited to fixed nodes across a lattice design, or may not permit use of various wire thicknesses, thereby impeding the requisite flexibility and conformability for the human heart.

These different ways of securement (as mentioned above) may assist in distributing the valve replacement embodiment's 2100 (e.g., the implant's) workload across the entire device 2100, and may provide for maximum stability while preserving the LVOT and preventing paravalvular leaks and trauma to the native heart wall. In addition, such multiple ways of securement and multi-point anchoring systems may enable methods (as also described herein) allowing a simpler and more secure approach to Transcatheter Mitral valve replacement and resulting in a safer overall procedure for patients.

Delivery Method Embodiments

FIGS. 71-79 show embodiments of methods and/or systems for delivering a valve replacement, incorporating valve replacement embodiments such as valve replacement embodiment 2100.

Figure 71:
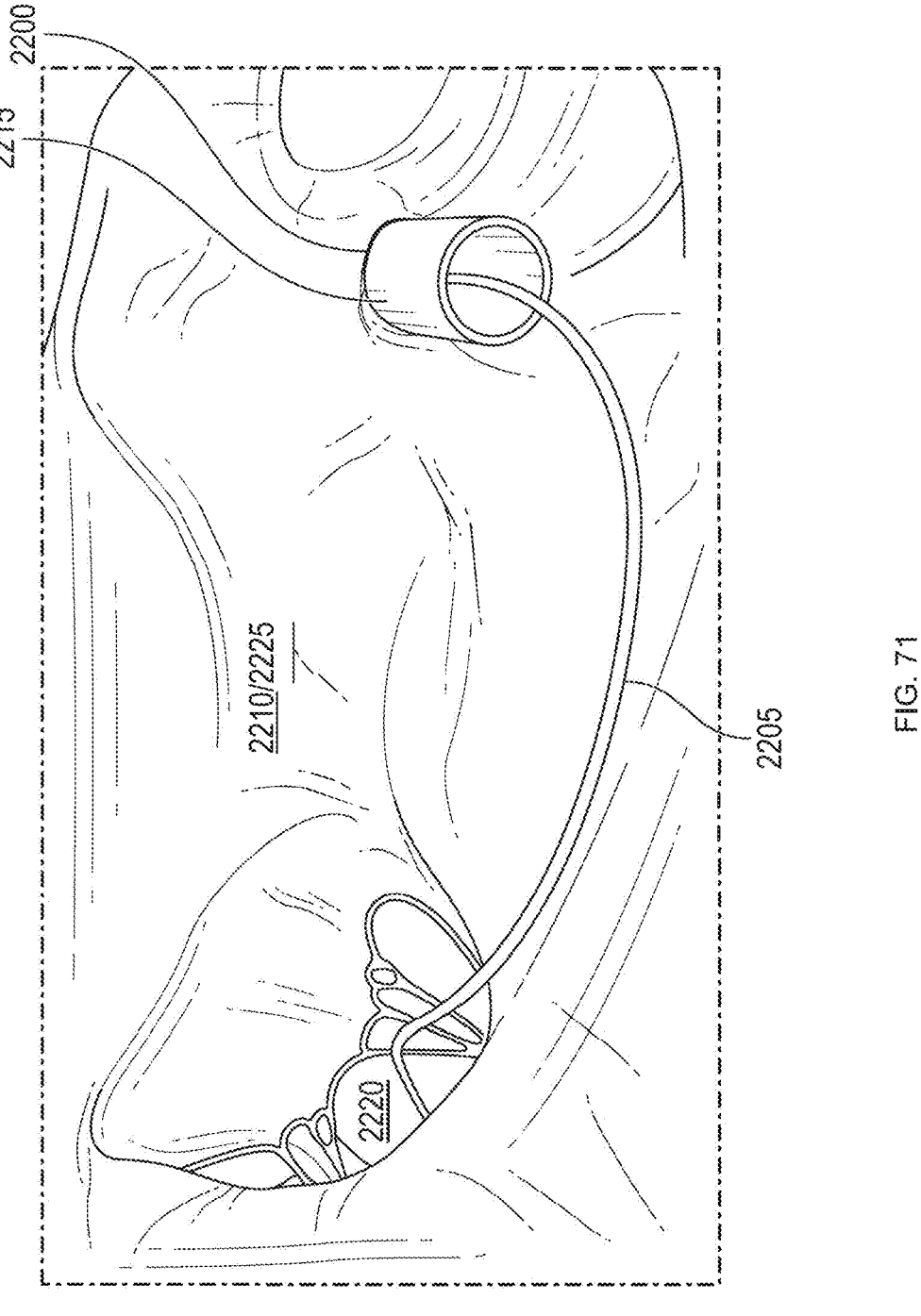
FIGS. 71-79 generally illustrate steps for deployment of embodiments of a valve replacement as described herein.

As an initial step of a method embodiment described herein, a sheathed valve/implant 2215 may be positioned over a mitral valve through a transeptal procedure. For example, FIG. 71 shows a transeptal puncture 2200 (in e.g., the transfemoral area) through which a guidewire 2205 may enter the left atrium 2210. The guidewire 2205 may be used by the method and/or system to assist in delivering a valve replacement, such as valve replacement embodiment 2100.

The method and/or system described herein may allow a broad plane of movement, allowing flection/deflection of the guidewire (and/or other delivery system components) in several directions, such as in the medial and lateral and anterior and posterior directions. Utilizing such directionality, the guidewire 2205 may also enter the mitral valve 2220.

Figure 72:
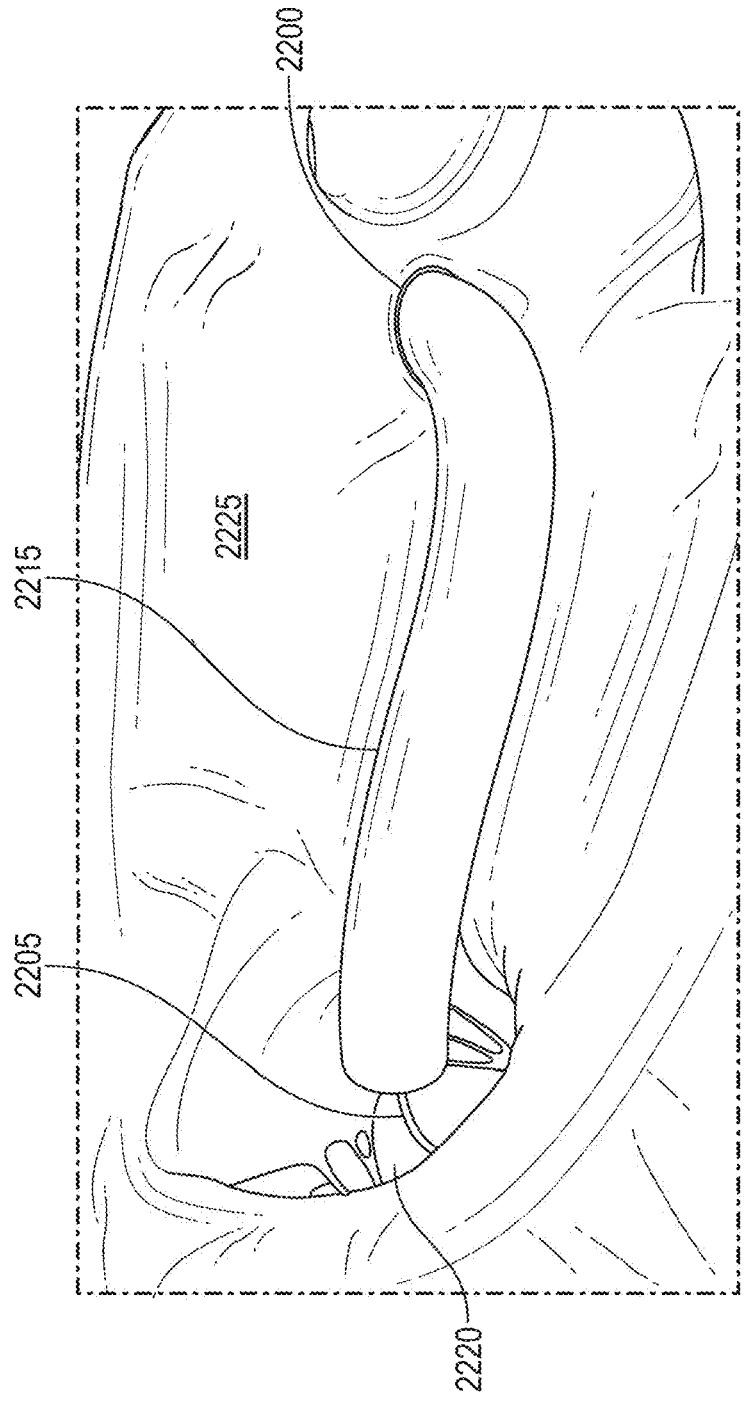

FIG. 72 shows next a sheathed valve/implant 2215 entering the atrium 2210 along the guidewire 2205.

Following the guidewire 2205, the sheathed valve/implant 2215 may be centered over the mitral valve 2220, in order to enter the ventricle 2225 over the wire 2205. Some embodiments of the delivery method described herein may also include verifying that there is clearance over the mitral valve 2220 and that there is proper flection for movement before further advancing downward. In some examples, the method may include tracking the sheathed valve/implant 2215 as it moves down through the native heart structure.

Figure 73:
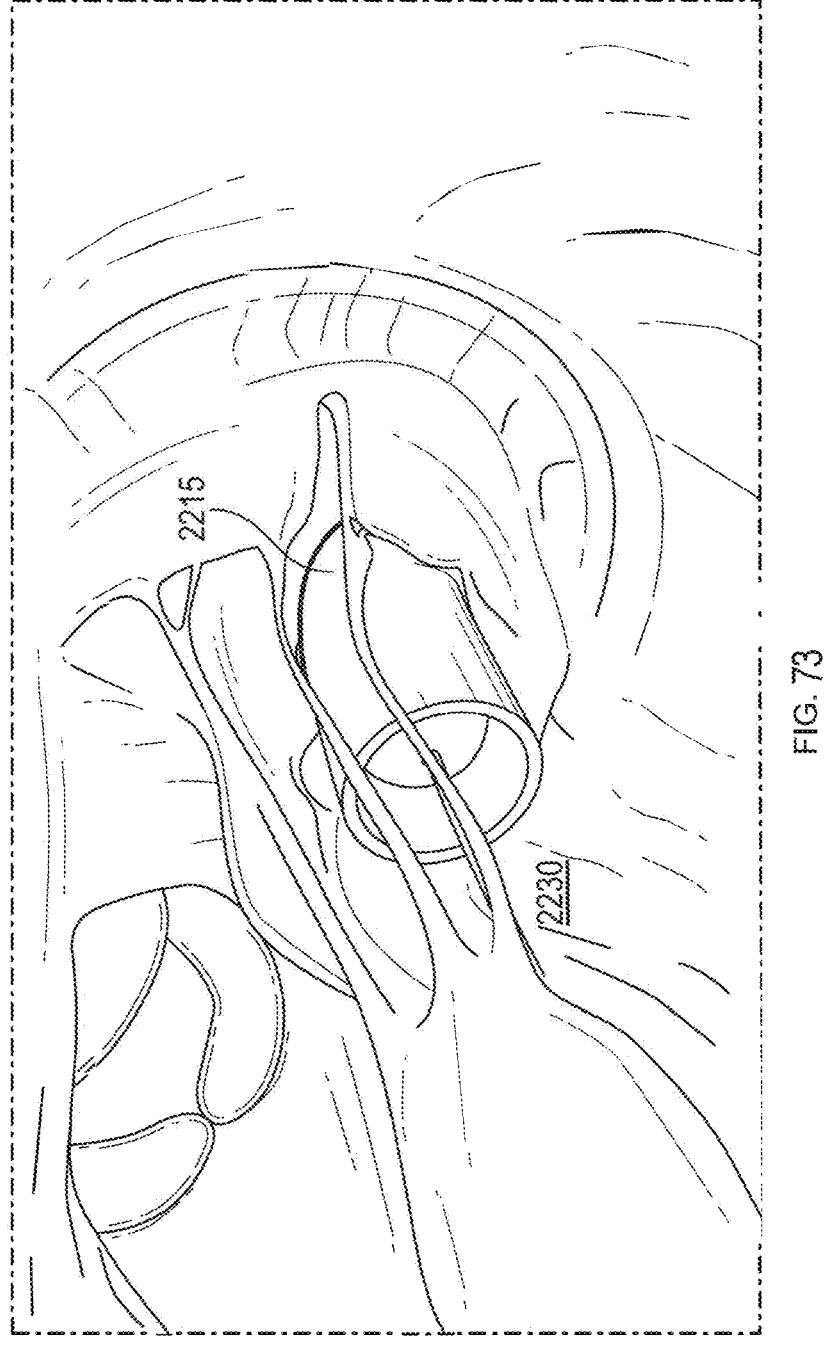

As shown in FIG. 73, the sheathed valve/implant 2215 may then be moved down into the ventricle 2230 from the septal puncture. Some method embodiments may include a step of testing a path or runway before moving further into the ventricle 2230, retracting, and then returning to move further down into the ventricle 2230, to ensure that the path is not obstructed and that a correct path has been chosen.

Figure 74:
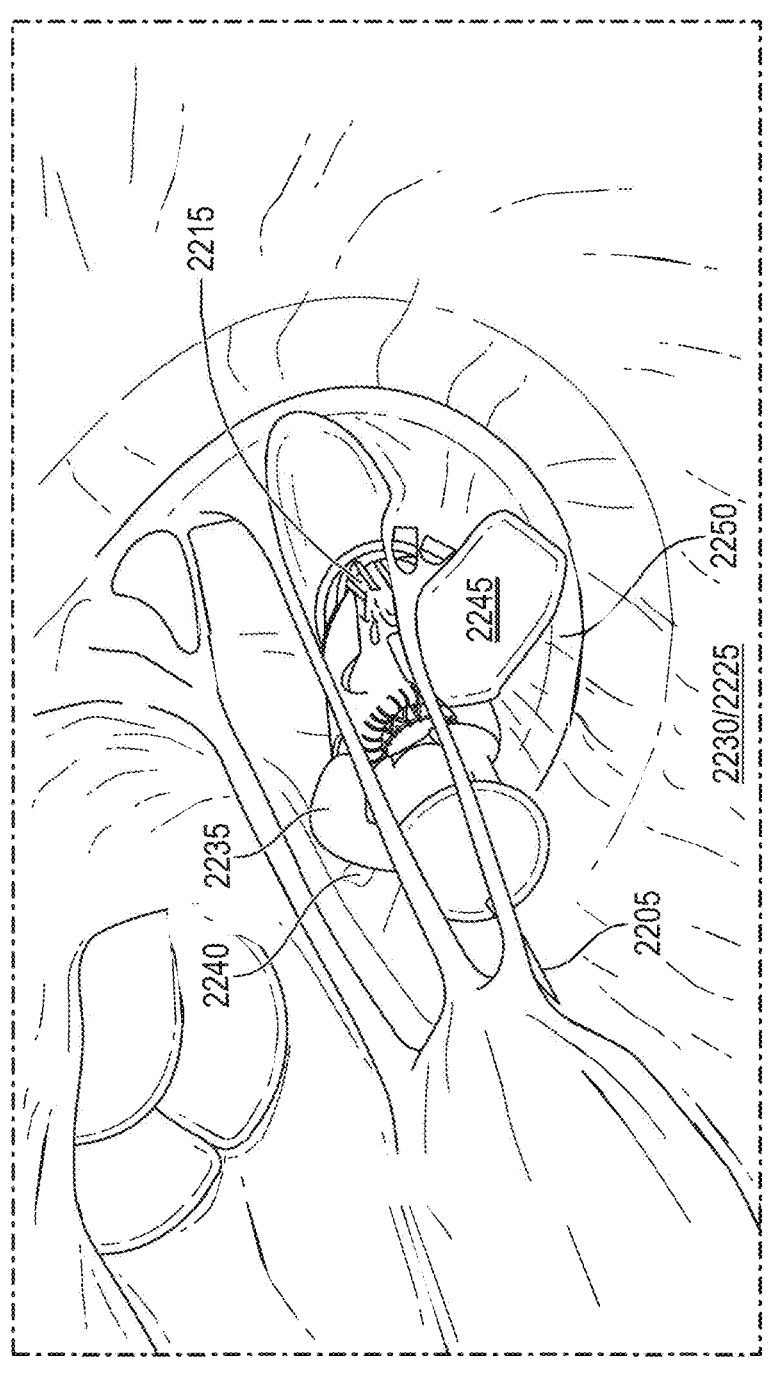

FIG. 74 shows, from the ventricle perspective, the sheathed valve/implant 2215 moving further down into the ventricle 2225/2230 for deployment of sub-annular anchors. In some examples, the anterior clip 2235 may be released or extended prior to moving down in order to determine the location of the anterior clip 2235 in relation to the 360° of the device 2215. Then, as the device 2215 (including the implant) is advanced into the ventricle, and based on the determined position of the anterior clip 2235, the anterior clip 2235 may be oriented or lined up with the location of the anterior leaflet 2240.

In some embodiments, once in the ventricle 2225, the anterior clip 2235 (which may also be referred to as the A2 clip 2235) may be unsheathed so that it is aligned with the anterior leaflet 2240. Then, after finishing entering the ventricle, the anterior clip 2235 may gently slide across the surface of the anterior leaflet 2240 into a predetermined position (e.g., the A2 region) for securing the anterior leaflet 2240. In some embodiments, the position may include the anterior leaflet 2240 being behind the anterior clip 2235. The anterior clip 2235 may be used to envelope the anterior leaflet 2240, and in some embodiments, the anterior leaflet 2240 may also be secured, which may include the anterior clip 2235 grabbing the anterior leaflet 2240 and/or a particular area thereof (e.g., the A2 region), to provide sub-annular securement and prevent migration of the valve replacement into the atrium.

Next, once the anterior leaflet 2240 is secured within the anterior clip 2235, the posterior clip 2245 which may be referred to as the P2 clip 2245) may be unsheathed or released so that it is proximate to the posterior leaflet 2250. In some embodiments, the posterior leaflet 2250 may be behind the posterior clip 2245. In some embodiments, the posterior clip 2245 may be used to envelope the posterior leaflet 2250, and in some embodiments, the posterior leaflet 2250 may also be secured, which may include the posterior clip 2245 grabbing the posterior leaflet 2250 and/or a particular area thereof (e.g., the P2 region), to provide sub-annular securement and prevent migration of the valve replacement into the atrium.

Securing both the anterior and posterior leaflets 2240, 2250 may prevent those native leaflets 2240, 2250 from interfering with the functioning of new leaflets 2265, which may be artificial or bovine leaflets. Once the clips 2235, 2245 are both in proper positions (in the inter-commissural or commissure-to-commissure space) and secured, the device 2215 may be slightly retracted towards the atrium 2230. In embodiments, the clips 2235, 2245 provide securement by a distal end of the clips (the free end opposite where it is attached to the valve replacement) pressing up against an underside of the annulus to prevent dislodgement or migration of the valve replacement.

In some embodiments, the clips 2235, 2245 may include two vertical, smaller loop structures configured to open and close and connect with the leaflets 2240, 2250, thereby enveloping (but not necessarily "pinching") the leaflets 2240, 2250. In this manner, for example, the clips 2235, 2245 may envelope the anterior leaflet 2240 (which may be closer to aortic valve 2405) and the posterior leaflet 2250, and/or parts thereof. In some embodiments, an anterior clip 2235 may be an A2 clip for securing the A2 anterior region of the anterior leaflet 2240, while the posterior clip 2245 may be a P2 clip for securing the posterior region or a particular part thereof. In some embodiments, enveloping native leaflets 2240, 2250 at these regions may provide a particular desirable form of securement (but other forms are contemplated).

Figure 75:
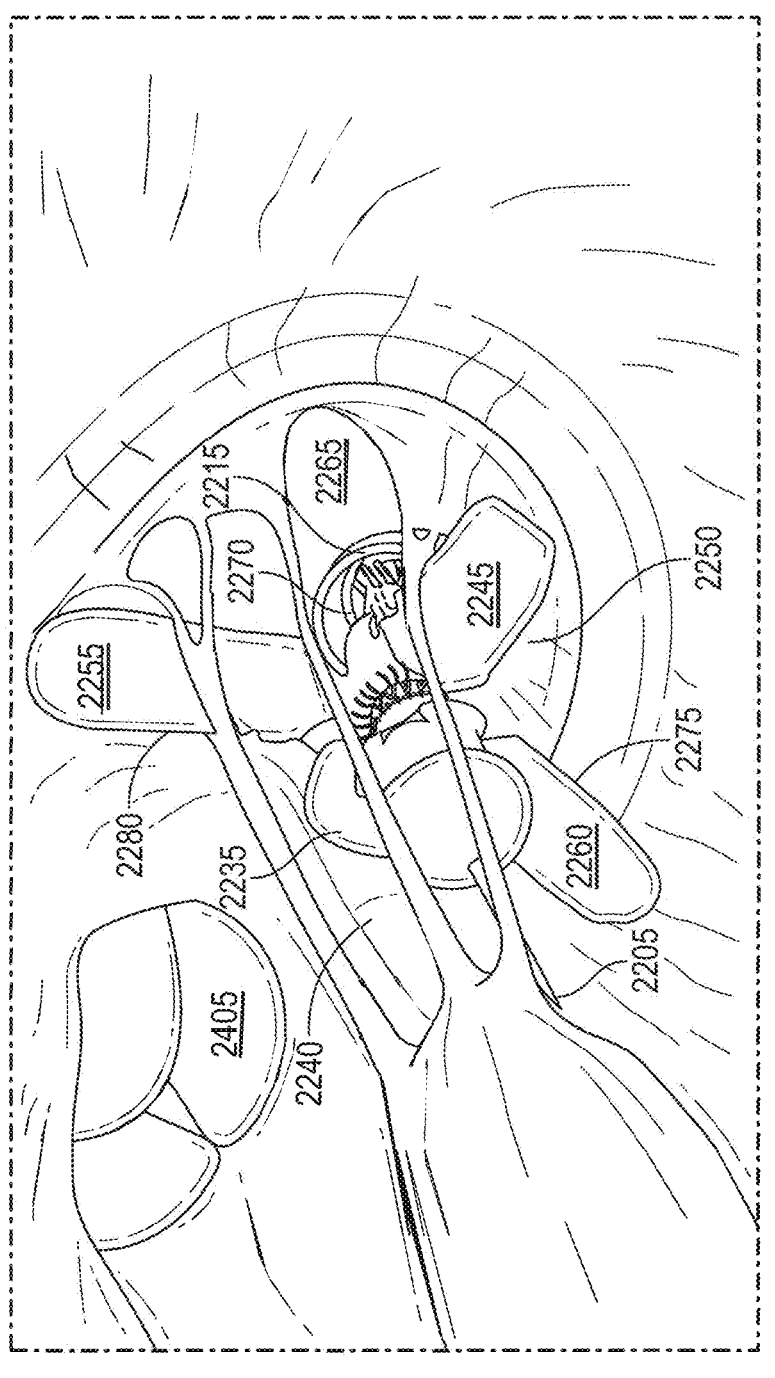
Figure 76:
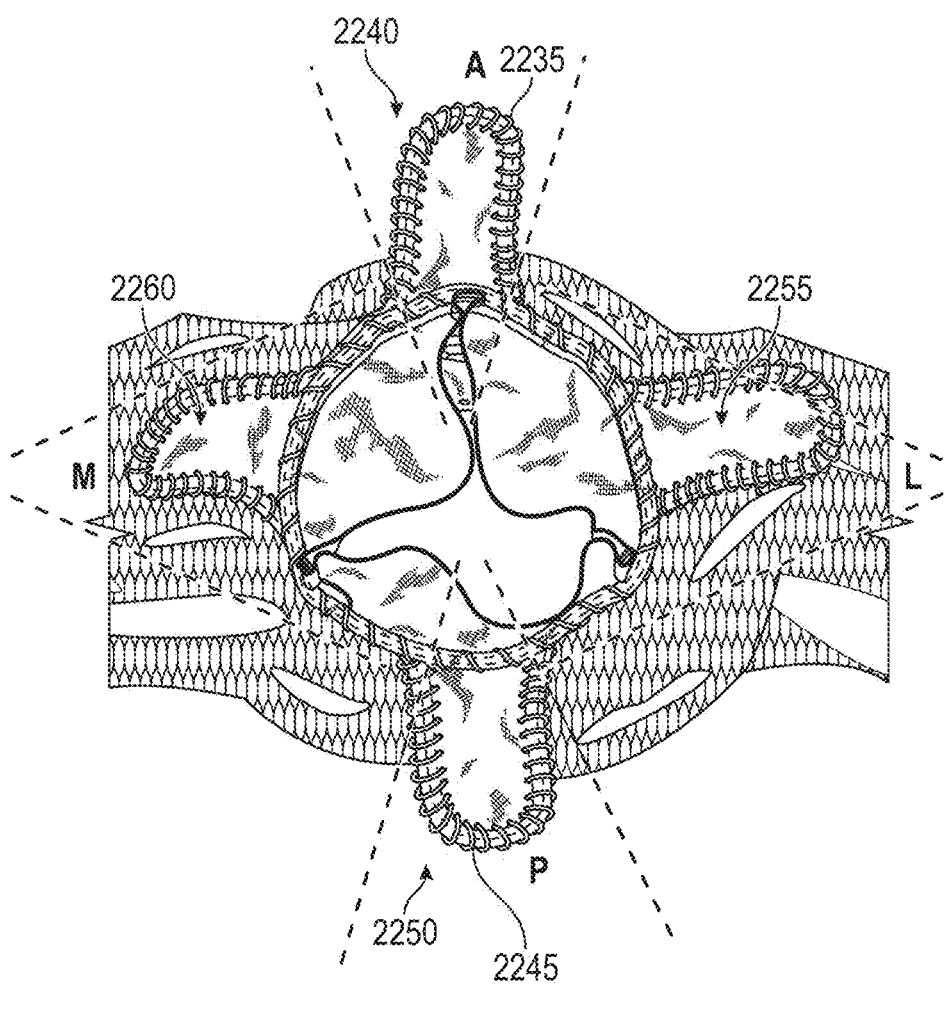

FIG. 75 generally illustrates an embodiment of a valve replacement as disclosed herein. FIG. 76 also generally illustrates an embodiment of a valve replacement as disclosed herein. Relatedly, embodiments of the method described herein may further include releasing medial and lateral strut anchors 2255, 2260, as shown in FIGS. 75 and 76. Some method embodiments may include first pulling up the device 2215 towards the atrium, and determining or verifying that the strut anchors 2255, 2260 are below the annulus 2265 and not in the atrium 2230. Some ways of so determining include, e.g., using echo technology, and using 3D and 2D imaging to identify locations of the tips of the anchors, and/or to otherwise identify locations of the anchors (and to ledges, which are further explained below).

In some embodiments, the clips 2235, 2245 may be released or extended based on some trigger mechanism to be controlled by an operator, which may involve, e.g., pulling a type of (e.g., a first) string.

FIG. 75 shows unsheathed medial anchor 2260 and lateral anchor 2255. Note that in embodiments unsheathing may not allow for release/expansion of P2 and stabilizers. In embodiments, a suture tether release will allow for release/expansion of P2 and stabilizers. In these embodiments, prior to a tether pull, P2 and stabilizers are held against the valve body by the tethers. In some embodiments, the extended or released medial 2260 and lateral anchors 2255 may anchor to, or rest in, the trigone area (which may be proximal to the anterior region of the sub-annular portion of the native heart) of the native tissues, and potentially in between chordae. In some embodiments, there may be desired target areas of native tissue for the anchors. For example, the medial anchor 2260 may rest on/in the medial area 2275 of native heart tissue while the lateral anchor 2255 may rest on/in the lateral area 2280 of native heart tissue.

In some embodiments, the distance or diameter from the medial and lateral anchors 2255, 2260 to the anterior and posterior clips 2235, 2245 may be in a range of 65° to 115°, and not necessarily 90°, and in some embodiments about 75°, from each other (see FIGS. 58 and 63). In some examples, the design of the device 2215 is such that the medial and lateral anchors 2255, 2260 and the anterior and posterior clips 2235, 2245 are spaced so that appropriately grabbing the anterior and posterior leaflets 2240, 2250 using the clips 2235, 2245 results in the medial and lateral anchors 2260, 2255 aligning with predesignated and proper positions for anchoring. Thus, unsheathing the anchors 2255, 2260 assists in achieving full securement on the ventricular side.

In some embodiments, operators may control not only the movement and directionality of the guidewire 2205 and device 2215, but also the releasing and unsheathing (and sequence thereof) of the clips 2235, 2245 and anchors 2255, 2260, and many aspects of delivery. It is anticipated that the relative simplicity associated with such steps, and with regard to placement, will enable a broad group of qualified operators. In some embodiments, the anchors 2255, 2260 may also be released or extended based on some trigger mechanism to be controlled by an operator, which may involve, e.g., pulling a type of (e.g., a second) string.

Figure 77:
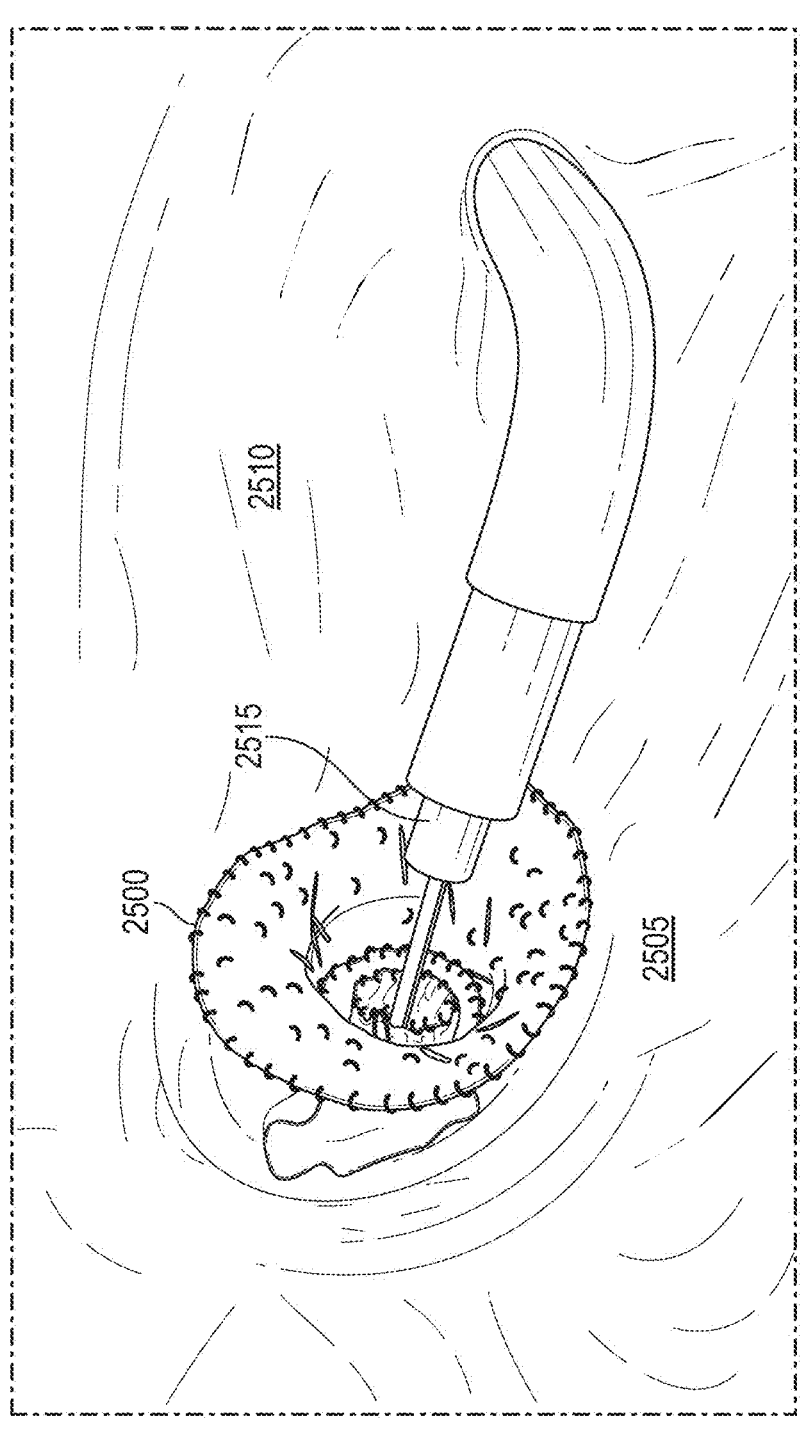

Embodiments of the delivery method described herein may also include unsheathing the flange 2500 in the annulus 2505 on the atrial side 2510, as shown in FIG. 77 (from the dorsal perspective). In some embodiments, deploying the flange 2500 may be triggered by or occur in relation to the pulling back or removing the sheath 2515.

Figure 78:
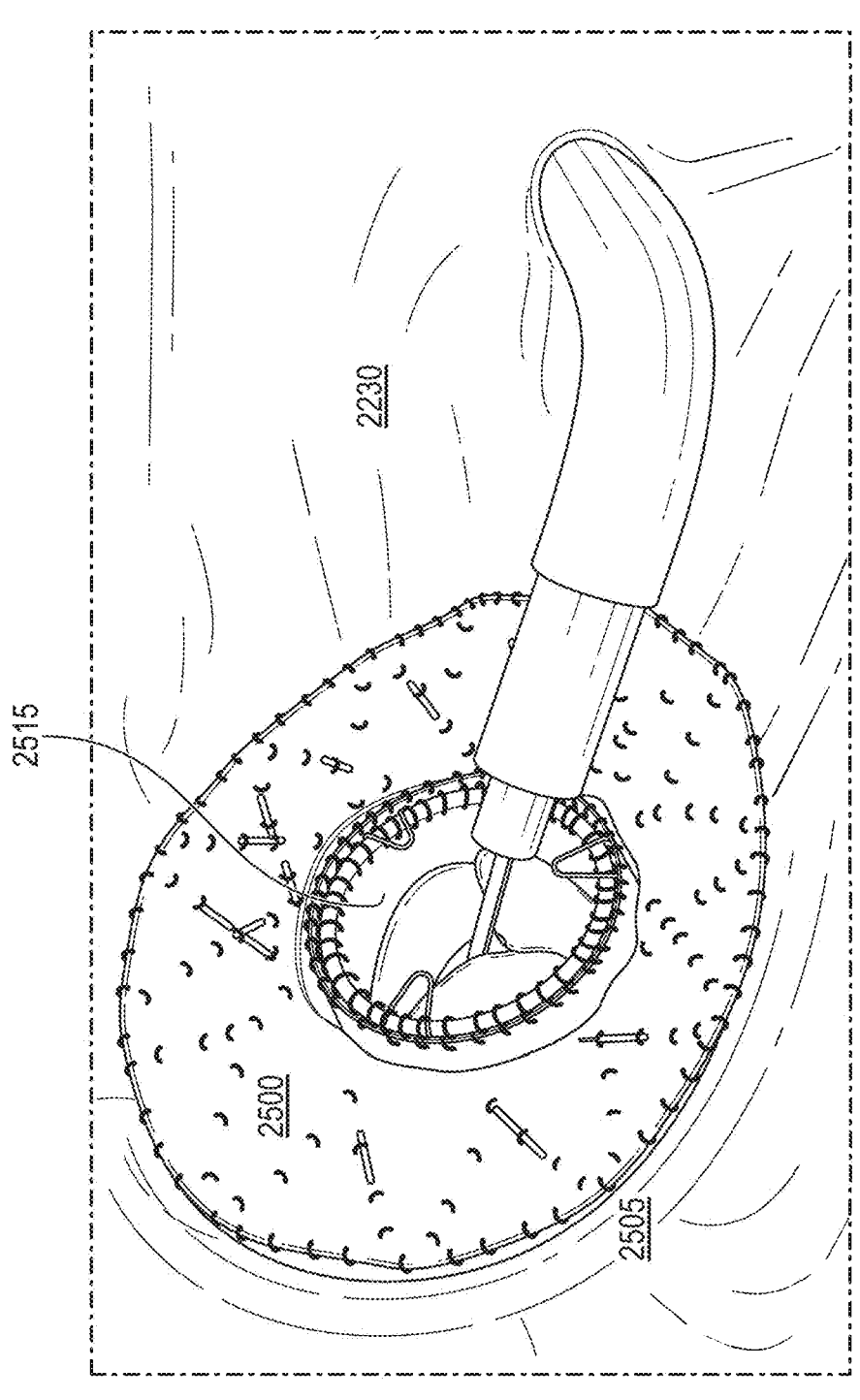

As shown in FIG. 78, releasing and deploying the flange 2500 may cinch it onto the annulus 2505, and/or to ledges thereof or just above the annulus 2505. In some respects, this may assist in sandwiching or trapping the annulus 2505 between the flange 2500 and the anchors 2255, 2260 and clips 2235, 2245, thereby creating a greater level of securement while still permitting an acceptable range of movement. (For example, as explained above, the device may move with the contractions of the heart, not only with the squeezing of the heart, but also with the twist of the heart.) Such securement may assist in preventing the device 2215 and components thereof from inadvertently being injected or migrating into the atrium 2230/ventricle 2225.

Figure 79:
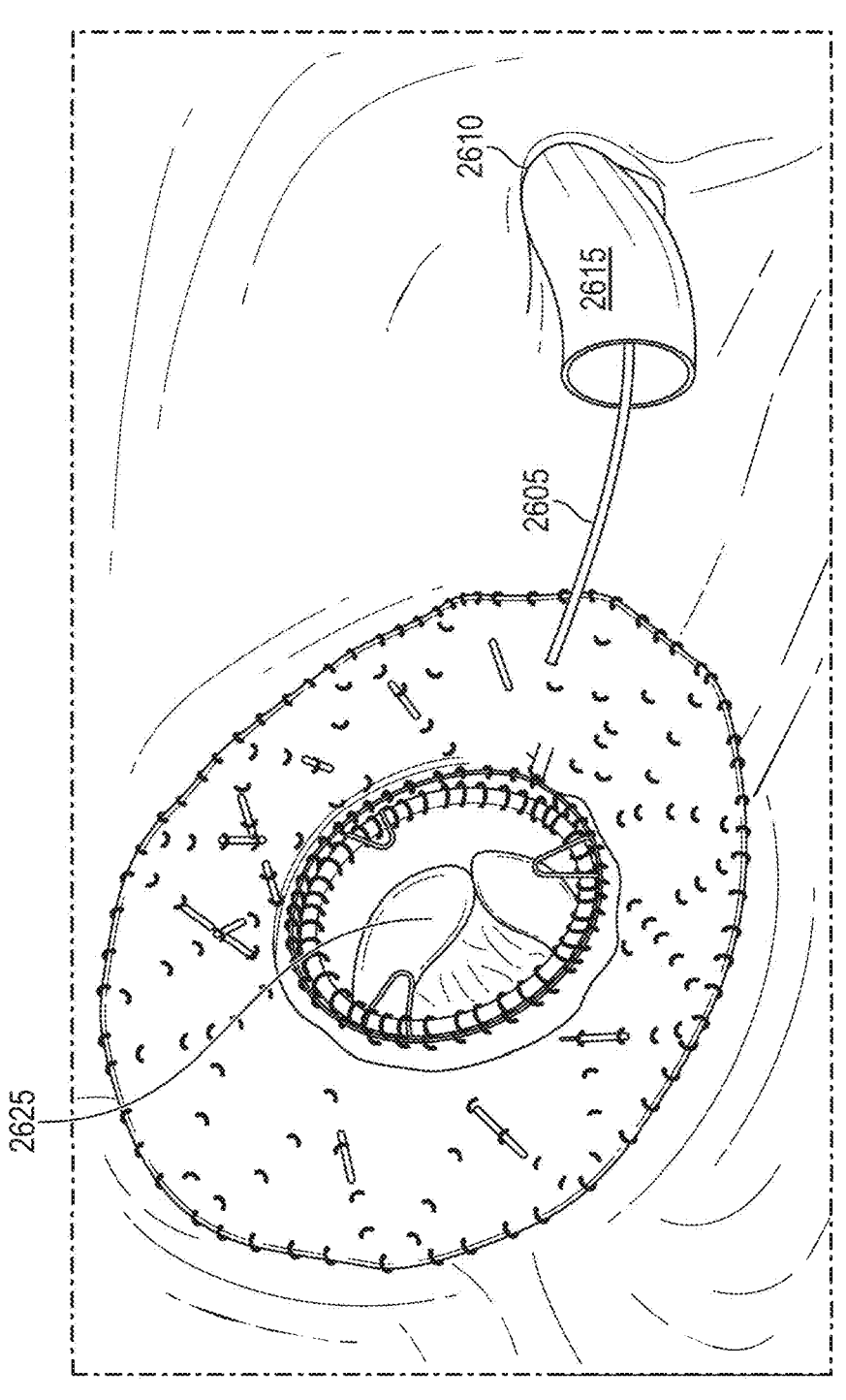

Then, once the device 2215 is in place as described above, the tube may retract and the guidewire may be removed, as shown in FIG. 79.

Implant Delivery Devices

FIG. 80 is a flow diagram generally illustrating a method 5000 of delivering a replacement heart valve, in accordance with aspects of the disclosure. In some embodiments, the method 5000 may include the step 5005 of advancing a catheter device embodiment for carrying heart valve toward the mitral annulus. The method 5000 may include the step 5010 of pushing the catheter device embodiment through the mitral annulus.

The method 5000 may further include the step 5015 of deploying at least one clip from the catheter device embodiment in the ventricle. The method 5000 may further include the step 5020 of, in the ventricle, securing the at least one clip to at least one native leaflet. The method 5000 may further include the step 5025 of, in the ventricle, deploying at least one anchor from the catheter device embodiment.

The method 5000 may further include the step 5030 of, in the ventricle, securing the at least one anchor to native heart tissue. The method 5000 may further include the step 5035 of, in the atrium, releasing a flange to fit over the mitral annulus.

Figures 81, 82:
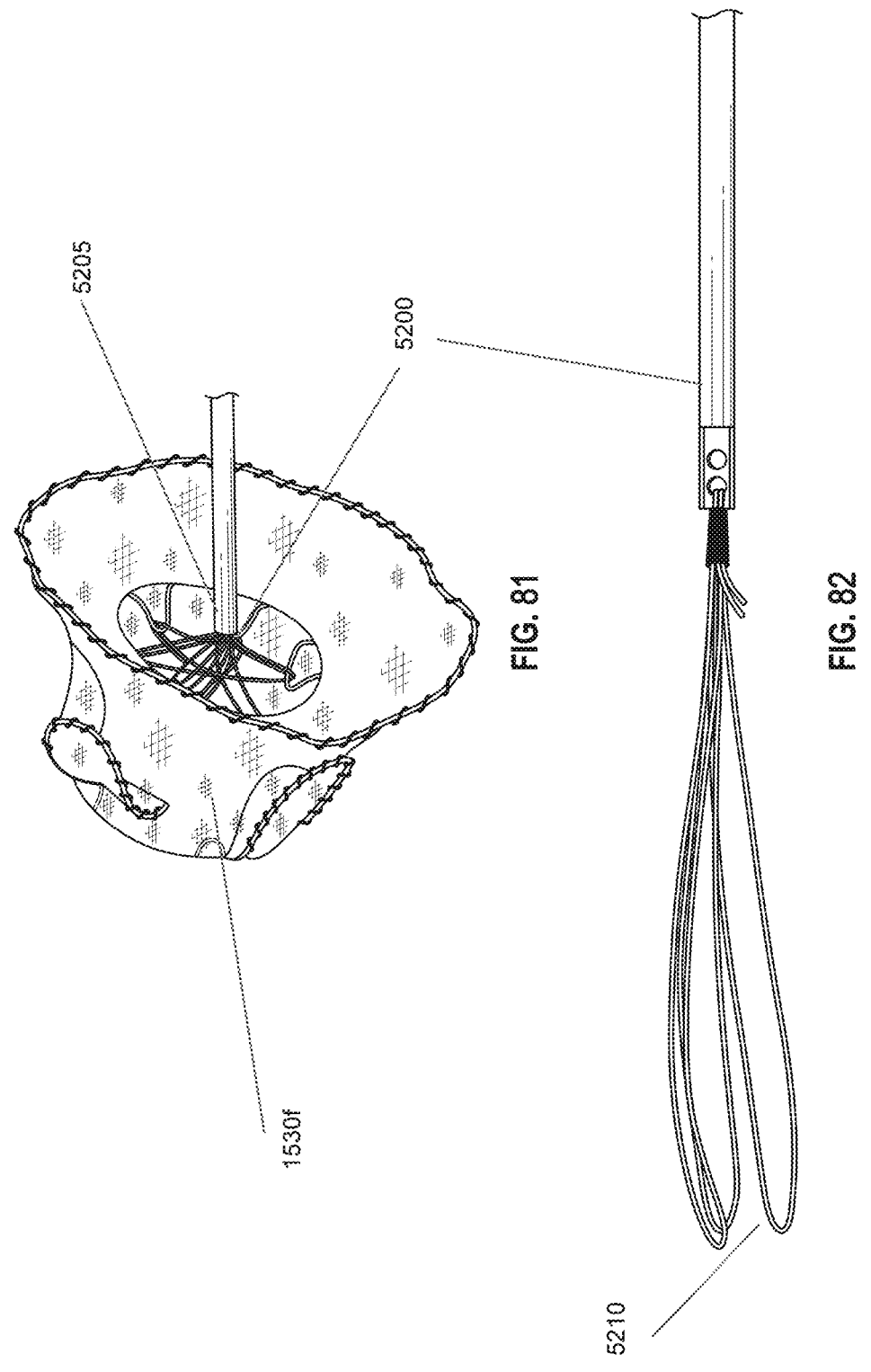
FIGS. 81-86 generally illustrate embodiments of a valve replacement and delivery mechanisms as disclosed herein.

FIGS. 81-87 show a replacement heart valve delivery system 5200. As shown in FIG. 81, the delivery system 5200 attaches to the heart valve/implant 1530f, in some embodiments, using suture. In some embodiments, the delivery system attaches to the heart valve/implant at the end of a laser cut hypotube lumen 5205. In some embodiments, as shown in FIG. 82, three suture loops 5210 route through 2 exposed implant apices each. This embodiment may assist in distributing the load of the device loading and deployment. It also allows for symmetric opening of the valve as slack is given to the mechanism during deployment. In embodiments, the number and placement of suture loops may be modified depending on the implant design and the suture loops may be used for valve-in-valve deployments.

The heart valve delivery system may utilize a number of components, such as, some embodiments, two lumens and release suture to control deployment. In some embodiments, one lumen may be an inner attachment lumen (IAL). In some embodiments, the IAL may include, contain, and/or interact with suture loops (and bundle), a loop connection (e.g., an IAL plate along with a wire), and a laser cut hypotube (LCHT).

Some heart valve delivery system embodiments may also have an outer attachment lumen (OAL), or an outer LCHT, that encapsulates the IAL, with the IAL, in embodiments, being composed of the sutures, IAL plate, wire, and LCHT. In embodiments, the OAL is basically an outer LCHT with the LCHT being a component of a lumen of the OAL.

In some examples, a first LCHT may encapsulate the IAL to contain it therein, and a second LCHT may encapsulate the OAL to contain it therein. Some delivery system embodiments may also have a release suture, such as an independent suture running from a distal end back to a handle or a more rigid component like a wire to prevent the suture from going back through the IAL plate. This assembly is then pulled inside of the OAL during loading. When the IAL is pulled into the OAL, this tightens the suture loops and reduces the valve diameter.

During deployment of the valve, in embodiments, the implant sheath is retracted fully and exposes the atrial flange. The valve cannot come to its fully diameter as it is still constrained by the IAL/OAL. The IAL is then advanced to loosen the suture loops and fully expand the valve via suture slack. This allows for slow and controlled expansion of the valve to its final diameter. After expansion, the valve is fully released by retracting the release suture, which frees the suture loops from the IAL. The advantage of this design is you only need to pull the release suture a couple of inches to release the valve (instead of a long length over the delivery system). The implant is then released and the delivery system can be removed.

Figure 83:
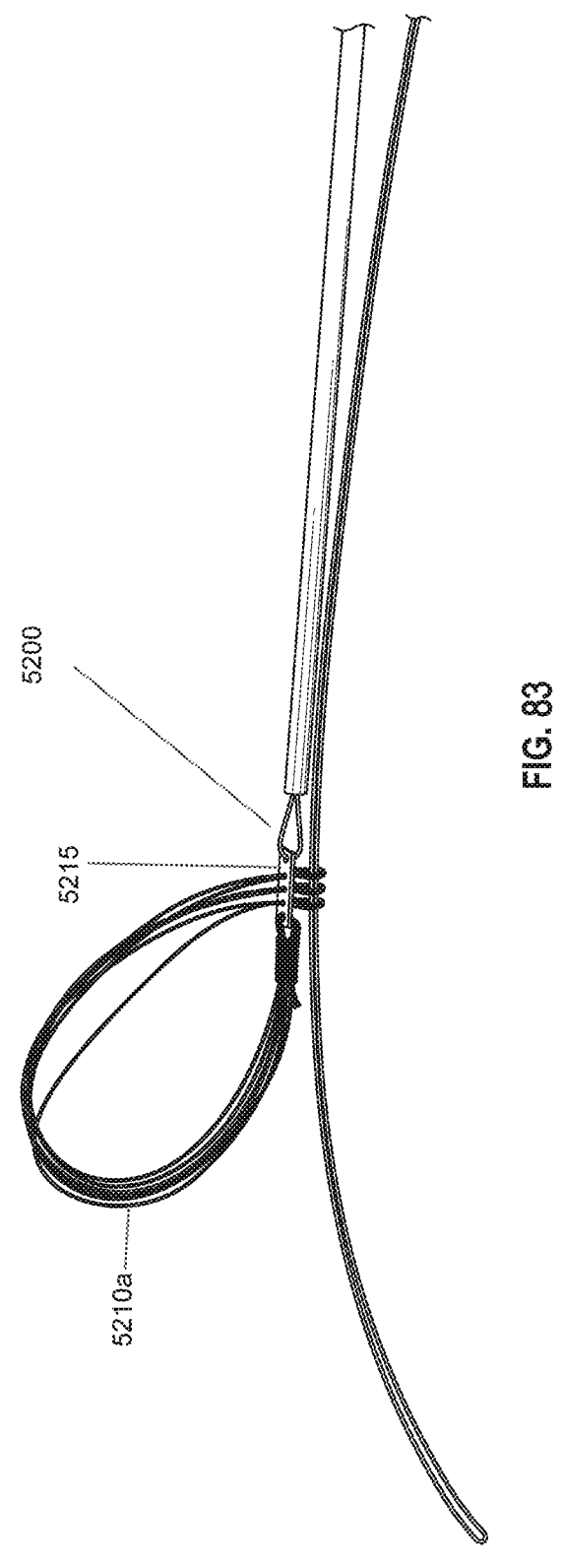

FIG. 83 shows a replacement heart valve delivery system embodiment, with suture loops 5210a tied together into a bundle (similar to the knot bundle of FIG. 81 above). The knot bundle may be tied directly to a metal connector 5215 (e.g., an IAL plate). In alternative embodiments, instead of an IAL plate to hold the suture bundle, a nitinol wire hook can be used, with the suture loop bundle looped and wrapped around the bent back nitinol wire hook, wherein when the wire hook is exposed and withdrawn back into the OAL, the hook inverts and the suture loops are pushed off to release the suture bundle and the connected replacement valve features.

Figure 84:
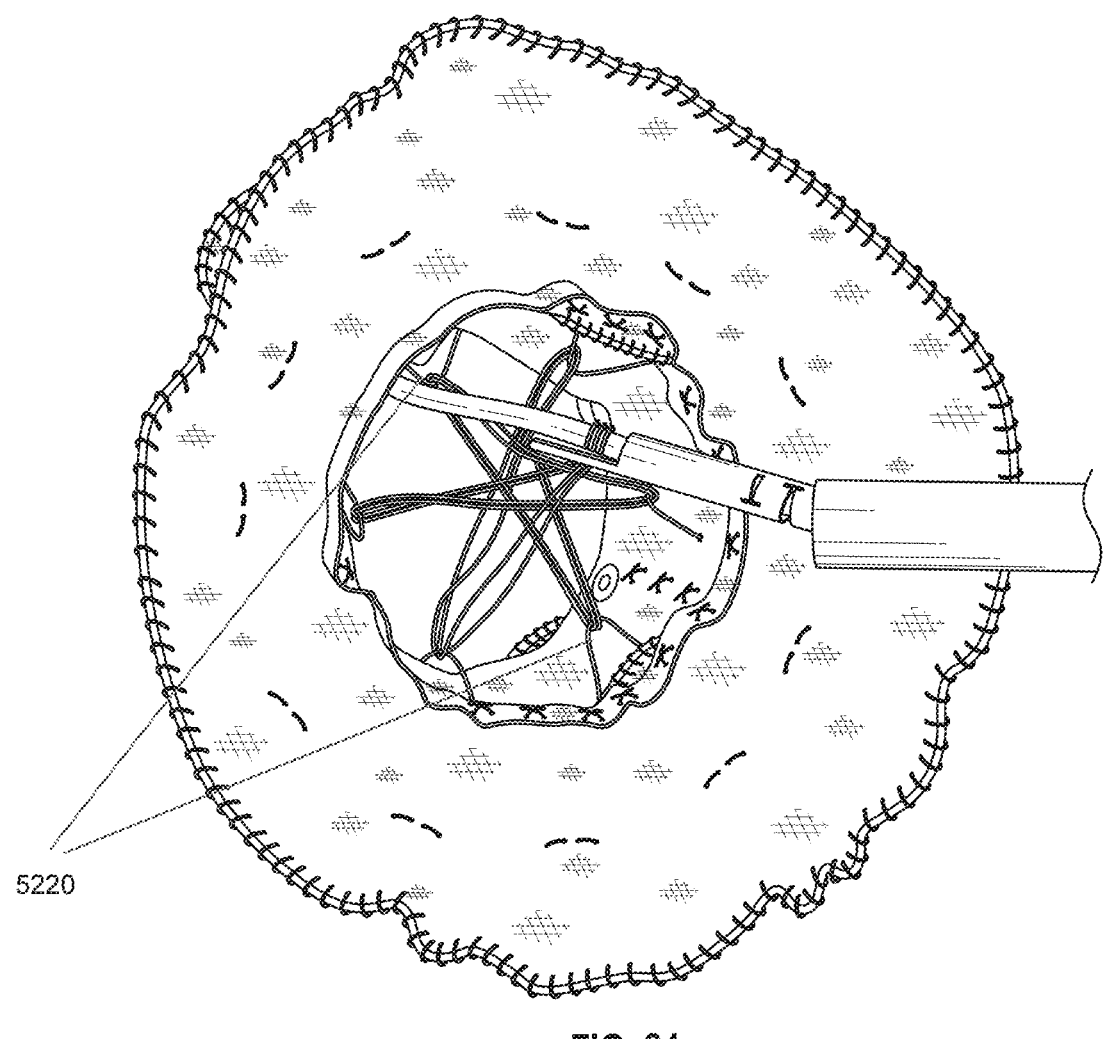

FIG. 84 shows a replacement heart valve delivery system embodiment, illustrating that each loop may then be routed individually through 2 exposed apices 5220 located across from each other on the implant. After routing through the apices 5220, each loop (of, e.g., three suture loops) is brought back to the metal connector (e.g., IAL plate), where each loop may be pushed through a free hole located on the metal connector (e.g., IAL plate).

Figure 85:
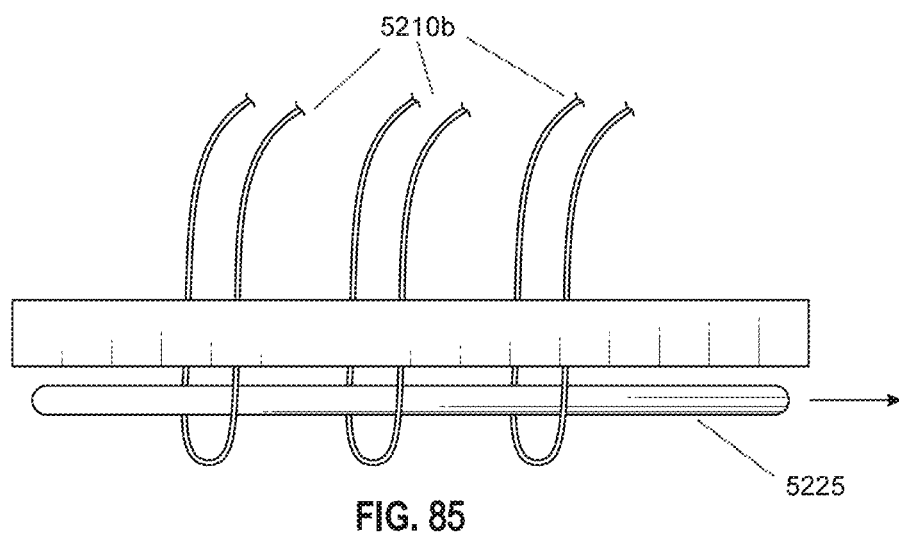

As shown in FIG. 85, the release suture 5225 can then be placed through the suture loop 5210b tips to prevent them from disengaging/popping back through the IAL plate.

This assembly of components including suture loops and release suture may then be pulled inside of the OAL during loading. In addition, in some embodiments, pulling the IAL into the OAL tightens the suture loops, reducing the valve diameter.

In some embodiments, during deployment of the valve, the implant sheath is retracted fully and exposes the atrial flange. However, at that point, the IAL/OAL still constrains the valve from expanding to its full diameter. In embodiments, the replacement valve may also still be moved at this point in the atrial direction if needed for final seating. Accordingly, next the IAL may be advanced to loosen the suture loops and fully expand the valve by providing suture slack. In some examples, this may allow for slow and controlled expansion of the valve to its final diameter.

After expansion, in some embodiments, the valve may be fully released by retracting the release suture 5225, which frees the suture loops from the IAL. One advantage of this design/embodiment is the release suture 5225 need only be pulled a few inches to release the valve (instead of a long length over the delivery system). At this point, the implant is released and delivery system can be removed/retracted.

Figure 86:
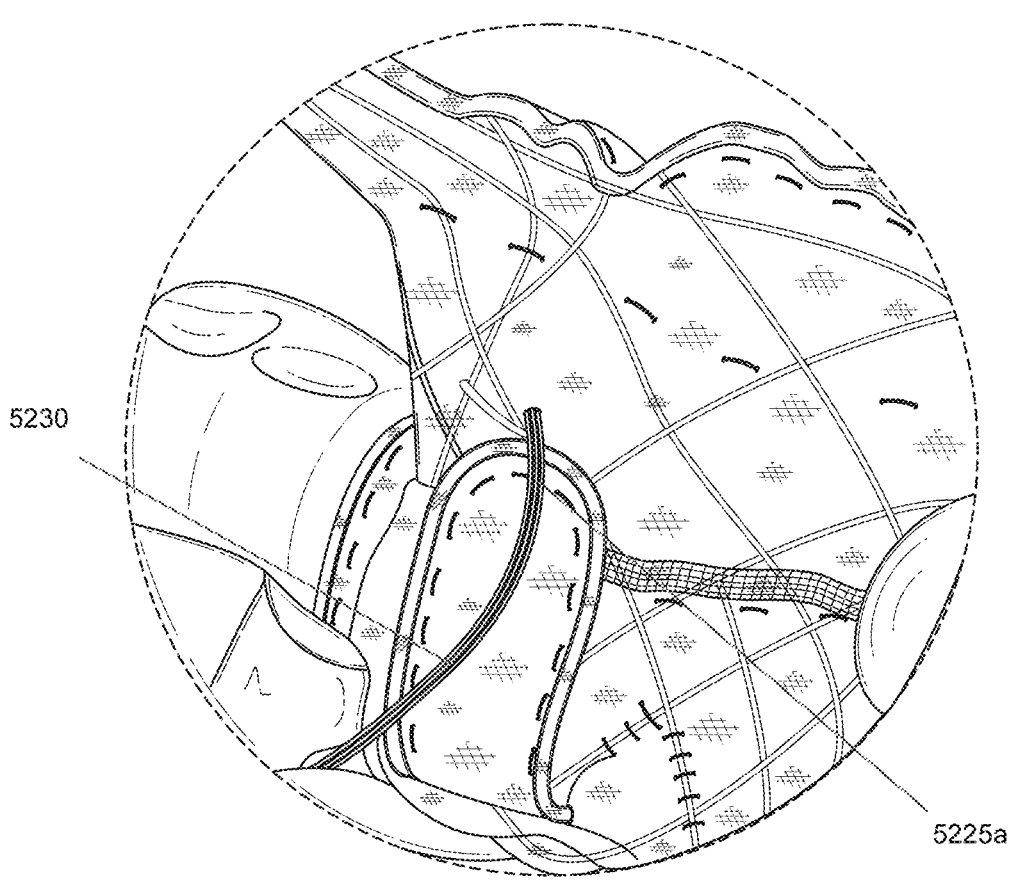

Various attachment techniques were tried in addition to this such as the double hole image above and nitinol wire hook pictured below. Similar mechanism but the loops would wrap around the bent back niti wire. The wire would be exposed, then when its withdrawn into the OAL, the hook inverts and the suture loops pushed off to release FIG. 86 shows a staged stabilizer and P2 deployment mechanism, which in some embodiments utilizes a suture mechanism similar to the release mechanism described above. Some embodiments are used in connection with a "pin suture method," which may feature a permanent suture loop tied into the valve at predetermined areas/features to control (e.g., a P2 clip, A2 clip, medial and/or lateral stabilizers).

In some examples, the suture loop 5225*a* is attached to the main valve body frame, proximate the flange. In some embodiments, the suture loop 5225*a* may then be pushed through a cloth corresponding to an intended stabilizer or A2 or P2 clip, where a "pin suture" or "tether" may be inserted into suture loop 5225*a*. Such insertion may prevent the stabilizer or A2 or P2 clip from expanding and maintain it/them tightly against the valve body. Similar mechanisms may allow controlling as many arm features as desired, including all or some of the stabilizers and A2 and P2 clips, and to individually deploy such features. In embodiments, a temporary pin suture is placed during manufacturing and then replaced bedside with delivery system pin suture.

Thus, FIG. 86 shows a closeup view of a permanent suture loop, a stabilizer, and temporary pin suture 5230 holding the stabilizer tight. Similar to the release mechanism described above, if the pin suture 5230 were to be pulled, the loop 5225*a* would disengage from the clip, and allow the clip to expand. In some embodiments, temporary pin sutures 5230 may also keep the suture loop 5225*a* engaged during sterilization and shipment. And in some embodiments, during bedside loading a real pin suture is attached to the delivery system, in preparation for deployment.

Figure 87:
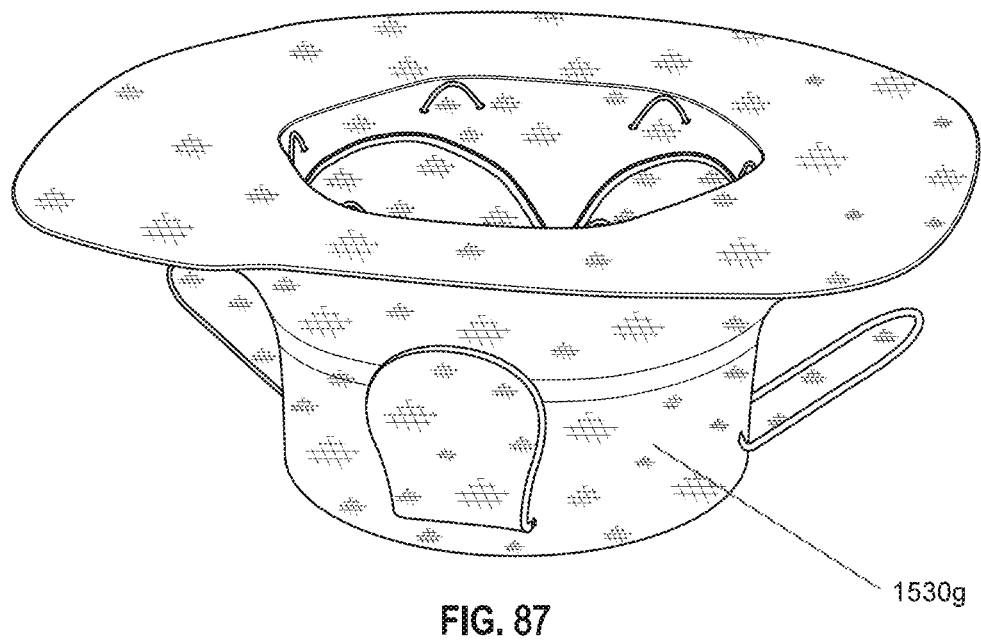
FIG. 87 generally illustrates an embodiment of a valve replacement as disclosed herein.

FIG. 87 shows a replacement heart valve 1530*g* after being deployed and expanded using the delivery system 5200 described above.

Other embodiments may include combinations and sub-combinations of features described or shown in the several figures, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, "feature" or "features" can refer to structures and/or functions of an apparatus, article of manufacture or system, and/or the steps, acts, or modalities of a method.

References throughout this specification to "one embodiment," "an embodiment," "an example embodiment," etc., indicate that the embodiment described may include a particular feature, structure, or characteristic, but every embodiment may not necessarily include that particular feature, structure, or characteristic. Moreover, such phrases are not necessarily referring to the same embodiment. Further, when a particular feature, structure, or characteristic is described in connection with one embodiment, it will be within the knowledge of one skilled in the art to affect such feature, structure, or characteristic in connection with other embodiments whether or not explicitly described.

Unless the context clearly indicates otherwise (1) the word "and" indicates the conjunctive; (2) the word "or" indicates the disjunctive; (3) when the article is phrased in the disjunctive, followed by the words "or both," both the conjunctive and disjunctive are intended; and (4) the word "and" or "or" between the last two items in a series applies to the entire series.

Where a group is expressed using the term "one or more" followed by a plural noun, any further use of that noun to refer to one or more members of the group shall indicate both the singular and the plural form of the noun. For example, a group expressed as having "one or more members" followed by a reference to "the members" of the group shall mean "the member" if there is only one member of the group.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

What is claimed:

1. A prosthetic mitral valve, comprising:
   a tubular body comprising a first braided wire, an inflow end and an outflow end, and a height between the inflow and outflow ends;
   a flange comprising a second braided wire woven into the first braided wire of the tubular body, the flange comprising a portion extending radially outwardly from an intermediate portion of the height of the tubular body and towards the inflow end of the tubular body, and the flange comprising a curved section and a D-shaped perimeter, wherein the flange's curved section comprises a convex section and a concave section with an inflection point therebetween;
   a medial stabilizer extending medially from a lower portion of the height of the tubular body at the outflow end;
   a lateral stabilizer extending laterally from a lower portion of the height of the tubular body at the outflow end;
   a posterior leaflet clip extending posteriorly from a lower portion of the height of the tubular body at the outflow end, the posterior leaflet clip configured to capture a P2 region of a native posterior mitral leaflet; and
   an anterior leaflet clip extending anteriorly from a lower portion of the height of the tubular body at the outflow end, the anterior leaflet clip configured to capture an A2 region of a native anterior mitral leaflet.

2. A prosthetic mitral valve as in claim 1, wherein the first braided wire of the tubular body comprises at least 8 peaks and no more than 16 peaks the outflow end and at least 8 peaks and no more than 16 peaks at the inflow end of the tubular body.

3. A prosthetic mitral valve as in claim 2, wherein the second braided wire of the flange comprises at least 8 peaks and no more than 16 peaks at the outflow end of the tubular body and at least 8 peaks and no more than 16 peaks along the D-shaped perimeter of the flange.

4. A prosthetic mitral valve as in claim 3, wherein the first braided wire of the tubular body comprises 12 peaks at the outflow end and 12 peaks at the inflow end of the tubular body and wherein the second braided wire of the flange comprises between 12 peaks at the outflow end of the tubular body and 12 peaks along the D-shaped perimeter of the flange.

5. A prosthetic mitral valve as in claim 1, wherein the posterior and anterior leaflet clips extend from a lower third portion of the receiver, are inclined towards a left atrium when deployed in the native mitral valve, and resist migration of the prosthetic mitral valve towards the inflow end.

6. A prosthetic mitral valve as in claim 1, wherein the medial and lateral stabilizers are inclined towards a left atrium when deployed in the native mitral valve and resist migration of the prosthetic mitral valve towards the inflow end.

7. A prosthetic mitral valve as in claim 1, wherein at least a portion of the flange is configured to rest in a supra-annular space when deployed in the native mitral valve and resist migration of the prosthetic mitral valve towards the outflow end.

8. A prosthetic mitral valve as in claim 1, wherein at least a portion of the flange's D-shaped perimeter is configured to rest on top of the atrial floor and wherein at least a portion of the flange's D-shaped perimeter is configured to rest at an aortic-mitral curtain area when the flange is deployed in the native mitral valve.

9. A prosthetic mitral valve as in claim 1, wherein the second braided wire of the flange comprises peaks along the D-shaped perimeter of the flange, wherein the peaks of the flange comprise a petal shape near the inflow end of the tubular body.

10. A prosthetic mitral valve as in claim 1, wherein at least a portion of the flange's curved section is configured to rest in an intra-annular space of a native mitral annulus when deployed in a native mitral valve, and wherein at least a portion of the flange's concave portion is configured to rest in a supra-annular space of the native mitral annulus when deployed in the native mitral valve.

11. A prosthetic mitral valve as in claim 10, wherein at least a portion of the flange's curved section transitions into the D-shaped perimeter and wherein at least a portion of the flange's D-shaped perimeter comprises a circular flange section that is configured to rest in an intra-annular space when deployed in the native mitral valve.

12. A prosthetic mitral valve, comprising:
a receiver body comprising a first braided wire, an inflow end and an outflow end, and a height between the inflow and outflow ends;
a flange comprising a second braided wire woven into the first braided wire of the receiver body, the flange comprising a portion extending radially outwardly from an intermediate portion of the height of the receiver body and towards the inflow end of the receiver body, and the flange comprising a curved section and a D-shaped perimeter, wherein at least a portion of the flange's curved section is configured to rest in an intra-annular space of a native mitral annulus when deployed in a native mitral valve, and wherein at least a portion of the flange's D-shaped perimeter is configured to rest on top of the native mitral annulus when deployed in the native mitral valve, wherein the flange resists migration of the prosthetic mitral valve towards the outflow end.

13. A prosthetic mitral valve as in claim 12, wherein the height of the receiver body is between 17 to 26 millimeters and wherein the receiver body has an inner diameter of between 25 to 34 millimeters.

14. A prosthetic mitral valve as in claim 13, further comprising an anterior leaflet clip extending anteriorly from a lower portion of the height of the receiver body at the outflow end, the anterior leaflet clip configured to capture an A2 region of a native anterior mitral leaflet, a posterior leaflet clip extending posteriorly from a lower portion of the height of the receiver body at the outflow end, the posterior leaflet clip configured to capture a P2 region of a native posterior mitral leaflet, wherein the anterior and posterior leaflet clips extend from the first braided wire of the receiver body.

15. A prosthetic mitral valve as in claim 14, wherein the anterior leaflet clip comprises a curved wire that exits the receiver body at a first location along a circumference of the receiver body and re-enters the receiver body at a second location along the circumference of the receiver body, wherein the first and second locations along the circumference of the receiver body are separated by a width of between 4 to 15 millimeters and wherein the curved wire of the anterior leaflet clip comprises a widest point between the curved wire of between 8 to 16 millimeters.

16. A prosthetic mitral valve as in claim 15, wherein the posterior leaflet clip comprises a curved wire that exits the receiver body at a third location along the circumference of the receiver body and re-enters the receiver body at a fourth location along the circumference of the receiver body, wherein the third and fourth locations along the circumference of the receiver body are separated by a width of between 4 to 15 millimeters and wherein the curved wire of the posterior leaflet clip comprises a widest point between the curved wire of between 6 to 14 millimeters.

17. A prosthetic mitral valve as in claim 16, wherein the anterior and posterior leaflet clips each comprise a height of between 10 to 19 millimeters.

18. A prosthetic mitral valve as in claim 13, further comprising a medial stabilizer extending medially from a lower portion of the height of the receiver body at the outflow end and a lateral stabilizer extending laterally from a lower portion of the height of the receiver body at the outflow end, wherein the medial and lateral stabilizers extend from the second braided wire of the flange.

19. A prosthetic mitral valve as in claim 18, wherein the medial stabilizer comprises a curved wire that exits the receiver body at a fifth location along the circumference of the receiver body and re-enters the receiver body at a sixth location along the circumference of the receiver body, wherein the fifth and sixth locations along the circumference of the receiver body are separated by a width of between 4 to 15 millimeters and wherein the curved wire of the medial stabilizer comprises a widest point between the curved wire of between 6 to 18 millimeters.

20. A prosthetic mitral valve as in claim 19, wherein the lateral stabilizer comprises a curved wire that exits the receiver body at a seventh location along the circumference of the receiver body and re-enters the receiver body at an eighth location along the circumference of the receiver body, wherein the seventh and eighth locations along the circumference of the receiver body are separated by a width of between 4 to 15 millimeters and wherein the curved wire of the lateral stabilizer comprises a widest point between the curved wire of between 6 to 18 millimeters.

21. A prosthetic mitral valve as in claim 20, wherein the medial and lateral stabilizers each comprise a height of between 7 to 15 millimeters.

22. A prosthetic mitral valve, comprising:
a tubular body comprising a first braided wire, an inflow end and an outflow end, and a height between the inflow and outflow ends;
a flange comprising a second braided wire woven into the first braided wire of the tubular body, the flange comprising a portion extending radially outwardly from an intermediate portion of the height of the tubular body and towards the inflow end of the tubular body, and the flange comprising a curved section and a D-shaped perimeter, wherein at least a portion of the flange's curved section is configured to rest in an intra-annular space of a native mitral annulus when deployed in a native mitral valve, and wherein at least a portion of the flange's D-shaped perimeter is configured to rest on top of the native mitral annulus when deployed in the native mitral valve;
wherein the flange resists migration of the prosthetic mitral valve towards the outflow end;
a medial stabilizer extending medially from a lower portion of the height of the tubular body at the outflow end, wherein the medial stabilizer extends from the second braided wire of the flange;

a lateral stabilizer extending laterally from a lower portion of the height of the tubular body at the outflow end, wherein the lateral stabilizer extends from the second braided wire of the flange;

a posterior leaflet clip extending posteriorly from a lower portion of the height of the tubular body at the outflow end, the posterior leaflet clip configured to capture a P2 region of a native posterior mitral leaflet, wherein the posterior leaflet clip extends from the first braided wire of the tubular body; and an anterior leaflet clip extending anteriorly from a lower portion of the height of the tubular body at the outflow end, the anterior leaflet clip configured to capture an A2 region of a native anterior mitral leaflet, wherein the anterior leaflet clip extends from the first braided wire of the tubular body, wherein the medial and lateral stabilizers and posterior and anterior leaflet clips resist migration of the prosthetic mitral valve towards the inflow end.

23. A prosthetic mitral valve as in claim 22, wherein the anterior leaflet clip comprises a curved wire that exits the tubular body at a first location along a circumference of the tubular body and re-enters the tubular body at a second location along the circumference of the receiver tubular, wherein the first and second locations along the circumference of the tubular body are separated by a width of between 4 to 15 millimeters and wherein the curved wire of the anterior leaflet clip comprises a widest point between the curved wire of between 8 to 16 millimeters.

24. A prosthetic mitral valve as in claim 23, wherein the posterior leaflet clip comprises a curved wire that exits the tubular body at a third location along the circumference of the tubular body and re-enters the tubular body at a fourth location along the circumference of the tubular body, wherein the third and fourth locations along the circumference of the tubular body are separated by a width of between 4 to 15 millimeters and wherein the curved wire of the posterior leaflet clip comprises a widest point between the curved wire of between 6 to 14 millimeters.

25. A prosthetic mitral valve as in claim 24, wherein the medial and lateral stabilizers each comprise a curved wire having a widest point between 6 to 18 millimeters and a height of between 7 to 15 millimeters, and wherein each of the medial and lateral stabilizers enter and exit the tubular body at different locations along the circumference of the tubular body.

26. A prosthetic mitral valve, comprising:

a tubular body comprising a first braided wire, an inflow end and an outflow end, and a height between the inflow and outflow ends; and a flange comprising a second braided wire woven into the first braided wire of the tubular body, the flange comprising a portion extending radially outwardly from an intermediate portion of the height of the tubular body and towards the inflow end of the tubular body, and the flange comprising a curved section and a D-shaped perimeter;

a medial stabilizer extending medially from a lower portion of the height of the tubular body at the outflow end;

a lateral stabilizer extending laterally from a lower portion of the height of the tubular body at the outflow end;

a posterior leaflet clip extending posteriorly from a lower portion of the height of the tubular body at the outflow end; and an anterior leaflet clip extending anteriorly from a lower portion of the height of the tubular body at the outflow end, wherein the tubular body is undersized in comparison to a native mitral annulus of a native mitral valve in one of more of an anterior-to-posterior (A-P) and commissure-to-commissure (C-C) directions, wherein the tubular body does not exert radial force against the native annulus in the undersized directions when deployed in the native mitral valve.

27. A prosthetic mitral valve as in claim 26, wherein the height of the tubular body is between 17 to 26 millimeters and wherein the tubular body has an inner diameter of between 25 to 34 millimeters.

28. A prosthetic mitral valve as in claim 27, wherein the tubular body in an uncompressed configuration has an inner diameter of at least 32 mm and is deliverable to the native mitral valve in a compressed configuration that is no more than 28Fr in outer diameter.

29. The prosthetic mitral valve of claim 28, wherein the tubular body in an uncompressed configuration has an inner diameter of at least 29 mm and is deliverable to the native mitral valve in a compressed configuration that is no more than 26Fr in outer diameter.

30. The prosthetic mitral valve of claim 29, wherein the flange of the prosthetic mitral valve resists migration towards the outflow end when deployed in the native mitral valve and wherein one or more of the posterior and anterior leaflet clips and medial and lateral stabilizers resist migration towards the inflow end when deployed in the native mitral valve.

* * * * *